United States Patent
Kikuchi et al.

(10) Patent No.: US 12,187,685 B2
(45) Date of Patent: Jan. 7, 2025

(54) PHARMACEUTICAL COMPOSITIONS COMPRISING WRN HELICASE INHIBITORS

(71) Applicant: Vividion Therapeutics, Inc., San Diego, CA (US)

(72) Inventors: Shota Kikuchi, San Diego, CA (US); Betty Lam, San Diego, CA (US); Jason Green, San Diego, CA (US); Don Rogness, San Diego, CA (US); David Weinstein, San Diego, CA (US); Larry Burgess, San Diego, CA (US); Benjamin Horning, San Diego, CA (US); Kelsey Lamb, San Diego, CA (US); Zachary Owyang, San Diego, CA (US); Robert Malmstrom, San Diego, CA (US)

(73) Assignee: Vividion Therapeutics, Inc.

( * ) Notice: Subject to any disclaimer, the term of this patent is extended or adjusted under 35 U.S.C. 154(b) by 0 days.

(21) Appl. No.: 18/370,519

(22) Filed: Sep. 20, 2023

(65) Prior Publication Data
US 2024/0140915 A1 May 2, 2024

Related U.S. Application Data

(63) Continuation of application No. 18/218,149, filed on Jul. 5, 2023, now abandoned.

(60) Provisional application No. 63/367,781, filed on Jul. 6, 2022.

(51) Int. Cl.
| | |
|---|---|
| C07D 237/34 | (2006.01) |
| A61P 35/00 | (2006.01) |
| C07D 239/34 | (2006.01) |
| C07D 403/06 | (2006.01) |
| C07K 14/00 | (2006.01) |

(52) U.S. Cl.
CPC ............ C07D 239/34 (2013.01); A61P 35/00 (2018.01); C07D 403/06 (2013.01); C07K 14/001 (2013.01)

(58) Field of Classification Search
None
See application file for complete search history.

(56) References Cited

FOREIGN PATENT DOCUMENTS

| | | |
|---|---|---|
| WO | 2019/241802 A2 | 12/2019 |
| WO | 2020/097389 A1 | 5/2020 |
| WO | 2022/006534 A1 | 1/2022 |
| WO | 2023/062575 A1 | 4/2023 |

OTHER PUBLICATIONS

Grant & Hackh's Chemical Dictionary (5th Ed. 1987) at p. 148.*
Chemical Abstract Registry No. 1452880-32-8, indexed in the Registry File on STN CAS Online Sep. 20, 2013.*
Chemical Abstract Registry No. 1609842-07-0, indexed in the Registry File on STN CAS Online Jun. 6, 2014.*
The International Search Report & Written Opinion, mailed on Nov. 9, 2023, in related PCT Appl. No. PCT/US2023/026886.
Stefan G. Kathman et al: "A Fragment-Based Method to Discover Irreversible Covalent Inhibitors of Cysteine Proteases", Journal of Medicinal Chemistry, vol. 57, No. 11, May 28, 2014, pp. 4969-4974, XP055494263.
Czerwinska Jolanta et al: "Catalytic activities of Werner protein are affected by adduction with 4-hydroxy-2-nonenal", Nucleic Acids Research, vol. 42, No. 17, Aug. 28, 2014, pp. 11119-11135, XP093096691.
Aggarwal Monika et al: "Inhibition of helicase activity by a small molecule impairs Werner syndrome helicase (WRN) function in the cellular response to DNA damage or replication stress", Proceedings of the National Academy of Sciences, vol. 108, No. 4, Jan. 10, 2011, pp. 1525-1530, XP093012713. (Supporting information included.).
Smita B Gunnoo et al: "Chemical Protein Modification through Cysteine", Chembiochem, John Wiley & Sons, Inc, Hoboken, USA, vol. 17, No. 7, Mar. 9, 2016, pp. 529-553, XP072199174.

* cited by examiner

*Primary Examiner* — Po-Chih Chen

(57) ABSTRACT

Disclosed are compounds of Formula (I):

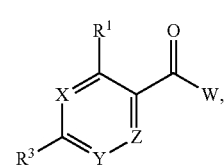

or pharmaceutically acceptable salts or solvates thereof, wherein $R^1$, $R^3$, X, Y, Z, and W are as defined herein. The compounds are, for example, inhibitors of WRN helicase and useful in treating a proliferative disease, such as cancer.

23 Claims, No Drawings

Specification includes a Sequence Listing.

PHARMACEUTICAL COMPOSITIONS COMPRISING WRN HELICASE INHIBITORS

CROSS-REFERENCE TO RELATED APPLICATIONS

This application is a Continuation Application of U.S. application Ser. No. 18/218,149, filed Jul. 5, 2023, which claims the benefit of and priority to U.S. Provisional Patent Application No. 63/367,781, filed on Jul. 6, 2022. Each of prior mentioned applications is hereby incorporated by reference herein in its entirety.

SEQUENCE LISTING

The instant application contains a Sequence Listing which has been submitted electronically in XML format and is hereby incorporated by reference in its entirety. Said XML copy, created on Nov. 17, 2023, is named 036844-109326_P38040-US2 SL.xml and is 8,069 bytes in size.

FIELD OF DISCLOSURE

This invention relates to compounds that are inhibitors of Werner syndrome helicase (WRN helicase), pharmaceutical compositions comprising said inhibitors and methods of treatment using said inhibitors.

BACKGROUND OF THE DISCLOSURE

RECQ helicases are 3' to 5' DNA unwinding DNA-dependent ATPases. Three RECQ helicases, BLM, Werner (WRN) and RECQL4, cause human syndromes that overlap, but are also distinct symptomatically, when their expression is altered or lost (de Renty C, Ellis N A. Ageing Res Rev 2017; 33:36-51). WRN was identified as a potential synthetic lethal target for cancer that expresses high levels of microsatellite instability (MSI-H cancer) in 2019 by multiple groups independently (Chan, E. M. et al., Nature 2019, 568, 551-556; Behan, F. M. et al., Nature 2019, 568, 511-516; Lieb et al. eLife 2019, 8, e43333). There are a few reports describing identification of small molecules that inhibit WRN helicase activity with unknown mechanism (Aggarwal et al., Cancer Res. 2013, 73, 5497; Aggarwal et al., PNAS 2011, 108, 4, 1525-1530; Sommers et al., PLoS ONE 2019, 14(1), e0210525).

There is therefore a need to provide novel inhibitors of WRN helicase for the treatment of MSI-H cancer.

SUMMARY OF THE DISCLOSURE

Some embodiments described herein relate to a compound of Formula (I):

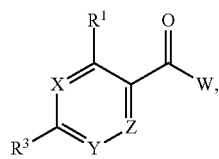

(I)

or a pharmaceutically acceptable salt or solvate thereof, wherein:
X is $CR^2$ or N;
Y is $CR^4$ or N;
Z is $CR^5$ or N;
or Y and Z taken together form an optionally substituted five- to six-membered heteroaryl, or an optionally substituted five- to six-membered heterocyclyl; with the proviso that X, Y, and Z are not simultaneously N;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
or $R^1$ together with the carbon atoms to which it is shown attached and X form an optionally substituted five- to six-membered heterocyclyl;
$R^2$ is H, optionally substituted $C_1$-$C_6$ alkyl, or halo;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);
or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;
$R^4$ is H, $C_1$-$C_6$ alkyl, cyano, or halo,
or $R^4$ together with the carbon atom to which it is shown attached and Z form an optionally substituted five- to six-membered heteroaryl;
or $R^3$ and $R^4$ taken together with the carbon atoms to which they are shown attached form an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;
$R^5$ is H, $C_1$-$C_6$ alkyl, —$NR_2$, or —N(R)—C(=O)—($C_1$-$C_6$ alkyl);
each R independently is H, or optionally substituted $C_1$-$C_6$ alkyl;
W is $W^1$, $W^2$, $W^3$, $W^4$, or $W^5$;
$W^1$ is:

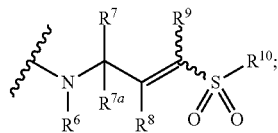

wherein:
the bonds represented by ⌇⌇⌇ indicate that

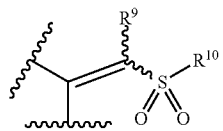

can exist as either a (Z)- or (E)-geometric isomer wherein

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl;
 or $R^6$ together with the nitrogen atom to which it is shown attached and $R^7$ and $R^{7a}$ with the carbon atom to which they are shown attached form an azetidinyl ring;
 or $R^6$ together with the nitrogen atom to which it is shown attached and $R^7$, $R^{7a}$, and $R^8$ together with the carbon atoms to which they are shown attached form an azetidinyl or pyrrolodinyl ring;
 or $R^6$ together with the nitrogen atom to which it is shown attached and $R^7$, $R^{7a}$, $R^8$, and $R^9$ together with the carbon atoms to which they are shown attached form a dihydropyrrolyl ring;
 or $R^7$, $R^{7a}$, $R^8$, $R^9$, and $R^{10}$ together with the carbon atoms to which they are shown attached form a 2,3-dihydrothiophene 1,1-dioxide ring; or
$R^8$, $R^9$, and $R^{10}$ together with the carbon atoms to which they are shown attached form a 1,1-dioxido-2H-thietyl ring;
$W^2$ is:

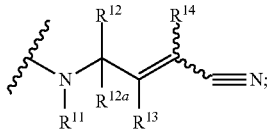

wherein:
the bonds represented by ∼∼∼∼ indicate that

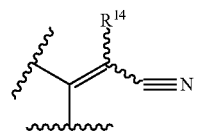

can exist as either a (Z)- or (E)-geometric isomer, wherein

indicates the point of attachment;

$R^{11}$ is H;
$R^{12}$ is H or optionally substituted $C_1$-$C_6$ alkyl;
$R^{12a}$ is H; and
$R^{13}$ and $R^{14}$ are each H;
 or $R^{11}$ together with the nitrogen atom to which it is shown attached and $R^{12}$, $R^{12a}$, and $R^{13}$ together with the carbon atoms to which they are shown attached form an optionally substituted azetidinyl ring;
$W^3$ is:

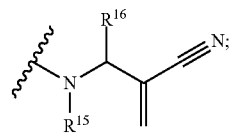

wherein:

indicates the point of attachment;
$R^{15}$ is H;
$R^{16}$ is H or optionally substituted $C_1$-$C_6$ alkyl, or optionally substituted $C_3$-$C_8$ cycloalkyl;
$W^4$ is:

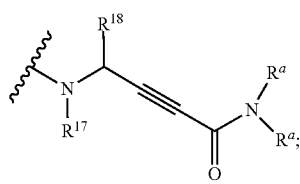

wherein:

indicates the point of attachment;
$R^{17}$ is H;
$R^{18}$ is H or optionally substituted $C_1$-$C_6$ alkyl; and
each $R^a$ independently is optionally substituted $C_1$-$C_6$ alkyl;
$W^5$ is:

wherein:

the bond represented by ⌇⌇⌇⌇ indicates that

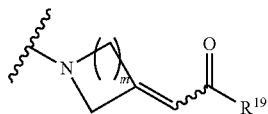

can exist as either a (Z)- or (E)-geometric isomer, and wherein

indicates the point of attachment;

m is 1, 2, or 3; and $R^{19}$ is selected from the group consisting of $C_1$-$C_6$ alkyl and —O—($C_1$-$C_6$ alkyl).

Some embodiments described herein relate to a compound of Formula (II):

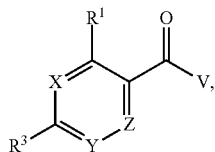

or a pharmaceutically acceptable salt or solvate thereof, wherein:

X is $CR^2$ or N;

Y is $CR^4$ or N;

Z is $CR^5$ or N;

or Y and Z taken together form an optionally substituted five- to six-membered heteroaryl, or an optionally substituted five- to six-membered heterocyclyl;

with the proviso that X, Y, and Z are not simultaneously N;

$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;

or $R^1$ together with the carbon atoms to which it is shown attached and X form an optionally substituted five- to six-membered heterocyclyl;

$R^2$ is H, optionally substituted $C_1$-$C_6$ alkyl, or halo;

$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);

or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;

$R^4$ is H, $C_1$-$C_6$ alkyl, cyano, or halo;

or $R^4$ together with the carbon atom to which it is shown attached and Z form an optionally substituted five- to six-membered heteroaryl;

or $R^3$ and $R^4$ taken together with the carbon atoms to which they are shown attached and $R^3$ taken form an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;

$R^5$ is H, $C_1$-$C_6$ alkyl, —$NR_2$, or —N(R)—C(=O)—($C_1$-$C_6$ alkyl);

each R independently is H, or optionally substituted $C_1$-$C_6$ alkyl; and

V comprises an electrophile that reacts and forms a covalent bond with the sulfur atom at cysteine 727 as set forth in SEQ ID NO: 1 or a variant thereof.

Some embodiments described herein also provides a pharmaceutical composition comprising a compound of Formula (I) or Formula (II) (or any of the embodiments thereof described herein), or a pharmaceutically acceptable salt or solvate thereof; and a pharmaceutically acceptable excipient.

Some embodiments described herein also provide a method of treating a disease (such as a proliferative disease, e.g., cancer) in a patient which method comprises administering to the patient in need thereof, a therapeutically effective amount of a compound of Formula (I) or Formula (II) (or any of the embodiments thereof described herein), and/or a pharmaceutically acceptable salt thereof.

Some embodiments described herein also provide a method of inhibiting WRN helicase (Werner syndrome ATP-dependent helicase) in a subject in need of such inhibition, comprising administering to the subject a therapeutically effective amount of at least one compound of Formula (I) or Formula (II) (or any of the embodiments thereof described herein), or a pharmaceutically acceptable salt or solvate thereof.

Some embodiments described herein also provide a method of inhibiting WRN helicase (Werner syndrome ATP-dependent helicase) comprising effecting a non-naturally occurring covalent modification at cysteine 727 as set forth in SEQ ID NO: 1 or the variant thereof, the modification resulting from a bond forming reaction between an electrophile and the cysteine 727 as set forth in SEQ ID NO:1 or a variant thereof, wherein a sulfur atom at the cysteine residue undergoes a reaction with the electrophile.

Some embodiments described herein also provide a modified WRN helicase protein comprising a non-naturally occurring small molecule fragment having a covalent bond to cysteine 727 of the WRN helicase protein, wherein the modified WRN helicase protein comprises SEQ ID NO: 1 or a variant thereof as set forth herein and has the structure of Formula (III):

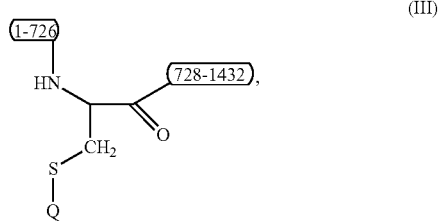

wherein:
S is the sulfur atom of Cysteine 727 in SEQ ID NO: 1 or a variant thereof,
1-726 and 728-1432 represent amino acid positions 1-726 and 7288-1432 respectively of SEQ ID NO: 1 or the variant thereof; and
Q is $Q^1$, $Q^2$, $Q^3$, $Q^4$, or $Q^5$; wherein:
$Q^1$ is:

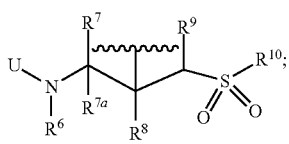

wherein:

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl;
  or $R^6$ together with the nitrogen atom to which it is shown attached and $R^7$ and $R^{7a}$ with the carbon atom to which they are shown attached form an azetidinyl ring;
  or $R^6$ together with the nitrogen atom to which it is shown attached and $R^7$, $R^{7a}$, and $R^8$ together with the carbon atoms to which they are shown attached form an azetidinyl or pyrrolodinyl ring;
  or $R^6$ together with the nitrogen atom to which it is shown attached and $R^7$, $R^{7a}$, $R^8$, and $R^9$ together with the carbon atoms to which they are shown attached form a dihydropyrrolyl ring;
  or $R^7$, $R^{7a}$, $R^8$, $R^9$, and $R^{10}$ together with the carbon atoms to which they are shown attached form a 2,3-dihydrothiophene 1,1-dioxide;
  or $R^8$, $R^9$, and $R^{10}$ together with the carbon atoms to which they are shown attached form a 1,1-dioxido-2H-thietyl ring;
$Q^2$ is:

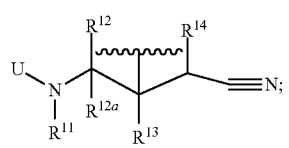

wherein:

indicates the point of attachment;
$R^{11}$ is H;
$R^{12}$ is H or optionally substituted $C_1$-$C_6$ alkyl;
$R^{12a}$ is H; and
$R^{13}$ and $R^{14}$ are each H;
  or $R^{11}$ together with the nitrogen atom to which it is shown attached and $R^{12}$, $R^{12a}$, and $R^{13}$ together with the carbon atoms to which they are shown attached form an optionally substituted azetidinyl ring;
$Q^3$ is:

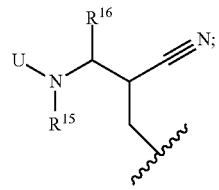

wherein:

indicates the point of attachment;
$R^{15}$ is H; and
$R^{16}$ is H or optionally substituted $C_1$-$C_6$ alkyl, or optionally substituted $C_3$-$C_8$ cycloalkyl;
$Q^4$ is:

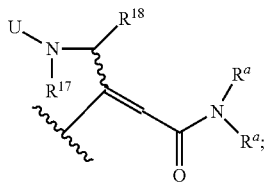

wherein:

indicates the point of attachment;
$R^{11}$ is H;
$R^{18}$ is H or optionally substituted $C_1$-$C_6$ alkyl; and
each $R^a$ independently is optionally substituted $C_1$-$C_6$ alkyl;

$Q^5$ is:

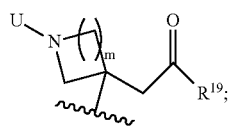

wherein:

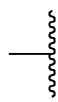

indicates the point of attachment;
m is 1, 2, or 3; and
$R^{19}$ is selected from the group consisting of $C_1$-$C_6$ alkyl and —O—($C_1$-$C_6$ alkyl); and
U is:

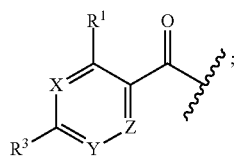

wherein:

indicates the point of attachment;
X is $CR^2$ or N;
Y is $CR^4$ or N;
Z is $CR^5$ or N;
or Y and Z taken together form an optionally substituted five- to six-membered heteroaryl, or an optionally substituted five- to six-membered heterocyclyl;
with the proviso that X, Y, and Z are not simultaneously N;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
or $R^1$ together with the carbon atoms to which it is shown attached and X form an optionally substituted five- to six-membered heterocyclyl;
$R^2$ is H, optionally substituted $C_1$-$C_6$ alkyl, or halo;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);
or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;
$R^4$ is H, $C_1$-$C_6$ alkyl, cyano, or halo,
or $R^4$ together with the carbon atom to which it is shown attached and Z form an optionally substituted five- to six-membered heteroaryl;
or $R^3$ and $R^4$ taken together with the carbon atoms to which they are shown attached form an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;
$R^5$ is H, $C_1$-$C_6$ alkyl, —$NR_2$, or —N(R)—C(=O)—($C_1$-$C_6$ alkyl); and
each R independently is H, or optionally substituted $C_1$-$C_6$ alkyl.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE DISCLOSURE

Definitions

Unless otherwise stated, the following terms used in the specification and claims are defined for the purposes of this Application and have the following meaning. All undefined technical and scientific terms used in this Application have the meaning as commonly understood by one of ordinary skill in the art to which this disclosure belongs.

As used herein, "a" or "an" entity refers to one or more of that entity; for example, a compound refers to one or more compounds or at least one compound unless stated otherwise. As such, the terms "a" (or "an"), "one or more", and "at least one" can be used interchangeably herein.

"Patient" includes both human and animals. "Patient" and "subject" are used interchangeably herein.

When a range of values is listed, it is intended to encompass each value and sub-range within the range. For example, "$C_{1-6}$ alkyl" (or "$C_1$-$C_6$ alkyl") is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 15 carbon atoms ("$C_{1-15}$ alkyl"). In some embodiments, an alkyl group has 1 to 14 carbon atoms ("$C_{1-14}$ alkyl"). In some embodiments, an alkyl group has 1 to 13 carbon atoms ("$C_{1-13}$ alkyl"). In some embodiments, an alkyl group has 1 to 12 carbon atoms ("$C_{1-12}$ alkyl"). In some embodiments, an alkyl group has 1 to 11 carbon atoms ("$C_{1-11}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like.

"Alkenyl" refers to a radical of a straight-chain or branched hydrocarbon group having from 2 to 10 carbon atoms and 1, 2, 3, or 4 carbon-carbon double bonds ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

"Alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

"Carbocyclyl", "Cycloalkyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

In some embodiments, "carbocyclyl" is a monocyclic, saturated carbocyclyl group having from 3 to 14 ring carbon atoms ("$C_{3-14}$ cycloalkyl"). In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$).

"Cycloalkenyl" refers to a radical of a non-aromatic cyclic hydrocarbon group having from 3 to 14 ring carbon atoms ("C$_{3-14}$ cycloalkyl") and zero heteroatoms in the non-aromatic ring system, wherein at least 2 carbon atoms have a carbon-carbon double bond. In some embodiments, the cycloalkenyl group has 3 to 14 ring carbon atoms and at least one double bond. In some embodiments, the cycloalkenyl group has 3 to 10 ring atoms and at least one double bond. In some embodiments, the cycloalkenyl group has 3 to 6 ring atoms and at least one double bond. In some embodiments, the cycloalkenyl has two double compounds.

"Heterocyclyl" or "heterocyclic" refers to a group or radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl (α-naphthyl) and 2-naphthyl (β-naphthyl)). In some embodiments, an aryl group has 14 ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

"Heteroaryl" refers to a radical of a 5-14 membered monocyclic or polycyclic (e.g., bicyclic, tricyclic) 4n+2 aromatic ring system (e.g., having 6, 10, or 14 pi electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. The term "heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl.

Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Saturated" refers to a ring moiety that does not contain a double or triple bond, i.e., the ring contains all single bonds.

Alkyl, alkenyl, cycloalkenyl, cycloalkyl, heterocyclyl, aryl, and heteroaryl groups may be optionally substituted. "Optionally substituted" refers to a group which may be substituted or unsubstituted. In general, the term "substituted" means that at least one hydrogen present on a group is replaced with a non-hydrogen substituent, and which upon substitution results in a stable compound, e.g., a compound which does not spontaneously undergo transformation such as by rearrangement, cyclization, elimination, or other reaction. Heteroatoms such as nitrogen, oxygen, and sulfur may have hydrogen substituents and/or non-hydrogen substituents which satisfy the valencies of the heteroatoms and results in the formation of a stable compound.

Exemplary non-hydrogen substituents may be selected from the group consisting of halogen, —CN, —NO$_2$, —N$_3$, —SO$_2$H, —SO$_3$H, —OH, —OR$^{aa}$, —N(R$^{bb}$)$_2$, —N(OR$^{cc}$)R$^{bb}$, —SH, —SR$^{aa}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —S(=O)R$^{aa}$, —OS(=O)R$^{aa}$, —B(OR$^{cc}$)$_2$, C$_{1-10}$ alkyl, C$_{2-10}$ alkenyl, C$_{2-10}$ alkynyl, C$_{3-14}$ cycloalkyl, 3- to 14-membered heterocyclyl, C$_{6-14}$ aryl, and 5- to 14-membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups, or two geminal hydrogens on a carbon atom are replaced with the group =O;

each instance of R$^{aa}$ is, independently, selected from the group consisting of C$_{1-10}$ alkyl, C$_{1-10}$ perhaloalkyl, C$_{2-10}$ alkenyl, C$_{2-10}$ alkynyl, C$_{3-14}$ carbocyclyl, 3- to 14-membered heterocyclyl, C$_{6-14}$ aryl, and 5- to 14-membered heteroaryl, or two R$^{aa}$ groups are joined to form a 3- to 14-membered heterocyclyl or 5- to 14-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from the group consisting of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —SO$_2$N(R$^{cc}$)$_2$, —SOR$^{aa}$, C$_{1-10}$ alkyl, C$_{1-10}$ perhaloalkyl, C$_{2-10}$ alkenyl, C$_{2-10}$ alkynyl, C$_{3-14}$ carbocyclyl, 3- to 14-membered heterocyclyl, C$_{6-14}$ aryl, and 5- to 14-membered heteroaryl, or two R$^{bb}$ groups are joined to form a 3- to 14-membered heterocyclyl or 5- to 14-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from the group consisting of hydrogen, C$_{1-10}$ alkyl, C$_{1-10}$ perhaloalkyl, C$_{2-10}$ alkenyl, C$_{2-10}$ alkynyl, C$_{3-14}$ carbocyclyl, 3- to 14-membered heterocyclyl, C$_{6-14}$ aryl, and 5- to 14-membered heteroaryl, or two R$^{cc}$ groups are joined to form a 3- to 14-membered heterocyclyl or 5- to 14-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; and each instance of R$^{dd}$ is, independently, selected from the group consisting of halogen, —CN, —NO$_2$, —N$_3$, —SO$_2$H, —SO₃H, —OH, —OC$_{1-6}$ alkyl, —ON(C$_{1-6}$ alkyl)$_2$, —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —SC$_{1-6}$ alkyl, —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —B(OH)$_2$, —B(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3- to 10-membered heterocyclyl, and 5- to 10-membered heteroaryl; or two geminal R$^d$ substituents on a carbon atom may be joined to form =O.

In preferred embodiments, optional substituents are selected from the group consisting of halogen, cyano, hydroxyl, amino, deuterio, —OC$_{1-6}$ alkyl, aryl, oxo, —SC$_{1-6}$ alkyl, —N(C$_{1-6}$ alkyl)$_2$, —O(aryl), C$_{1-6}$ alkyl, —OC$_{1-6}$ cycloalkyl, halogen substituted —OC$_{1-6}$ alkyl and C$_{1-6}$ cycloalkyl. In more preferred embodiments, optional substituents are selected from the group consisting of fluoro, chloro, trifluoromethyl, cyano, hydroxyl, amino, deutorio, methoxy, methyl, ethyl, phenyl, oxo, methylsulfanyl, dimethylamino, phenoxy, tert-butoxy, cyclopropoxy, difluoromethoxy, cyclopropyl and cyclohexyl. In preferred embodiments, optional substituents are selected from the group consisting of fluoro, trifluormethyl, hydroxyl, deutorio, methyl, phenyl and cyclopropyl.

"Halo" or "halogen" refers to fluorine (fluoro, —F), chlorine (chloro, —Cl), bromine (bromo, —Br), or iodine (iodo, —I).

It should be noted that in hetero-atom containing ring systems described herein, there are no hydroxyl groups on carbon atoms adjacent to a N, O or S, as well as there are no N or S groups on carbon adjacent to another heteroatom. Thus, for example, in the ring:

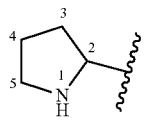

there is no —OH attached directly to carbons marked 2 and 5.

It should also be noted that tautomeric forms such as, for example, the moieties:

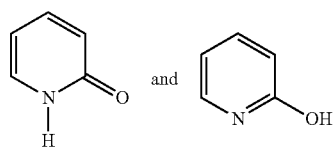 [SMILES: O=c1cccc[nH]1 ; Oc1ccccn1]

are considered equivalent unless otherwise specified.

As used herein, the term "composition" is intended to encompass a product comprising the specified ingredients in the specified amounts, as well as any product which results, directly or indirectly, from combination of the specified ingredients in the specified amounts.

"Electrophile" is a chemical species that forms bonds with nucleophiles by accepting an electron pair. Such electrophiles are often involved in Michael addition reactions which involve the nucleophilic addition of a nucleophile to an α,β-unsaturated carbonyl compound containing an electron withdrawing group. It belongs to the larger class of conjugate additions and is widely used for the mild formation of C—C bonds. The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile.

"Effective amount" or "therapeutically effective amount" is meant to describe an amount of compound or a composition described herein that is effective in inhibiting the above-noted enzyme, diseases or conditions, and thus producing the desired therapeutic, ameliorative, inhibitory and/or preventative effect.

"Salt" includes any and all salts. "Pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts include those derived from inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Solvate" includes any and all solvates. As used herein, the term "pharmaceutically acceptable solvate," is a solvate formed from the association of one or more solvent molecules to one or more molecules of a compound as disclosed herein. The term solvate includes hydrates (where the solvent molecule is water) (e.g., hemi-hydrate, mono-hydrate, dihydrate, trihydrate, tetrahydrate, and the like).

"Microsatellite instability" or "MSI" as used herein, is defined as alterations in the lengths of microsatellites due to deletion or insertion of repeating units to produce novel length alleles in tumor DNA when compared with the normal/germline DNA from the same individual. A tumor that has an "MSI-High" (MSI-H) phenotype is a tumor that has a change in DNA sequence length in at least two of the evaluated mononucleotide or dinucleotide microsatellite loci (e.g., BAT25, BAT26, D2S123, D5S346, and D17S250). Methods of identifying MSI-H tumor status are well known in the art and include, e.g., polymerase chain reaction (PCR) tests for MSI status. Mononucleotide or dinucleotide markers used for the characterization of MSI status include, but are not limited to, BAT25, BAT26, D2S123, D5S346, and D17S250; also known as the Bethesda panel.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. According to Cahn-Ingold Prelog Convention, the asymmetric carbon atom (chiral carbon atom) can be of the "R" or "S" configuration. Isomers can be isolated from mixtures by methods known to those skilled in the art, including chiral high performance liquid chromatography (HPLC). Compounds described herein can be in the form of individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{8}F$, replacement of a carbon by a $^{13}C$- or $^{14}C$-enriched carbon, and/or replacement of an oxygen atom with $^{18}O$, are within the scope of the disclosure. Other examples of isotopes include $^{15}N$, $^{18}O$, $^{17}O$, $^{31}P$, $^{32}P$, $^{35}S$, $^{18}F$, $^{36}Cl$ and $^{123}I$. Compounds with such isotopically enriched atoms are useful, for example, as analytical tools or probes in biological assays.

Certain isotopically-labelled compounds of Formula (I), (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes, for example, those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single Photon Emission Computed Tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half-lives ($t_{1/2}$>1 day), can generally be prepared by following procedures analogous to those disclosed in the Schemes and/or in the Examples herein below, by substituting an appropriate isotopically labeled reagent for a non-isotopically labeled reagent.

The present invention provides a series of potent and selective WRN inhibitors that engage cysteine 727 (C727) of WRN via irreversible covalent binding of electrophilic groups. In one embodiment, these inhibitors exhibited potent helicase inhibition, reduction of viability only in MSI cell lines not in MSS cell lines and complete tumor growth inhibition of MSI cell line xenograft mouse models. In one embodiment, ATP cooperativity of these inhibitors (potency improves in the presence of ATP or ADP: i.e., cellular assay or lysate supplemented with ATP) which is a surprising and unexpected feature of these compounds.

The compounds described herein can also be used in combination with one or more additional therapeutic and/or prophylactic agents (see below "Combination Therapies").

In other embodiments, disclosed herein are methods of inhibiting a WRN helicase. In some embodiments, the method includes administering a compound disclosed herein. In some embodiments, the method includes administering ATP. In some embodiments, the method includes administering a compound disclosed herein and ATP. In some embodiments, the method includes administering ADP. In some embodiments, the method includes administering a compound disclosed herein and ADP. The administration may be in vivo. For example, the WRN helicase may be inhibited in vivo. The administration may be to a subject. The administration may be to a cell. The administration may be in vitro. For example, the WRN helicase may be inhibited in vitro.

Disclosed herein, in some embodiments, are methods of performing a WRN helicase activity assay. Some embodiments include methods of measuring a WRN helicase activity. The method may include contacting a WRN helicase with a WRN helicase substrate. The method may include administering a WRN helicase substrate. The method may include contacting a WRN helicase with ATP. The method may include administering ATP. The method may include administering a WRN helicase substrate and ATP. The method may include contacting a WRN helicase with ADP. The method may include administering ADP. The method may include administering a WRN helicase substrate and ADP. The administration may be in vivo. For example, the WRN helicase activity assay may be performed in cultured cells. The administration may be to a cell. The administration may be in vitro. For example, the WRN helicase activity assay may be performed in vitro. In some embodiments, the measurement is performed after administration of ADP. In some embodiments, the measurement is performed after administration of ATP.

EMBODIMENTS

Examples of embodiments of the present application include the following:

Embodiment 1

A compound of Formula (I):

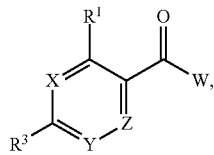

(I)

or a pharmaceutically acceptable salt or solvate thereof, wherein:
X is $CR^2$ or N;
Y is $CR^4$ or N;
Z is $CR^5$ or N;
or Y and Z taken together form an optionally substituted five- to six-membered heteroaryl, or an optionally substituted five- to six-membered heterocyclyl;
with the proviso that X, Y, and Z are not simultaneously N;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
or $R^1$ together with the carbon atoms to which it is shown attached and X form an optionally substituted five- to six-membered heterocyclyl;
$R^2$ is H, optionally substituted $C_1$-$C_6$ alkyl, or halo;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);
or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;
$R^4$ is H, $C_1$-$C_6$ alkyl, cyano, or halo;
or $R^4$ together with the carbon atom to which it is shown attached and Z form an optionally substituted five- to six-membered heteroaryl;
or $R^3$ and $R^4$ taken together with the carbon atoms to which they are shown attached form an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;
$R^5$ is H, $C_1$-$C_6$ alkyl, —$NR_2$, or —N(R)—C(=O)—($C_1$-$C_6$ alkyl);
each R independently is H, or optionally substituted $C_1$-$C_6$ alkyl;
W is $W^1$, $W^2$, $W^3$, $W^4$, or $W^5$;
$W^1$ is:

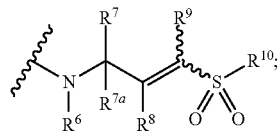

wherein:
the bonds represented by ⌇ indicate that

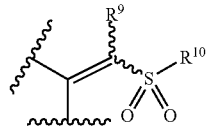

can exist as either a (Z)- or (E)-geometric isomer wherein

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl; or
$R^6$ together with the nitrogen atom to which it is shown attached and $R^7$ and $R^{7a}$ together with the carbon atom to which they are shown attached form an azetidinyl ring;
or $R^6$ together with the nitrogen atom to which it is shown attached and $R^7$, $R^{7a}$, and $R^8$ together with the carbon atoms to which they are shown attached form an azetidinyl or pyrrolodinyl ring;
or $R^6$ together with the nitrogen atom to which it is shown attached and $R^7$, $R^{7a}$, $R^8$, and $R^9$ together with the carbon atoms to which they are shown attached form a dihydropyrrolyl ring; or
$R^7$, $R^{7a}$, $R^8$, $R^9$, and $R^{10}$ together with the carbon atoms to which they are shown attached form a 2,3-dihydrothiophene 1,1-dioxide;
or $R^8$, $R^9$, and $R^{10}$ together with the carbon atoms to which they are shown attached form a 1,1-dioxido-2H-thietyl ring;

$W^2$ is:

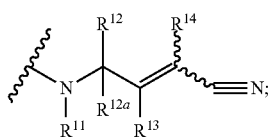

wherein:

the bonds represented by ~~~~ indicate that

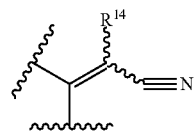

can exist as either a (Z)- or (E)-geometric isomer, wherein

indicates the point of attachment;

$R^{11}$ is H;
$R^{12}$ is H or optionally substituted $C_1$-$C_6$ alkyl;
$R^{12a}$ is H; and
$R^{13}$ and $R^{14}$ are each H;
  or $R^{11}$ together with the nitrogen atom to which it is shown attached and $R^{12}$, $R^{12a}$, and $R^{13}$ together with the carbon atoms to which they are shown attached form an optionally substituted azetidinyl ring;

$W^3$ is:

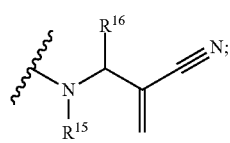

wherein:

indicates the point of attachment;
$R^5$ is H;
$R^{16}$ is H or optionally substituted $C_1$-$C_6$ alkyl, or optionally substituted $C_3$-$C_8$ cycloalkyl;

$W^4$ is:

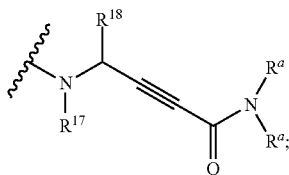

wherein:

indicates the point of attachment;
$R^{17}$ is H;
$R^{18}$ is H or optionally substituted $C_1$-$C_6$ alkyl; and
each $R^a$ independently is optionally substituted $C_1$-$C_6$ alkyl; and $W^5$ is:

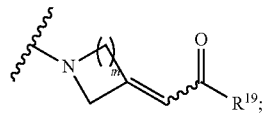

wherein:
the bond represented by ~~~~ indicates that

can exist as either a (Z)- or (E)-geometric isomer, and wherein

indicates the point of attachment;
m is 1, 2, or 3; and
$R^{19}$ is selected from the group consisting of $C_1$-$C_6$ alkyl and —O—($C_1$-$C_6$ alkyl).

Embodiment 1A

A compound of Formula (I):

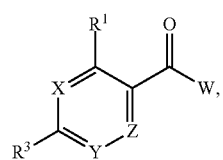

(I)

or a pharmaceutically acceptable salt thereof, wherein:

X is CR² or N;

Y is CR⁴ or N;

Z is CR⁵ or N;

or Y and Z taken together form an optionally substituted five- to six-membered heteroaryl, or an optionally substituted five- to six-membered heterocyclyl;

with the proviso that X, Y, and Z are not simultaneously N;

R¹ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;

or R¹ together with the carbon atoms to which it is shown attached and X form an optionally substituted five- to six-membered heterocyclyl;

R² is H, optionally substituted $C_1$-$C_6$ alkyl, or halo;

R³ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —NR₂, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);

or R³ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;

R⁴ is H, $C_1$-$C_6$ alkyl, cyano, or halo;

or R⁴ together with the carbon atom to which it is shown attached and Z form an optionally substituted five- to six-membered heteroaryl;

or R³ and R⁴ taken together with the carbon atoms to which they are shown attached form an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;

R⁵ is H, $C_1$-$C_6$ alkyl, —NR₂, or —N(R)—C(=O)—($C_1$-$C_6$ alkyl);

each R independently is H, or optionally substituted $C_1$-$C_6$ alkyl;

W is W¹, W², W³, W⁴, or W⁵;

W¹ is:

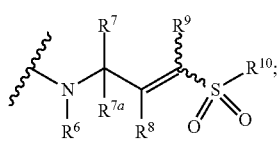

wherein:

the bonds represented by ∼∼∼ indicate that

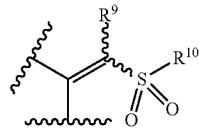

can exist as either a (Z)- or (E)-geometric isomer wherein

indicates the point of attachment;

R⁶ is H;

R⁷ is H, optionally substituted $C_1$-$C_6$ alkyl, optionally substituted $C_3$-$C_8$ cycloalkyl, or optionally substituted five- to six-membered heterocyclyl;

R⁷ᵃ is H or deuterium;

R⁸ is H;

R⁹ is H; and

R¹⁰ is optionally substituted $C_1$-$C_6$ alkyl, optionally substituted $C_3$-$C_8$ cycloalkyl, or optionally substituted five- to six-membered heterocyclyl; or R⁶ together with the nitrogen atom to which it is shown attached and R⁷ and R⁷ᵃ together with the carbon atom to which they are shown attached form an azetidinyl ring;

or R⁶ together with the nitrogen atom to which it is shown attached and R⁷, R⁷ᵃ, and R⁸ together with the carbon atoms to which they are shown attached form an azetidinyl or pyrrolodinyl ring;

or R⁶ together with the nitrogen atom to which it is shown attached and R⁷, R⁷ᵃ, R⁸, and R⁹ together with the carbon atoms to which they are shown attached form a dihydropyrrolyl ring; or R⁷, R⁷ᵃ, R⁸, R⁹, and R¹⁰ together with the carbon atoms to which they are shown attached form a 2,3-dihydrothiophene 1,1-dioxide;

or R⁸, R⁹, and R¹⁰ together with the carbon atoms to which they are shown attached form a 1,1-dioxido-2H-thietyl ring;

W² is:

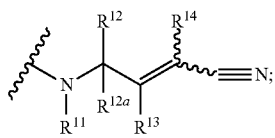

wherein:

the bonds represented by ∼∼∼ indicate that

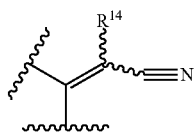

can exist as either a (Z)- or (E)-geometric isomer, wherein indicates the point of attachment;
$R^{11}$ is H;
$R^{12}$ is H or optionally substituted $C_1$-$C_6$ alkyl;
$R^{12a}$ is H; and
$R^{13}$ and $R^{14}$ are each H;
or $R^{11}$ together with the nitrogen atom to which it is shown attached and $R^{12}$, $R^{12a}$, and $R^{13}$ together with the carbon atoms to which they are shown attached form an optionally substituted azetidinyl ring;
$W^3$ is:

wherein:

indicates the point of attachment;
$R^{15}$ is H;
$R^{16}$ is H or optionally substituted $C_1$-$C_6$ alkyl, or optionally substituted $C_3$-$C_8$ cycloalkyl;
$W^4$ is:

wherein:

indicates the point of attachment;
$R^{11}$ is H;
$R^{18}$ is H or optionally substituted $C_1$-$C_6$ alkyl; and
each $R^a$ independently is optionally substituted $C_1$-$C_6$ alkyl; and $W^5$ is:

wherein:
the bond represented by ∼∼∼ indicates that can exist as either a (Z)- or (E)-geometric isomer, and wherein indicates the point of attachment;
m is 1, 2, or 3; and
$R^{19}$ is selected from the group consisting of $C_1$-$C_6$ alkyl and —O—($C_1$-$C_6$ alkyl).

Embodiment 1B

A compound of Formula (I):

(I)

wherein:
X is $CR^2$ or N;
Y is $CR^4$ or N;
Z is $CR^5$ or N;
or Y and Z taken together form an optionally substituted five- to six-membered heteroaryl, or an optionally substituted five- to six-membered heterocyclyl;
with the proviso that X, Y, and Z are not simultaneously N;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
or $R^1$ together with the carbon atoms to which it is shown attached and X form an optionally substituted five- to six-membered heterocyclyl;
$R^2$ is H, optionally substituted $C_1$-$C_6$ alkyl, or halo;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);

or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;

$R^4$ is H, $C_1$-$C_6$ alkyl, cyano, or halo;

or $R^4$ together with the carbon atom to which it is shown attached and Z form an optionally substituted five- to six-membered heteroaryl;

or $R^3$ and $R^4$ taken together with the carbon atoms to which they are shown attached form an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;

$R^5$ is H, $C_1$-$C_6$ alkyl, —$NR_2$, or —N(R)—C(=O)—($C_1$-$C_6$ alkyl);

each R independently is H, or optionally substituted $C_1$-$C_6$ alkyl;

W is $W^1$, $W^2$, $W^3$, $W^4$, or $W^5$;

$W^1$ is:

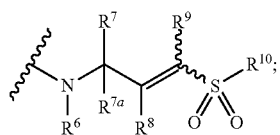

wherein:
the bonds represented by ∿∿∿ indicate that

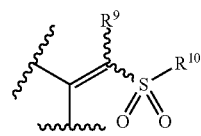

can exist as either a (Z)- or (E)-geometric isomer wherein

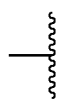

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl; or $R^6$ together with the nitrogen atom to which it is shown attached and $R^7$ and $R^{7a}$ together with the carbon atom to which they are shown attached form an azetidinyl ring;

or $R^6$ together with the nitrogen atom to which it is shown attached and $R^7$, $R^{7a}$, and $R^8$ together with the carbon atoms to which they are shown attached form an azetidinyl or pyrrolodinyl ring;

or $R^6$ together with the nitrogen atom to which it is shown attached and $R^7$, $R^{7a}$, $R^8$, and $R^9$ together with the carbon atoms to which they are shown attached form a dihydropyrrolyl ring; or $R^7$, $R^{7a}$, $R^8$, $R^9$, and $R^{10}$ together with the carbon atoms to which they are shown attached form a 2,3-dihydrothiophene 1,1-dioxide;

or $R^8$, $R^9$, and $R^{10}$ together with the carbon atoms to which they are shown attached form a 1,1-dioxido-2H-thietyl ring;

$W^2$ is:

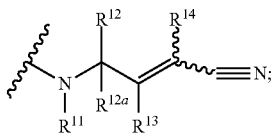

wherein:
the bonds represented by ∿∿∿ indicate that

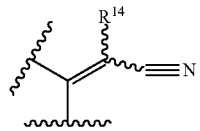

can exist as either a (Z)- or (E)-geometric isomer, wherein

indicates the point of attachment;
$R^{11}$ is H;
$R^{12}$ is H or optionally substituted $C_1$-$C_6$ alkyl;
$R^{12a}$ is H; and
$R^{13}$ and $R^{14}$ are each H;
or $R^{11}$ together with the nitrogen atom to which it is shown attached and $R^{12}$, $R^{12a}$, and $R^{13}$ together with the carbon atoms to which they are shown attached form an optionally substituted azetidinyl ring;
$W^3$ is:

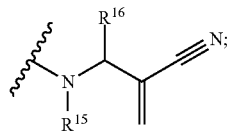

wherein:

indicates the point of attachment;
$R^5$ is H;
$R^{16}$ is H or optionally substituted $C_1$-$C_6$ alkyl, or optionally substituted $C_3$-$C_8$ cycloalkyl;
$W^4$ is:

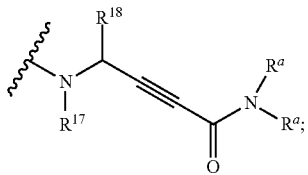

wherein:

indicates the point of attachment;
$R^{17}$ is H;
$R^{18}$ is H or optionally substituted $C_1$-$C_6$ alkyl; and
each $R^a$ independently is optionally substituted $C_1$-$C_6$ alkyl; and
$W^5$ is:

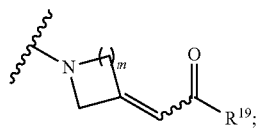

wherein:
the bond represented by ~~~~ indicates that

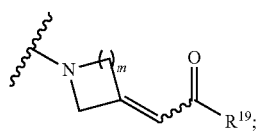

can exist as either a (Z)- or (E)-geometric isomer, and wherein

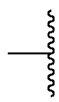

indicates the point of attachment;

m is 1, 2, or 3; and
$R^{19}$ is selected from the group consisting of $C_1$-$C_6$ alkyl and —O—($C_1$-$C_6$ alkyl).

Embodiment 2

The compound according to Embodiment 1, or a pharmaceutically acceptable salt or solvate thereof, wherein:
X is N;
Y is N; and
Z is $CR^5$;
or Y and Z taken together form an optionally substituted five- to six-membered heteroaryl, or an optionally substituted five- to six-membered heterocyclyl.
In other words, when X is N, Y is N, and Z is $CR^5$, Formula (I) is represented by Formula (IA):

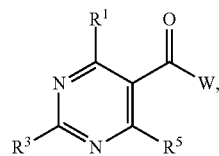

(I-A)

wherein $R^1$, $R^3$, $R^5$, and W are as defined for Formula (I).

Embodiment 2.1

The compound according to Embodiment 1, or a pharmaceutically acceptable salt or solvate thereof, wherein:
X is N;
Y is N;
Z is $CR^5$;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl); $R^5$ is H, $C_1$-$C_6$ alkyl, —$NR_2$, or —N(R)—C(=O)—($C_1$-$C_6$ alkyl);
each R independently is H, or optionally substituted $C_1$-$C_6$ alkyl;
W is $W^1$;
$W^1$ is:

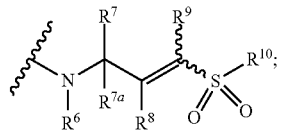

wherein:
the bonds represented by ⁓⁓⁓ indicate that

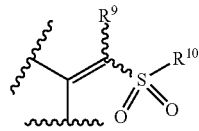

can exist as either a (Z)- or (E)-geometric isomer wherein

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl.

Embodiment 2.1A

The compound according to Embodiment 1, or a pharmaceutically acceptable salt thereof, wherein:
X is N;
Y is N;
Z is CR;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl); $R^5$ is H, $C_1$-$C_6$ alkyl, —$NR_2$, or —N(R)—C(=O)—($C_1$-$C_6$ alkyl); each R independently is H, or optionally substituted $C_1$-$C_6$ alkyl;
W is $W^1$;
$W^1$ is:

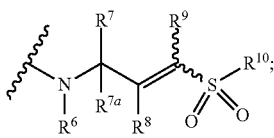

wherein:
the bonds represented by ⁓⁓⁓ indicate that

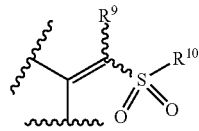

can exist as either a (Z)- or (E)-geometric isomer wherein

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl.

Embodiment 2.1B

The compound according to Embodiment 1, wherein:
X is N;
Y is N;
Z is $CR^5$;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl); $R^5$ is H, $C_1$-$C_6$ alkyl, —$NR_2$, or —N(R)—C(=O)—($C_1$-$C_6$ alkyl);
each R independently is H, or optionally substituted $C_1$-$C_6$ alkyl;
W is $W^1$;
$W^1$ is:

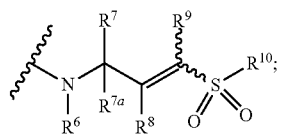

wherein:
the bonds represented by 〜〜 indicate that

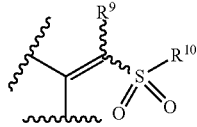

can exist as either a (Z)- or (E)-geometric isomer wherein

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl.

Embodiment 2.2

The compound according to Embodiment 2.1, or a pharmaceutically acceptable salt or solvate thereof, wherein:
$R^1$ is —O—($C_6$-$C_{10}$ aryl);
$R^3$ is fluoro substituted $C_1$-$C_6$ alkyl;
$R^5$ is H;
$R^6$ is H;
$R^7$ is $C_3$-$C_8$ cycloalkyl;
$R^{7a}$ is H or deuterium;
$R^8$ is H;
$R^9$ is H; and
$R^{10}$ is $C_1$-$C_6$ alkyl.

Embodiment 2.2A

The compound according to Embodiment 2.1, or a pharmaceutically acceptable salt thereof, wherein:
$R^1$ is —O—($C_6$-$C_{10}$ aryl);
$R^3$ is fluoro substituted $C_1$-$C_6$ alkyl;
$R^5$ is H;
$R^6$ is H;
$R^7$ is $C_3$-$C_8$ cycloalkyl;
$R^{7a}$ is H or deuterium;
$R^8$ is H;
$R^9$ is H; and
$R^{10}$ is $C_1$-$C_6$ alkyl.

Embodiment 2.2B

The compound according to Embodiment 2.1, wherein:
$R^1$ is —O—($C_6$-$C_{10}$ aryl);
$R^3$ is fluoro substituted $C_1$-$C_6$ alkyl;
$R^5$ is H;
$R^6$ is H;
$R^7$ is $C_3$-$C_8$ cycloalkyl;

$R^{7a}$ is H or deuterium;
$R^8$ is H;
$R^9$ is H; and
$R^{10}$ is $C_1$-$C_6$ alkyl.

Embodiment 3

The compound according to Embodiment 1, or a pharmaceutically acceptable salt or solvate thereof, wherein:
X is $CR^2$;
Y is $CR^4$; and
Z is $CR^5$;
or Y and Z taken together form an optionally substituted five- to six-membered heteroaryl, or an optionally substituted five- to six-membered heteroaryl;
or $R^3$ taken together with the carbon atom to which it is shown attached and Y form an optionally substituted $C_3$-$C_8$ cycloalkyl or cycloalkenyl.

In other words, when X is $CR^2$, Y is $CR^4$, and Z is $CR^5$, Formula (I) is represented by Formula (IB):

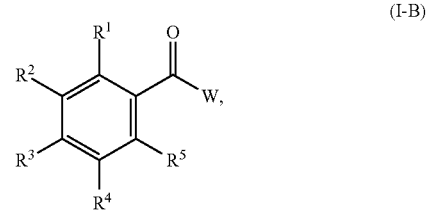

(I-B)

wherein $R^1$, $R^2$, $R^3$, $R^4$, $R^5$, and W are as defined for Formula (I).

Embodiment 4

The compound according to Embodiment 1, or a pharmaceutically acceptable salt or solvate thereof, wherein:
X is $CR^2$;
Y is N; and
Z is $CR^5$;
or $R^1$ together with the carbon atoms to which it is shown attached and X form an optionally substituted five- to six-membered heterocyclyl.

In other words, when X is $CR^2$, Y is N, and Z is $CR^5$, Formula (I) is represented by Formula (I-C):

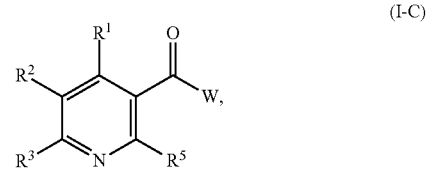

(I-C)

wherein $R^1$, $R^2$, $R^3$, $R^5$, and W are as defined for Formula (I).

Embodiment 5

The compound according to Embodiment 1, or a pharmaceutically acceptable salt or solvate thereof, wherein:
X is N;
Y is $CR^4$; and
Z is $CR^5$;

or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl.

In other words, when X is N, Y is $CR^4$, and Z is $CR^5$, Formula (I) is represented by Formula (I-D):

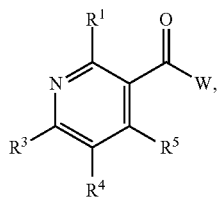

(I-D)

wherein $R^1$, $R^3$, $R^4$, $R^5$, and W are as defined for Formula (I).

Embodiment 6

The compound according to Embodiment 1, or a pharmaceutically acceptable salt or solvate thereof, wherein:
X is N;
Y is $CR^4$; and
Z is N.

In other words, when X is N, Y is $CR^4$, and Z is N, Formula (I) is represented by Formula (I-E):

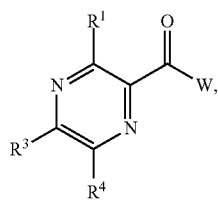

(I-E)

wherein $R^1$, $R^3$, $R^4$, and W are as defined for Formula (I).

Embodiment 7

The compound according to Embodiment 1, or a pharmaceutically acceptable salt or solvate thereof, wherein:
X is $CR^2$;
Y is $CR^4$; and
Z is N.

In other words, when X is $CR^2$, Y is $CR^4$, and Z is N, Formula (I) is represented by Formula (I-F):

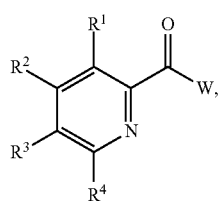

(I-F)

wherein $R^1$, $R^2$, $R^3$, $R^4$, and W are as defined for Formula (I).

Embodiment 8

The compound according to any one of Embodiments 1-7, or a pharmaceutically acceptable salt or solvate thereof, wherein:

in $R^1$:
the optional substituents of the —O—(optionally substituted $C_3$-$C_8$ cycloalkyl) are 1-3 substituents selected from the group consisting of halo, cyano, and hydroxy; or when there are two substituents on the same ring carbon atom of the $C_3$-$C_8$ cycloalkyl, the substituents together with the ring carbon atom to which they are attached form a $C_3$-$C_6$ cycloalkyl; or when there are two substituents on adjacent ring carbon atoms of the $C_3$-$C_8$ cycloalkyl, the substituents taken together with the ring carbon atoms to which they are attached form a $C_3$-$C_6$ cycloalkyl;

the optional substituents of the —O—(optionally substituted $C_6$-$C_{10}$ aryl) are 1-3 substituents selected from the group consisting of halo, $C_1$-$C_6$ alkyl, cyano, hydroxy, and —$NH_2$, or 1-5 deuterium atoms;

or when $R^1$ together with the carbon atoms to which it is shown attached and X form an optionally substituted five- to six-membered heterocyclyl, two substituents on the same ring carbon atom of the five- to six-membered heterocyclyl together with the ring carbon atom to which they are attached form a five- to six-membered cycloalkyl;

in $R^3$:
the optional substituents of the optionally substituted $C_3$-$C_8$ cycloalkyl are 1-3 substituents selected from hydroxy, halo, $C_1$-$C_6$ alkyl, and $C_6$-$C_{10}$ aryl; or when there are two substituents on the same carbon atom of the $C_3$-$C_8$ cycloalkyl, the substituents together with the ring carbon atom to which they are attached form a $C_3$-$C_6$ cycloalkyl; or when there are two substituents on adjacent ring carbon atoms of the $C_3$-$C_8$ cycloalkyl, the substituents taken together with the ring carbon atoms to which they are attached form $C_6$-$C_{10}$ aryl;

or when $R^3$ taken together with the carbon atom to which it is shown attached and Y form an optionally substituted $C_3$-$C_8$ cycloalkyl or cycloalkenyl, the optional substituents are 1-3 substituents selected from the group consisting of halo, and $C_1$-$C_6$ alkyl; or two geminal hydrogens on a ring carbon atom of the $C_3$-$C_8$ cycloalkyl or cycloalkenyl can be replaced with the group =O;

or when $R^3$ taken together with the carbon atom to which it is shown attached and Y form an optionally substituted five- to six-membered heterocyclyl or heterocyclenyl, the optional substituents are 1-3 substituents selected from the group consisting of halo and $C_1$-$C_6$ alkyl;

the optional substituents of the optionally substituted $C_6$-$C_{10}$ aryl are 1-3 substituents selected from the group consisting of halo;

the optional substituents of the optionally substituted $C_1$-$C_6$ alkyl or $C_6$ alkenyl are 1-5 substituents selected from the group consisting of halo, hydroxy, —O—($C_1$-$C_6$ alkyl), and optionally substituted $C_3$-$C_6$ cycloalkyl, wherein the optional substituents of the $C_3$-$C_6$ cycloalkyl are 1-3 substituents selected from the group consisting of $C_1$-$C_6$ alkyl;

the optional substituents of the $C_1$-$C_6$ alkyl of R of —$NR_2$ are 1-3 substituents selected from the group consisting of halo; and the optional substituents of the optionally substituted four- to six-membered heterocyclyl are 1-3 substituents selected from the group consisting of —O—($C_1$-$C_6$ alkyl), $C_1$-$C_6$ alkyl, halo; or when there are two substituents on the same carbon atom of the optionally substituted four- to six-membered heterocyclyl, the substituents together with the ring carbon atom to which they are attached form a $C_3$-$C_6$ cycloalkyl.

Embodiment 9

The compound according to any one of Embodiments 1-8, or a pharmaceutically acceptable salt or solvate thereof, wherein:

the optionally substituted five- to six-membered heterocyclyl formed by $R^1$ together with the carbon atoms to which it is shown attached is

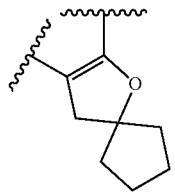 [SMILES: *C1=C(*)OC2(CCCC2)C1]

wherein the double bond shown is between the carbon bearing the $R^1$ group and X;

the optionally substituted $C_6$-$C_{10}$ aryl formed by $R^3$ taken together with the carbon atom to which it is shown attached and Y is

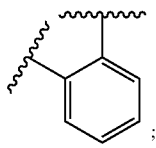 [SMILES: *c1ccccc1*]

the optionally substituted five- to six-membered heterocyclenyl formed by $R^3$ taken together with the carbon atom to which it is shown attached and Y is

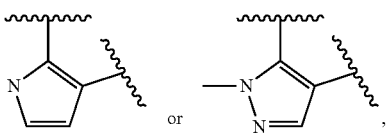

wherein the carbon-carbon double bond shown between the two carbons bearing the

groups is between the carbon bearing the $R^3$ group and Y; when $R^3$ taken together with the carbon atom to which it is shown attached and Y form an optionally substituted $C_3$-$C_8$ cycloalkyl or cycloalkenyl, the optionally substituted $C_3$-$C_8$ cycloalkyl or cycloalkenyl is

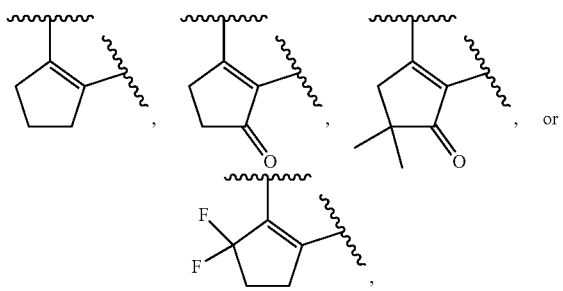

wherein the carbon-carbon double bond shown is between the carbon bearing the $R^3$ group and Y; and wherein the optionally substituted five- to six-membered heteroaryl formed by $R^4$ together with the carbon atom to which it is shown attached and Z is

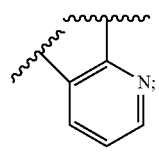 [SMILES: *c1cccnc1*]

wherein in each structure

indicates the point of attachment.

Embodiment 10

The compound according to any one of Embodiments 1-9, or a pharmaceutically acceptable salt or solvate thereof, wherein:

in $R^1$:

the —O-(optionally substituted $C_3$-$C_8$ cycloalkyl) is —O-cyclobutyl, —O-cyclopropyl, —O-cyclohexyl, —O-cyclopentyl, —O-(4,4-difluorocyclohexyl), —O-(spiro[2.3]hexan-5-yl), —O-(spiro[3.3]heptan-2-yl), —O-(3-chlorocyclobutyl), —O-(bicyclo[3.1.0]hexan-3-yl), —O-(bicyclo[2.2.1]heptan-1-yl), —O-(1-cyanocyclopentanyl), —O-(3,3-difluorocyclobutyl), —O-(2-hydroxycyclohexyl), —O-cycloheptyl, —O-(2-fluorocyclohexyl), —O-(3,3-difluorocyclopentyl), —O-(2-fluorocyclohexyl), or —O-(2,2-difluorocyclopentyl), the —O-(optionally substituted $C_1$-$C_6$ alkyl) is ethoxy, isopropoxy, or cyclopropylmethyloxy;

the —O-(optionally substituted $C_6$-$C_{10}$ aryl) is phenoxy, 4-chlorophenoxy, 3-fluorophenoxy, 2-chlorophenoxy, 3-chlorophenoxy, 2-fluorophenoxy, p-tolyloxy, 3,5-difluorophenoxy, 4-fluoro-3-methylphenoxy, 3,5-dichlorophenoxy, 4-cyanophenoxy, 3,4-dimethylphenoxy, m-tolyloxy, 4-ethylphenoxy, 3-ethylphenoxy, o-tolyloxy, 2-hydroxyphenoxy, 3-hydroxyphenoxy, 4-hydroxyphenoxy, 3-chloro-5-fluorophenoxy, 3-aminophenoxy, naphthalen-1-oxy, or phenoxy-d5;

the —O-(optionally substituted five- to six-membered heteroaryl) is pyridine-2-yloxy, or pyridine-3-yloxy;

the —O-(optionally substituted five- to six-membered heterocyclyl) is tetrahydro-2H-pyran-4-yl, or tetrahydro-2H-pyran-3-yl; and the optionally substituted $C_3$-$C_8$ cycloalkyl is cyclohexyl;

in $R^2$:

the optionally substituted $C_1$-$C_6$ alkyl is methyl; and in $R^3$:

the optionally substituted $C_3$-$C_8$ cycloalkyl is cyclopentyl, cyclobutyl, cyclohexyl, cyclopropyl, hydroxycyclopentyl, fluorocyclopentyl, methylcyclobutyl, methylcyclopropyl, phenylcyclopropyl, methylcyclopentyl, difluorocyclobutyl, fluorocyclopentyl, bicyclo[4.2.0]octa-1,3,5-trien-7-yl, or (trifluoromethyl)cyclopropyl, or spiro[2.3]hexan-5-yl;

the optionally substituted $C_3$-$C_8$ cycloalkenyl is cyclopentenyl;

the optionally substituted $C_6$-$C_{10}$ aryl is phenyl;

the optionally substituted $C_1$-$C_6$ alkyl is methyl, ethyl, isopropyl, tert-butyl, cyclopropylmethyl, cyclobutylmethyl, cyclopentylmethyl, cyclohexylmethyl, trifluoromethyl, trifluoroethyl, hydroxypropanyl, fluropropanyl, methoxypropanyl, difluoroethyl, difluoropropyl, (methylcyclopropyl)methyl, perfluoroethyl, or cyclopropyldifluoromethyl;

the optionally substituted $C_1$-$C_6$ alkenyl is 2-methylprop-1-en-1-yl;

the $NR_2$ is —N(H)(cyclopentyl), —N(H)(methyl), —N(methyl)(ethyl), —N(methyl)(isopropyl), —N(ethyl)$_2$, or —N(methyl)(trifluoroethyl);

the —N(R)(optionally substituted $C_3$-$C_8$ cycloalkyl) is N(methyl)(cyclopropyl);

the —S-(optionally substituted $C_1$-$C_6$ alkyl) is methylthiol;

the —O-(optionally substituted $C_1$-$C_6$ alkyl) is trifluoroethoxy, or methoxy;

the —O-(optionally substituted $C_3$-$C_8$ cycloalkyl) is cyclopentyloxy, or cyclopropyloxy; and the optionally substituted four- to six-membered heterocyclyl or hetrocyclenyl is tetrahydrofuranyl, 7-azabicyclo[2.2.1]heptan-7-yl, bicyclo[1.1.1]pentan-1-yl, methoxyazetadin-1-yl, 2-azaspiro[3.3]heptan-2-yl, tetrahydropyranyl, tetrahydro-2H-pyran-3-yl, tetrahydro-2H-pyran-4-yl, dihydropyranyl, 5,6-dihydro-2H-pyran-3-yl, dimethylpyrrolidinyl, 2,2-dimethylpyrrolidin-1-yl, difluoropyrrolidinyl, methylcyclobutyl, pyrrolidinyl, pyrrolidine-1-yl, methylpyrrolidinyl, 2-methylpyrrolidin-1-yl, azetidinyl, azetidine-1-yl, fluoroazetidinyl, 3-fluoroazetidin-1-yl, difluoroazetidinyl, or 3,3-difluoro-azetidin-1-yl;

in $R^5$:

the $C_1$-$C_6$ alkyl is methyl;

the —$NR_2$ is —$NH_2$; and the —N(R)—C(=O)—($C_1$-$C_6$ alkyl) is —N(H)—C(=O)—$CH_3$.

Embodiment 11

The compound according to any one of Embodiments 1-10, or a pharmaceutically acceptable salt or solvate thereof, wherein W is $W^1$, i.e., W is

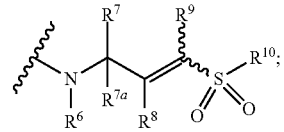

wherein $R^6$, $R^7$, $R^{7a}$, $R^8$, $R^9$, and $R^{10}$ are as defined in Embodiment 1; and the bonds represented by ∿∿∿ indicate that

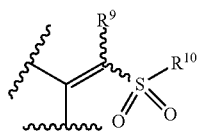

can exist as either a (Z)- or (E)-geometric isomer wherein

indicates the point of attachment.

Embodiment 12

The compound according to Embodiment 11, or a pharmaceutically acceptable salt or solvate thereof, wherein:

the optionally substituted $C_1$-$C_6$ alkyl of $R^7$ is methyl, ethyl, isopropyl, methoxymethyl, cyclopropylmethyl, cyclopropyloxymethyl, tolyl, —CH($CH_3$)—$OCH_3$, difluoroethyl, phenoxymethyl, —$CH_2$—C(=O)—N($CH_3$)$_2$, or tert-butoxymethyl, difluoromethoxymethyl;

the optionally substituted $C_3$-$C_8$ cycloalkyl of $R^7$ is cyclopropyl, cyclobutyl, difluorocyclobutyl, —$CH_2$—S—$CH_3$, difluorocyclohexyl;

the optionally substituted five- to six-membered heterocyclyl of $R^7$ is tetrahydropyranyl, or tetrahydro-2H-pyran-4-yl;

the optionally substituted $C_1$-$C_6$ alkyl of $R^{10}$ is methyl;

the optionally substituted $C_3$-$C_8$ cycloalkyl of $R^{10}$ is cyclopropyl;

the optionally five- to six-membered heterocyclyl of $R^{10}$ is tetrahydropyranyl or tetrahydro-2H-pyran-4-yl;

or wherein $W^1$ is:

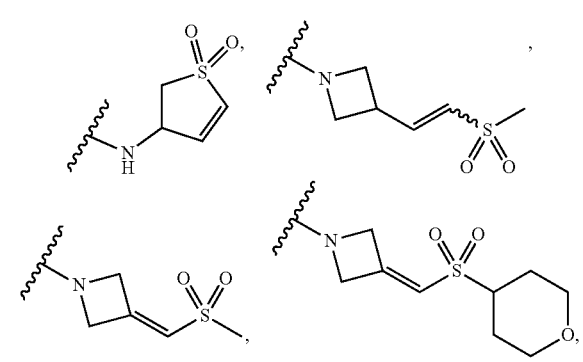

-continued

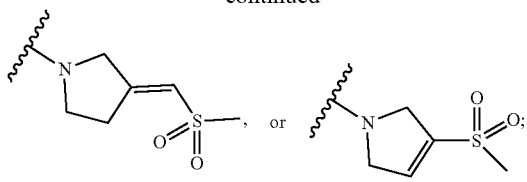

wherein in each structure above,

indicates the point of attachment.

Embodiment 13

The compound according to any one of Embodiments 1-10, or a pharmaceutically acceptable salt or solvate thereof, wherein W is $W^2$, i.e., W is

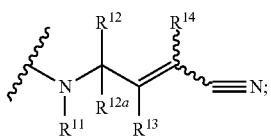

wherein:
the bonds represented by ∿∿∿ indicate that

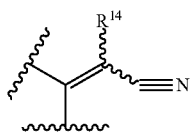

can exist as either a (Z)- or (E)-geometric isomer, wherein

indicates the point of attachment; and
$R^{11}$, $R^{12}$, $R^{12a}$, $R^{13}$, and $R^{14}$ are as defined in Embodiment 1.

Embodiment 14

The compound according to Embodiment 13, or a pharmaceutically acceptable salt or solvate thereof, wherein $W^2$ is:

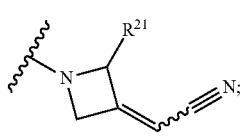

wherein:
$R^{21}$ is H or $C_1$-$C_6$ alkyl;
the bond represented by ∿∿∿ indicates that

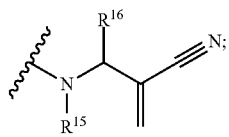

can exist as either a (Z)- or (E)-geometric isomer, and wherein

indicates the point of attachment.

Embodiment 15

The compound according to any one of Embodiments 1-10, or a pharmaceutically acceptable salt or solvate thereof, wherein W is $W^3$, i.e., W is

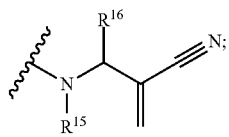

wherein:

indicates the point of attachment; and
$R^{15}$ and $R^{16}$ are as defined in Embodiment 1.

Embodiment 16

The compound according to Embodiment 15, or a pharmaceutically acceptable salt or solvate thereof, wherein:
the optionally substituted $C_1$-$C_6$ alkyl of $R^{16}$ is methyl; and
the optionally substituted $C_3$-$C_8$ cycloalkyl of $R^{16}$ is cyclopropyl.

Embodiment 17

The compound according to any one of Embodiments 1-10, or a pharmaceutically acceptable salt or solvate thereof, wherein W is $W^4$, i.e., W is

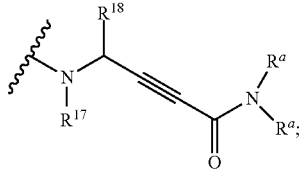

wherein:

indicates the point of attachment; and
$R^{17}$, $R^{18}$, and $R^a$ are as defined in Embodiment 1.

Embodiment 18

The compound according to Embodiment 17, or a pharmaceutically acceptable salt or solvate thereof, wherein:
the optionally substituted $C_1$-$C_6$ alkyl of $R^{18}$ is methyl; and
the optionally substituted $C_1$-$C_6$ alkyl is methyl.

Embodiment 19

The compound according to any one of Embodiments 1-10, or a pharmaceutically acceptable salt or solvate thereof, wherein W is $W^5$, i.e., W is

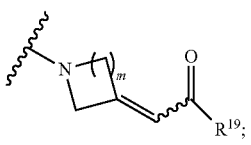

wherein:
the bond represented by ~~~ indicates that

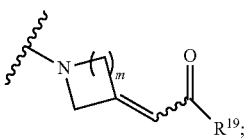

can exist as either a (Z)- or (E)-geometric isomer, and wherein

indicates the point of attachment; and
m and $R^{19}$ are as defined in Embodiment 1.

Embodiment 20

The compound according to Embodiment 19, or a pharmaceutically acceptable salt or solvate thereof, wherein:
the $C_1$-$C_6$ alkyl of $R^{19}$ is methyl; and
the —O—($C_1$-$C_6$ alkyl) of $R^{19}$ is methoxy.

Embodiment 21

The compound according to any one of Embodiments 2 and 8-12, or a pharmaceutically acceptable salt or solvate thereof, wherein the compound is selected from the group consisting of:
(E)-N-(3-(methylsulfonyl)allyl)-4-phenoxy-2-(pyrrolidin-1-yl)pyrimidine-5-carboxamide;
(S,E)-N-(4-(methylsulfonyl)but-3-en-2-yl)-4-phenoxy-2-phenylpyrimidine-5-carboxamide;
(S,E)-2-methyl-N-(4-(methylsulfonyl)but-3-en-2-yl)-4-phenoxypyrimidine-5-carboxamide;
(R,E)-2-cyclopentyl-N-(4-(methylsulfonyl)but-3-en-2-yl)-4-phenoxypyrimidine-5-carboxamide;
(S,E)-2-cyclopentyl-N-(4-(methylsulfonyl)but-3-en-2-yl)-4-phenoxypyrimidine-5-carboxamide;
(S,E)-2-ethyl-N-(4-(methylsulfonyl)but-3-en-2-yl)-4-phenoxypyrimidine-5-carboxamide;
(E)-2-cyclopentyl-N-(3-(methylsulfonyl)allyl)-4-phenoxypyrimidine-5-carboxamide;
(E)-2-isopropyl-N-(3-(methylsulfonyl)allyl)-4-phenoxypyrimidine-5-carboxamide;
(R,E)-2-cyclobutyl-N-(4-(methylsulfonyl)but-3-en-2-yl)-4-phenoxypyrimidine-5-carboxamide;
(S,E)-2-cyclobutyl-N-(4-(methylsulfonyl)but-3-en-2-yl)-4-phenoxypyrimidine-5-carboxamide;
(S,E)-2-cyclohexyl-N-(4-(methylsulfonyl)but-3-en-2-yl)-4-phenoxypyrimidine-5-carboxamide;
(E)-2-ethyl-N-(3-(methylsulfonyl)allyl)-4-phenoxypyrimidine-5-carboxamide;
(S,E)-2-isopropyl-N-(4-(methylsulfonyl)but-3-en-2-yl)-4-phenoxypyrimidine-5-carboxamide;
(S,E)-2-(cyclopentylamino)-N-(4-(methylsulfonyl)but-3-en-2-yl)-4-phenoxypyrimidine-5-carboxamide;
(E)-2-cyclopropyl-N-(3-(methylsulfonyl)allyl)-4-phenoxypyrimidine-5-carboxamide;
(S,E)-2-cyclopropyl-N-(4-(methylsulfonyl)but-3-en-2-yl)-4-phenoxypyrimidine-5-carboxamide;
(E)-2-(tert-butyl)-N-(3-(methylsulfonyl)allyl)-4-phenoxypyrimidine-5-carboxamide;
(R,Z)-2-cyclopentyl-N-(4-(methylsulfonyl)but-3-en-2-yl)-4-phenoxypyrimidine-5-carboxamide;
(S,Z)-2-cyclopentyl-N-(4-(methylsulfonyl)but-3-en-2-yl)-4-phenoxypyrimidine-5-carboxamide;
(E)-2-cyclobutyl-N-(3-(methylsulfonyl)allyl)-4-phenoxypyrimidine-5-carboxamide;
(E)-4-(4-chlorophenoxy)-2-cyclopentyl-N-(3-(methylsulfonyl)allyl)pyrimidine-5-carboxamide;
(S,E)-4-(4-chlorophenoxy)-2-cyclopentyl-N-(4-(methylsulfonyl)but-3-en-2-yl)pyrimidine-5-carboxamide;
(E)-2-cyclopentyl-4-(3-fluorophenoxy)-N-(3-(methylsulfonyl)allyl)pyrimidine-5-carboxamide;
(E)-2-cyclohexyl-N-(3-(methylsulfonyl)allyl)-4-phenoxypyrimidine-5-carboxamide;
(E)-N-(3-(methylsulfonyl)allyl)-2-(methylthio)-4-phenoxypyrimidine-5-carboxamide;

2-cyclopropyl-N-((1,1-dioxido-2H-thiet-3-yl)methyl)-4-phenoxypyrimidine-5-carboxamide;
2-cyclopropyl-N-(1,1-dioxido-2,3-dihydrothiophen-3-yl)-4-phenoxypyrimidine-5-carboxamide;
(E)-2-cyclopentyl-4-(4-fluorophenoxy)-N-(3-(methylsulfonyl)allyl)pyrimidine-5-carboxamide;
(S,E)-2-cyclopentyl-4-(4-fluorophenoxy)-N-(4-(methylsulfonyl)but-3-en-2-yl)pyrimidine-5-carboxamide;
(S,E)-4-(2-chlorophenoxy)-2-cyclopentyl-N-(4-(methylsulfonyl)but-3-en-2-yl)pyrimidine-5-carboxamide;
(S,E)-4-(3-chlorophenoxy)-2-cyclopentyl-N-(4-(methylsulfonyl)but-3-en-2-yl)pyrimidine-5-carboxamide;
(S,E)-2-cyclopentyl-4-(3-fluorophenoxy)-N-(4-(methylsulfonyl)but-3-en-2-yl)pyrimidine-5-carboxamide;
(S,E)-2-cyclopentyl-4-(2-fluorophenoxy)-N-(4-(methylsulfonyl)but-3-en-2-yl)pyrimidine-5-carboxamide;
(S,E)-4-(cyclohexyloxy)-2-cyclopentyl-N-(4-(methylsulfonyl)but-3-en-2-yl)pyrimidine-5-carboxamide;
(E)-2-cyclopentyl-N-methyl-N-(3-(methylsulfonyl)allyl)-4-phenoxypyrimidine-5-carboxamide;
(E)-2-cyclopentyl-N-(3-(methylsulfonyl)allyl)-4-(p-tolyloxy)pyrimidine-5-carboxamide;
(E)-N-(3-(methylsulfonyl)allyl)-4-phenoxy-2-(1H-pyrazol-5-yl)pyrimidine-5-carboxamide;
(E)-4-(3-chlorophenoxy)-2-cyclopentyl-N-(3-(methylsulfonyl)allyl)pyrimidine-5-carboxamide;
(S,E)-2-cyclopentyl-4-(3,5-difluorophenoxy)-N-(4-(methylsulfonyl)but-3-en-2-yl)pyrimidine-5-carboxamide;
(S,E)-2-cyclopentyl-4-(4-fluoro-3-methylphenoxy)-N-(4-(methylsulfonyl)but-3-en-2-yl)pyrimidine-5-carboxamide;
(S,E)-2-cyclopentyl-4-(3,5-dichlorophenoxy)-N-(4-(methylsulfonyl)but-3-en-2-yl)pyrimidine-5-carboxamide;
(S,E)-2-(cyclopentyloxy)-N-(4-(methylsulfonyl)but-3-en-2-yl)-4-phenoxypyrimidine-5-carboxamide; (2-cyclopropyl-4-phenoxypyrimidin-5-yl)(3-((methylsulfonyl)methylene)azetidin-1-yl)methanone;
(S,E)-2-cyclopentyl-4-(cyclopentyloxy)-N-(4-(methylsulfonyl)but-3-en-2-yl)pyrimidine-5-carboxamide;
(S,E)-4-(4-cyanophenoxy)-2-cyclopentyl-N-(4-(methylsulfonyl)but-3-en-2-yl)pyrimidine-5-carboxamide;
(S,E)-N-(4-(methylsulfonyl)but-3-en-2-yl)-4-phenoxy-2-(tetrahydro-2H-pyran-4-yl)pyrimidine-5-carboxamide;
(S,E)-2-cyclopentyl-4-(3,4-dimethylphenoxy)-N-(4-(methylsulfonyl)but-3-en-2-yl)pyrimidine-5-carboxamide;
(S,E)-2-cyclopentyl-N-(4-(methylsulfonyl)but-3-en-2-yl)-4-(m-tolyloxy)pyrimidine-5-carboxamide;
(S,E)-2-(tert-butyl)-N-(4-(methylsulfonyl)but-3-en-2-yl)-4-phenoxypyrimidine-5-carboxamide;
(S,E)-2-cyclopentyl-4-(4-ethylphenoxy)-N-(4-(methylsulfonyl)but-3-en-2-yl)pyrimidine-5-carboxamide;
(S,E)-2-cyclopentyl-4-(3-ethylphenoxy)-N-(4-(methylsulfonyl)but-3-en-2-yl)pyrimidine-5-carboxamide;
(S,E)-2-cyclopentyl-N-(4-(methylsulfonyl)but-3-en-2-yl)-4-(o-tolyloxy)pyrimidine-5-carboxamide;
(S,E)-2-cyclopentyl-N-(4-(methylsulfonyl)but-3-en-2-yl)-4-((tetrahydro-2H-pyran-4-yl)oxy)pyrimidine-5-carboxamide;
(S,E)-2-(cyclopropylmethyl)-N-(4-(methylsulfonyl)but-3-en-2-yl)-4-phenoxypyrimidine-5-carboxamide;
(S,E)-4-cyclobutoxy-2-cyclopentyl-N-(4-(methylsulfonyl)but-3-en-2-yl)pyrimidine-5-carboxamide;
(S,E)-2-(1-hydroxycyclopentyl)-N-(4-(methylsulfonyl)but-3-en-2-yl)-4-phenoxypyrimidine-5-carboxamide;
(S,E)-2-cyclopentyl-N-(1-(methylsulfonyl)pent-1-en-3-yl)-4-phenoxypyrimidine-5-carboxamide;
N—((S,E)-4-(methylsulfonyl)but-3-en-2-yl)-4-phenoxy-2-(tetrahydrofuran-2-yl)pyrimidine-5-carboxamide;
(S,E)-2-cyclopentyl-N-(4-(methylsulfonyl)but-3-en-2-yl)-4-(pyridin-2-yloxy)pyrimidine-5-carboxamide;
(S,E)-2-cyclopentyl-N-(4-(methylsulfonyl)but-3-en-2-yl)-4-(pyridin-3-yloxy)pyrimidine-5-carboxamide;
(S,E)-2-cyclopropyl-N-(4-(methylsulfonyl)but-3-en-2-yl)-4-(spiro[3.3]heptan-2-yloxy)pyrimidine-5-carboxamide;
(S,E)-N-(4-(methylsulfonyl)but-3-en-2-yl)-4-phenoxy-2-(trifluoromethyl)pyrimidine-5-carboxamide;
(S,E)-2-(tert-butyl)-4-(cyclohexyloxy)-N-(4-(methylsulfonyl)but-3-en-2-yl)pyrimidine-5-carboxamide;
(S,E)-2-(tert-butyl)-4-((4,4-difluorocyclohexyl)oxy)-N-(4-(methylsulfonyl)but-3-en-2-yl)pyrimidine-5-carboxamide;
2-cyclopentyl-N—((S,E)-4-(methylsulfonyl)but-3-en-2-yl)-4-(((S)-tetrahydro-2H-pyran-3-yl)oxy)pyrimidine-5-carboxamide;
(S,E)-2-cyclopropyl-N-(4-(methylsulfonyl)but-3-en-2-yl)-4-(spiro[2.3]hexan-5-yloxy)pyrimidine-5-carboxamide;
(S,E)-2-cyclopropyl-4-(cyclopropylmethoxy)-N-(4-(methylsulfonyl)but-3-en-2-yl)pyrimidine-5-carboxamide;
4-((1R,3S)-3-chlorocyclobutoxy)-2-cyclopropyl-N—((S,E)-4-(methylsulfonyl)but-3-en-2-yl)pyrimidine-5-carboxamide;
(S,E)-4-cyclohexyl-2-cyclopentyl-N-(4-(methylsulfonyl)but-3-en-2-yl)pyrimidine-5-carboxamide; 4-[[(1S,5R)-3-bicyclo[3.1.0]hexanyl]oxy]-2-tert-butyl-N—[(E,1S)-1-methyl-3-methylsulfonyl-allyl]pyrimidine-5-carboxamide;
(S,E)-2-(tert-butyl)-4-((1-cyanocyclopentyl)oxy)-N-(4-(methylsulfonyl)but-3-en-2-yl)pyrimidine-5-carboxamide;
(S,E)-2-(tert-butyl)-4-(3,3-difluorocyclobutoxy)-N-(4-(methylsulfonyl)but-3-en-2-yl)pyrimidine-5-carboxamide;
(S,E)-2-cyclopentyl-4-methyl-N-(4-(methylsulfonyl)but-3-en-2-yl)-6-phenoxypyrimidine-5-carboxamide;
(S,E)-2-(1-fluorocyclopentyl)-N-(4-(methylsulfonyl)but-3-en-2-yl)-4-phenoxypyrimidine-5-carboxamide;
(S,E)-2-cyclopentyl-4-(3-hydroxyphenoxy)-N-(4-(methylsulfonyl)but-3-en-2-yl)pyrimidine-5-carboxamide;
(S,E)-2-cyclopentyl-4-(4-hydroxyphenoxy)-N-(4-(methylsulfonyl)but-3-en-2-yl)pyrimidine-5-carboxamide;
(2-(tert-butyl)-4-phenoxypyrimidin-5-yl)(3-((methylsulfonyl)methylene)azetidin-1-yl)methanone;
(S,E)-2-(tert-butyl)-4-(cyclopentyloxy)-N-(4-(methylsulfonyl)but-3-en-2-yl)pyrimidine-5-carboxamide;
(S,E)-2-(cyclopentylmethyl)-N-(4-(methylsulfonyl)but-3-en-2-yl)-4-phenoxypyrimidine-5-carboxamide;
(S,E)-2-(7-azabicyclo[2.2.1]heptan-7-yl)-N-(4-(methylsulfonyl)but-3-en-2-yl)-4-phenoxypyrimidine-5-carboxamide;
N—((S,E)-4-(methylsulfonyl)but-3-en-2-yl)-4-phenoxy-2-(tetrahydrofuran-3-yl)pyrimidine-5-carboxamide;
(S,E)-4-(3-chloro-5-fluorophenoxy)-2-cyclopentyl-N-(4-(methylsulfonyl)but-3-en-2-yl)pyrimidine-5-carboxamide;
(S,E)-2-(cyclohexylmethyl)-N-(4-(methylsulfonyl)but-3-en-2-yl)-4-phenoxypyrimidine-5-carboxamide;
(S,E)-4-(3-aminophenoxy)-2-cyclopentyl-N-(4-(methylsulfonyl)but-3-en-2-yl)pyrimidine-5-carboxamide;
(S,E)-2-(cyclobutylmethyl)-N-(4-(methylsulfonyl)but-3-en-2-yl)-4-phenoxypyrimidine-5-carboxamide;
(S,E)-2-cyclopropyl-N-(4-(cyclopropylsulfonyl)but-3-en-2-yl)-4-phenoxypyrimidine-5-carboxamide; (Z)-(2-cyclopropyl-4-phenoxypyrimidin-5-yl)(3-(2-(methylsulfonyl)

vinyl)azetidin-1-yl)methanone; (E)-(2-cyclopropyl-4-phenoxypyrimidin-5-yl)(3-(2-(methylsulfonyl)vinyl)azetidin-1-yl)methanone;
(S,E)-4-(cyclopentyloxy)-2-cyclopropyl-N-(4-(methylsulfonyl)but-3-en-2-yl)pyrimidine-5-carboxamide;
2-cyclopentyl-4-(((1R,2R)-2-hydroxycyclohexyl)oxy)-N—((S,E)-4-(methylsulfonyl)but-3-en-2-yl)pyrimidine-5-carboxamide;
(S,E)-4-amino-2-cyclopentyl-N-(4-(methylsulfonyl)but-3-en-2-yl)-6-phenoxypyrimidine-5-carboxamide;
(S,E)-2-cyclopentyl-N-(4-(methylsulfonyl)but-3-en-2-yl)-4-(naphthalen-1-yloxy)pyrimidine-5-carboxamide;
(R,E)-2-(2-fluorophenyl)-N-(4-(methylsulfonyl)but-3-en-2-yl)-4-phenoxypyrimidine-5-carboxamide;
(S,E)-2-cyclopentyl-4-(2-hydroxyphenoxy)-N-(4-(methylsulfonyl)but-3-en-2-yl)pyrimidine-5-carboxamide;
(S,E)-4-(cycloheptyloxy)-2-cyclopentyl-N-(4-(methylsulfonyl)but-3-en-2-yl)pyrimidine-5-carboxamide;
2-cyclopentyl-4-(((1S,2R)-2-hydroxycyclohexyl)oxy)-N—((S,E)-4-(methylsulfonyl)but-3-en-2-yl)pyrimidine-5-carboxamide;
2-cyclopentyl-4-(((1R,2S)-2-hydroxycyclohexyl)oxy)-N—((S,E)-4-(methylsulfonyl)but-3-en-2-yl)pyrimidine-5-carboxamide;
(S,E)-2-(bicyclo[1.1.1]pentan-1-yl)-N-(4-(methylsulfonyl)but-3-en-2-yl)-4-phenoxypyrimidine-5-carboxamide;
2-((1S,3R)-3-methylcyclobutyl)-N—((S,E)-4-(methylsulfonyl)but-3-en-2-yl)-4-phenoxypyrimidine-5-carboxamide;
2-((1R,3S)-3-methylcyclobutyl)-N—((S,E)-4-(methylsulfonyl)but-3-en-2-yl)-4-phenoxypyrimidine-5-carboxamide;
(S,E)-2-(3-methoxyazetidin-1-yl)-N-(4-(methylsulfonyl)but-3-en-2-yl)-4-phenoxypyrimidine-5-carboxamide;
2-cyclopropyl-4-((3,3-difluorocyclopentyl)oxy)-N—((S,E)-4-(methylsulfonyl)but-3-en-2-yl)pyrimidine-5-carboxamide;
2-cyclopropyl-4-(((S)-2,2-difluorocyclopentyl)oxy)-N—((S,E)-4-(methylsulfonyl)but-3-en-2-yl)pyrimidine-5-carboxamide;
2-cyclopropyl-4-(((R)-2,2-difluorocyclopentyl)oxy)-N—((S,E)-4-(methylsulfonyl)but-3-en-2-yl)pyrimidine-5-carboxamide;
(S,E)-N-(4-(methylsulfonyl)but-3-en-2-yl)-4-phenoxy-2-(2-azaspiro[3.3]heptan-2-yl)pyrimidine-5-carboxamide;
2-(bicyclo[4.2.0]octa-1,3,5-trien-7-yl)-N—((S,E)-4-(methylsulfonyl)but-3-en-2-yl)-4-phenoxypyrimidine-5-carboxamide;
N—((S,E)-4-(methylsulfonyl)but-3-en-2-yl)-4-phenoxy-2-(tetrahydro-2H-pyran-3-yl)pyrimidine-5-carboxamide;
(S,E)-2-(5,6-dihydro-2H-pyran-3-yl)-N-(4-(methylsulfonyl)but-3-en-2-yl)-4-phenoxypyrimidine-5-carboxamide;
(S,E)-2-cyclopentyl-N-(4-methyl-1-(methylsulfonyl)pent-1-en-3-yl)-4-phenoxypyrimidine-5-carboxamide;
(S,E)-2-(2-hydroxypropan-2-yl)-N-(4-(methylsulfonyl)but-3-en-2-yl)-4-phenoxypyrimidine-5-carboxamide;
(S,E)-2-isobutyl-N-(4-(methylsulfonyl)but-3-en-2-yl)-4-phenoxypyrimidine-5-carboxamide;
(S,E)-2-(2-methylprop-1-en-1-yl)-N-(4-(methylsulfonyl)but-3-en-2-yl)-4-phenoxypyrimidine-5-carboxamide;
2-((2R,5S)-2,5-dimethylpyrrolidin-1-yl)-N—((S,E)-4-(methylsulfonyl)but-3-en-2-yl)-4-phenoxypyrimidine-5-carboxamide;
2-((2R,5R)-2,5-dimethylpyrrolidin-1-yl)-N—((S,E)-4-(methylsulfonyl)but-3-en-2-yl)-4-phenoxypyrimidine-5-carboxamide;
(S,E)-4-(bicyclo[2.2.1]heptan-1-yloxy)-2-cyclopropyl-N-(4-(methylsulfonyl)but-3-en-2-yl)pyrimidine-5-carboxamide;
(S,E)-2-(3,3-difluoropyrrolidin-1-yl)-N-(4-(methylsulfonyl)but-3-en-2-yl)-4-phenoxypyrimidine-5-carboxamide;
(S,E)-2-(2-methoxypropan-2-yl)-N-(4-(methylsulfonyl)but-3-en-2-yl)-4-phenoxypyrimidine-5-carboxamide;
(S,E)-2-(1,1-difluoroethyl)-N-(4-(methylsulfonyl)but-3-en-2-yl)-4-phenoxypyrimidine-5-carboxamide;
(S,E)-2-cyclopentyl-N-(1-cyclopropyl-3-(methylsulfonyl)allyl)-4-phenoxypyrimidine-5-carboxamide;
(S,E)-2-(1-methylcyclopropyl)-N-(4-(methylsulfonyl)but-3-en-2-yl)-4-phenoxypyrimidine-5-carboxamide;
(2-(1-methylcyclopropyl)-4-phenoxypyrimidin-5-yl)(3-((methylsulfonyl)methylene)azetidin-1-yl)methanone;
(2-(tert-butyl)-4-phenoxypyrimidin-5-yl)(3-(((tetrahydro-2H-pyran-4-yl)sulfonyl)methylene)azetidin-1-yl)methanone;
(2-((1S,3S)-3-methylcyclobutyl)-4-phenoxypyrimidin-5-yl)(3-((methylsulfonyl)methylene)azetidin-1-yl)methanone;
(2-((1r,3r)-3-methylcyclobutyl)-4-phenoxypyrimidin-5-yl)(3-((methylsulfonyl)methylene)azetidin-1-yl)methanone;
(S,E)-N-(4-(methylsulfonyl)but-3-en-2-yl)-4-phenoxy-2-(pyrrolidin-1-yl)pyrimidine-5-carboxamide;
(S,E)-2-(2,2-dimethylpyrrolidin-1-yl)-N-(4-(methylsulfonyl)but-3-en-2-yl)-4-phenoxypyrimidine-5-carboxamide;
2-((S)-2-methylpyrrolidin-1-yl)-N—((S,E)-4-(methylsulfonyl)but-3-en-2-yl)-4-phenoxypyrimidine-5-carboxamide;
2-((R)-2-methylpyrrolidin-1-yl)-N—((S,E)-4-(methylsulfonyl)but-3-en-2-yl)-4-phenoxypyrimidine-5-carboxamide;
1-(1-(2-(tert-butyl)-4-phenoxypyrimidine-5-carbonyl)azetidin-3-ylidene)propan-2-one;
(S,E)-2-((1-methylcyclopropyl)methyl)-N-(4-(methylsulfonyl)but-3-en-2-yl)-4-phenoxypyrimidine-5-carboxamide;
(2-((1-methylcyclopropyl)methyl)-4-phenoxypyrimidin-5-yl)(3-((methylsulfonyl)methylene)azetidin-1-yl)methanone;
(E)-(2-cyclopropyl-4-phenoxypyrimidin-5-yl)(3-((methylsulfonyl)methylene)pyrrolidin-1-yl)methanone;
(S,E)-2-(tert-butyl)-N-(4-(methylsulfonyl)but-3-en-2-yl)-4-(phenoxy-d5)pyrimidine-5-carboxamide;
(S,E)-2-cyclopropyl-N-(4-(methylsulfonyl)but-3-en-2-yl)-4-(phenoxy-d5)pyrimidine-5-carboxamide;
(R,E)-2-(tert-butyl)-N-(1-methoxy-4-(methylsulfonyl)but-3-en-2-yl)-4-phenoxypyrimidine-5-carboxamide;
(S,E)-2-(tert-butyl)-N-(1-methoxy-4-(methylsulfonyl)but-3-en-2-yl)-4-phenoxypyrimidine-5-carboxamide;
(S,E)-N-(4-(methylsulfonyl)but-3-en-2-yl)-4-phenoxy-2-(1-phenylcyclopropyl)pyrimidine-5-carboxamide;
2-((1R,3S)-3-methylcyclopentyl)-N—((S,E)-4-(methylsulfonyl)but-3-en-2-yl)-4-phenoxypyrimidine-5-carboxamide;
(S,E)-2-(tert-butyl)-N-(1-cyclopropyl-4-(methylsulfonyl)but-3-en-2-yl)-4-phenoxypyrimidine-5-carboxamide;
(S,E)-2-cyclopropyl-N-(1-cyclopropyl-4-(methylsulfonyl)but-3-en-2-yl)-4-phenoxypyrimidine-5-carboxamide;
(S,E)-2-(3,3-difluorocyclobutyl)-N-(4-(methylsulfonyl)but-3-en-2-yl)-4-phenoxypyrimidine-5-carboxamide;
(R,E)-2-(1,1-difluoroethyl)-N-(1-methoxy-4-(methylsulfonyl)but-3-en-2-yl)-4-phenoxypyrimidine-5-carboxamide;
(S,E)-2-(tert-butyl)-N-(1-cyclopropyl-3-(methylsulfonyl)allyl)-4-phenoxypyrimidine-5-carboxamide;
(S,E)-2-(tert-butyl)-N-(1-cyclobutyl-3-(methylsulfonyl)allyl)-4-phenoxypyrimidine-5-carboxamide;
(S,E)-N-(1-cyclobutyl-3-(methylsulfonyl)allyl)-2-cyclopropyl-4-phenoxypyrimidine-5-carboxamide;
(S,E)-2-(tert-butyl)-N-(1-(3,3-difluorocyclobutyl)-3-(methylsulfonyl)allyl)-4-phenoxypyrimidine-5-carboxamide;

(S,E)-2-cyclopropyl-N-(1-(3,3-difluorocyclobutyl)-3-(methylsulfonyl)allyl)-4-phenoxypyrimidine-5-carboxamide;
(S,E)-2-(1-fluorocyclopropyl)-N-(4-(methylsulfonyl)but-3-en-2-yl)-4-phenoxypyrimidine-5-carboxamide;
(S,E)-N-(1-cyclopropyl-3-(methylsulfonyl)allyl)-2-(1,1-difluoroethyl)-4-phenoxypyrimidine-5-carboxamide;
(E)-2-(tert-butyl)-N-(1-(2-(methylsulfonyl)vinyl)cyclopropyl)-4-phenoxypyrimidine-5-carboxamide;
(S,E)-4-acetamido-2-cyclopentyl-N-(4-(methylsulfonyl)but-3-en-2-yl)-6-phenoxypyrimidine-5-carboxamide;
(R,E)-2-(tert-butyl)-N-(4-(methylsulfonyl)-1-(methylthio)but-3-en-2-yl)-4-phenoxypyrimidine-5-carboxamide;
(R,E)-2-cyclopropyl-N-(4-(methylsulfonyl)-1-(methylthio)but-3-en-2-yl)-4-phenoxypyrimidine-5-carboxamide;
(S,E)-N-(4-(methylsulfonyl)but-3-en-2-yl)-2-(perfluoroethyl)-4-phenoxypyrimidine-5-carboxamide;
(S,E)-N-(1-cyclopropyl-3-(methylsulfonyl)allyl)-2-isopropyl-4-phenoxypyrimidine-5-carboxamide;
(S,E)-2-cyclopropyl-N-(1-cyclopropyl-3-(methylsulfonyl)allyl)-4-phenoxypyrimidine-5-carboxamide;
(S,E)-N-(1-cyclopropyl-3-(methylsulfonyl)allyl)-2-(2-fluoropropan-2-yl)-4-phenoxypyrimidine-5-carboxamide;
N—((S,E)-1-cyclopropyl-3-(methylsulfonyl)allyl)-2-((1S,3S)-3-methylcyclobutyl)-4-phenoxypyrimidine-5-carboxamide;
N—((S,E)-1-cyclopropyl-3-(methylsulfonyl)allyl)-2-((1R,3R)-3-methylcyclobutyl)-4-phenoxypyrimidine-5-carboxamide;
(2-cyclopropyl-4-phenoxypyrimidin-5-yl)(3-(methylsulfonyl)-2,5-dihydro-1H-pyrrol-1-yl)methanone;
(S,E)-2-cyclopropyl-N-(4-(methylsulfonyl)-1-phenylbut-3-en-2-yl)-4-phenoxypyrimidine-5-carboxamide;
(S,Z)-2-cyclopropyl-N-(4-(methylsulfonyl)-1-phenylbut-3-en-2-yl)-4-phenoxypyrimidine-5-carboxamide;
2-(tert-butyl)-N-((3R,4R,E)-4-methoxy-1-(methylsulfonyl)pent-1-en-3-yl)-4-phenoxypyrimidine-5-carboxamide;
(S,E)-2-(tert-butyl)-N-(3-(methylsulfonyl)-1-(tetrahydro-2H-pyran-4-yl)allyl)-4-phenoxypyrimidine-5-carboxamide;
2-cyclopropyl-N-((3R,4R,E)-4-methoxy-1-(methylsulfonyl)pent-1-en-3-yl)-4-phenoxypyrimidine-5-carboxamide;
(S,E)-2-cyclopropyl-N-(3-(methylsulfonyl)-1-(tetrahydro-2H-pyran-4-yl)allyl)-4-phenoxypyrimidine-5-carboxamide;
(S,E)-N-(1-cyclopropyl-3-(methylsulfonyl)allyl)-2-(cyclopropylmethyl)-4-phenoxypyrimidine-5-carboxamide;
(S,E)-2-(tert-butyl)-N-(4-(methylsulfonyl)-1-phenylbut-3-en-2-yl)-4-phenoxypyrimidine-5-carboxamide;
(S,Z)-2-(tert-butyl)-N-(4-(methylsulfonyl)-1-phenylbut-3-en-2-yl)-4-phenoxypyrimidine-5-carboxamide;
(R,E)-2-cyclopentyl-N-(1-methoxy-4-(methylsulfonyl)but-3-en-2-yl)-4-phenoxypyrimidine-5-carboxamide;
(S,E)-2-cyclobutyl-N-(1-cyclopropyl-3-(methylsulfonyl)allyl)-4-phenoxypyrimidine-5-carboxamide;
(S,E)-N-(1-cyclopropyl-3-(methylsulfonyl)allyl)-2-(cyclopropyldifluoromethyl)-4-phenoxypyrimidine-5-carboxamide;
(S,E)-2-(cyclopropyldifluoromethyl)-N-(4-(methylsulfonyl)but-3-en-2-yl)-4-phenoxypyrimidine-5-carboxamide;
(R,E)-2-(cyclopropyldifluoromethyl)-N-(1-methoxy-4-(methylsulfonyl)but-3-en-2-yl)-4-phenoxypyrimidine-5-carboxamide;
(S,E)-2-(1,1-difluoroethyl)-4-phenoxy-N-(5,5,5-trifluoro-1-(methylsulfonyl)pent-1-en-3-yl)pyrimidine-5-carboxamide;
(S,E)-N-(1-cyclobutyl-3-(methylsulfonyl)allyl)-2-cyclopentyl-4-phenoxypyrimidine-5-carboxamide;
(E)-2-(tert-butyl)-N-(4-(methylsulfonyl)-1-phenoxybut-3-en-2-yl)-4-phenoxypyrimidine-5-carboxamide;
(S,E)-N-(1-cyclobutyl-3-(methylsulfonyl)allyl)-2-(cyclopropyldifluoromethyl)-4-phenoxypyrimidine-5-carboxamide;
(S,E)-N-(1-cyclobutyl-3-(methylsulfonyl)allyl)-2-(1,1-difluoroethyl)-4-phenoxypyrimidine-5-carboxamide;
(S,E)-2-(tert-butyl)-N-(5-(dimethylamino)-1-(methylsulfonyl)-5-oxopent-1-en-3-yl)-4-phenoxypyrimidine-5-carboxamide;
(R,E)-2-(1,1-difluoroethyl)-4-phenoxy-N-(5,5,5-trifluoro-1-(methylsulfonyl)pent-1-en-3-yl)pyrimidine-5-carboxamide;
(S,E)-N-(1-cyclopropyl-3-(methylsulfonyl)allyl)-2-(perfluoroethyl)-4-phenoxypyrimidine-5-carboxamide;
(R,E)-N-(1-methoxy-4-(methylsulfonyl)but-3-en-2-yl)-2-(perfluoroethyl)-4-phenoxypyrimidine-5-carboxamide;
(S,E)-N-(1-cyclopropyl-3-(methylsulfonyl)allyl)-4-phenoxy-2-(trifluoromethyl)pyrimidine-5-carboxamide;
(S,E)-N-(4-(methylsulfonyl)but-3-en-2-yl)-4-phenoxy-2-(1-(trifluoromethyl)cyclopropyl)pyrimidine-5-carboxamide;
(S,E)-N-(1-cyclopropyl-3-(methylsulfonyl)allyl)-4-phenoxy-2-(1-(trifluoromethyl)cyclopropyl)pyrimidine-5-carboxamide;
(S,E)-N-(1-cyclopropyl-3-(methylsulfonyl)allyl)-4-phenoxy-2-(2,2,2-trifluoroethyl)pyrimidine-5-carboxamide;
(S,E)-N-(1-cyclopropyl-3-(methylsulfonyl)allyl)-2-(1-fluorocyclopropyl)-4-phenoxypyrimidine-5-carboxamide;
(S,E)-2-(tert-butyl)-N-(1-(4,4-difluorocyclohexyl)-3-(methylsulfonyl)allyl)-4-phenoxypyrimidine-5-carboxamide;
(S,E)-2-(tert-butyl)-N-(5,5-difluoro-1-(methylsulfonyl)pent-1-en-3-yl)-4-phenoxypyrimidine-5-carboxamide;
(S,E)-N-(5,5-difluoro-1-(methylsulfonyl)pent-1-en-3-yl)-2-(1,1-difluoroethyl)-4-phenoxypyrimidine-5-carboxamide;
(S,E)-N-(1-(4,4-difluorocyclohexyl)-3-(methylsulfonyl)allyl)-2-(1,1-difluoroethyl)-4-phenoxypyrimidine-5-carboxamide;
(R,E)-N-(4-(methylsulfonyl)but-3-en-2-yl)-4-phenoxy-2-(2,2,2-trifluoroethyl)pyrimidine-5-carboxamide;
4-(((1R,3S,5S)-bicyclo[3.1.0]hexan-3-yl)oxy)-2-(tert-butyl)-N—((E)-3-(methylsulfonyl)allyl)pyrimidine-5-carboxamide;
4-(((1R,3S,5S)-bicyclo[3.1.0]hexan-3-yl)oxy)-2-cyclopropyl-N—((E)-3-(methylsulfonyl)allyl)pyrimidine-5-carboxamide;
(R,E)-N-(1-(tert-butoxy)-4-(methylsulfonyl)but-3-en-2-yl)-2-(1,1-difluoroethyl)-4-phenoxypyrimidine-5-carboxamide;
(R,E)-2-(tert-butyl)-N-(4-(methylsulfonyl)-1-phenoxybut-3-en-2-yl)-4-phenoxypyrimidine-5-carboxamide;
(S,E)-2-(tert-butyl)-N-(4-(methylsulfonyl)-1-phenoxybut-3-en-2-yl)-4-phenoxypyrimidine-5-carboxamide;
(S,E)-N-(4-(methylsulfonyl)but-3-en-2-yl)-4-phenoxy-2-(spiro[2.3]hexan-5-yl)pyrimidine-5-carboxamide;
(R,E)-2-(1,1-difluoroethyl)-N-(1-(difluoromethoxy)-4-(methylsulfonyl)but-3-en-2-yl)-4-phenoxypyrimidine-5-carboxamide;
(S,E)-2-(1,1-difluoroethyl)-N-(5-(dimethylamino)-1-(methylsulfonyl)-5-oxopent-1-en-3-yl)-4-phenoxypyrimidine-5-carboxamide;
N—((S,E)-1-cyclopropyl-3-(methylsulfonyl)allyl)-2-(cyclopropylfluoromethyl)-4-phenoxypyrimidine-5-carboxamide;

4-(((1R,3S,5S)-bicyclo[3.1.0]hexan-3-yl)oxy)-2-(tert-butyl)-N—((S,E)-1-cyclopropyl-3-(methylsulfonyl)allyl)pyrimidine-5-carboxamide;
(S,E)-N-(1-(3,3-difluorocyclobutyl)-3-(methylsulfonyl)allyl)-2-(1,1-difluoroethyl)-4-phenoxypyrimidine-5-carboxamide;
(R,E)-N-(1-(3,3-difluorocyclobutyl)-3-(methylsulfonyl)allyl)-2-(1,1-difluoroethyl)-4-phenoxypyrimidine-5-carboxamide;
(S,E)-2-(cyclopropyldifluoromethyl)-N-(1-(3,3-difluorocyclobutyl)-3-(methylsulfonyl)allyl)-4-phenoxypyrimidine-5-carboxamide;
(R,E)-2-(cyclopropyldifluoromethyl)-N-(1-(3,3-difluorocyclobutyl)-3-(methylsulfonyl)allyl)-4-phenoxypyrimidine-5-carboxamide;
2-(1,1-difluoroethyl)-N-((3R,4S,E)-4-methoxy-1-(methylsulfonyl)pent-1-en-3-yl)-4-phenoxypyrimidine-5-carboxamide;
4-(((1R,3R,5S)-bicyclo[3.1.0]hexan-3-yl)oxy)-N—((S,E)-1-cyclopropyl-3-(methylsulfonyl)allyl)-2-(1,1-difluoroethyl)pyrimidine-5-carboxamide;
(R,E)-N-(1-cyclopropoxy-4-(methylsulfonyl)but-3-en-2-yl)-2-(1,1-difluoroethyl)-4-phenoxypyrimidine-5-carboxamide;
(S,E)-N-(1-cyclopropyl-3-(methylsulfonyl)allyl)-2-(dimethylamino)-4-phenoxypyrimidine-5-carboxamide;
(S,E)-N-(1-cyclopropyl-3-(methylsulfonyl)allyl)-2-(methylamino)-4-phenoxypyrimidine-5-carboxamide;
(S,E)-2-cyclopropoxy-N-(1-cyclopropyl-3-(methylsulfonyl)allyl)-4-phenoxypyrimidine-5-carboxamide;
(S,E)-N-(1-cyclopropyl-3-(methylsulfonyl)allyl)-4-phenoxy-2-(2,2,2-trifluoroethoxy)pyrimidine-5-carboxamide;
(S,E)-N-(1-cyclopropyl-3-(methylsulfonyl)allyl)-2-(diethylamino)-4-phenoxypyrimidine-5-carboxamide;
(S,E)-2-(cyclopropyl(methyl)amino)-N-(1-cyclopropyl-3-(methylsulfonyl)allyl)-4-phenoxypyrimidine-5-carboxamide;
(S,E)-N-(1-cyclopropyl-3-(methylsulfonyl)allyl)-2-methoxy-4-phenoxypyrimidine-5-carboxamide;
(S,E)-2-(azetidin-1-yl)-N-(1-cyclopropyl-3-(methylsulfonyl)allyl)-4-phenoxypyrimidine-5-carboxamide;
(S,E)-N-(1-cyclopropyl-3-(methylsulfonyl)allyl)-2-(methyl(2,2,2-trifluoroethyl)amino)-4-phenoxypyrimidine-5-carboxamide;
(S,E)-N-(1-cyclopropyl-3-(methylsulfonyl)allyl)-2-(3-fluoroazetidin-1-yl)-4-phenoxypyrimidine-5-carboxamide;
(S,E)-N-(1-cyclopropyl-3-(methylsulfonyl)allyl)-2-(ethyl(methyl)amino)-4-phenoxypyrimidine-5-carboxamide;
(S,E)-N-(1-cyclopropyl-3-(methylsulfonyl)allyl)-1-methyl-6-phenoxy-1H-pyrazolo[3,4-b]pyridine-5-carboxamide;
(S,E)-N-(1-cyclopropyl-3-(methylsulfonyl)allyl)-2-(3,3-difluoroazetidin-1-yl)-4-phenoxypyrimidine-5-carboxamide;
(S,E)-N-(1-cyclopropyl-3-(methylsulfonyl)allyl)-2-(1,1-difluoropropyl)-4-phenoxypyrimidine-5-carboxamide;
(S,E)-N-(1-cyclopropyl-3-(methylsulfonyl)allyl-1-d)-2-(1,1-difluoroethyl)-4-phenoxypyrimidine-5-carboxamide;
(S)—N-(3-cyanobut-3-en-2-yl)-2-(cyclopropyldifluoromethyl)-4-phenoxypyrimidine-5-carboxamide;
(S,E)-N-(1-cyclopropyl-3-(methylsulfonyl)allyl)-2-(cyclopropyldifluoromethyl)-4-(phenoxy-d5)pyrimidine-5-carboxamide;
(S,E)-N-(1-cyclopropyl-3-(methylsulfonyl)allyl-1-d)-2-(1,1-difluoroethyl)-4-phenoxypyrimidine-5-carboxamide; and
(S,E)-N-(1-cyclopropyl-3-(methylsulfonyl)allyl)-2-(cyclopropyldifluoromethyl)-4-(phenoxy-d5)pyrimidine-5-carboxamide.

Embodiment 21A

The compound according to Embodiment 21, or a pharmaceutically acceptable salt or solvate thereof, wherein when the R or S stereochemical configuration at one or more chiral carbons is specified, the compound includes a mixture of R or S configurations at that carbon;
or a mixture of (E) or (Z) geometric isomers of the aforementioned compounds.

Embodiment 21.1

The compound according to any one of Embodiments 2 and 8-12, or a pharmaceutically acceptable salt or solvate thereof, wherein the compound is:
(S,E)-N-(1-cyclopropyl-3-(methylsulfonyl)allyl)-2-(1,1-difluoroethyl)-4-phenoxypyrimidine-5-carboxamide.

Embodiment 21.1A

The compound according to Embodiment 21.1, or a pharmaceutically acceptable salt or solvate thereof, wherein when the R or S stereochemical configuration at one or more chiral carbons is specified, the compound includes a mixture of R or S configurations at that carbon;
or a mixture of (E) or (Z) geometric isomers of the aforementioned compounds.

Embodiment 21.2

The compound according to any one of Embodiments 2 and 8-12, or a pharmaceutically acceptable salt thereof, wherein the compound is:
(S,E)-N-(1-cyclopropyl-3-(methylsulfonyl)allyl)-2-(1,1-difluoroethyl)-4-phenoxypyrimidine-5-carboxamide.

Embodiment 21.2A

The compound according to Embodiment 21.2, or a pharmaceutically acceptable salt thereof, wherein when the R or S stereochemical configuration at one or more chiral carbons is specified, the compound includes a mixture of R or S configurations at that carbon;
or a mixture of (E) or (Z) geometric isomers of the aforementioned compounds.

Embodiment 21.3

The compound according to any one of Embodiments 2 and 8-12, wherein the compound is:
(S,E)-N-(1-cyclopropyl-3-(methylsulfonyl)allyl)-2-(1,1-difluoroethyl)-4-phenoxypyrimidine-5-carboxamide.

Embodiment 21.3A

The compound according to Embodiment 21.3, wherein when the R or S stereochemical configuration at one or more chiral carbons is specified, the compound includes a mixture of R or S configurations at that carbon;
or a mixture of (E) or (Z) geometric isomers of the aforementioned compounds.

Embodiment 22

The compound according to any one of Embodiments 3 and 8-12, or a pharmaceutically acceptable salt or solvate thereof, wherein the compound is selected from the group consisting of:
(E)-2-cyclobutoxy-4-cyclopentyl-N-(3-(methylsulfonyl)allyl)benzamide;
(E)-4-cyclopentyl-2-ethoxy-N-(3-(methylsulfonyl)allyl)benzamide;
(E)-4-cyclopentyl-2-isopropoxy-N-(3-(methylsulfonyl)allyl)benzamide;
(E)-4-cyclopentyl-N-(3-(methylsulfonyl)allyl)-2-phenoxybenzamide;
(E)-4-cyclopentyl-2-cyclopropoxy-N-(3-(methylsulfonyl)allyl)benzamide;
4-cyclopentyl-2-cyclopropoxy-N-((1,1-dioxido-2H-thiet-3-yl)methyl)benzamide;
(E)-2-cyclobutoxy-4-cyclopentyl-N-(3-(methylsulfonyl)allyl)benzamide;
(E)-4-cyclopentyl-2-ethoxy-N-(3-(methylsulfonyl)allyl)benzamide;
(E)-4-cyclopentyl-2-isopropoxy-N-(3-(methylsulfonyl)allyl)benzamide;
(E)-4-cyclopentyl-N-(3-(methylsulfonyl)allyl)-2-phenoxybenzamide;
(E)-4-cyclopentyl-2-cyclopropoxy-N-(3-(methylsulfonyl)allyl)benzamide; 4-cyclopentyl-2-cyclopropoxy-N-((1,1-dioxido-2H-thiet-3-yl)methyl)benzamide;
(S,E)-5-cyclopentyl-N-(4-(methylsulfonyl)but-3-en-2-yl)quinoline-8-carboxamide;
(S,E)-6-(cyclopent-1-en-1-yl)-N-(4-(methylsulfonyl)but-3-en-2-yl)-4-phenoxynicotinamide;
(E)-4-cyclopentyl-2-(cyclopentyloxy)-N-(3-(methylsulfonyl)allyl)benzamide;
rac-(R,E)-4-cyclopentyl-N-(4-(methylsulfonyl)but-3-en-2-yl)-2-phenoxybenzamide;
(S,E)-N-(4-(methylsulfonyl)but-3-en-2-yl)-3-oxo-6-phenoxy-2,3-dihydro-1H-indene-5-carboxamide;
(S,E)-2,2-dimethyl-N-(4-(methylsulfonyl)but-3-en-2-yl)-3-oxo-6-phenoxy-2,3-dihydro-1H-indene-5-carboxamide; and
2,2-dimethyl-6-(3-((methylsulfonyl)methylene)azetidine-1-carbonyl)-5-phenoxy-2,3-dihydro-1H-inden-1-one.

Embodiment 22A

The compound according to Embodiment 22, or a pharmaceutically acceptable salt or solvate thereof, wherein when the R or S stereochemical configuration at one or more chiral carbon atoms is specified, the compound includes a mixture of R or S configurations at those carbon atoms;
or a mixture of (E) or (Z) geometric isomers of the aforementioned compounds.

Embodiment 23

The compound according to any one of Embodiments 4 and 8-12, wherein the compound is selected from the group consisting of:
(S,E)-6-cyclopentyl-N-(4-(methylsulfonyl)but-3-en-2-yl)-4-phenoxynicotinamide;
(S,E)-6-cyclopentyl-N-(4-(methylsulfonyl)but-3-en-2-yl)-2-phenoxynicotinamide;
(S,E)-6-(cyclopent-1-en-1-yl)-N-(4-(methylsulfonyl)but-3-en-2-yl)-4-phenoxynicotinamide;
(S,E)-6-(cyclopent-1-en-1-yl)-N-(4-(methylsulfonyl)but-3-en-2-yl)-2-phenoxynicotinamide;
(S,E)-6-cyclopropyl-5-methyl-N-(4-(methylsulfonyl)but-3-en-2-yl)-4-phenoxynicotinamide;
(S,E)-6-(tert-butyl)-N-(4-(methylsulfonyl)but-3-en-2-yl)-4-phenoxynicotinamide; and
(S,E)-N-(1-cyclopropyl-3-(methylsulfonyl)allyl)-6-(1,1-difluoroethyl)-4-phenoxynicotinamide.

Embodiment 23A

The compound according to Embodiment 23, or a pharmaceutically acceptable salt or solvate thereof, wherein when the (R) or (S) stereochemical configuration at one or more chiral carbon atoms is specified, the compound includes a mixture of (R) or (S) configurations at those carbon atoms;
or a mixture of (E) and (Z) geometric isomers of the aforementioned compounds.

Embodiment 24

The compound according to any one of Embodiments 5 and 8-12, or a pharmaceutically acceptable salt or solvate thereof, wherein the compound is selected from the group consisting of:
(S,E)-6-cyclopentyl-N-(4-(methylsulfonyl)but-3-en-2-yl)-2-phenoxynicotinamide;
(S,E)-6-(cyclopent-1-en-1-yl)-N-(4-(methylsulfonyl)but-3-en-2-yl)-2-phenoxynicotinamide;
(S,E)-N-(4-(methylsulfonyl)but-3-en-2-yl)-2-phenoxyquinoline-3-carboxamide;
(S,E)-5-cyano-6-cyclopentyl-N-(4-(methylsulfonyl)but-3-en-2-yl)-2-phenoxynicotinamide;
(S,E)-6-(cyclopent-1-en-1-yl)-5-fluoro-N-(4-(methylsulfonyl)but-3-en-2-yl)-2-phenoxynicotinamide;
(S,E)-6-cyclopropyl-5-fluoro-N-(4-(methylsulfonyl)but-3-en-2-yl)-4-phenoxynicotinamide;
(S,E)-N-(4-(methylsulfonyl)but-3-en-2-yl)-2-phenoxy-6,7-dihydro-5H-cyclopenta[b]pyridine-3-carboxamide;
(S,E)-6-cyclopentyl-5-methyl-N-(4-(methylsulfonyl)but-3-en-2-yl)-2-phenoxynicotinamide;
(S,E)-N-(1-cyclopropyl-3-(methylsulfonyl)allyl)-6-(1,1-difluoroethyl)-2-phenoxynicotinamide;
S,E)-6-(1,1-difluoroethyl)-N-(4-(methylsulfonyl)but-3-en-2-yl)-2-phenoxynicotinamide;
(S,E)-N-(1-cyclopropyl-3-(methylsulfonyl)allyl)-1-methyl-6-phenoxy-1H-pyrrolo[2,3-b]pyridine-5-carboxamide;
(S,E)-N-(1-cyclopropyl-3-(methylsulfonyl)allyl)-1-methyl-6-phenoxy-1H-pyrazolo[3,4-b]pyridine-5-carboxamide;
(S,E)-N-(1-cyclopropyl-3-(methylsulfonyl)allyl)-6-(1,1-difluoroethyl)-5-fluoro-2-phenoxynicotinamide;
(S,E)-N-(1-cyclopropyl-3-(methylsulfonyl)allyl)-7,7-difluoro-2-phenoxy-6,7-dihydro-5H-cyclopenta[b]pyridine-3-carboxamide;
(S,E)-N-(1-cyclopropyl-3-(methylsulfonyl)allyl)-3-methyl-5-phenoxy-3H-imidazo[4,5-b]pyridine-6-carboxamide; and
(S,E)-N-(1-cyclopropyl-3-(methylsulfonyl)allyl)-6-(cyclopropyldifluoromethyl)-5-fluoro-2-phenoxynicotinamide.

Embodiment 24A

The compound according to Embodiment 24, or a pharmaceutically acceptable salt or solvate thereof, wherein when the (R) or (S) stereochemical configuration at one or more chiral carbon atoms is specified, the compound includes a mixture of R or S configurations at that carbon;
or a mixture of (E) or (Z) geometric isomers of the aforementioned compounds.

Embodiment 25

The compound according to any one of Embodiments 6 and 8-12, or a pharmaceutically acceptable salt or solvate thereof, wherein the compound is:
(S,E)-5-(cyclopent-1-en-1-yl)-N-(4-(methylsulfonyl)but-3-en-2-yl)-3-phenoxypyrazine-2-carboxamide.

Embodiment 25A

The compound according to Embodiment 25, or a pharmaceutically acceptable salt or solvate thereof, wherein when the (R) or (S) stereochemical configuration at one or more chiral carbon atoms is specified, the compound includes a mixture of (R) or (S) configurations at those carbon atoms;
or a mixture of E or Z geometric isomers of the aforementioned compounds.

Embodiment 26

The compound according to any one of Embodiments 7 and 8-12, or a pharmaceutically acceptable salt or solvate thereof, wherein the compound is:
(S,E)-5-cyclopentyl-N-(4-(methylsulfonyl)but-3-en-2-yl)-3-phenoxypicolinamide.

Embodiment 26A

The compound according to Embodiment 26, or a pharmaceutically acceptable salt or solvate thereof, wherein when the (R) or (S) stereochemical configuration at one or more chiral carbon atoms is specified, the compound includes a mixture of (R) or (S) configurations at those carbon atoms;
or a mixture of E or Z geometric isomers of the aforementioned compounds.

Embodiment 27

The compound according to any one of Embodiments 2, 8-10, and 13-14, or a pharmaceutically acceptable salt or solvate thereof, wherein the compound is selected from the group consisting of:
2-(1-(2-cyclopropyl-4-phenoxypyrimidine-5-carbonyl)azetidin-3-ylidene)acetonitrile;
2-(1-(2-cyclopropyl-4-phenoxypyrimidine-5-carbonyl)-2-methylazetidin-3-ylidene)acetonitrile;
(E)-N-(3-cyanoallyl)-2-cyclopropyl-4-phenoxypyrimidine-5-carboxamide; and
(Z)—N-(3-cyanoallyl)-2-cyclopropyl-4-phenoxypyrimidine-5-carboxamide.

Embodiment 27A

The compound according to Embodiment 27, or a pharmaceutically acceptable salt or solvate thereof, wherein an (E) or (Z) geometric isomer of a compound has been specified, a mixture of (E) or (Z) geometric isomers of said compounds.

Embodiment 28

The compound according to any one of Embodiments 2, 8-10, and 15-16, or a pharmaceutically acceptable salt or solvate thereof, wherein the compound is selected from the group consisting of:
N-(2-cyanoallyl)-2-cyclopropyl-4-phenoxypyrimidine-5-carboxamide;
2-(tert-butyl)-N-(2-cyanoallyl)-4-phenoxypyrimidine-5-carboxamide;
N-(2-cyanoallyl)-2-(1,1-difluoroethyl)-4-phenoxypyrimidine-5-carboxamide;
N-(2-cyanoallyl)-2-cyclopentyl-4-phenoxypyrimidine-5-carboxamide;
N-(2-cyanoallyl)-2-(cyclopropyldifluoromethyl)-4-phenoxypyrimidine-5-carboxamide;
(R)—N-(3-cyanobut-3-en-2-yl)-2-(1,1-difluoroethyl)-4-phenoxypyrimidine-5-carboxamide;
(S)—N-(3-cyanobut-3-en-2-yl)-2-(1,1-difluoroethyl)-4-phenoxypyrimidine-5-carboxamide;
(S)—N-(3-cyanobut-3-en-2-yl)-2-(cyclopropyldifluoromethyl)-4-phenoxypyrimidine-5-carboxamide; and
(S)—N-(2-cyano-1-cyclopropylallyl)-2-(1,1-difluoroethyl)-4-phenoxypyrimidine-5-carboxamide.

Embodiment 28A

The compound according to Embodiment 28, or a pharmaceutically acceptable salt or solvate thereof, wherein when the (R) or (S) stereochemical configuration at one or more chiral carbon atoms is specified, the compound includes a mixture of (R) or (S) configurations at those carbon atoms.

Embodiment 29

The compound according to any one of Embodiments 2, 8-10, and 17-18, or a pharmaceutically acceptable salt or solvate thereof, wherein the compound is:
(S)-2-(1,1-difluoroethyl)-N-(5-(dimethylamino)-5-oxopent-3-yn-2-yl)-4-phenoxypyrimidine-5-carboxamide.

Embodiment 29A

The compound according to Embodiment 29, or a pharmaceutically acceptable salt or solvate thereof, wherein when the (R) or (S) stereochemical configuration at one or more chiral carbon atoms is specified, the compound includes a mixture of (R) or (S) configurations at those carbon.

Embodiment 30

The compound according to any one of Embodiments 2, 8-10, and 19-20, or a pharmaceutically acceptable salt or solvate thereof, wherein the compound is selected from the group consisting of:
1-(1-(2-(tert-butyl)-4-phenoxypyrimidine-5-carbonyl)azetidin-3-ylidene)propan-2-one; and
methyl 2-(1-(2-(tert-butyl)-4-phenoxypyrimidine-5-carbonyl)azetidin-3-ylidene)acetate.

Embodiment 31

A compound according to any one of Embodiments 1-30, 2.1, 2.2, 21.1, 21.1A and 21A-29A, or a pharmaceutically acceptable salt or solvate thereof, and a pharmaceutically acceptable carrier or excipient.

Embodiment 31A

A compound according to any one of Embodiments 1-30, 2.1, 2.2, 21.1, 21.1A and 21A-29A, or a pharmaceutically acceptable salt thereof, and a pharmaceutically acceptable carrier or excipient.

Embodiment 31B

A compound according to any one of Embodiments 1-30, 2.1, 2.2, 21.1, 21.1A and 21A-29A, and a pharmaceutically acceptable carrier or excipient.

Embodiment 31.1

A compound according to any one of Embodiments 1-30 and 21A-29A, or a pharmaceutically acceptable salt.

Embodiment 31.1A

A compound according to any one of Embodiments 1-30 and 21A-29A.

Embodiment 32

A method of treating a proliferative disease in a patient in need thereof, the method comprising administering to the patient a therapeutically effective amount of a compound according to any one of Embodiments 1-30, 2.1, 2.2, 21.1, 21.1A and 21A-29A, or a pharmaceutically acceptable salt or solvate thereof.

Embodiment 32A

The method according to Embodiment 32, the method comprising administering to the patient a therapeutically effective amount of a compound according to any one of Embodiments 1-30, 2.1, 2.2, 21.1, 21.1A and 21A-29A, or a pharmaceutically acceptable salt thereof.

Embodiment 32B

The method according to Embodiment 32, the method comprising administering to the patient a therapeutically effective amount of a compound according to any one of Embodiments 1-30, 2.1, 2.2, 21.1, 21.1A and 21A-29A.

Embodiment 33

The method according to Embodiment 32, wherein the proliferative disease is cancer.

Embodiment 34

The method according to Embodiment 33, wherein the cancer is selected from the group consisting of colon cancer, colorectal cancer, gastric cancer, endometrium cancer, ovarian cancer, hepatobiliary tract cancer, urinary tract cancer, brain cancer, skin cancer, and MSI-H cancer.

Embodiment 35

A method of inhibiting WRN helicase (Werner syndrome ATP-dependent helicase) in a subject in need of such inhibition, comprising administering to the subject a therapeutically effective amount of at least one compound according to any of Embodiments 1-30, 2.1, 2.2, 21.1, 21.1A and 21A-29A, or a pharmaceutically acceptable salt or solvate thereof.

Embodiment 35A

A method of inhibiting WRN helicase (Werner syndrome ATP-dependent helicase) in a subject in need of such inhibition, comprising administering to the subject a therapeutically effective amount of at least one compound according to any of Embodiments 1-30, 2.1, 2.2, 21.1, 21.1A and 21A-29A, or a pharmaceutically acceptable salt thereof.

Embodiment 35B

A method of inhibiting WRN helicase (Werner syndrome ATP-dependent helicase) in a subject in need of such inhibition, comprising administering to the subject a therapeutically effective amount of at least one compound according to any of Embodiments 1-30, 2.1, 2.2, 21.1, 21.1A and 21A-29A.

Embodiment 36

A method of inhibiting WRN helicase (Werner syndrome ATP-dependent helicase) comprising effecting a non-naturally occurring covalent modification at cysteine 727 as set forth in SEQ ID NO: 1 or a variant thereof, the modification resulting from a bond forming reaction between an electrophile and the cysteine 727 as set forth in SEQ ID NO: 1 or the variant thereof, wherein a sulfur atom at the cysteine residue undergoes a reaction with the electrophile.

Embodiment 37

The method according to Embodiment 36, wherein the electrophile comprises at least one chemical moiety selected from the group consisting of: a vinyl sulfone, an alkynyl sulfone, a vinyl sulfonamide, a vinyl sulfoxide, an alkynyl sulfoxide, a vinyl sulfoximine, an alkynyl sulfoximine, an acrylamide, an acrylonitrile, an alkynenitrile, an enone, a ynone, an enoate, and a ynoate.

Embodiment 38

The method according to Embodiment 37, wherein:
the vinyl sulfone is represented by the structure

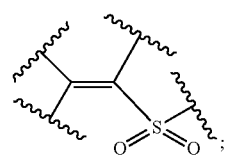 [SMILES: *C(*)=C(*)S(*)(=O)=O]

the alkynyl sulfone is represented by the structure

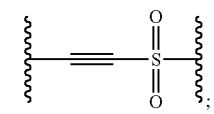

the vinyl sulfonamide is represented by the structure

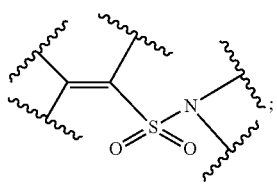 [SMILES: *C(*)=C(*)S(=O)(=O)N(*)*]

the vinyl sulfoxide is represented by the structure

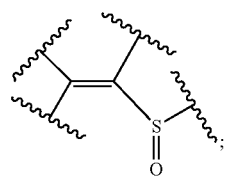 [SMILES: *C(*)=C(*)S(*)=O]

the alkynyl sulfoxide is represented by the structure

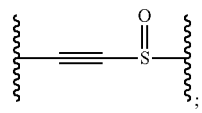 [SMILES: *C#CS(*)=O]

the vinyl sulfoximine is represented by the structure

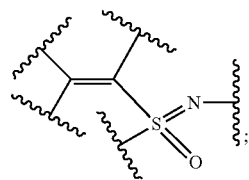 [SMILES: *N=S(*)(=O)C(*)=C(*)*]

the alkynyl sulfoximine is represented by the structure

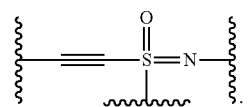

the acrylamide is represented by the formula

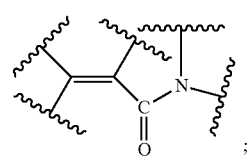 [SMILES: *C(*)=C(*)C(=O)N(*)*]

the acrylonitrile is represented by the structure

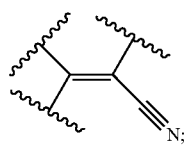

the enone is represented by the structure

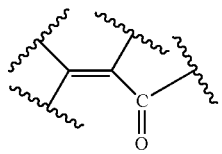

the ynone is represented by the structure

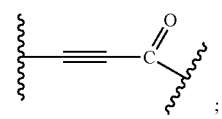 [SMILES: *C#CC(*)=O]

the enoate is represented by the structure

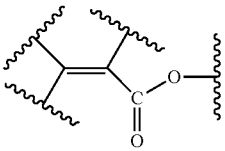

the ynoate is represented by the structure

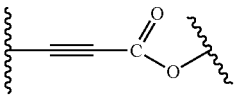

wherein:

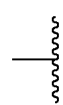

represents a possible point of attachment of the chemical moiety to the remainder of the electrophile.

Embodiment 39

A compound of Formula (II):

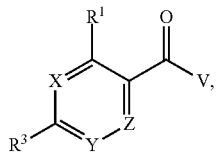

or a pharmaceutically acceptable salt or solvate thereof, wherein:
X is $CR^2$ or N;
Y is $CR^4$ or N;
Z is $CR^5$ or N;
  or Y and Z taken together form an optionally substituted five- to six-membered heteroaryl, or an optionally substituted five- to six-membered heterocyclyl;
with the proviso that X, Y, and Z are not simultaneously N;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
  or $R^1$ together with the carbon atoms to which it is shown attached and X form an optionally substituted five- to six-membered heterocyclyl;
$R^2$ is H, optionally substituted $C_1$-$C_6$ alkyl, or halo;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);
  or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;
$R^4$ is H, $C_1$-$C_6$ alkyl, cyano, or halo;
  or $R^4$ together with the carbon atom to which it is shown attached and Z form an optionally substituted five- to six-membered heteroaryl;
  or R and $R^4$ taken together with the carbon atoms to which they are shown attached and $R^3$ taken from an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;
$R^5$ is H, $C_1$-$C_6$ alkyl, —$NR_2$, or —N(R)—C(=O)—($C_1$-$C_6$ alkyl);
each R independently is H, or optionally substituted $C_1$-$C_6$ alkyl; and
V comprises an electrophile that reacts and forms a covalent bond with the sulfur atom at cysteine 727 as set forth in SEQ ID NO: 1 or variants thereof.

Embodiment 40

The compound according to Embodiment 39, or a pharmaceutically acceptable salt or solvate thereof, wherein the electrophile comprises at least one chemical moiety selected from the group consisting of a vinylsulfone, an alkynylsulfone, a vinylsulfonamide, a vinylsulfoxide, an alkynylsulfoxide, a vinylsulfoximine, an alkynylsulfoximine, an acrylamide, an acrylonitrile, an alkynenitrile, an enone, a ynone, an enoate, and a ynoate.

Embodiment 41

The compound according to Embodiment 40, or a pharmaceutically acceptable salt or solvate thereof, wherein:
the vinyl sulfone is represented by the structure

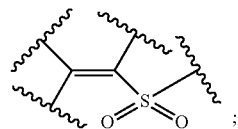 [SMILES: *C(*)=C(*)S(*)(=O)=O]

the alkynyl sulfone is represented by the structure

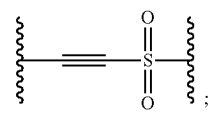 [SMILES: *C#CS(*)(=O)=O]

the vinyl sulfonamide is represented by the structure

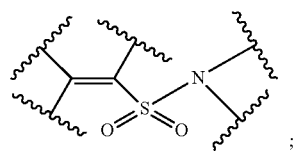 [SMILES: *C(*)=C(*)S(=O)(=O)N(*)*]

the vinyl sulfoxide is represented by the structure

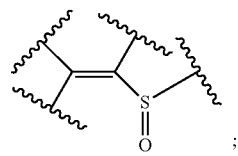 [SMILES: *C(*)=C(*)S(*)=O]

the alkynyl sulfoxide is represented by the structure

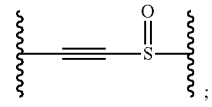

the vinyl sulfoximine is represented by the structure

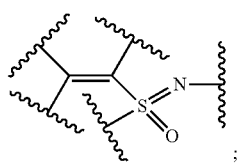 [SMILES: *N=S(*)(=O)C(*)=C(*)*]

the alkynyl sulfoximine is represented by the structure

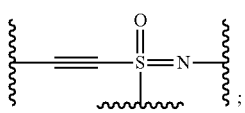

the acrylamide is represented by the formula

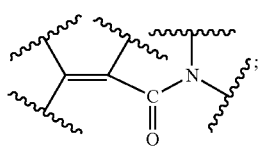 [SMILES: *C(*)=C(*)C(=O)N(*)*]

the acrylonitrile is represented by the structure

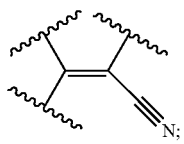 [SMILES: *C(*)=C(*)C#N]

the enone is represented by the structure

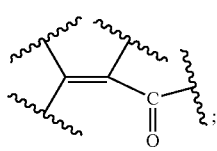 [SMILES: *C(=O)C(*)=C(*)*]

the ynone is represented by the structure

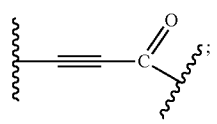 [SMILES: *C#CC(*)=O]

the enoate is represented by the structure

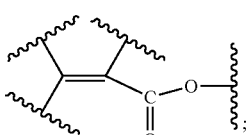

and
the ynoate is represented by the structure

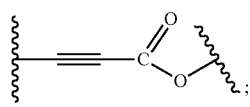 [SMILES: *C#CC(=O)O*]

wherein:

represents a possible point of attachment of the chemical moiety to the remainder of the electrophile.

Embodiment 42

A compound according to any one of Embodiments 39-41, or a pharmaceutically acceptable salt or solvate thereof, and a pharmaceutically acceptable carrier or excipient.

Embodiment 42A

A compound according to any one of Embodiments 39-41, or a pharmaceutically acceptable salt, and a pharmaceutically acceptable carrier or excipient.

Embodiment 42B

A compound according to any one of Embodiments 39-41, and a pharmaceutically acceptable carrier or excipient.

Embodiment 42.1

A compound according to any one of Embodiments 39-41, or a pharmaceutically acceptable salt.

Embodiment 42.1A

A compound according to any one of Embodiments 39-41.

Embodiment 43

A method of treating a proliferative disease in a patient in need thereof, the method comprising administering to the patient a therapeutically effective amount of a compound according to any one of Embodiments 39-41, or a pharmaceutically acceptable salt or solvate thereof.

Embodiment 43A

The method of Embodiment 43, the method comprising administering to the patient a therapeutically effective amount of a compound according to any one of Embodiments 39-41, or a pharmaceutically acceptable salt thereof.

Embodiment 43B

The method of Embodiment 43, the method comprising administering to the patient a therapeutically effective amount of a compound according to any one of Embodiments 39-41.

Embodiment 44

The method of Embodiment 43, wherein the proliferative disease is cancer.

Embodiment 45

The method of Embodiment 44, wherein the cancer is selected from the group consisting of colon cancer, colorectal cancer, gastric cancer, endometrium cancer, ovarian cancer, hepatobiliary tract cancer, urinary tract cancer, brain cancer, skin cancer, and MSI-H cancer.

Embodiment 46

A modified WRN helicase protein comprising a non-naturally occurring small molecule fragment having a covalent bond to cysteine 727 of the WRN helicase protein, wherein the modified WRN helicase protein comprises SEQ ID NO: 1 or a variant thereof; and has the structure of Formula (III):

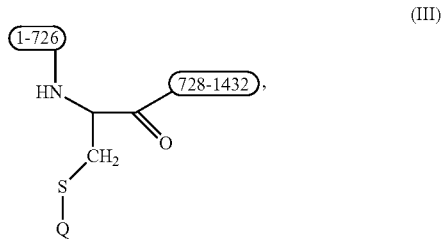
(III)

wherein:
S is the sulfur atom of Cysteine 727 in SEQ ID NO: 1 or a variant thereof,
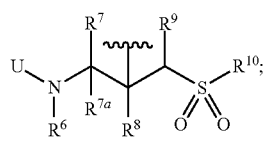 and 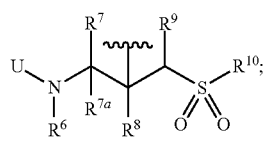 represent amino acid positions 1-726 and 728-1432 respectively of SEQ ID NO: 1 or the variant thereof; and
Q is $Q^1$, $Q^2$, $Q^3$, $Q^4$, or $Q^5$; wherein:
$Q^1$ is:

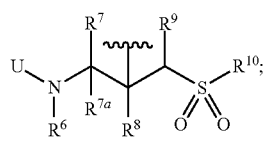

wherein:

indicates the point of attachment;

$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl;
or $R^6$ together with the nitrogen atom to which it is shown attached and $R^7$ and $R^{7a}$ with the carbon atom to which they are shown attached form an azetidinyl ring;
or $R^6$ together with the nitrogen atom to which it is shown attached and $R^7$, $R^{7a}$, and $R^8$ together with the carbon atoms to which they are shown attached form an azetidinyl or pyrrolodinyl ring;
or $R^6$ together with the nitrogen atom to which it is shown attached and $R^7$, $R^{7a}$, $R^8$, and $R^9$ together with the carbon atoms to which they are shown attached form a dihydropyrrolyl ring;
or $R^7$, $R^{7a}$, $R^8$, $R^9$, and $R^{10}$ together with the carbon atoms to which they are shown attached form a 2,3-dihydrothiophene 1,1-dioxide;
or $R^8$, $R^9$, and $R^{10}$ together with the carbon atoms to which they are shown attached form a 2,3-dihydrothiophene 1,1-dioxide;
$Q^2$ is:

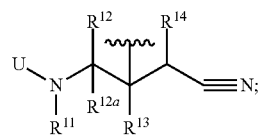

wherein:

indicates the point of attachment;
$R^{11}$ is H;
$R^{12}$ is H or optionally substituted $C_1$-$C_6$ alkyl;
$R^{12a}$ is H; and
$R^{13}$ and $R^{14}$ are each H;
or $R^{11}$ together with the nitrogen atom to which it is shown attached and $R^{12}$, $R^{12a}$, and $R^{13}$ together with the carbon atoms to which they are shown attached form an optionally substituted azetidinyl ring;
$Q^3$ is:

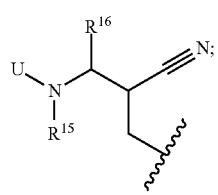

wherein:

indicates the point of attachment;
$R^{15}$ is H; and
$R^{16}$ is H or optionally substituted $C_1$-$C_6$ alkyl, or optionally substituted $C_3$-$C_8$ cycloalkyl;
$Q^4$ is:

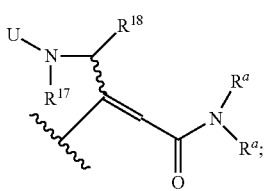

wherein:

indicates the point of attachment;
$R^{17}$ is H;
$R^{18}$ is H or optionally substituted $C_1$-$C_6$ alkyl; and
each $R^a$ independently is optionally substituted $C_1$-$C_6$ alkyl;
$Q^5$ is:

wherein:

indicates the point of attachment;
m is 1, 2, or 3; and
$R^{19}$ is selected from the group consisting of $C_1$-$C_6$ alkyl and —O—($C_1$-$C_6$ alkyl); and
U is:

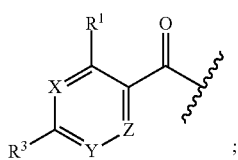

wherein:

indicates the point of attachment;
X is $CR^2$ or N;
Y is $CR^4$ or N;
Z is $CR^5$ or N;
or Y and Z taken together form an optionally substituted five- to six-membered heteroaryl, or an optionally substituted five- to six-membered heterocyclyl;
with the proviso that X, Y, and Z are not simultaneously N;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
or $R^1$ together with the carbon atoms to which it is shown attached and X form an optionally substituted five- to six-membered heterocyclyl;
$R^2$ is H, optionally substituted $C_1$-$C_6$ alkyl, or halo;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);
or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl;
$R^4$ is H, $C_1$-$C_6$ alkyl, cyano, halo;
or $R^4$ together with the carbon atom to which it is shown attached and Z form an optionally substituted five- to six-membered heteroaryl;
or $R^3$ and $R^4$ taken together with the carbon atoms to which they are shown attached form an optionally substituted $C_6$-$C_{10}$ aryl, an optionally substituted $C_4$-$C_8$ cycloalkyl or cycloalkenyl, or an optionally substituted five- to six-membered heterocyclyl or heterocyclenyl;
$R^5$ is H, $C_1$-$C_6$ alkyl, —$NR_2$, or —N(R)—C(=O)—($C_1$-$C_6$ alkyl); and
each R independently is H, or optionally substituted $C_1$-$C_6$ alkyl.

Embodiment 47

The modified WRN helicase protein according to Embodiment 46, wherein:
X is N;
Y is N; and
Z is $CR^5$; or Y and Z taken together form an optionally substituted five- to six-membered heteroaryl, or an optionally substituted five- to six-membered heterocyclyl.

In other words, when X is N, Y is N, and Z is $CR^5$, U is

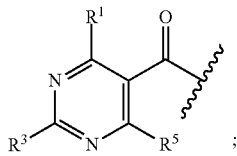

wherein $R^1$, $R^3$, and $R^5$ are as defined in Embodiment 46.

Embodiment 48

The modified WRN helicase protein according to Embodiment 46, wherein:
X is $CR^2$;
Y is $CR^4$; and
Z is $CR^5$;
or Y and Z taken together form an optionally substituted five- to six-membered heteroaryl, or an optionally substituted five- to six-membered heteroaryl;
or $R^3$ taken together with the carbon atom to which it is shown attached and Y form an optionally substituted $C_3$-$C_8$ cycloalkyl or cycloalkenyl.

In other words, when X is $CR^2$, Y is $CR^4$, and Z is $CR^5$, U is

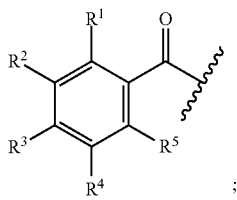

wherein $R^1$, $R^2$, $R^3$, $R^4$, and $R^5$ are as defined in Embodiment 46.

Embodiment 49

The modified WRN helicase protein according to Embodiment 46, wherein:
X is $CR^2$;
Y is N; and
Z is $CR^5$;
or $R^1$ together with the carbon atoms to which it is shown attached and X form an optionally substituted five- to six-membered heterocyclyl.

In other words, when X is $CR^2$, Y is N, and Z is $CR^5$, U is

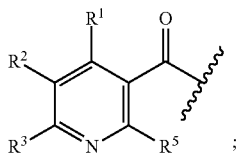

wherein $R^1$, $R^2$, $R^3$, and $R^5$ are as defined in Embodiment 46.

Embodiment 50

The modified WRN helicase protein according to Embodiment 46, wherein:
X is N;
Y is $CR^4$; and
Z is $CR^5$;
or $R^3$ taken together with the carbon atom to which it is shown attached and Y form an optionally substituted $C_6$-$C_{10}$ aryl, an optionally substituted $C_3$-$C_8$ cycloalkyl or cycloalkenyl, or an optionally substituted five- to six-membered heterocyclyl or heterocyclenyl.

In other words, when X is N, Y is $CR^4$, and Z is $CR^5$, U is

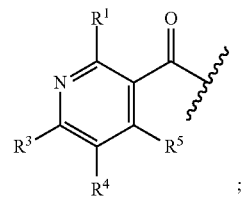

wherein $R^1$, $R^3$, $R^4$, and $R^5$ are as defined in Embodiment 46.

Embodiment 51

The modified WRN helicase protein according to Embodiment 46, wherein:
X is N;
Y is $CR^4$; and
Z is N.

In other words, when X is N, Y is $CR^4$, and Z is N, U is

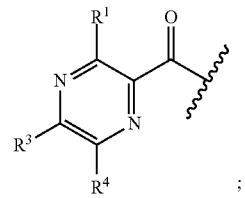

wherein $R^1$, $R^3$, and $R^4$ are as defined in Embodiment 46.

Embodiment 52

The modified WRN helicase protein according to Embodiment 46, wherein:
X is $CR^2$;
Y is $CR^4$; and
Z is N.

In other words, when X is $CR^2$, Y is $CR^4$, and Z is N, U is

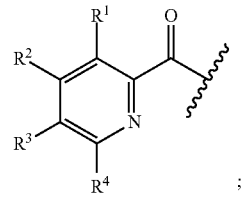

wherein $R^1$, $R^2$, $R^3$, and $R^4$ are as defined in Embodiment 46.

Embodiment 53

The modified WRN helicase protein according to any one of Embodiments 46-52, wherein:
in $R^1$:
the optional substituents of the —O-(optionally substituted $C_3$-$C_8$ cycloalkyl) are 1-3 substituents selected from the group consisting of halo, cyano, and hydroxy; or when there are two substituents on the same ring carbon atom of the $C_3$-$C_8$ cycloalkyl, the substituents together with the ring carbon atom to which they are attached form a $C_3$-$C_6$ cycloalkyl; or when there are two substituents on adjacent ring carbon atoms of the $C_3$-$C_8$ cycloalkyl, the substituents taken together with the ring carbon atoms to which they are attached form a $C_3$-$C_6$ cycloalkyl;
the optional substituents of the —O-(optionally substituted $C_6$-$C_{10}$ aryl are 1-3 substituents selected from the group consisting of halo, $C_1$-$C_6$ alkyl, cyano, hydroxy, and —NH$_2$, or 1-5 deuterium atoms;
or when $R^1$ together with the carbon atoms to which it is shown attached and X form an optionally substituted five- to six-membered heterocyclyl, two substituents on the same ring carbon atom of the five- to six-membered heterocyclyl together with the ring carbon atom to which they are attached form a five- to six-membered cycloalkyl;
in $R^3$:
the optional substituents of the optionally substituted $C_3$-$C_8$ cycloalkyl are 1-3 substituents selected from hydroxy, halo, $C_1$-$C_6$ alkyl, and $C_6$-$C_{10}$ aryl; or when there are two substituents on the same carbon atom of the $C_3$-$C_8$ cycloalkyl, the substituents together with the ring carbon atom to which they are attached form a $C_3$-$C_6$ cycloalkyl; or when there are two substituents on adjacent ring carbon atoms of the $C_3$-$C_8$ cycloalkyl, the substituents taken together with the ring carbon atoms to which they are attached form $C_6$-$C_{10}$ aryl;
or when $R^3$ taken together with the carbon atom to which it is shown attached and Y form an optionally substituted $C_3$-$C_8$ cycloalkyl or cycloalkenyl, the optional substituents are 1-3 substituents selected from the group consisting of halo, and $C_1$-$C_6$ alkyl; or two geminal hydrogens on a ring carbon atom of the $C_3$-$C_8$ cycloalkyl or cycloalkenyl can be replaced with the group =O;
or when R taken together with the carbon atom to which it is shown attached and Y form an optionally substituted five- to six-membered heterocyclyl or heterocyclenyl, the optional substituents are 1-3 substituents selected from the group consisting of halo and $C_1$-$C_6$ alkyl;
the optional substituents of the optionally substituted $C_6$-$C_{10}$ aryl are 1-3 substituents selected from the group consisting of halo;
the optional substituents of the optionally substituted $C_1$-$C_6$ alkyl or $C_6$ alkenyl are 1-5 substituents selected from the group consisting of halo, hydroxy, —O—($C_1$-$C_6$ alkyl), and optionally substituted $C_3$-$C_6$ cycloalkyl, wherein the optional substituents of the $C_3$-$C_6$ cycloalkyl are 1-3 substituents selected from the group consisting of $C_1$-$C_6$ alkyl;
the optional substituents of the $C_1$-$C_6$ alkyl of R of —NR$_2$ are 1-3 substituents selected from the group consisting of halo; and the optional substituents of the optionally substituted four- to six-membered heterocyclyl are 1-3 substituents selected from the group consisting of —O—($C_1$-$C_6$ alkyl), $C_1$-$C_6$ alkyl, halo; or when there are two substituents on the same carbon atom of the optionally substituted four- to six-membered heterocyclyl, the substituents together with the ring carbon atom to which they are attached form a $C_3$-$C_6$ cycloalkyl.

Embodiment 54

The modified WRN helicase protein according to any one of Embodiments 46-53, wherein:
the optionally substituted five- to six-membered heterocyclyl formed by $R^1$ together with the carbon atoms to which it is shown attached is

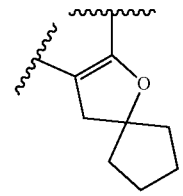 [SMILES: *C1=C(*)OC2(CCCC2)C1]

wherein the double bond shown is between the carbon bearing the $R^1$ group and X;
the optionally substituted $C_6$-$C_{10}$ aryl formed by $R^3$ taken together with the carbon atom to which it is shown attached and Y is

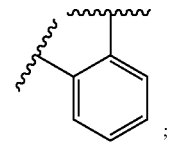 [SMILES: *c1ccccc1*];

the optionally substituted five- to six-membered heterocyclenyl formed by $R^3$ taken together with the carbon atom to which it is shown attached and Y is

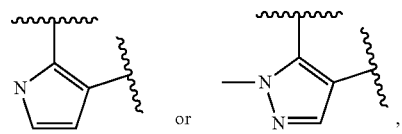, wherein the carbon-carbon double bond shown between the two carbons bearing the

groups is between the carbon bearing the R group and Y;
when $R^3$ taken together with the carbon atom to which it is shown attached and Y form an optionally substituted $C_3$-$C_8$ cycloalkyl or cycloalkenyl, the optionally substituted $C_3$-$C_8$ cycloalkyl or cycloalkenyl is

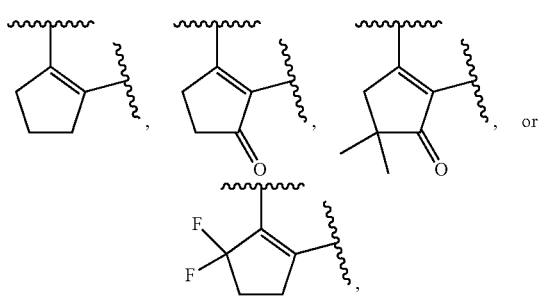

wherein the carbon-carbon double bond shown is between the carbon bearing the $R^3$ group and Y; and wherein the optionally substituted five- to six-membered heteroaryl formed by $R^4$ together with the carbon atom to which it is shown attached and Z is

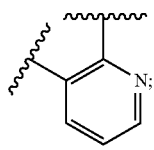

wherein in each structure

indicates the point of attachment.

Embodiment 55

The modified WRN helicase protein according to any one of Embodiments 46-54, wherein:

in $R^1$:
the —O-(optionally substituted $C_3$-$C_8$ cycloalkyl) is —O-cyclobutyl, —O-cyclopropyl, —O-cyclohexyl, —O-cyclopentyl, —O-(4,4-difluorocyclohexyl), —O-(spiro[2.3]hexan-5-yl), —O-(spiro[3.3]heptan-2-yl), —O-(3-chlorocyclobutyl), —O-(bicyclo[3.1.0]hexan-3-yl), —O-(bicyclo[2.2.1]heptan-1-yl), —O-(1-cyanocyclopentanyl), —O-(3,3-difluorocyclobutyl), —O-(2-hydroxycyclohexyl), —O-cycloheptyl, —O-(2-fluorocyclohexyl), —O-(3,3-difluorocyclopentyl), —O-(2-fluorocyclohexyl), or —O-(2,2-difluorocyclopentyl),
the —O-(optionally substituted $C_1$-$C_6$ alkyl) is ethoxy, isopropoxy, or cyclopropylmethyloxy;
the —O-(optionally substituted $C_6$-$C_{10}$ aryl) is phenoxy, 4-chlorophenoxy, 3-fluorophenoxy, 2-chlorophenoxy, 3-chlorophenoxy, 2-fluorophenoxy, p-tolyloxy, 3,5-difluorophenoxy, 4-fluoro-3-methylphenoxy, 3,5-dichlorophenoxy, 4-cyanophenoxy, 3,4-dimethylphenoxy, m-tolyloxy, 4-ethylphenoxy, 3-ethylphenoxy, o-tolyloxy, 2-hydroxyphenoxy, 3-hydroxyphenoxy, 4-hydroxyphenoxy, 3-chloro-5-fluorophenoxy, 3-aminophenoxy, naphthalen-1-oxy, or phenoxy-d5;
the —O-(optionally substituted five- to six-membered heteroaryl) is pyridine-2-yloxy, or pyridine-3-yloxy;
the —O-(optionally substituted five- to six-membered heterocyclyl) is —O-tetrahydro-2H-pyran-4-yl, or —O-tetrahydro-2H-pyran-3-yl; and the optionally substituted $C_3$-$C_8$ cycloalkyl is cyclohexyl;

in $R^2$:
the optionally substituted $C_1$-$C_6$ alkyl is methyl; and in $R^3$:
the optionally substituted $C_3$-$C_8$ cycloalkyl is cyclopentyl, cyclobutyl, cyclohexyl, cyclopropyl, hydroxycyclopentyl, fluorocyclopentyl, methylcyclobutyl, methylcyclopropyl, phenylcyclopropyl, methylcyclopentyl, difluorocyclobutyl, fluorocyclopentyl, bicyclo[4.2.0]octa-1,3,5-trien-7-yl, or (trifluoromethyl)cyclopropyl, or spiro[2.3]hexan-5-yl;
the optionally substituted $C_3$-$C_8$ cycloalkenyl is cyclopentenyl;
the optionally substituted $C_6$-$C_{10}$ aryl is phenyl;
the optionally substituted $C_1$-$C_6$ alkyl is methyl, ethyl, isopropyl, tert-butyl, cyclopropylmethyl, cyclobutylmethyl, cyclopentylmethyl, cyclohexylmethyl, trifluoromethyl, trifluoroethyl, hydroxypropanyl, fluropropanyl, methoxypropanyl, difluoroethyl, difluoropropyl, (methylcyclopropyl)methyl, perfluoroethyl, or cyclopropyldifluoromethyl;
the optionally substituted $C_1$-$C_6$ alkenyl is 2-methylprop-1-en-1-yl;
the $NR_2$ is —N(H)(cyclopentyl), —N(H)(methyl), —N(methyl)(ethyl), —N(methyl)(isopropyl), —N(ethyl)$_2$, or —N(methyl)(trifluoroethyl);
the —N(R)(optionally substituted $C_3$-$C_8$ cycloalkyl) is N(methyl)(cyclopropyl);
the —S-(optionally substituted $C_1$-$C_6$ alkyl) is methylthiol;
the —O-(optionally substituted $C_1$-$C_6$ alkyl) is trifluoroethoxy, or methoxy;
the —O-(optionally substituted $C_3$-$C_8$ cycloalkyl) is cyclopentyloxy, or cyclopropyloxy; and
the optionally substituted four- to six-membered heterocyclyl or hetrocyclenyl is tetrahydrofuranyl, 7-azabicyclo[2.2.1]heptan-7-yl, bicyclo[1.1.1]pentan-1-yl, methoxyazetadin-1-yl, 2-azaspiro[3.3]heptan-2-yl, tetrahydropyranyl, tetrahydro-2H-pyran-3-yl, tetrahydro-2H-pyran-4-yl, dihydropyranyl, 5,6-dihydro-2H-pyran-3-yl, dimethylpyrrolidinyl, 2,2-dimethylpyrrolidin-1-yl, difluoropyrrolidinyl, methylcyclobutyl, pyrrolidinyl, pyrrolidine-1-yl, methylpyrrolidinyl, 2-methylpyrrolidin-1-yl, azetidinyl, azetidine-1-yl, fluoroazetidinyl, 3-fluoroazetidin-1-yl, difluoroazetidinyl, or 3,3-difluoro-azetidin-1-yl;

in $R^5$:
the $C_1$-$C_6$ alkyl is methyl;
the —$NR_2$ is —$NH_2$; and
the —N(R)—C(=O)—($C_1$-$C_6$ alkyl) is —N(H)—C(=O)—$CH_3$.

Embodiment 56

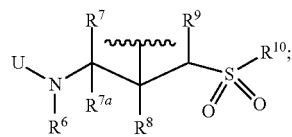

The modified WRN helicase protein according to any one of claims 46-55, wherein Q is $Q^1$, i.e., Q is: wherein

indicates the point of attachment and U, $R^6$, $R^7$, $R^{7a}$, $R^8$, $R^9$, and $R^{10}$ are as defined in Embodiment 46.

Embodiment 57

The modified WRN helicase protein according to Embodiment 56, wherein:
the optionally substituted $C_1$-$C_6$ alkyl of $R^7$ is methyl, ethyl, isopropyl, methoxymethyl, cyclopropylmethyl, cyclopropyloxymethyl, tolyl, —CH(CH$_3$)—OCH$_3$, difluoroethyl, phenoxymethyl, —CH$_2$—C(=O)—N(CH$_3$)$_2$, or tert-butoxymethyl, difluoromethoxymethyl;
the optionally substituted $C_3$-$C_8$ cycloalkyl of $R^7$ is cyclopropyl, cyclobutyl, difluorocyclobutyl, —CH$_2$—S—CH$_3$, difluorocyclohexyl;
the optionally substituted five- to six-membered heterocyclyl of $R^7$ is tetrahydropyranyl, or tetrahydro-2H-pyran-4-yl;
the optionally substituted $C_1$-$C_6$ alkyl of $R^{10}$ is methyl;
the optionally substituted $C_3$-$C_8$ cycloalkyl of $R^{10}$ is cyclopropyl; and
the optionally five- to six-membered heterocyclyl of $R^{10}$ is tetrahydropyranyl or tetrahydro-2H-pyran-4-yl;
or wherein $Q^1$ is:

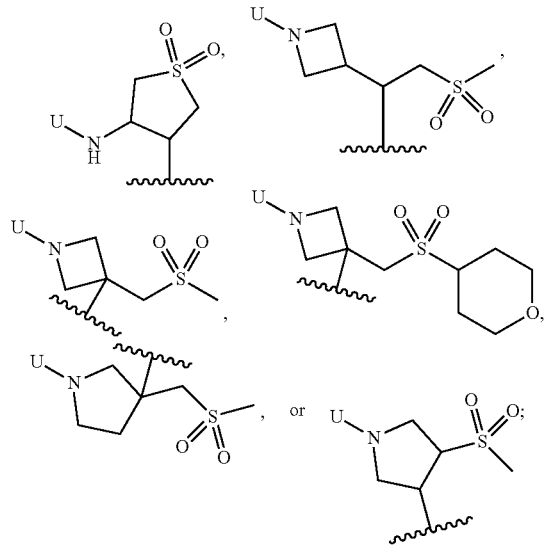

wherein in each structure

indicates the point of attachment.

Embodiment 58

The modified WRN helicase protein according to any one of Embodiments 46-55, wherein Q is $Q^2$, i.e., Q is:

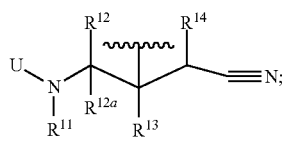

wherein

indicates the point of attachment, and U, $R^{11}$, $R^{12}$, $R^{12a}$, $R^{13}$, and $R^{14}$ are as defined in Embodiment 46.

Embodiment 59

The modified WRN helicase protein according to Embodiment 58, wherein $Q^2$ is

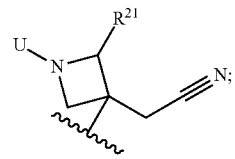

wherein $R^{21}$ is H or $C_1$-$C_6$ alkyl; wherein

indicates the point of attachment.

Embodiment 60

The modified WRN helicase protein according to any one of Embodiments 46-55, wherein Q is $Q^3$, i.e., Q is:

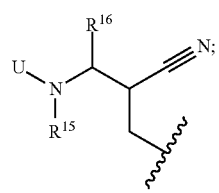

wherein

indicates the point of attachment, and U, $R^{15}$ and $R^{16}$ are as defined in Embodiment 46.

Embodiment 61

The modified WRN helicase protein according to Embodiment 60, wherein:
the optionally substituted $C_1$-$C_6$ alkyl of $R^{16}$ is methyl; and
the optionally substituted $C_3$-$C_8$ cycloalkyl of $R^{16}$ is cyclopropyl.

Embodiment 62

The modified WRN helicase protein according to any one of Embodiments 46-55, wherein Q is $Q^4$, i.e., Q is:

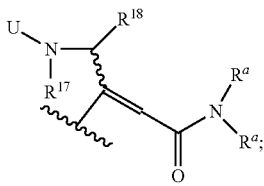

wherein

indicates the point of attachment, and U, $R^{17}$, $R^{18}$, and $R^a$ are as defined in Embodiment 46.

Embodiment 63

The modified WRN helicase protein according to Embodiment 62, wherein:
the optionally substituted $C_1$-$C_6$ alkyl of $R^{18}$ is methyl; and
the optionally substituted $C_1$-$C_6$ alkyl is methyl.

Embodiment 64

The modified WRN helicase protein according to any one of claims 46-55, wherein Q is $Q^5$, i.e., Q is:

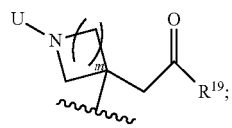

wherein

indicates the point of attachment, and U, m, and $R^{19}$ are as defined in Embodiment 46.

Embodiment 65

The modified WRN helicase protein according to Embodiment 64, wherein:
the $C_1$-$C_6$ alkyl of $R^{19}$ is methyl; and
the —O—($C_1$-$C_6$ alkyl) of $R^{19}$ is methoxy.

Embodiment 66

A compound according to any one of Embodiments 1 to 30, 2.1, 2.2, 21.1, 21.1A, 21A-29A and 39-41, or a pharmaceutically acceptable salt or solvate thereof, for use in the treatment of a proliferative disease.

Embodiment 66A

A compound according to any one of Embodiments 1 to 30, 2.1, 2.2, 21.1, 21.1A, 21A-29A and 39-41, or a pharmaceutically acceptable salt, for use in the treatment of a proliferative disease.

Embodiment 66B

A compound according to any one of Embodiments 1 to 30, 2.1, 2.2, 21.1, 21.1A, 21A-29A and 39-41 for use in the treatment of a proliferative disease.

Embodiment 67

A compound for use according to Embodiment 66, or a pharmaceutically acceptable salt or solvate thereof, wherein the proliferative disease is cancer.

Embodiment 67A

A compound for use according to Embodiment 66, or a pharmaceutically acceptable salt, wherein the proliferative disease is cancer.

Embodiment 67B

A compound for use according to Embodiment 66, wherein the proliferative disease is cancer.

Embodiment 68

A compound for use according to Embodiment 67, or a pharmaceutically acceptable salt or solvate thereof, wherein the cancer is selected from the group consisting of colon cancer, colorectal cancer, gastric cancer, endometrium cancer, ovarian cancer, hepatobiliary tract cancer, urinary tract cancer, brain cancer, skin cancer, and MSI-H cancer.

Embodiment 68A

A compound for use according to Embodiment 67, or a pharmaceutically acceptable salt, wherein the cancer is selected from the group consisting of colon cancer, colorectal cancer, gastric cancer, endometrium cancer, ovarian cancer, hepatobiliary tract cancer, urinary tract cancer, brain cancer, skin cancer, and MSI-H cancer.

Embodiment 68B

A compound for use according to Embodiment 67, wherein the cancer is selected from the group consisting of colon cancer, colorectal cancer, gastric cancer, endometrium cancer, ovarian cancer, hepatobiliary tract cancer, urinary tract cancer, brain cancer, skin cancer, and MSI-H cancer.

Embodiment 69

A method of measuring WRN helicase activity in an assay comprising ATP and a compound according to any of Embodiments 1-30, 2.1, 2.2, 21.1, 21.1A, 21A-29A and 39-41, or a pharmaceutically acceptable salt or solvate thereof. In some embodiments, the assay is an in vitro assay. In some embodiments, the assay is a WRN helicase activity assay.

Embodiment 69A

A method of measuring WRN helicase activity in an assay comprising ATP and a compound according to any of Embodiments 1-30, 2.1, 2.2, 21.1, 21.1A, 21A-29A and 39-41, or a pharmaceutically acceptable salt thereof. In some embodiments, the assay is an in vitro assay. In some embodiments, the assay is a WRN helicase activity assay.

Embodiment 69B

A method of measuring WRN helicase activity in an assay comprising ATP and a compound according to any of Embodiments 1-30, 2.1, 2.2, 21.1, 21.1A, 21A-29A and 39-41. In some embodiments, the assay is an in vitro assay. In some embodiments, the assay is a WRN helicase activity assay.

Administration and Pharmaceutical Composition

In general, the compounds described herein will be administered in a therapeutically effective amount by any of the accepted modes of administration for agents that serve similar utilities. Therapeutically effective amounts of a compound described herein may range from 0.01 to about 500 mg per kg patient body weight per day, which can be administered in single or multiple doses. A suitable dosage level may be from about 0.1 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound, i.e., the active ingredient, will depend upon numerous factors such as the severity of the disease to be treated, the age and relative health of the patient, the potency of the compound being utilized, the route and form of administration, and other factors.

In general, compounds described herein will be administered as pharmaceutical compositions by any one of the following routes: oral, systemic (e.g., transdermal, intranasal or by suppository), parenteral (e.g., intramuscular, intravenous, intrasternal or subcutaneous) topical (e.g., application to skin) administration, or through an implant. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound described herein in combination with at least one pharmaceutically acceptable carrier/excipient. Acceptable excipients are non-toxic, aid administration, and do not adversely affect the therapeutic benefit of the compound. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be chosen from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound described herein in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound described based on the total formulation, with the balance being one or more suitable pharmaceutical excipients. Preferably, the compound is present at a level of about 1-80 wt. %.

A compound described herein may be used in combination with one or more other drugs in the treatment of diseases or conditions for which a compound described herein or the other drugs may have utility, where the combination of the drugs together are safer or more effective than either drug alone. Such other drug(s) may be administered, by a route and in an amount commonly used therefore, contemporaneously or sequentially with a compound described herein. When a compound described herein is used contemporaneously with one or more other drugs, a pharmaceutical composition in unit dosage form containing such other drugs and a compound described herein is preferred. However, the combination therapy may also include therapies in which a compound described herein and one or more other drugs are administered on different overlapping schedules. It is also contemplated that when used in combination with one or more other active ingredients, a compound described herein and the other active ingredients may be used in lower doses than when each is used singly.

Accordingly, a pharmaceutical composition described herein also can include those that contain one or more other active ingredients, in addition to a compound described herein. Subjects that may be treated using the methods described herein are subjects having a cancer characterized by an MSI-H phenotype. In some embodiments, the MSI-H phenotype characterized by the presence of a DNA sequence length change in at least two of the mononucleotide or dinucleotide markers selected from the group consisting of BAT25, BAT26, D25123, D55346, and D175250. In some embodiments, the MSI-H phenotype characterized by the presence DNA sequence length changes in at least two mononucleotide markers selected from the group consisting of NR-21, NR-24, BAT-25, BAT-26, and NR-27/Mono-27 in the MSI analysis system marketed by Promega Corporation (Madison, Wisconsin, USA). In some embodiments, the cancer has a mismatch repair deficiency (MMRd). In some embodiments, the MMRd is caused by a mutation in the MLH1, MLH3, MSH2, MSH3, MSH6, PMS1, PMS2, and/or EPCAM genes. In some embodiments, the MMRd is caused by a mutation in the MLH1, MSH2, MSH6, PMS2, and/or EPCAM genes. In some embodiments, the MMRd is caused by a mutation in the MLH1 gene. In some embodiments, the cancer additionally has a mutation that results in a loss of function of ARID1A. In some embodiments, the MMRd is caused by mutation or epigenetic silencing of MMR gene promoters.

The types of cancer may include, for example, an MSI-H cancer, adrenocortical carcinoma, bladder carcinoma, breast carcinoma, cervical squamous cell carcinoma, endocervical adenocarcinoma, cholangiocarcinoma, chronic lymphocytic leukemia, a colorectal cancer, colon adenocarcinoma, an ovarian cancer, cutaneous T-cell lymphoma, lymphoid neoplasm diffuse large B-cell lymphoma, esophageal carcinoma, glioblastoma multiforme, head and neck squamous cell carcinoma, kidney chromophobe, kidney renal papillary cell carcinoma, acute myeloid leukemia, lower-grade glioma, liver hepatocellular carcinoma, lung adenocarcinoma, lung squamous cell carcinoma, mesothelioma, nasopharyngeal carcinoma, ovarian serous cystadenocarcinoma, pancreatic adenocarcinoma, pheochromocytoma, paraganglioma, prostate adenocarcinoma, rectal adenocarcinoma, sarcoma, skin cutaneous melanoma, stomach adenocarcinoma, testicular germ cell tumor, thyroid carcinoma, thymoma, uterine corpus endometrial carcinoma, uterine carcinosarcoma, uveal melanoma, pediatric acute myeloid leukemia, pediatric neuroblastoma, pediatric high-risk Wilms tumor, or any other type of cancer as described herein. The cancer may be of early or advanced stage (e.g., a recurrent or metastatic cancer). In some embodiments, the subject has received prior anticancer therapy. In some embodiments, the subject has not been previously treated with an anti-cancer therapy. In some embodiments, the cancer is resistant to immunotherapy (e.g., a checkpoint inhibitor as described herein). In some embodiments, the cancer is resistant to targeted therapy. In some embodiments, the therapeutic resistance is driven by the deficiency in MMR, such as resistance to endocrine treatment in breast cancers and resistance to targeted therapy (e.g., temozolomide) in glioblastomas.

MSI-H can be found in many types of cancers, including without limitation colorectal cancer, endometrial cancer, biliary cancer, bladder cancer, breast cancer, esophageal cancer, gastric or gastroesophageal junction cancer, pancreatic cancer, prostate cancer, renal cell cancer, retroperitoneal adenocarcinoma, sarcoma, small cell lung cancer, small intestinal cancer, and thyroid cancer.

Combination Therapies: An agent that reduces the level and/or activity of WRN in a cell in a subject as described herein, can be administered alone or in combination with an additional anti-cancer therapy. The anti-cancer therapy may be an additional therapeutic agent (e.g., other agents that treat cancer or symptoms associated therewith) or in combination with other types of therapies to treat cancer (e.g., radiological therapies or surgical procedures). In some embodiments, the second therapeutic agent is selected based on tumor type, tumor tissue of origin, tumor stage, or mutation status. In combination treatments, the dosages of one or more of the therapeutic agents may be reduced from standard dosages when administered alone. For example, doses may be determined empirically from drug combinations and permutations or may be deduced by isobolographic analysis (e.g., Black et al., Neurology 65: S3-S6 (2005)). In this case, dosages of the agents or compounds when combined should provide a therapeutic effect.

In some embodiments, the anti-cancer therapy is a checkpoint inhibitor. In some embodiments, the checkpoint inhibitor is an inhibitory antibody (e.g., a monospecific antibody, such as a monoclonal antibody). The antibody may be humanized or fully human. In some embodiments, the checkpoint inhibitor is a fusion protein, e.g., an Fc receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA4 antibody or a fusion protein, such as ipilimumab/YERVOY® or tremelimumab). In some embodiments, the checkpoint inhibitor is an inhibitor (e.g., an inhibitory antibody or small molecule inhibitor) of PD-1 (e.g., nivolumab/OPDIVO®; pembrolizumab/KEYTRUDA®; or pidilizumab/CT-011). In some embodiments, checkpoint inhibitor is an inhibitor (e.g., an inhibitory antibody or small molecule inhibitor) of PDL1 (e.g., MPDL3280A1RG7446/atezolizumab; MED14736/durvalumab; MSB0010718C/avelumab; BMS 936559/cemiplimab). In some embodiments, the checkpoint inhibitor is an inhibitor (e.g., an inhibitory antibody or Fc fusion or small molecule inhibitor) of PDL2 (e.g., a PDL2/Ig fusion protein, such as AMP 224). In some embodiments, the checkpoint inhibitor is an inhibitor (e.g., an inhibitory antibody or small molecule inhibitor) of B7-H3 (e.g., MGA271), B7-H4, BTLA, HVEM, TIM3, GAL9, LAGS, VISTA, KIR, 2B4, CDi60, CGEN-15049, CHK1, CHK2, A2aR, B-7 family ligands, or a combination thereof.

In some embodiments, the anti-cancer therapy is a biologic, such as a cytokine (e.g., interferon or an interleukin (e.g., IL-2)) used in cancer treatment. In some embodiments the biologic is an anti-angiogenic agent, such as an anti- VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (Rituximab); ZENAPAX® (Daclizumab); SIMIJLECT® (Basiliximab); SYNAGIS® (Palivizumab); REMICADE® (Infliximab); HERCEPTIN® (Trastuzumab); MYLOTARG™ (Gemtuzumab ozogamicin); CAMPATH® (Alemtuzumab); ZEVALIN® (Ibritumomab tiuxetan); HUMIRA® (Adalimumab); XOLAIR® (Omalizumab); BEXXAR® (Tositumomab-I-131); RAPTIVA® (Efalizumab); ERBITUX® (Cetuximab); AVASTIN® (Bevacizumab); TYSABRI® (Natalizumab); ACTEMRA® (Tocilizumab); VECTIBIX® (Panitumumab); LUCENTIS® (Ranibizumab); SOLIRIS® (Eculizumab); CIMZIA® (Certolizumab pegol); SIMPONI® (Golimumab); ILARIS® (Canakinumab); STELARA® (TJstekinumab); ARZERRA® (Ofatumumab); PROLIA® (Denosumab); Numax (Motavizumab); ABThrax (Raxibacumab); BENLYSTA® (Belimumab); YERVOY® (Ipilimumab); ADCETRTS® (Brentuximab Vedotin); PERJETA® (Pertuzumab); KADCYLA® (Ado-trastuzumab emtansine); and GAZYVA® (Obinutuzumab). Also included are antibody-drug conjugates.

In some embodiments, the anti-cancer therapy is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, ymca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin, irenotecan, oxaliplatin, capecitabine, paclitaxel, and doxetaxel. Non-limiting examples of chemotherapeutic agents include alkylating agents, such as thiotepa and cyclosphosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechiorethamine oxide hydrochloride, melphalan, novembichin, phenesterine, prednimustine, trofosfamide, uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamyci olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil; folic acid analogues, such as denopterin, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytarabine, dideoxyuridine, doxifluridine, enocitabine, floxuridine; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside; cyclophosphamide; thiotepa; taxoids, e.g., TAXOL® (paclitaxel; Bristol-Myers Squibb Oncology, Princeton, N.J.), ABRAXANE®, cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; platinum coordination complexes, such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; XELODA®; ibandronate; irinotecan (e.g., CPT-11); topoisomerase inhibitor RFS 2000; difluoromethylornithine (DMFO); retinoids, such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., Proc. Am. Soc. Clin. Oncol. 18:233a (1999), and Douillard et al., Lancet 355(9209):1041-1047 (2000).

In some embodiments, the anti-cancer therapy is a T cell adoptive transfer therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

The additional anti-cancer therapy may be a non-drug treatment. For example, the additional therapeutic agent is radiation therapy, cryotherapy, hyperthermia, and/or surgical excision of tumor tissue.

In any of the combination embodiments described herein, the agent that reduces the level and/or activity of WRN in a cell in a subject and additional therapeutic agents are administered simultaneously or sequentially, in either order. The agent that reduces the level and/or activity of WRN in a cell in a subject may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours, or up to 1-7, 1-14, 1-21, or 1-30 days before or after the additional therapeutic agent (e.g., an anti-cancer therapy).

EXAMPLES

Abbreviations
% Percent
° C. Degree Celsius
AcOH Acetic acid
AcONa Sodium acetate
aq. Aqueous
Boc Tert-butyloxycarbonyl
BuLi Butyllithium
CDI 1,1'-Carbonyldiimidazole
cm Centimeter
CO Carbon monoxide
$CO_2$ Carbon dioxide
$Cs_2CO_3$ Cesium carbonate
$D_2O$ Deuterium oxide, heavy water
DAST Diethylaminosulfur trifluoride
DBU 1,8-Diazabicyclo[5.4.0]undec-7-ene
DCE Dichloroethane
DCM Dichloromethane
DIAD Diisopropyl azodicarboxylate
DIBAL-H Diisobutylaluminum hydride
DIPEA N,N-Diisopropylethylamine
DMF Dimethylformamide
DMP Dess-Martin periodinane
DMSO Dimethyl sulfoxide
dtbbpy 4,4'-Di-tert-butyl-2,2'-bipyridine
EA Ethyl acetate
$Et_2O$ Diethyl ether
EtOAc Ethyl acetate
EtOH Ethanol
FA Formic acid
g Gram
h Hour
$H_2$ Hydrogen gas
$H_2O$ Water
HATU Hexafluorophosphate azabenzotriazole tetramethyl uronium
HBr Hydrobromic acid
HCl Hydrochloric acid
HPLC High-performance liquid chromatography
IBX 2-Iodoxybenzoic acid
IPA Isopropanol
$K_2CO_3$ Potassium carbonate
L Liter
LAH Lithium aluminum hydride
LC-MS Liquid chromatography-mass spectrometry
LED Light emitting diode
LiHMDS Lithium bis(trimethylsilyl)amide
M Molar
m/z Mass-to-charge ratio
MeCN Acetonitrile
MeOH Methanol
mg Milligram
$MgSO_4$ Magnesium sulfate (anhydrous)
min Minute
mL Milliliter
mm Millimeter
mmol Millimole
MTBE Methyl tertiary-butyl ether
N Normal
$N_2$ nitrogen gas
$Na_2S_2O_3$ Sodium thiosulfate
$Na_2SO_4$ Sodium sulfate (anhydrous)
$NaClO_2$ Sodium chlorite
NaH Sodium hydride
$NaHCO_3$ Sodium bicarbonate
NaHMDS Sodium bis(trimethylsilyl)amide
NaOEt Sodium ethoxide
NaOH Sodium hydroxide
NaOMe Sodium methoxide
$NH_4Cl$ Ammonium chloride
$NH_4HCO_3$ Ammonium bicarbonate
$O_2$ Oxygen gas
$Pd(OH)_2$ Palladium hydroxide
Pd/C Palladium on carbon
PE Petroleum ether
pH Potential of hydrogen
$POCl_3$ Phosphoryl chloride
$PPh_3$ Triphenylphosphine
psi Pound per square inch
PTSA p-Toluenesulfonic acid
rac Racemic
Rf Retardation factor
rt Room temperature
sat. Saturated
SFC Supercritical fluid chromatography
$SiO_2$ Silicon dioxide, Silica gel
$SO_2Cl_2$ Sulfuryl chloride
tBuOK Potassium tert-butoxide
TEA Triethylamine
TFA Trifluoroacetic acid
THF Tetrahydrofuran
TLC Thin-layer chromatography
μm Micrometer
W Watts
$ZnCl_2$ Zinc chloride

Example 1

(E)-2-cyclopentyl-N-(3-(methylsulfonyl)allyl)-4-phenoxypyrimidine-5-carboxamide

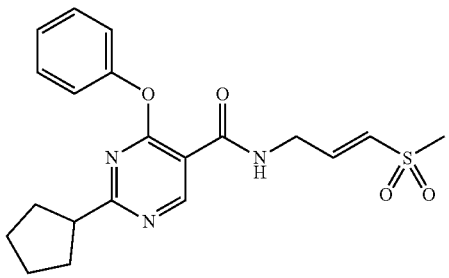 [SMILES: CS(=O)(=O)/C=C/CNC(=O)c1cnc(C2CCCC2)nc1Oc1ccccc1]

Procedure A

Step 1

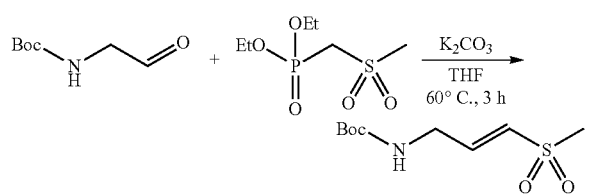

A mixture of diethyl ((methylsulfonyl)methyl)phosphonate (6 g, 26.06 mmol), N-Boc-2-aminoacetaldehyde (4.56 g, 28.67 mmol) and potassium carbonate (9.00 g, 65.16 mmol) in THF (50 mL, 0.521 M) was stirred at 60° C. for 3 hours. The reaction mixture was poured into ice water (100 mL) and extracted with EtOAc (3×100 mL). The combined organic layers were washed with brine (2×50 mL), dried over Na$_2$SO$_4$, filtered and concentrated under reduced pressure to give a residue. The residue was purified by flash silica gel chromatography (ISCO®; 120 g SepaFlash® Silica Flash Column, Eluent of 20~25% Ethyl acetate/Petroleum ether gradient at 100 mL/min) to afford tert-butyl N—[(E)-3-methylsulfonylallyl]carbamate (5 g, 82% yield) as a white solid.

Step 2

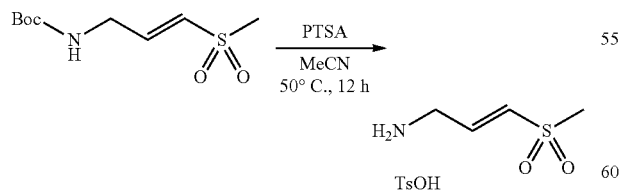

To a solution of tert-butyl N—[(E)-3-methylsulfonylallyl]carbamate (3 g, 12.75 mmol) in MeCN (40 mL, 0.319 M) was added p-toluenesulfonic acid monohydrate (2.91 g, 15.3 mmol). The mixture was stirred at 50° C. for 12 hours. The mixture was cooled to rt and concentrated under reduce pressure to afford the crude [(E)-3-methylsulfonylallyl] amine 4-methylbenzenesulfonic acid as a white solid (2.50 g, 64% yield).

Step 3

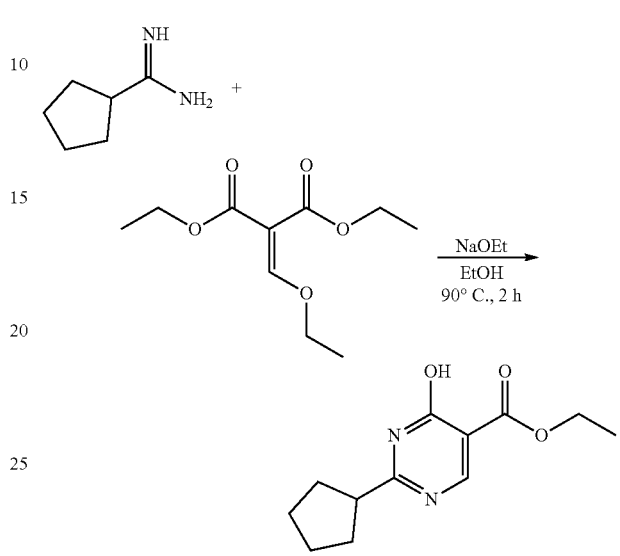

To a solution of cyclopentanecarboxamidine (1.0 g, 8.92 mmol) in ethanol (15 mL, 0.594 M) was added NaOEt (1.82 g, 26.75 mmol) at 0° C. A solution of diethyl ethoxymethylenemalonate (1.9 g, 8.92 mmol) in ethanol (5 mL) was added dropwise to the above mixture over 5 minutes. The mixture was heated at 90° C. for 2 hours. The reaction mixture was diluted with water (20 mL) and extracted with DCM (2×20 mL). The combined organic layers were washed with brine (20 mL), dried over Na$_2$SO$_4$, filtered and concentrated under reduced pressure to afford ethyl 2-cyclopentyl-4-hydroxy-pyrimidine-5-carboxylate as a yellow solid (1.3 g, 62%).

Step 4

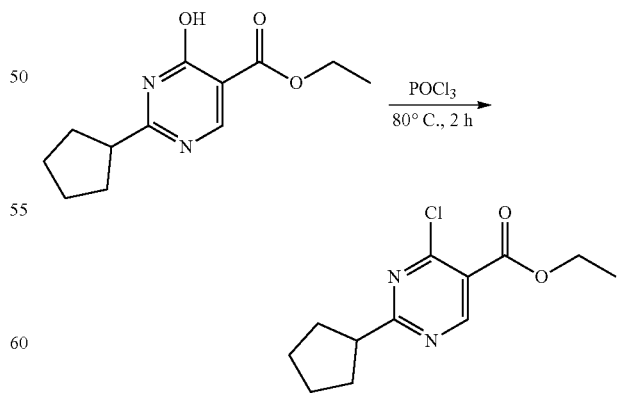

To a solution of ethyl 2-cyclopentyl-4-hydroxy-pyrimidine-5-carboxylate (500 mg, 2.12 mmol) in phosphorus oxychloride (5 mL, 53.64 mmol, 1.645 g/ml). The mixture was heated at 80° C. for 2 hours. The mixture was concentrated under reduced pressure to dryness to afford crude ethyl 4-chloro-2-cyclopentyl-pyrimidine-5-carboxylate as a brown oil (0.5 g).

Step 5

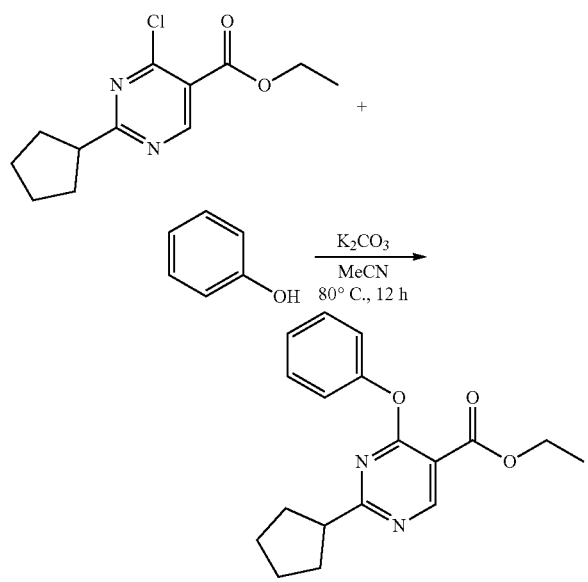

To a solution of ethyl 4-chloro-2-cyclopentyl-pyrimidine-5-carboxylate (200 mg, 0.79 mmol) and phenol (88.7 mg, 0.94 mmol) in MeCN (3 mL, 0.262 M) was added K$_2$CO$_3$ (326 mg, 2.36 mmol). The mixture was stirred at 80° C. for 12 hours. The reaction mixture was extracted with EtOAc (2×10 mL) and brine (10 mL), dried over Na$_2$SO$_4$, filtered and concentrated under reduced pressure to afford crude ethyl 2-cyclopentyl-4-phenoxy-pyrimidine-5-carboxylate as a white solid (240 mg).

Step 6

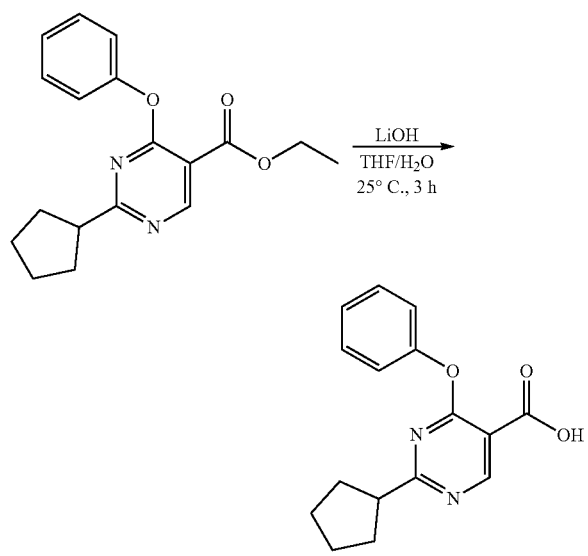

To a solution of ethyl 2-cyclopentyl-4-phenoxy-pyrimidine-5-carboxylate (240 mg, 0.77 mmol) in THF (3 mL, 0.128 M) was added lithium hydroxide monohydrate (96.9 mg, 2.31 mmol). The mixture was stirred at 25° C. for 3 hours. The aqueous phase was adjusted to around pH=5-6 by progressively adding 2M HCl. The precipitate was collected by filtration, washed with water and dried under reduced pressure to afford crude 2-cyclopentyl-4-phenoxy-pyrimidine-5-carboxylic acid as a white solid (200 mg).

Step 7

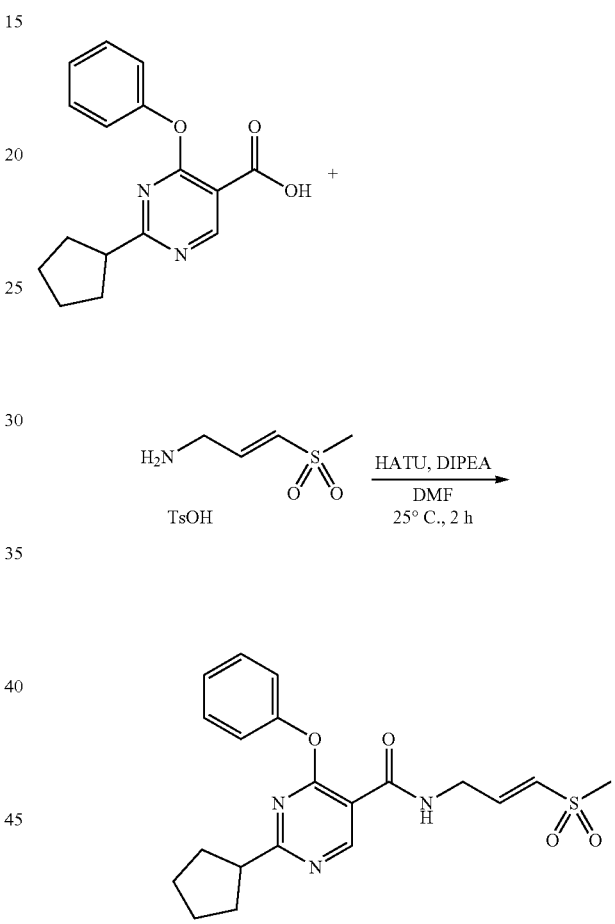

To a solution of 2-cyclopentyl-4-phenoxy-pyrimidine-5-carboxylic acid (100 mg, 0.35 mmol) in DMF (2 mL, 0.176 M) was added [(E)-3-methylsulfonylallyl]amine 4-methylbenzenesulfonic acid (113.5 mg, 0.37 mmol), HATU (200.6 mg, 0.53 mmol) and DIPEA (0.2 mL, 1.06 mmol) at 25° C. The mixture was stirred at 25° C. for 2 hours under N$_2$. The reaction mixture was diluted with water (5 mL) and extracted with EtOAc (3×10 mL). The combined organic layers were washed with brine (8 mL), dried over Na$_2$SO$_4$, filtered and concentrated under reduced pressure to give a residue. The residue was dissolved in DMF (2 mL), and the resulting solution was purified by prep-HPLC [column: Welch Xtimate C18 100*25 mm*3 um, eluent: water (0.04% HCl)/MeCN=25 to 65%, flow rate: 25 ml/min] to afford the title compound as a white solid (34.3 mg, 24% yield). LC-MS m/z: 402.1 [M+1].

Example 2

(S,E)-2-cyclopentyl-N-(4-(methylsulfonyl)but-3-en-2-yl)-4-phenoxypyrimidine-5-carboxamide

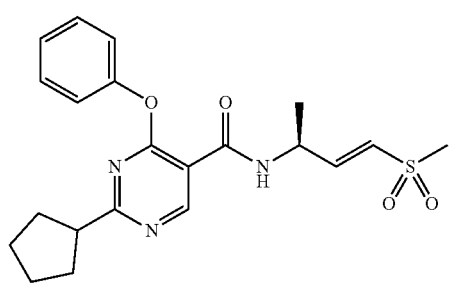 [SMILES: C[C@@H](/C=C/S(C)(=O)=O)NC(=O)c1cnc(C2CCCC2)nc1Oc1ccccc1]

Step 1

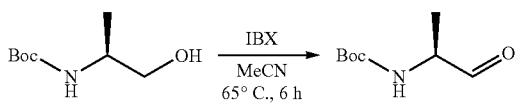

To a solution of Boc-L-alaninol (10 g, 57.07 mmol) in MeCN (1 L, 0.0571 M) was added 1-hydroxy-1-oxo-1,5,2-benziodoxol-3-one (40.0 g, 142.67 mmol) at 25° C. The reaction was stirred at 65° C. for 6 hours. The reaction mixture was filtered and concentrated under reduced pressure to afford crude tert-butyl N-[(1S)-1-methyl-2-oxo-ethyl]carbamate as a yellow oil (10 g).

Using tert-butyl N-[(1S)-1-methyl-2-oxo-ethyl]carbamate/NaH at Step 1 in Procedure A, the title compound was obtained. LC-MS m/z: 416.1 [M+1].

Example 3

(S,Z)-2-cyclopentyl-N-(4-(methylsulfonyl)but-3-en-2-yl)-4-phenoxypyrimidine-5-carboxamide

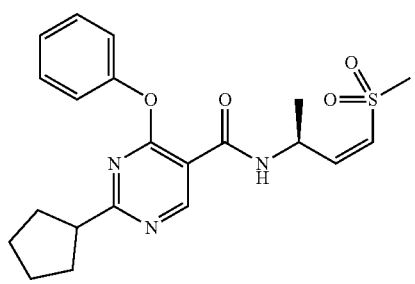 [SMILES: C[C@@H](/C=C\S(C)(=O)=O)NC(=O)c1cnc(C2CCCC2)nc1Oc1ccccc1]

Using the minor olefin isomer tert-butyl N—[(Z,1S)-1-methyl-3-methylsulfonyl-allyl]carbamate obtained at Step 1 for the compound of Example 2, the title compound was obtained. LC-MS m/z: 416.2 [M+1].

Example 4

(R,E)-2-cyclopentyl-N-(4-(methylsulfonyl)but-3-en-2-yl)-4-phenoxypyrimidine-5-carboxamide

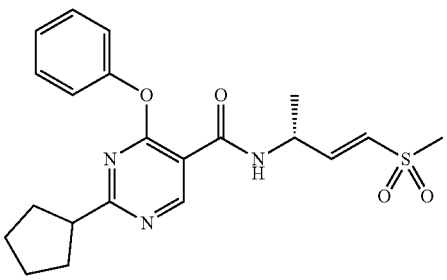 [SMILES: C[C@H](/C=C/S(C)(=O)=O)NC(=O)c1cnc(C2CCCC2)nc1Oc1ccccc1]

Using tert-butyl N-[(1R)-1-methyl-2-oxo-ethyl]carbamate/NaH at Step 1 in Procedure A, the title compound was obtained. LC-MS m/z: 416.1 [M+1].

Example 5

(R,Z)-2-cyclopentyl-N-(4-(methylsulfonyl)but-3-en-2-yl)-4-phenoxypyrimidine-5-carboxamide

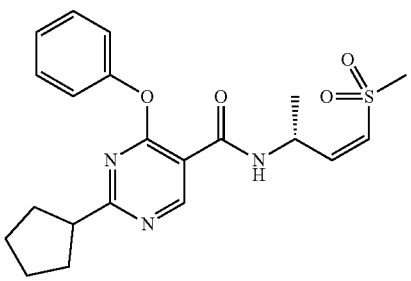 [SMILES: C[C@H](/C=C\S(C)(=O)=O)NC(=O)c1cnc(C2CCCC2)nc1Oc1ccccc1]

Using the minor olefin isomer tert-butyl N—[(Z,1R)-1-methyl-3-methylsulfonyl-allyl]carbamate obtained at Step 1 for the compound of Example 4, the title compound was obtained. LC-MS m/z: 416.2 [M+1].

Example 6

(S,E)-2-cyclopentyl-N-(1-(methylsulfonyl)pent-1-en-3-yl)-4-phenoxypyrimidine-5-carboxamide

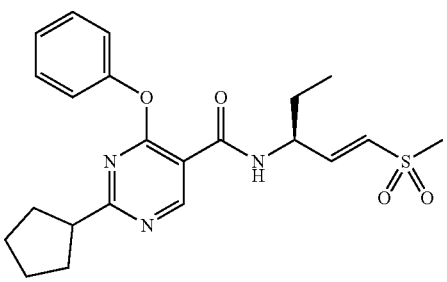 [SMILES: CC[C@@H](/C=C/S(C)(=O)=O)NC(=O)c1cnc(C2CCCC2)nc1Oc1ccccc1]

Using tert-butyl N-[(1S)-1-(hydroxymethyl)propyl]carbamate/IBX/MeCN to prepare 1-hydroxy-1-oxo-1,5,2-benziodoxol-3-one for Step 1 and NaH as the base for Step 1 in Procedure A, the title compound was obtained. LC-MS m/z: 430.2 [M+1].

Example 7

(S,E)-2-cyclopentyl-N-(4-methyl-1-(methylsulfonyl)pent-1-en-3-yl)-4-phenoxypyrimidine-5-carboxamide

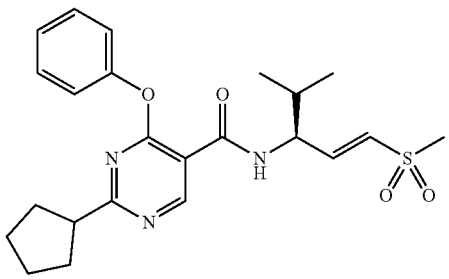 [SMILES: CC(C)[C@@H](/C=C/S(C)(=O)=O)NC(=O)c1cnc(C2CCCC2)nc1Oc1ccccc1]

Using Boc-D-valinol/IBX to prepare tert-butyl N-[(1S)-1-formyl-2-methyl-propyl]carbamate for Step 1 and NaH as the base at Step 1 in Procedure A, the title compound was obtained. LC-MS m/z: 444.2 [M+1].

Example 8

(S,E)-2-cyclopentyl-N-(1-cyclopropyl-3-(methylsulfonyl)allyl)-4-phenoxypyrimidine-5-carboxamide

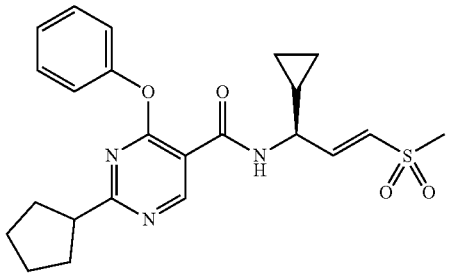 [SMILES: CS(=O)(=O)/C=C/[C@@H](NC(=O)c1cnc(C2CCCC2)nc1Oc1ccccc1)C1CC1]

Step 1

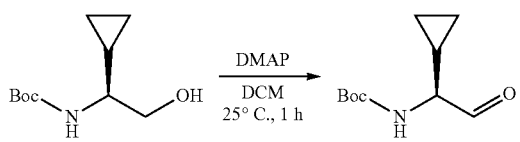

To a solution of tert-butyl N-[(1S)-1-cyclopropyl-2-hydroxy-ethyl]carbamate (500 mg, 2.48 mmol) in DCM (8 mL, 0.311 M) was added Dess-Martin periodinane (2.1 g, 4.97 mmol). The reaction mixture was stirred at 25° C. for 1 hour under N$_2$. The mixture was filtered and the filter cake was rinsed with DCM (3×15 mL). Then the combined filtrates were concentrated under reduced pressure to give a residue. The residue was purified by flash column chromatography (Biotage using a 12 g Agela flash silica gel column, eluted with 0% to 8% ethyl acetate in petroleum ether) to afford tert-butyl N-[(1S)-1-cyclopropyl-2-oxo-ethyl]carbamate as a colorless oil (300 mg, 61% yield).

Using N-[(1S)-1-cyclopropyl-2-oxo-ethyl]carbamate/NaH at Step 1 in Procedure A, the title compound was obtained. LC-MS m/z: 442.1 [M+1].

Example 9

(S,E)-N-(1-cyclobutyl-3-(methylsulfonyl)allyl)-2-cyclopentyl-4-phenoxypyrimidine-5-carboxamide

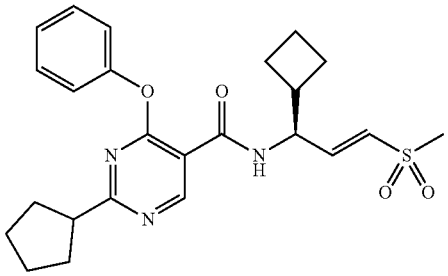 [SMILES: CS(=O)(=O)/C=C/[C@@H](NC(=O)c1cnc(C2CCCC2)nc1Oc1ccccc1)C1CCC1]

Using tert-butyl N-[(1S)-1-cyclobutyl-2-hydroxy-ethyl]carbamate/Dess-Martin Periodinane/DCM to prepare tert-butyl N-[(1S)-1-cyclobutyl-2-oxo-ethyl]carbamate for Step 1 and NaH as the base for Step 1 in Procedure A, the title compound was obtained. LC-MS m/z: 456.1 [M+1].

Example 10

(R,E)-2-cyclopentyl-N-(1-methoxy-4-(methylsulfonyl)but-3-en-2-yl)-4-phenoxypyrimidine-5-carboxamide

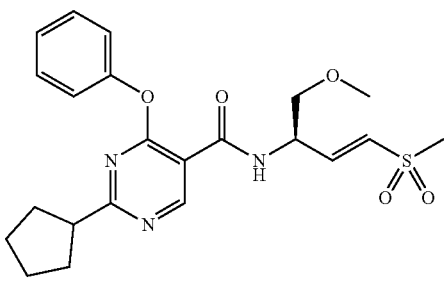 [SMILES: COC[C@@H](/C=C/S(C)(=O)=O)NC(=O)c1cnc(C2CCCC2)nc1Oc1ccccc1]

Step 1

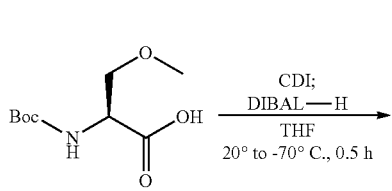

-continued

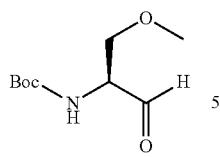

To a solution of (2S)-2-{[(tert-butoxy)carbonyl]amino}-3-methoxypropanoic acid (5 g, 22.81 mmol) in THF (100 mL, 0.228 M) was added 1,1'-carbonyl-diimidazole (4.07 g, 25.09 mmol). The mixture was stirred for 30 minutes at 20° C., then the mixture was added DIBAL-H (47.9 mL, 47.90 mmol, 1.23 g/ml) dropwise at −70° C. The mixture was quenched by adding sat. Seignette salt (100 mL) and stirred for 30 minutes, then extracted with DCM (3×50 mL). The combined organic layers were dried over Na$_2$SO$_4$, filtered and concentrated under reduced pressure to afford crude tert-butyl N-[(1S)-1-formyl-2-methoxy-ethyl]carbamate as a yellow oil (3.20 g).

Using tert-butyl N-[(1S)-1-formyl-2-methoxy-ethyl]carbamate/NaH at Step 1 in Procedure A, the title compound was obtained. LC-MS m/z: 446.1 [M+1].

Example 11

(S,E)-2-methyl-N-(4-(methylsulfonyl)but-3-en-2-yl)-4-phenoxypyrimidine-5-carboxamide

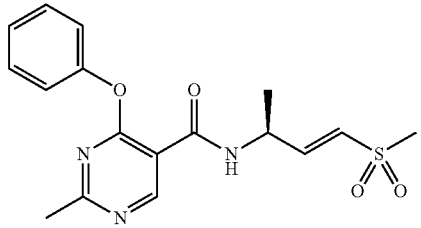 [SMILES: Cc1ncc(C(=O)N[C@@H](C)/C=C/S(C)(=O)=O)c(Oc2ccccc2)n1]

Using tert-butyl N-[(1S)-1-methyl-2-oxo-ethyl]carbamate/NaH at Step 1 and using ethyl 4-hydroxy-2-methyl-pyrimidine-5-carboxylate at Step 4 in Procedure A, the title compound was obtained. LC-MS m/z: 362.1 [M+1].

Example 12

(E)-2-ethyl-N-(3-(methylsulfonyl)allyl)-4-phenoxy-pyrimidine-5-carboxamide

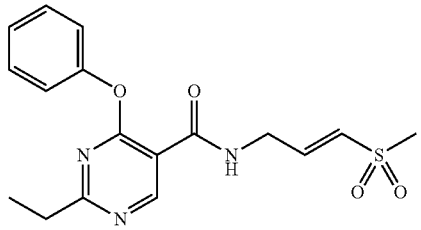 [SMILES: CCc1ncc(C(=O)NC/C=C/S(C)(=O)=O)c(Oc2ccccc2)n1]

Using propanamidine hydrochloride at Step 3 in Procedure A, the title compound was obtained. LC-MS m/z: 362.2 [M+1].

Example 13

(S,E)-2-ethyl-N-(4-(methylsulfonyl)but-3-en-2-yl)-4-phenoxypyrimidine-5-carboxamide

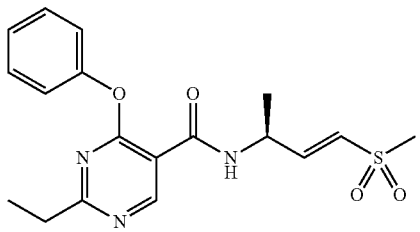 [SMILES: CCc1ncc(C(=O)N[C@@H](C)/C=C/S(C)(=O)=O)c(Oc2ccccc2)n1]

Using tert-butyl N-[(1S)-1-methyl-2-oxo-ethyl]carbamate/NaH at Step 1 and using propanamidine hydrochloride at Step 3 in Procedure A, the title compound was obtained. LC-MS m/z: 376.2 [M+1].

Example 14

(E)-2-isopropyl-N-(3-(methylsulfonyl)allyl)-4-phenoxypyrimidine-5-carboxamide

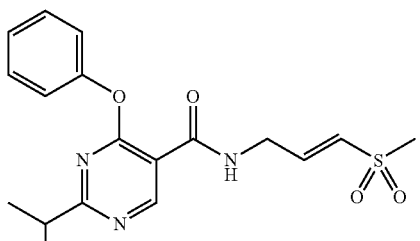

Using 2-methylpropanamidine hydrochloride at Step 3 in Procedure A, the title compound was obtained. LC-MS m/z: 376.1 [M+1].

Example 15

(S,E)-2-isopropyl-N-(4-(methylsulfonyl)but-3-en-2-yl)-4-phenoxypyrimidine-5-carboxamide

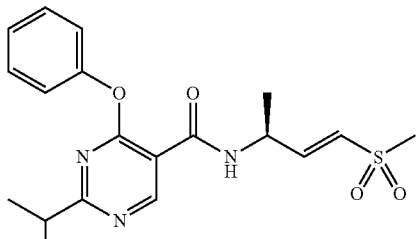

Using tert-butyl N-[(1S)-1-methyl-2-oxo-ethyl]carbamate/NaH at Step 1 and using 2-methylpropanamidine hydrochloride at Step 3 in Procedure A, the title compound was obtained. LC-MS m/z: 390.1 [M+1].

Example 16

(S,E)-N-(1-cyclopropyl-3-(methylsulfonyl)allyl)-2-isopropyl-4-phenoxypyrimidine-5-carboxamide

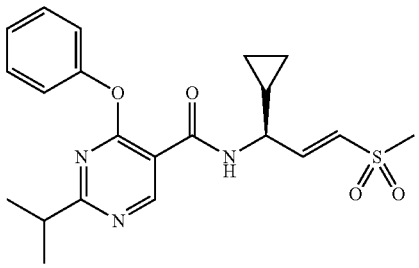 [SMILES: CC(C)c1ncc(C(=O)N[C@H](/C=C/S(C)(=O)=O)C2CC2)c(Oc2ccccc2)n1]

Using tert-butyl N-[(1S)-1-cyclopropyl-2-oxo-ethyl]carbamate/NaH for Step 1 and 2-methylpropanamidine hydrochloride at Step 3 in Procedure A, the title compound was obtained. LC-MS m/z: 416.1 [M+1].

Example 17

(E)-2-cyclopropyl-N-(3-(methylsulfonyl)allyl)-4-phenoxypyrimidine-5-carboxamide

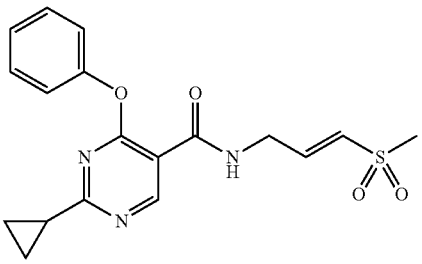 [SMILES: CS(=O)(=O)/C=C/CNC(=O)c1cnc(C2CC2)nc1Oc1ccccc1]

Using cyclopropanecarboxamidine at Step 3 in Procedure A, the title compound was obtained. LC-MS m/z: 374.0 [M+1].

Example 18

(S,E)-2-cyclopropyl-N-(4-(methylsulfonyl)but-3-en-2-yl)-4-phenoxypyrimidine-5-carboxamide

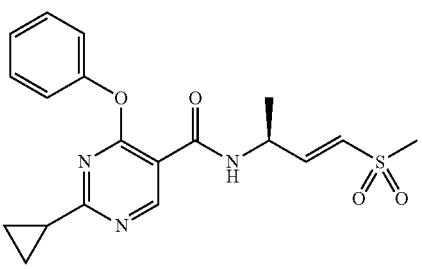 [SMILES: C[C@@H](/C=C/S(C)(=O)=O)NC(=O)c1cnc(C2CC2)nc1Oc1ccccc1]

Using tert-butyl N-[(1S)-1-methyl-2-oxo-ethyl]carbamate/NaH at Step 1 and using cyclopropanecarboxamidine at Step 3 in Procedure A, the title compound was obtained. LC-MS m/z: 388.0 [M+1].

Example 19

(S,E)-N-(1-cyclopropyl-3-(methylsulfonyl)allyl)-2-(2-fluoropropan-2-yl)-4-phenoxypyrimidine-5-carboxamide

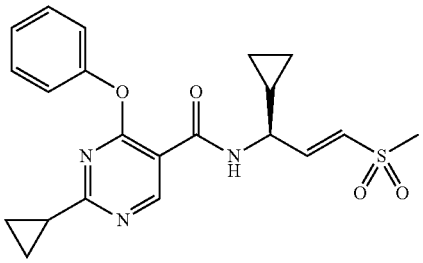 [SMILES: CS(=O)(=O)/C=C/[C@@H](NC(=O)c1cnc(C2CC2)nc1Oc1ccccc1)C1CC1]

Using tert-butyl N-[(1S)-1-cyclopropyl-2-oxo-ethyl]carbamate/NaH for Step 1 and cyclopropanecarboxamidine at Step 3 in Procedure A, the title compound was obtained. LC-MS m/z: 414.1 [M+1].

Examples 20 and 21

(S,E)-2-cyclopropyl-N-(4-(methylsulfonyl)-1-phenylbut-3-en-2-yl)-4-phenoxypyrimidine-5-carboxamide (Example 20)

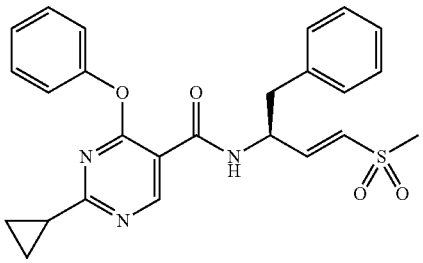 [SMILES: CS(=O)(=O)/C=C/[C@H](Cc1ccccc1)NC(=O)c1cnc(C2CC2)nc1Oc1ccccc1]

(S,Z)-2-cyclopropyl-N-(4-(methylsulfonyl)-1-phenylbut-3-en-2-yl)-4-phenoxypyrimidine-5-carboxamide (Example 21)

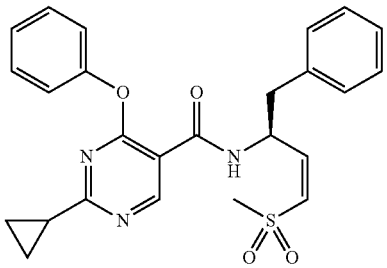 [SMILES: CS(=O)(=O)/C=C\[C@H](Cc1ccccc1)NC(=O)c1cnc(C2CC2)nc1Oc1ccccc1]

Using tert-butyl N-[(1S)-1-benzyl-2-oxo-ethyl]carbamate/NaH for Step 1 and cyclopropanecarboxamidine at Step 3 in Procedure A, the mixture of the title compounds was obtained. The mixture was separated by prep-HPLC (reverse phase, MeCN/H$_2$O (0.1% FA)=5-95%) to afford Peak 1 (E isomer, LC-MS m/z: 464.2 [M+1]) and Peak 2 (Z isomer, LC-MS m/z: 464.2 [M+1]).

Example 22

(2-cyclopropyl-4-phenoxypyrimidin-5-yl)(3-(2-(methylsulfonyl)vinyl)azetidin-1-yl)methanone

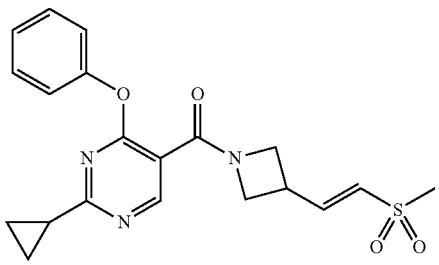 [SMILES: CS(=O)(=O)/C=C/C1CN(C(=O)c2cnc(C3CC3)nc2Oc2ccccc2)C1]

Using tert-butyl 3-formylazetidine-1-carboxylate/"BuLi for Step 1 and cyclopropanecarboxamidine at Step 3 in Procedure A, the title compound was obtained as a mixture of olefin isomer (E:Z=1.6:1). LC-MS m/z: 400.2 [M+1].

Examples 23 and 24

(Z)-(2-cyclopropyl-4-phenoxypyrimidin-5-yl)(3-(2-(methylsulfonyl)vinyl)azetidin-1-yl)methanone (Example 23)

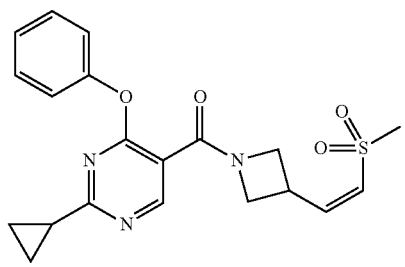 [SMILES: CS(=O)(=O)/C=C\C1CN(C(=O)c2cnc(C3CC3)nc2Oc2ccccc2)C1]

(E)-(2-cyclopropyl-4-phenoxypyrimidin-5-yl)(3-(2-(methylsulfonyl)vinyl)azetidin-1-yl)methanone (Example 24)

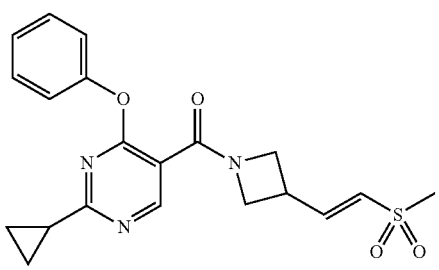 [SMILES: CS(=O)(=O)/C=C/C1CN(C(=O)c2cnc(C3CC3)nc2Oc2ccccc2)C1]

The compound of Example 22 was separated by chiral SFC (column: Chiralpak AS-3) to afford to afford Peak 1 (Z isomer, LC-MS m/z: 400.2 [M+1]) and Peak 2 (E isomer, LC-MS m/z: 400.2 [M+1]).

Example 25

(S,E)-2-cyclopropyl-N-(4-(cyclopropylsulfonyl)but-3-en-2-yl)-4-phenoxypyrimidine-5-carboxamide

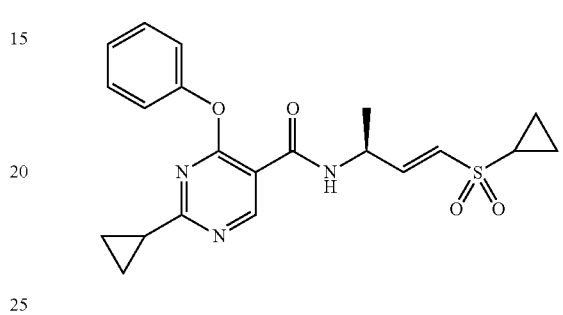

Step 1

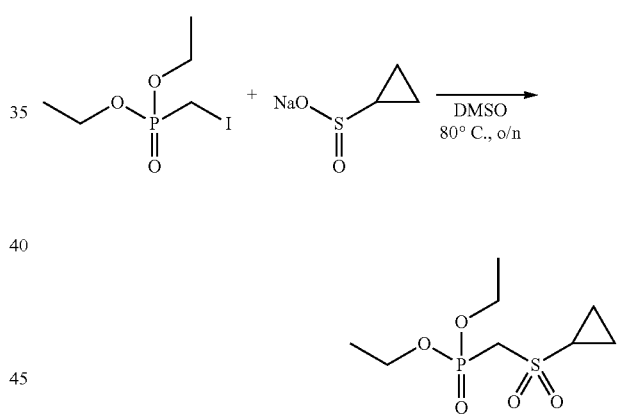

A solution of sodium cyclopropanesulfinate (922 mg, 7.19 mmol) in DMSO (6 mL, 0.600 M) was stirred for 1 hour at rt to completely dissolve the salt. Then diethyl iodomethylphosphonate (0.60 mL, 3.60 mmol) was added and the mixture was heated at 80° C. for overnight. Additional sodium cyclopropanesulfinate (922 mg, 7.19 mmol) was added and the mixture was heated at 100° C. for 1 hour. The mixture was diluted with EtOAc, washed with 1 M HCl and brine, dried over Na$_2$SO$_4$, and concentrated in reduced pressure to give a residue. The residue was purified via normal phase column chromatography using Biotage Isolera (0-10% MeOH/DCM) to afford diethoxyphosphorylmethylsulfonylcyclopropane as a yellow oil (432 mg, 47% yield).

Using diethoxyphosphorylmethylsulfonylcyclopropane/tert-butyl N-[(1S)-1-methyl-2-oxo-ethyl]carbamate/NaH at Step 1 and using cyclopropanecarboxamidine at Step 3 in Procedure A, the title compound was obtained. LC-MS m/z: 414.0 [M+1].

Example 26

(2-cyclopropyl-4-phenoxy-pyrimidin-5-yl)-[(3Z)-3-(methylsulfonylmethylene)pyrrolidin-1-yl]methanone

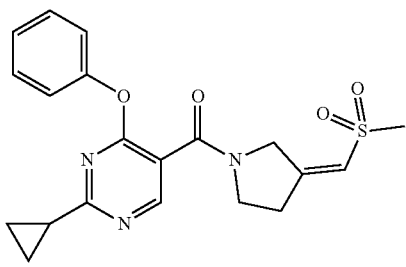 [SMILES: CS(=O)(=O)/C=C1/CCN(C(=O)c2cnc(C3CC3)nc2Oc2ccccc2)C1]

Using N-Boc-3-pyrrolidinone/NaH for Step 1 and cyclopropanecarboxamidine at Step 3 in Procedure A, the title compound was obtained. LC-MS m/z: 400.0 [M+1].

Example 27

2-cyclopropyl-N-(1,1-dioxido-2,3-dihydrothiophen-3-yl)-4-phenoxypyrimidine-5-carboxamide

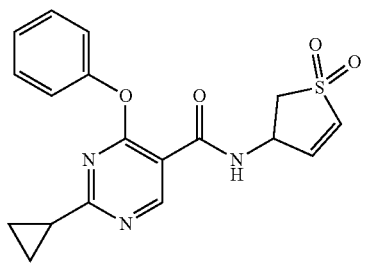 [SMILES: O=C(NC1C=CS(=O)(=O)C1)c1cnc(C2CC2)nc1Oc1ccccc1]

Following Step 7 in Procedure A with 2-cyclopropyl-4-phenoxy-pyrimidine-5-carboxylic acid and 3-amino-2,3-dihydrothiophene 1,1-dioxide, the title compound was obtained. LC-MS m/z: 372.0 [M+1].

Example 28

(S,E)-2-cyclopropyl-N-(1-cyclopropyl-4-(methylsulfonyl)but-3-en-2-yl)-4-phenoxypyrimidine-5-carboxamide

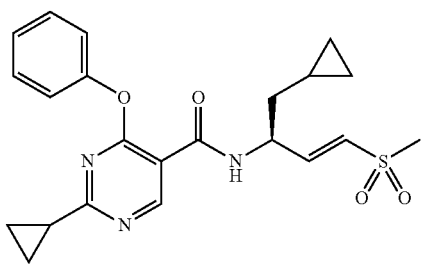 [SMILES: CS(=O)(=O)/C=C/[C@H](CC1CC1)NC(=O)c1cnc(C2CC2)nc1Oc1ccccc1]

Step 1

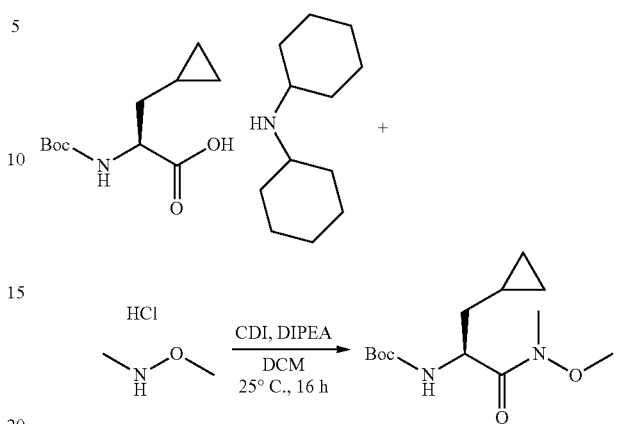

CDI (592 mg, 3.65 mmol) was added slowly to a solution of (2S)-2-(tert-butoxycarbonylamino)-3-cyclopropyl-propanoic acid; N-cyclohexylcyclohexanamine (1.0 g, 2.44 mmol) in DCM and stirred at rt for 30 minutes until CO$_2$ evolution ceased. DIPEA (0.64 mL, 3.65 mmol) was added dropwise to the reaction mixture followed by the addition of solid N,O-dimethylhydroxylamine hydrochloride (356 mg, 3.65 mmol). After the addition was complete, the resulting mixture was stirred at rt for 16 hours. The reaction was then quenched by the addition of water and the resulting solution was extracted with DCM (3×20 mL). The combined organic layers were washed with brine, dried over anhydrous Na$_2$SO$_4$, and filtered. The filtrate was concentrated to afford crude tert-butyl N-[(1S)-1-(cyclopropylmethyl)-2-[methoxy(methyl)amino]-2-oxo-ethyl]carbamate (356 mg).

Step 2

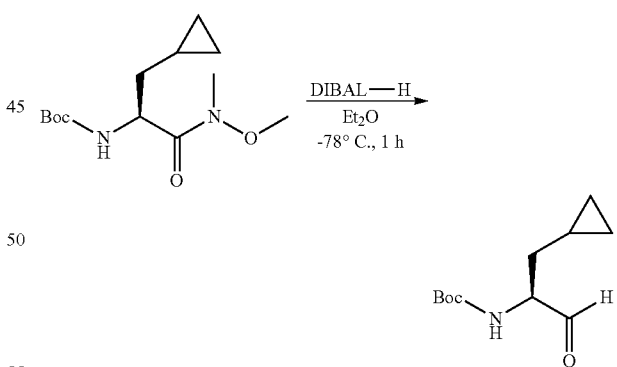

DIBAL-H (0.86 mL, 4.8 mmol) was added dropwise to a solution of tert-butyl N-[(1S)-1-(cyclopropylmethyl)-2-[methoxy(methyl)amino]-2-oxo-ethyl]carbamate (356 mg, 1.31 mmol) in Et$_2$O at −78° C. After 1 hour, the excess DIBAL-H was quenched by the addition of EtOAc, and the mixture was stirred for an additional 15 minutes at −78° C. The reaction mixture was poured into a mixture of citric acid and Et$_2$O (15 mL), and the layers were lightly shaken and then separated. The aqueous layer was then washed with Et$_2$O (3×20 mL). The combined organic layers were dried over Na$_2$SO$_4$ and concentrated under reduced pressure. The residue was purified via normal phase chromatography (SiO₂, EtOAc/heptanes=0-100%) to afford tert-butyl N-[(1S)-1-(cyclopropylmethyl)-2-oxo-ethyl]carbamate (209.8 mg, 74% yield).

Using tert-butyl N-[(1S)-1-(cyclopropylmethyl)-2-oxo-ethyl]carbamate/Cs2CO3 at Step 1 and cyclopropanecarboxamidine at Step 3 in Procedure A, the title compound was obtained. LC-MS m/z: 428.0 [M+1].

Example 29

(S,E)-N-(1-cyclobutyl-3-(methylsulfonyl)allyl)-2-cyclopropyl-4-phenoxypyrimidine-5-carboxamide

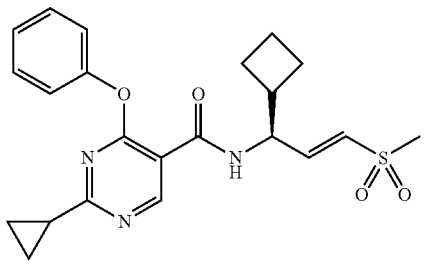 [SMILES: CS(=O)(=O)/C=C/[C@@H](NC(=O)c1cnc(C2CC2)nc1Oc1ccccc1)C1CCC1]

Using (2S)-2-(tert-butoxycarbonylamino)-2-cyclobutyl-acetic acid at Step 1 and following the procedure for the compound of Example 28, the title compound was obtained. LC-MS m/z: 428.0 [M+1].

Example 30

(S,E)-2-cyclopropyl-N-(1-(3,3-difluorocyclobutyl)-3-(methylsulfonyl)allyl)-4-phenoxypyrimidine-5-carboxamide

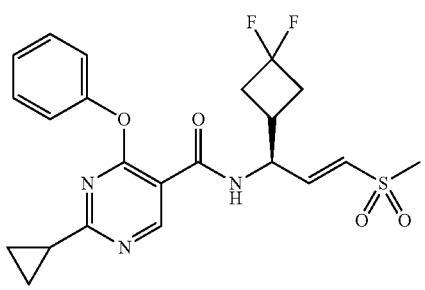 [SMILES: CS(=O)(=O)/C=C/[C@@H](NC(=O)c1cnc(C2CC2)nc1Oc1ccccc1)C1CC(F)(F)C1]

Using (2S)-2-(tert-butoxycarbonylamino)-2-(3,3-difluorocyclobutyl)acetic acid at Step 1 and following the procedure for the compound of Example 28, the title compound was obtained. LC-MS m/z: 464.0 [M+1].

Example 31

(R,E)-2-cyclopropyl-N-(4-(methylsulfonyl)-1-(methylthio)but-3-en-2-yl)-4-phenoxypyrimidine-5-carboxamide

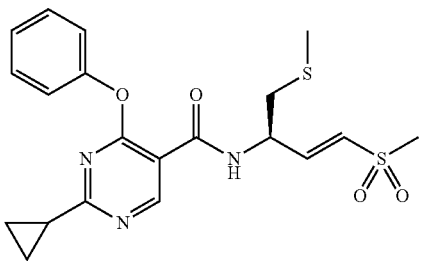 [SMILES: CSC[C@@H](/C=C/S(C)(=O)=O)NC(=O)c1cnc(C2CC2)nc1Oc1ccccc1]

Using (2R)-2-(tert-butoxycarbonylamino)-3-methylsulfanyl-propanoic acid at Step 1 and following the procedure for the compound of Example 28, the title compound was obtained. LC-MS m/z: 434.0 [M+1].

Example 32

2-cyclopropyl-N-((3R,4R,E)-4-methoxy-1-(methylsulfonyl)pent-1-en-3-yl)-4-phenoxypyrimidine-5-carboxamide

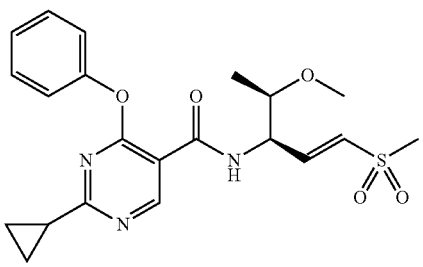 [SMILES: CO[C@H](C)[C@@H](/C=C/S(C)(=O)=O)NC(=O)c1cnc(C2CC2)nc1Oc1ccccc1]

Using (2S,3R)-2-(tert-butoxycarbonylamino)-3-methoxy-butanoic acid at Step 1 to follow the procedure for the compound of Example 28, the title compound was obtained. LC-MS m/z: 432.0 [M+1].

Example 33

(S,E)-2-cyclopropyl-N-(3-(methylsulfonyl)-1-(tetrahydro-2H-pyran-4-yl)allyl)-4-phenoxypyrimidine-5-carboxamide

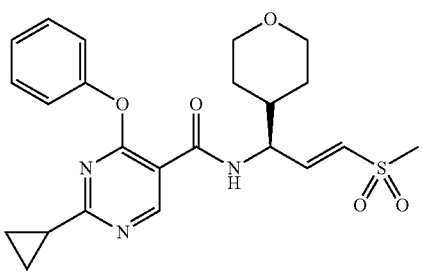 [SMILES: CS(=O)(=O)/C=C/[C@@H](NC(=O)c1cnc(C2CC2)nc1Oc1ccccc1)C1CCOCC1]

Using (2S)-2-(tert-butoxycarbonylamino)-2-tetrahydropyran-4-yl-acetic acid at Step 1 to follow the procedure for the compound of Example 28, the title compound was obtained. LC-MS m/z: 458.0 [M+1].

Example 34

(2-cyclopropyl-4-phenoxypyrimidin-5-yl)(3-(methylsulfonyl)-2,5-dihydro-1H-pyrrol-1-yl)methanone

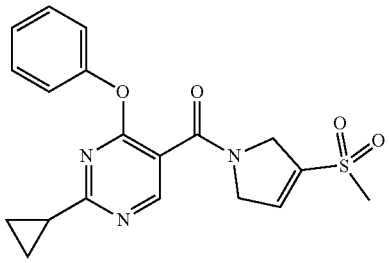 [SMILES: CS(=O)(=O)C1=CCN(C(=O)c2cnc(C3CC3)nc2Oc2ccccc2)C1]

Step 1

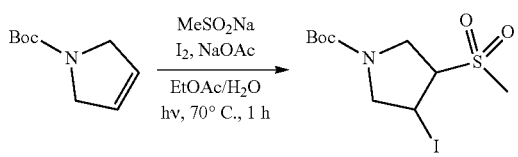 [SMILES: CC(C)(C)OC(=O)N1CC=CC1 ; CC(C)(C)OC(=O)N1CC(I)C(S(C)(=O)=O)C1]

A mixture of tert-butyl 2,5-dihydro-1h-pyrrole-1-carboxylate (1 g, 5.91 mmol), sodium methanesulfinate (1.2 g, 11.82 mmol), iodine (1.65 g, 6.50 mmol) and sodium acetate (727 mg, 8.86 mmol) in ethyl acetate (15 mL, 0.236 M) and water (10 mL, 0.236 M) was stirred at 70° C. (illuminated by 1000 W lamp) for 1 hour. The reaction mixture was poured into saturated aqueous Na$_2$S$_2$O$_3$ (15 mL) and extracted with EtOAc (3×15 mL). The combined organic layers were washed with brine (2×10 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 30~60% Ethyl acetate/Petroleum ether gradient at 100 mL/min) to afford tert-butyl 3-iodo-4-methylsulfonyl-pyrrolidine-1-carboxylate as yellow oil (600 mg, 27% yield).

Step 2

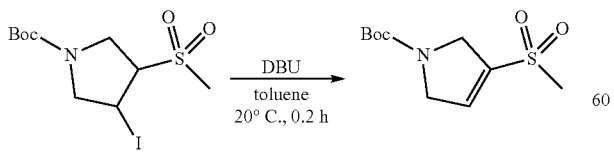

To a mixture of tert-butyl 3-iodo-4-methylsulfonyl-pyrrolidine-1-carboxylate (600 mg, 1.60 mmol in toluene (3 mL, 0.533 M) was added 1,8-diazabicyclo[5.4.0]undec-7-ene (292.1 mg, 1.92 mmol) at 20° C. and the mixture was stirred at 20° C. for 0.5 hour. The mixture was washed with aq. HCl (1N, 3 mL), sat. NaHCO$_3$ (3 mL) and brine (3 mL), dried over Na$_2$SO$_4$, filtered and concentrated under reduced pressure. The residue was purified by prep-TLC (SiO$_2$, PE:EtOAc=1:1) to afford tert-butyl 3-methylsulfonyl-2,5-dihydropyrrole-1-carboxylate as a white solid (400 mg).

Using tert-butyl 3-methylsulfonyl-2,5-dihydropyrrole-1-carboxylate at Step 2 and cyclopropanecarboxamidine at Step 3 in Procedure A, the title compound was obtained. LC-MS m/z: 386.0 [M+1].

Example 35

(S,E)-2-(cyclopropylmethyl)-N-(4-(methylsulfonyl)but-3-en-2-yl)-4-phenoxypyrimidine-5-carboxamide

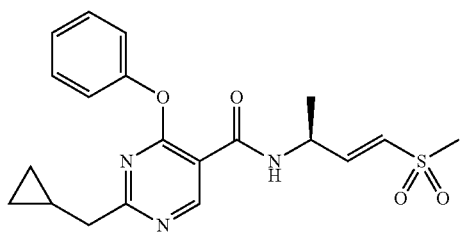 [SMILES: C[C@@H](/C=C/S(C)(=O)=O)NC(=O)c1cnc(CC2CC2)nc1Oc1ccccc1]

Using tert-butyl N-[(1S)-1-methyl-2-oxo-ethyl]carbamate/NaH at Step 1 and 2-cyclopropylacetamidine at Step 3 in Procedure A, the title compound was obtained. LC-MS m/z: 402.1 [M+1].

Example 36

(S,E)-N-(1-cyclopropyl-3-(methylsulfonyl)allyl)-2-(cyclopropylmethyl)-4-phenoxypyrimidine-5-carboxamide

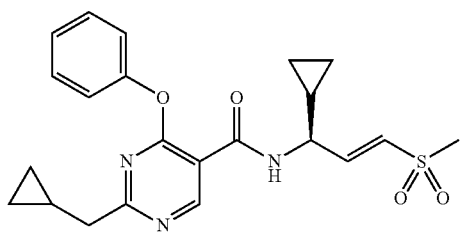

Using tert-butyl N-[(1S)-1-cyclopropyl-2-oxo-ethyl]carbamate/NaH for Step 1 and 2-cyclopropylacetamidine at Step 3 in Procedure A, the title compound was obtained. LC-MS m/z: 428.1 [M+1].

Example 37

N—((S,E)-1-cyclopropyl-3-(methylsulfonyl)allyl)-2-(cyclopropylfluoromethyl)-4-phenoxypyrimidine-5-carboxamide

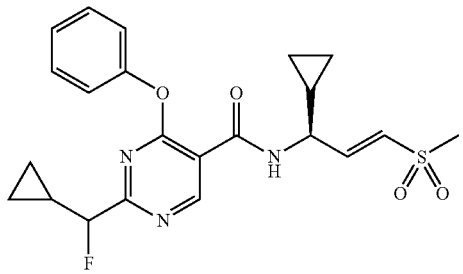 [SMILES: CS(=O)(=O)/C=C/[C@@H](NC(=O)c1cnc(C(F)C2CC2)nc1Oc1ccccc1)C1CC1]

Step 1

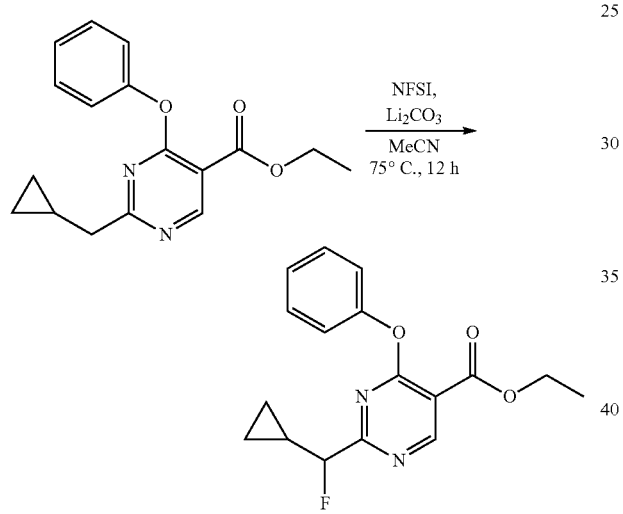

To a solution of ethyl 2-(cyclopropylmethyl)-4-phenoxy-pyrimidine-5-carboxylate (100.3 mg, 0.34 mmol) in MeCN (10 mL, 0.034 M) was added lithium carbonate (127.6 mg, 1.68 mmol) and N-fluorobenzenesulfonimide (530.3 mg, 1.68 mmol). The mixture was stirred at 75° C. for 12 hours under $N_2$. After cooling to room temperature, the reaction mixture was concentrated under reduced pressure to give a residue. The residue was diluted with $H_2O$ (8 mL) and the aqueous phase was extracted with EtOAc (3×10 mL). The combined organic layers were dried over anhydrous $Na_2SO_4$, filtered and concentrated under reduced pressure to give a residue. The residue was dissolved in DMF (1 mL), and the resulting solution was purified by prep-HPLC (Waters Xbridge BEH C18 100*30 mm*10 um, gradient water ($NH_4HCO_3$)-MeCN: 30-50% B, 25 mL/min) to afford ethyl 2-[cyclopropyl(fluoro)methyl]-4-phenoxy-pyrimidine-5-carboxylate as a yellow solid (10 mg, 9.4% yield).

Following Step 6 with ethyl 2-[cyclopropyl(fluoro)methyl]-4-phenoxy-pyrimidine-5-carboxylate and Step 7 with [(E,1S)-1-cyclopropyl-3-methylsulfonyl-allyl]amine 4-methylbenzenesulfonic acid in Procedure A, the title compound was obtained. LC-MS m/z: 446.1 [M+1].

Example 38

(S,E)-2-(1-methylcyclopropyl)-N-(4-(methylsulfonyl)but-3-en-2-yl)-4-phenoxypyrimidine-5-carboxamide

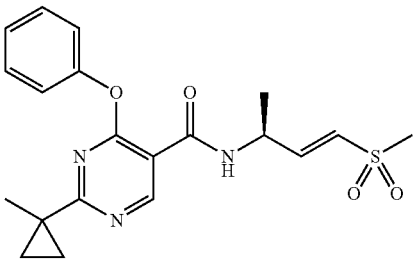

Using tert-butyl N-[(1S)-1-methyl-2-oxo-ethyl]carbamate/NaH at Step 1 and 1-methylcyclopropanecarboxamidine hydrochloride at Step 3 in Procedure A, the title compound was obtained. LC-MS m/z: 402.0 [M+1].

Example 39

(2-(1-methylcyclopropyl)-4-phenoxypyrimidin-5-yl)(3-((methylsulfonyl)methylene)azetidin-1-yl)methanone

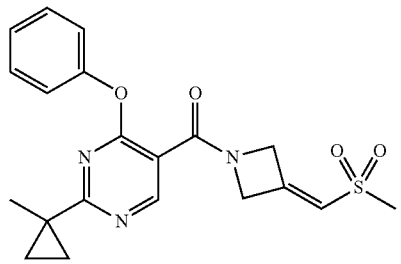

Using t-butyl 3-oxoazetidine-1-carboxylate/NaH at Step 1 and 1-methylcyclopropanecarboxamidine hydrochloride at Step 3 in Procedure A, the title compound was obtained. LC-MS m/z: 400.0 [M+1].

Example 40

(S,E)-2-((1-methylcyclopropyl)methyl)-N-(4-(methylsulfonyl)but-3-en-2-yl)-4-phenoxypyrimidine-5-carboxamide

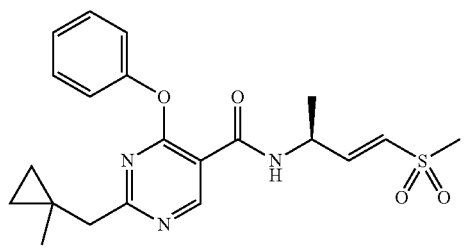 [SMILES: C[C@@H](/C=C/S(C)(=O)=O)NC(=O)c1cnc(CC2(C)CC2)nc1Oc1ccccc1]

Using tert-butyl N-[(1S)-1-methyl-2-oxo-ethyl]carbamate/NaH at Step 1 and 2-(1-methylcyclopropyl)acetamidine at Step 3 in Procedure A, the title compound was obtained. LC-MS m/z: 416.0 [M+1].

Example 41

(2-((1-methylcyclopropyl)methyl)-4-phenoxypyrimidin-5-yl)(3-((methylsulfonyl)methylene)azetidin-1-yl)methanone

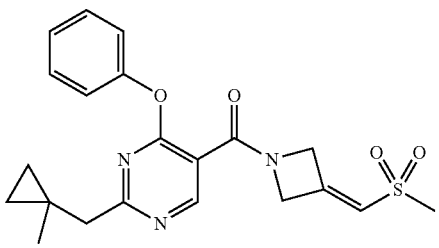 [SMILES: CC1(Cc2ncc(C(=O)N3CC(=CS(C)(=O)=O)C3)c(Oc3ccccc3)n2)CC1]

Using t-butyl 3-oxoazetidine-1-carboxylate/NaH at Step 1 and 2-(1-methylcyclopropyl)acetamidine at Step 3 in Procedure A, the title compound was obtained. LC-MS m/z: 414.0 [M+1].

Example 42

(S,E)-N-(4-(methylsulfonyl)but-3-en-2-yl)-4-phenoxy-2-(1-phenylcyclopropyl)pyrimidine-5-carboxamide

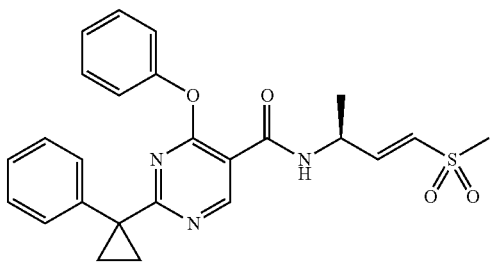 [SMILES: C[C@@H](/C=C/S(C)(=O)=O)NC(=O)c1cnc(C2(c3ccccc3)CC2)nc1Oc1ccccc1]

Using tert-butyl N-[(1S)-1-methyl-2-oxo-ethyl]carbamate/NaH at Step 1 and 1-phenylcyclopropanecarboxamidine at Step 3 in Procedure A, the title compound was obtained. LC-MS m/z: 464.0 [M+1].

Example 43

(E)-2-cyclobutyl-N-(3-(methylsulfonyl)allyl)-4-phenoxypyrimidine-5-carboxamide

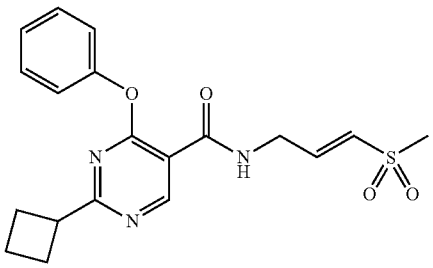 [SMILES: CS(=O)(=O)/C=C/CNC(=O)c1cnc(C2CCC2)nc1Oc1ccccc1]

Using cyclobutanecarboxamidine at Step 3 in Procedure A, the title compound was obtained. LC-MS m/z: 388.1 [M+1].

Example 44

(S,E)-2-cyclobutyl-N-(4-(methylsulfonyl)but-3-en-2-yl)-4-phenoxypyrimidine-5-carboxamide

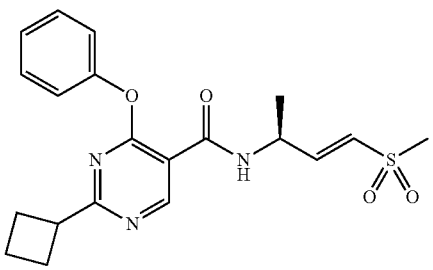 [SMILES: C[C@@H](/C=C/S(C)(=O)=O)NC(=O)c1cnc(C2CCC2)nc1Oc1ccccc1]

Using tert-butyl N-[(1S)-1-methyl-2-oxo-ethyl]carbamate/NaH at Step 1 and using cyclobutanecarboxamidine hydrochloride at Step 3 in Procedure A, the title compound was obtained. LC-MS m/z: 402.1 [M+1].

Example 45

(S,E)-2-cyclobutyl-N-(1-cyclopropyl-3-(methylsulfonyl)allyl)-4-phenoxypyrimidine-5-carboxamide

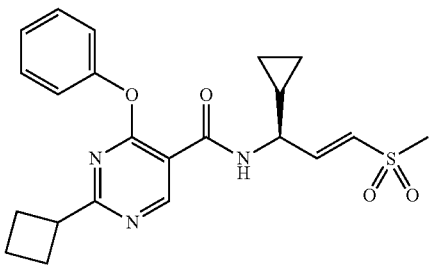 [SMILES: CS(=O)(=O)/C=C/[C@@H](NC(=O)c1cnc(C2CCC2)nc1Oc1ccccc1)C1CC1]

Using tert-butyl N-[(1S)-1-cyclopropyl-2-oxo-ethyl]carbamate/NaH for Step 1 and cyclobutanecarboxamidine hydrochloride at Step 3 in Procedure A, the title compound was obtained. LC-MS m/z: 428.1 [M+1].

Examples 46 and 47

2-((1s,3R)-3-methylcyclobutyl)-N—((S,E)-4-(methylsulfonyl)but-3-en-2-yl)-4-phenoxypyrimidine-5-carboxamide (Example 46)

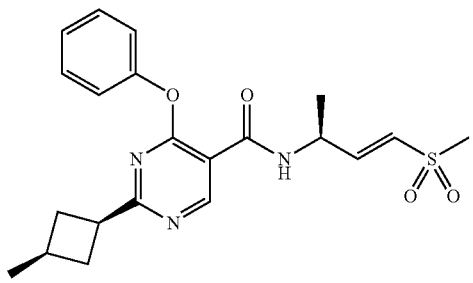

2-((1r,3S)-3-methylcyclobutyl)-N—((S,E)-4-(methylsulfonyl)but-3-en-2-yl)-4-phenoxypyrimidine-5-carboxamide (Example 47)

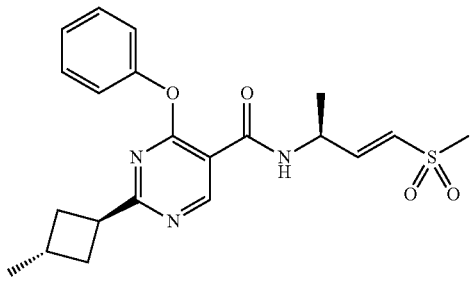

Using tert-butyl N-[(1S)-1-methyl-2-oxo-ethyl]carbamate/NaH for Step 1 and 3-methylcyclobutanecarboxamidine at Step 3 in Procedure A, the mixture of the title compounds was obtained. The mixture was separated by chiral HPLC (column: Chiralpak AD-3) to afford Peak 1 (compound of Example 46) (LC-MS m/z: 416.2 [M+1]) and Peak 2 (Compound of Example 47) (LC-MS m/z: 416.2 [M+1]).

Examples 48 and 49

N—((S,E)-1-cyclopropyl-3-(methylsulfonyl)allyl)-2-((1s,3R)-3-methylcyclobutyl)-4-phenoxypyrimidine-5-carboxamide (Example 48)

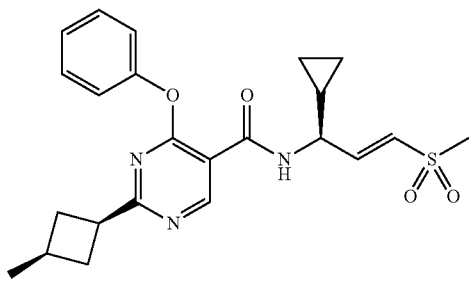

N—((S,E)-1-cyclopropyl-3-(methylsulfonyl)allyl)-2-((1r,3S)-3-methylcyclobutyl)-4-phenoxypyrimidine-5-carboxamide (Example 49)

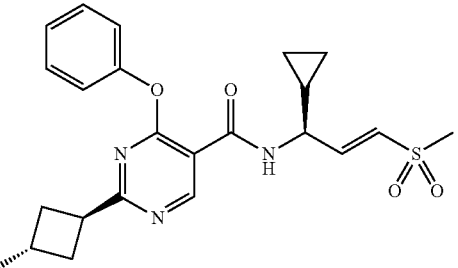

Using tert-butyl N-[(1S)-1-cyclopropyl-2-oxo-ethyl]carbamate/NaH for Step 1 and 3-methylcyclobutanecarboxamidine at Step 3 in Procedure A, the mixture of the title compounds was obtained. The mixture was separated by chiral HPLC (column: Waters Xbridge BEH C18 (100*30 mm*10 um), mobile phase water (NH$_4$HCO$_3$)-MeCN, gradient 30-65% B, flow rate: 60 mL/min) to afford Peak 1 (Compound of Example 48) (LC-MS m/z: 442.2 [M+1]) and Peak 2 (Compound of Example 49)
((LC-MS m/z: 442.2 [M+1]).

Examples 50 and 51

(2-((1s,3s)-3-methylcyclobutyl)-4-phenoxypyrimidin-5-yl)(3-((methylsulfonyl)methylene)azetidin-1-yl)methanone (Example 50)

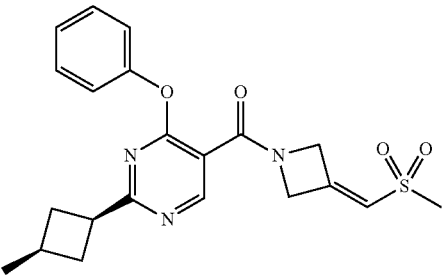

(2-((1r,3r)-3-methylcyclobutyl)-4-phenoxypyrimidin-5-yl)(3-((methylsulfonyl)methylene)azetidin-1-yl)methanone (Example 51)

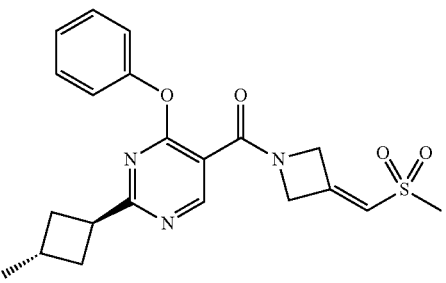

Using t-butyl 3-oxoazetidine-1-carboxylate/NaH for Step 1 and 3-methylcyclobutanecarboxamidine at Step 3 in Procedure A, the mixture of the title compounds was obtained. The mixture was separated by chiral SFC (column: Daicel ChiralPak IC (250 mm*30 mm*10 um), mobile phase neutral MeOH) to afford Peak 1 (LC-MS m/z: 414.1 [M+1]) and Peak 2 (LC-MS m/z: 414.2 [M+1]).

Example 52

2-(bicyclo[4.2.0]octa-1,3,5-trien-7-yl)-N—((S,E)-4-(methylsulfonyl)but-3-en-2-yl)-4-phenoxypyrimidine-5-carboxamide

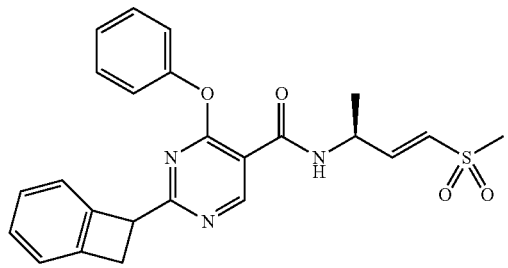 [SMILES: C[C@@H](/C=C/S(C)(=O)=O)NC(=O)c1cnc(C2Cc3ccccc32)nc1Oc1ccccc1]

Using tert-butyl N-[(1S)-1-methyl-2-oxo-ethyl]carbamate/NaH at Step 1 and bicyclo[4.2.0]octa-1,3,5-triene-7-carboxamidine at Step 3 in Procedure A, the title compound was obtained. LC-MS m/z: 450.0 [M+1].

Example 53

(S,E)-2-(cyclobutylmethyl)-N-(4-(methylsulfonyl)but-3-en-2-yl)-4-phenoxypyrimidine-5-carboxamide

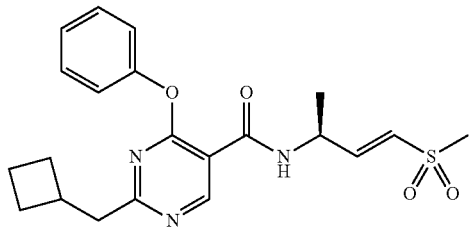 [SMILES: C[C@@H](/C=C/S(C)(=O)=O)NC(=O)c1cnc(CC2CCC2)nc1Oc1ccccc1]

Using tert-butyl N-[(1S)-1-methyl-2-oxo-ethyl]carbamate/NaH at Step 1 and 2-cyclobutylacetamidine at Step 3 in Procedure A, the title compound was obtained. LC-MS m/z: 416.2 [M+1].

Example 54

(S,E)-2-(cyclopentylmethyl)-N-(4-(methylsulfonyl)but-3-en-2-yl)-4-phenoxypyrimidine-5-carboxamide

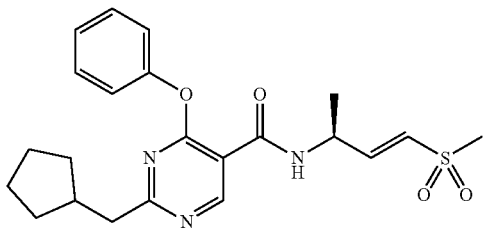

Using tert-butyl N-[(1S)-1-methyl-2-oxo-ethyl]carbamate/NaH at Step 1 and 2-cyclopentylacetamidine at Step 3 in Procedure A, the title compound was obtained. LC-MS m/z: 430.2 [M+1].

Example 55

(S,E)-N-(4-(methylsulfonyl)but-3-en-2-yl)-4-phenoxy-2-(spiro[2.3]hexan-5-yl)pyrimidine-5-carboxamide

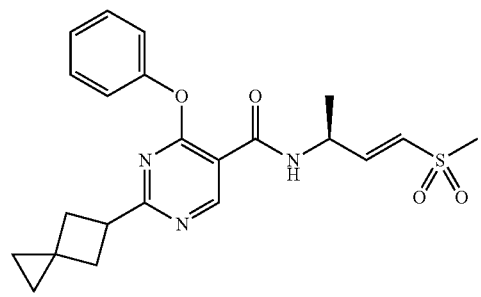 [SMILES: C[C@@H](/C=C/S(C)(=O)=O)NC(=O)c1cnc(C2CC3(CC3)C2)nc1Oc1ccccc1]

Step 1

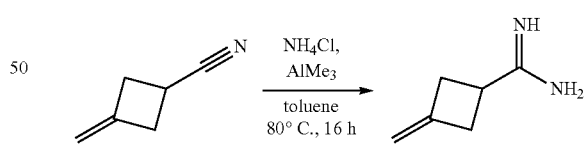

To a solution of ammonium chloride (1.90 g, 35.43 mmol) in toluene (50 mL, 0.644 M) was added trimethylaluminum (16.1 mL, 32.21 mmol, 2 M) at 0° C. The reaction was stirred at 25° C. for 2 hours. Then 3-methylenecyclobutanecarbonitrile (3 g, 32.21 mmol) was added dropwise in the mixture. The mixture was stirred at 80° C. for 16 hours under N₂. The reaction mixture was cooled to temperature and slowly poured into a slurry of silica gel in DCM (15 mL) and stirred for 10 minutes. The silica was filtered and washed with MeOH (3×20 mL). The filtrate and wash were combined and concentrated under reduced pressure to afford crude 3-methylenecyclobutanecarboxamidine as a white solid (2.35 g, 66% yield).

Step 2

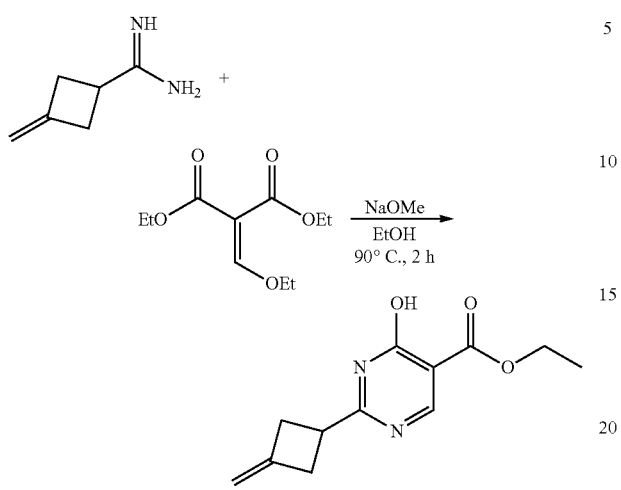

To a solution of 3-methylenecyclobutanecarboxamidine (4.3 g, 39.03 mmol) in ethanol (40 mL, 0.781 M) was added sodium methanolate (23.4 mL, 117.1 mmol, 5 M) at 0° C. A solution of diethyl ethoxymethylenemalonate (8.44 g, 39.03 mmol) in ethanol (10 mL, 0.781 M) was added dropwise to the mixture over 5 minutes. The mixture was stirred at 90° C. for 2 hours under $N_2$. The reaction mixture was concentrated under reduced pressure to give a residue. The residue was diluted with $H_2O$ (5 mL) and adjusted pH to ~6 with saturated aqueous citric acid and extracted with DCM (3×50 mL). The combined organic layers were dried over $Na_2SO_4$, filtered and concentrated under reduced pressure to give a residue. The residue was triturated with MTBE (15 mL). The resulting solid was collected by filtration, washed with MTBE (20 mL) and dried to afford ethyl 4-hydroxy-2-(3-methylenecyclobutyl)pyrimidine-5-carboxylate as a light yellow solid (3.6 g, 39% yield).

Step 3

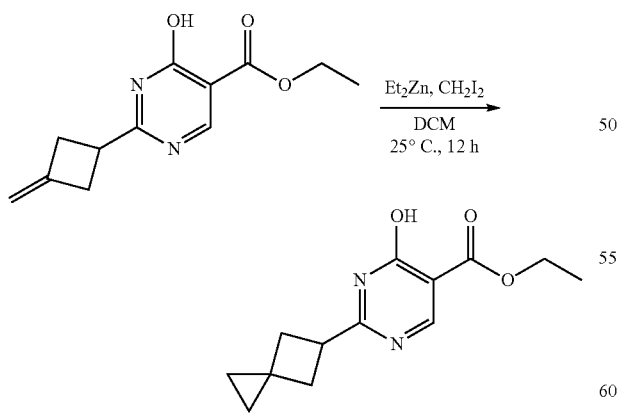

Diiodomethane (1.7 mL, 21.35 mmol) was added to diethylzinc (21.4 mL, 21.35 mmol, 1M) at 0° C. The mixture was stirred at 0° C. for 0.5 hour. Then ethyl 4-hydroxy-2-(3-methylenecyclobutyl)pyrimidine-5-carboxylate (500 mg, 2.13 mmol) in DCM (1 mL, 2.135 M) was added slowly to the mixture at 0° C. After stirring for 2 hours at the temperature, the mixture was allowed to warm to rt and stirred at 25° C. for 12 hours. The mixture was then filtered and the filter cake was rinsed with EtOAc (3×5 mL). The combined filtrates were concentrated under reduced pressure to afford crude ethyl 4-hydroxy-2-spiro[2.3]hexan-5-yl-pyrimidine-5-carboxylate (160 mg).

Using ethyl 4-hydroxy-2-spiro[2.3]hexan-5-yl-pyrimidine-5-carboxylate to follow Step 4, 5, 6 and 7 (using [(E,1S)-1-methyl-3-methylsulfonyl-allyl]amine 4-methylbenzenesulfonic acid) in Procedure A, the title compound was obtained. LC-MS m/z: 428.2 [M+1].

Example 56

(E)-2-(tert-butyl)-N-(3-(methylsulfonyl)allyl)-4-phenoxypyrimidine-5-carboxamide

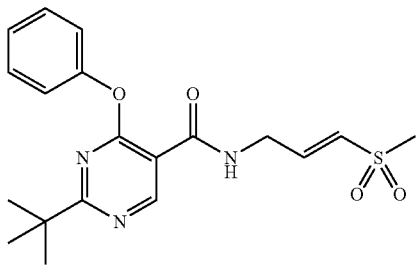 [SMILES: CC(C)(C)c1ncc(C(=O)NC/C=C/S(C)(=O)=O)c(Oc2ccccc2)n1]

Using 2,2-dimethylpropanamidine hydrochloride at Step 3 in Procedure A, the title compound was obtained. LC-MS m/z: 390.1 [M+1].

Example 57

(S,E)-2-(tert-butyl)-N-(4-(methylsulfonyl)but-3-en-2-yl)-4-phenoxypyrimidine-5-carboxamide

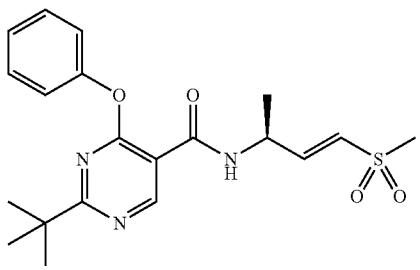 [SMILES: C[C@@H](/C=C/S(C)(=O)=O)NC(=O)c1cnc(C(C)(C)C)nc1Oc1ccccc1]

Using tert-butyl N-[(1S)-1-methyl-2-oxo-ethyl]carbamate/NaH at Step 1 and 2,2-dimethylpropanamidine hydrochloride at Step 3 in Procedure A, the title compound was obtained. LC-MS m/z: 404.2 [M+1].

Example 58

(S,E)-2-(tert-butyl)-N-(1-cyclopropyl-3-(methyl-sulfonyl)allyl)-4-phenoxypyrimidine-5-carboxamide

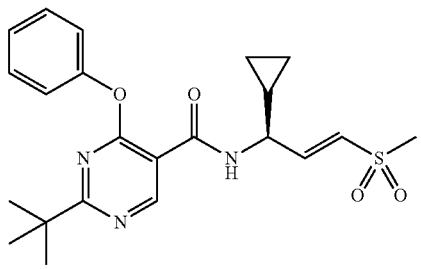 [SMILES: CC(C)(C)c1ncc(C(=O)N[C@H](/C=C/S(C)(=O)=O)C2CC2)c(Oc2ccccc2)n1]

Using tert-butyl N-[(1S)-1-cyclopropyl-2-oxo-ethyl]carbamate/NaH for Step 1 and 2,2-dimethylpropanamidine hydrochloride at Step 3 in Procedure A, the title compound was obtained. LC-MS m/z: 430.2 [M+1].

Example 59

2-(tert-butyl)-N-(1-(2-(methylsulfonyl)vinyl)cyclopropyl)-4-phenoxypyrimidine-5-carboxamide

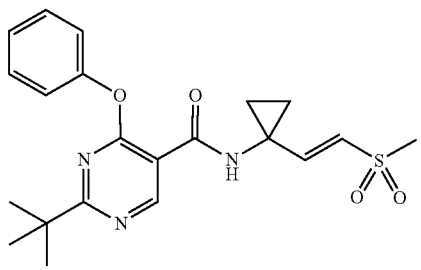 [SMILES: CC(C)(C)c1ncc(C(=O)NC2(/C=C/S(C)(=O)=O)CC2)c(Oc2ccccc2)n1]

Using tert-butyl N-[1-(hydroxymethyl)cyclopropyl]carbamate/Dess-Martin Periodinane/DCM to prepare (1-formyl-cyclopropyl)-carbamic acid tert-butyl ester for Step 1 and using NaH as the base at Step 1 and 2,2-dimethylpropanamidine hydrochloride at Step 3 in Procedure A, the title compound was obtained as a mixture of olefin isomers (E:Z=3.7:1). LC-MS m/z: 416.2 [M+1].

Examples 60 and 61

(S,E)-2-(tert-butyl)-N-(4-(methylsulfonyl)-1-phenyl-but-3-en-2-yl)-4-phenoxypyrimidine-5-carboxamide (Example 60)

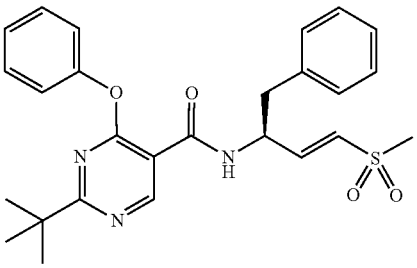 [SMILES: CC(C)(C)c1ncc(C(=O)N[C@H](/C=C/S(C)(=O)=O)Cc2ccccc2)c(Oc2ccccc2)n1]

(S,Z)-2-(tert-butyl)-N-(4-(methylsulfonyl)-1-phenyl-but-3-en-2-yl)-4-phenoxypyrimidine-5-carboxamide (Example 61)

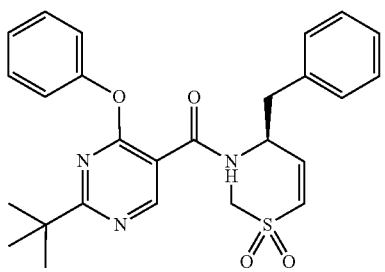 [SMILES: CC(C)(C)c1ncc(C(=O)N2CS(=O)(=O)C=C[C@@H]2Cc2ccccc2)c(Oc2ccccc2)n1]

Using tert-butyl N-[(1S)-1-benzyl-2-oxo-ethyl]carbamate/NaH for Step 1 and 2,2-dimethylpropanamidine hydrochloride at Step 3 in Procedure A, the mixture of the title compounds was obtained. The mixture was separated by prep-HPLC (reverse phase, MeCN/H$_2$O (0.1% FA)=5-95%) to afford Peak 1 (E isomer, LC-MS m/z: 480.2 [M+1]) and Peak 2 (Z isomer, LC-MS m/z: 480.0 [M+1]).

Example 62

(2-(tert-butyl)-4-phenoxypyrimidin-5-yl)(3-(((tetrahydro-2H-pyran-4-yl)sulfonyl)methylene)azetidin-1-yl)methanone

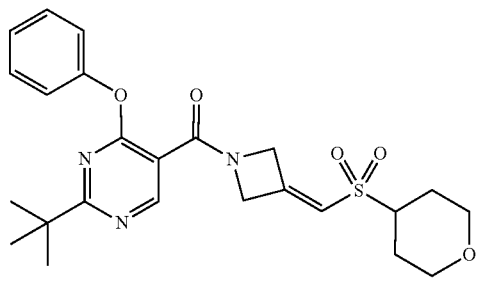 [SMILES: CC(C)(C)c1ncc(C(=O)N2CC(=CS(=O)(=O)C3CCOCC3)C2)c(Oc2ccccc2)n1]

Step 1

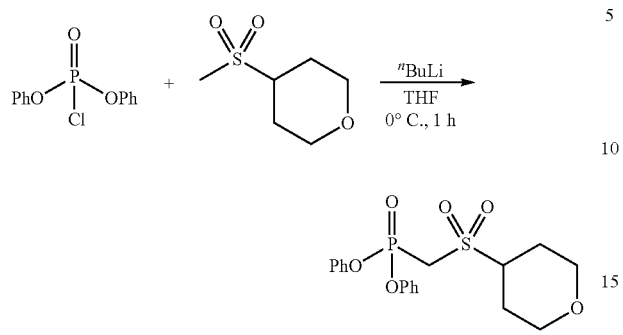

To a solution of 4-methylsulfonyltetrahydropyran (580 mg, 3.53 mmol) in THF (5 mL, 0.122 M), n-butyllithium solution (3.1 mL, 7.77 mmol, 2.5 M) was added at 0° C. The mixture was stirred at 0° C. for 0.5 hour, then diphenyl phosphorochloridate (948.8 mg, 3.53 mmol) was added. The mixture was stirred at 0° C. for 1 hour. The reaction mixture was poured into saturated aqueous NH$_4$Cl (30 mL) and extracted with EtOAc (3×30 mL). The combined organic layers were washed with brine (3×30 mL), dried over Na$_2$SO$_4$, filtered and concentrated under reduced pressure to give a residue. The residue was purified by flash silica gel chromatography (ISCO®; 12 g SepaFlash® Silica Flash Column, eluent of 0~40% ethyl acetate/petroleum ether gradient at 100 mL/min) to afford 4-(diphenoxyphosphorylmethylsulfonyl)tetrahydropyran as a yellow solid (1.0 g, 72% yield).

Using 4-(diphenoxyphosphorylmethylsulfonyl)tetrahydropyran/t-butyl 3-oxoazetidine-1-carboxylate/NaH at Step 1 and 2,2-dimethylpropanamidine hydrochloride at Step 3 in Procedure A, the title compound was obtained. LC-MS m/z: 472.1 [M+1].

Example 63

(R,E)-2-(tert-butyl)-N-(1-methoxy-4-(methylsulfonyl)but-3-en-2-yl)-4-phenoxypyrimidine-5-carboxamide

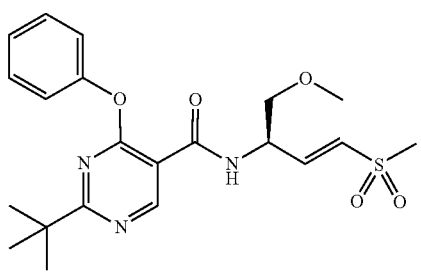 [SMILES: COC[C@@H](/C=C/S(C)(=O)=O)NC(=O)c1cnc(C(C)(C)C)nc1Oc1ccccc1]

Using tert-butyl N-[(1S)-1-formyl-2-methoxy-ethyl]carbamate/NaH at Step 1 and 2,2-dimethylpropanamidine hydrochloride at Step 3 in Procedure A, the title compound was obtained. LC-MS m/z: 434.2 [M+1].

Example 64

(S,E)-2-(tert-butyl)-N-(1-methoxy-4-(methylsulfonyl)but-3-en-2-yl)-4-phenoxypyrimidine-5-carboxamide

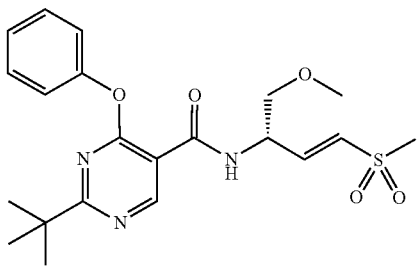 [SMILES: COC[C@H](/C=C/S(C)(=O)=O)NC(=O)c1cnc(C(C)(C)C)nc1Oc1ccccc1]

Using (2R)-2-{[(tert-butoxy)carbonyl]amino}-3-methoxypropanoic acid at the first step to follow the procedure for the compound of Example 63, the title compound was obtained. LC-MS m/z: 434.2 [M+1].

Example 65

(S,E)-2-(tert-butyl)-N-(1-cyclopropyl-4-(methylsulfonyl)but-3-en-2-yl)-4-phenoxypyrimidine-5-carboxamide

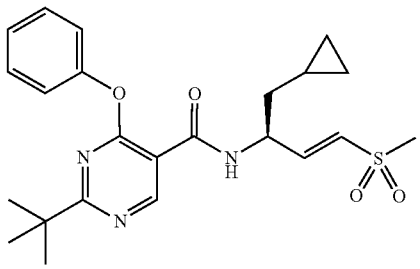 [SMILES: CC(C)(C)c1ncc(C(=O)N[C@H](/C=C/S(C)(=O)=O)CC2CC2)c(Oc2ccccc2)n1]

Using tert-butyl N-[(1S)-1-(cyclopropylmethyl)-2-oxo-ethyl]carbamate/Cs$_2$CO$_3$ at Step 1 and 2,2-dimethylpropanamidine hydrochloride at Step 3 in Procedure A, the title compound was obtained. LC-MS m/z: 444.2 [M+1].

Example 66

(S,E)-2-(tert-butyl)-N-(1-cyclobutyl-3-(methylsulfonyl)allyl)-4-phenoxypyrimidine-5-carboxamide

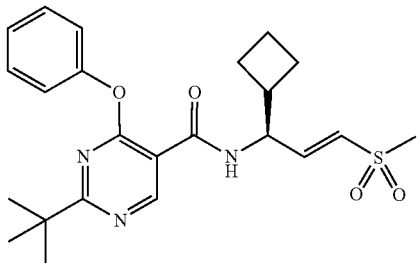 [SMILES: CC(C)(C)c1ncc(C(=O)N[C@H](/C=C/S(C)(=O)=O)C2CCC2)c(Oc2ccccc2)n1]

Using tert-butyl N-[(1S)-1-cyclobutyl-2-oxo-ethyl]carbamate/Cs₂CO₃ at Step 1 and 2,2-dimethylpropanamidine hydrochloride at Step 3 in Procedure A, the title compound was obtained. LC-MS m/z: 444.2 [M+1].

Example 67

(S,E)-2-(tert-butyl)-N-(1-(3,3-difluorocyclobutyl)-3-(methylsulfonyl)allyl)-4-phenoxypyrimidine-5-carboxamide

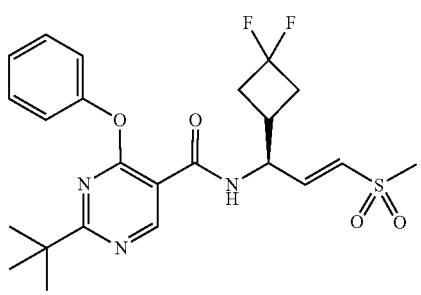 [SMILES: CC(C)(C)c1ncc(C(=O)N[C@H](/C=C/S(C)(=O)=O)C2CC(F)(F)C2)c(Oc2ccccc2)n1]

Using tert-butyl N-[(1S)-1-(3,3-difluorocyclobutyl)-2-oxo-ethyl]carbamate/Cs₂CO₃ at Step 1 and 2,2-dimethylpropanamidine hydrochloride at Step 3 in Procedure A, the title compound was obtained. LC-MS m/z: 480.2 [M+1].

Example 68

(R,E)-2-(tert-butyl)-N-(4-(methylsulfonyl)-1-(methylthio)but-3-en-2-yl)-4-phenoxypyrimidine-5-carboxamide

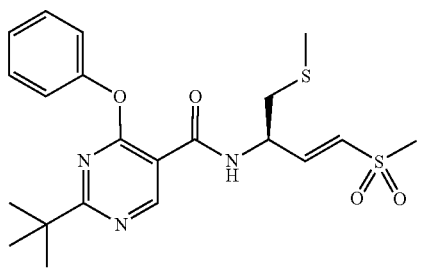 [SMILES: CSC[C@@H](/C=C/S(C)(=O)=O)NC(=O)c1cnc(C(C)(C)C)nc1Oc1ccccc1]

Using tert-butyl N-[(1R)-1-formyl-2-methylsulfanyl-ethyl]carbamate/Cs₂CO₃ at Step 1 and 2,2-dimethylpropanamidine hydrochloride at Step 3 in Procedure A, the title compound was obtained. LC-MS m/z: 450.0 [M+1].

Example 69

2-(tert-butyl)-N-((3R,4R,E)-4-methoxy-1-(methylsulfonyl)pent-1-en-3-yl)-4-phenoxypyrimidine-5-carboxamide

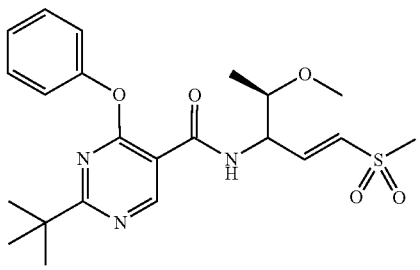 [SMILES: CO[C@H](C)C(/C=C/S(C)(=O)=O)NC(=O)c1cnc(C(C)(C)C)nc1Oc1ccccc1]

Using tert-butyl N-[(1S,2R)-1-formyl-2-methoxy-propyl]carbamate/Cs₂CO₃ at Step 1 and 2,2-dimethylpropanamidine hydrochloride at Step 3 in Procedure A, the title compound was obtained. LC-MS m/z: 448.2 [M+1].

Example 70

(S,E)-2-(tert-butyl)-N-(3-(methylsulfonyl)-1-(tetrahydro-2H-pyran-4-yl)allyl)-4-phenoxypyrimidine-5-carboxamide

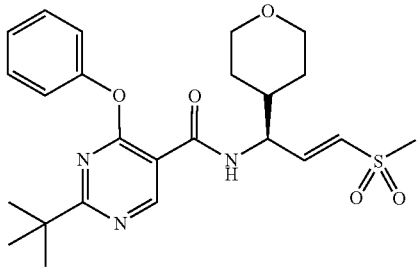 [SMILES: CC(C)(C)c1ncc(C(=O)N[C@H](/C=C/S(C)(=O)=O)C2CCOCC2)c(Oc2ccccc2)n1]

Using tert-butyl N-[(1S)-2-oxo-1-tetrahydropyran-4-yl-ethyl]carbamate/Cs₂CO₃ at Step 1 and 2,2-dimethylpropanamidine hydrochloride at Step 3 in Procedure A, the title compound was obtained. LC-MS m/z: 474.2 [M+1].

Example 71

(S,E)-2-(tert-butyl)-N-(5-(dimethylamino)-1-(methylsulfonyl)-5-oxopent-1-en-3-yl)-4-phenoxypyrimidine-5-carboxamide

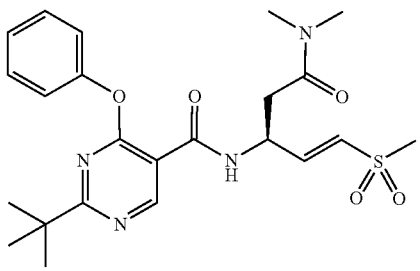 [SMILES: CN(C)C(=O)C[C@@H](/C=C/S(C)(=O)=O)NC(=O)c1cnc(C(C)(C)C)nc1Oc1ccccc1]

Using (2S)-2-(tert-butoxycarbonylamino)-4-(dimethylamino)-4-oxo-butanoic acid at Step 1 and following Step 2 of the procedure for the compound of Example 28, tert-butyl N-[(1S)-3-(dimethylamino)-1-formyl-3-oxo-propyl]carbamate was obtained. Using tert-butyl N-[(1S)-3-(dimethylamino)-1-formyl-3-oxo-propyl]carbamate/Cs₂CO₃ at Step 1 and 2,2-dimethylpropanamidine hydrochloride at Step 3 in Procedure A, the title compound was obtained. LC-MS m/z: 475.2 [M+1].

Example 72

(S,E)-2-(tert-butyl)-N-(1-(4,4-difluorocyclohexyl)-3-(methylsulfonyl)allyl)-4-phenoxypyrimidine-5-carboxamide

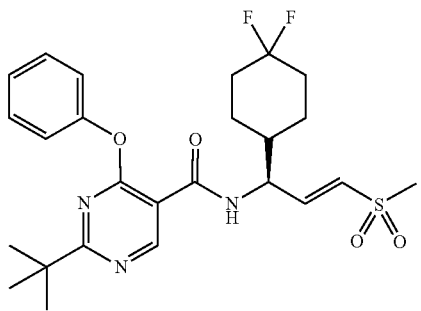 [SMILES: CC(C)(C)c1ncc(C(=O)N[C@H](/C=C/S(C)(=O)=O)C2CCC(F)(F)CC2)c(Oc2ccccc2)n1]

Using (2S)-2-(tert-butoxycarbonylamino)-2-(4,4-difluorocyclohexyl)acetic acid at Step 1 and following Step 2 of the procedure for the compound of Example 28, tert-butyl N-[(1S)-1-(4,4-difluorocyclohexyl)-2-oxo-ethyl]carbamate was obtained. Using tert-butyl N-[(1S)-1-(4,4-difluorocyclohexyl)-2-oxo-ethyl]carbamate/Cs₂CO₃ at Step 1 and 2,2-dimethylpropanamidine hydrochloride at Step 3 in Procedure A, the title compound was obtained. LC-MS m/z: 508.2 [M+1].

Example 73

(S,E)-2-(tert-butyl)-N-(5,5-difluoro-1-(methylsulfonyl)pent-1-en-3-yl)-4-phenoxypyrimidine-5-carboxamide

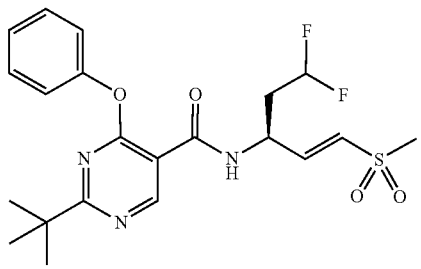 [SMILES: CC(C)(C)c1ncc(C(=O)N[C@H](/C=C/S(C)(=O)=O)CC(F)F)c(Oc2ccccc2)n1]

Using (2S)-2-(tert-butoxycarbonylamino)-4,4-difluoro-butanoic acid at Step 1 and following Step 2 of the procedure for the compound of Example 28, tert-butyl N-[(1S)-3,3-difluoro-1-formyl-propyl]carbamate was obtained. Using tert-butyl N-[(1S)-3,3-difluoro-1-formyl-propyl]carbamate/Cs₂CO₃ at Step 1 and 2,2-dimethylpropanamidine hydrochloride at Step 3 in Procedure A, the title compound was obtained. LC-MS m/z: 454.0 [M+1].

Examples 74 and 75

(R,E)-2-(tert-butyl)-N-(4-(methylsulfonyl)-1-phenoxybut-3-en-2-yl)-4-phenoxypyrimidine-5-carboxamide/(S,E)-2-(tert-butyl)-N-(4-(methylsulfonyl)-1-phenoxybut-3-en-2-yl)-4-phenoxypyrimidine-5-carboxamide

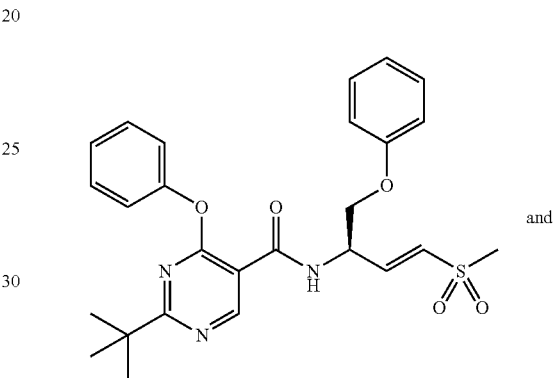

and

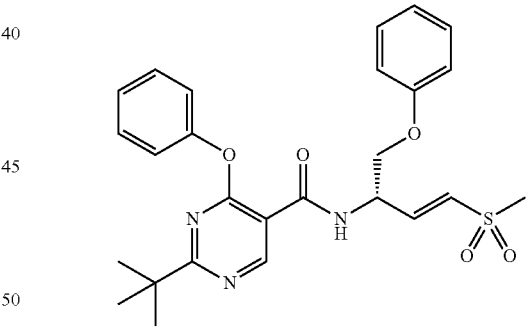

2-(tert-butoxycarbonylamino)-3-phenoxy-propanoic acid was converted to tert-butyl N-(1-formyl-2-phenoxy-ethyl)carbamate via LiBH4 reduction followed by DMP oxidation. Using tert-butyl N-(1-formyl-2-phenoxy-ethyl)carbamate/NaH at Step 1 and 2,2-dimethylpropanamidine hydrochloride at Step 3 in Procedure A, the mixture of the title compounds was obtained. The mixture was separated by chiral SFC (column: Chiralpak IG-3) to afford Peak 1 (LC-MS m/z: 496.3 [M+1]) and Peak 2 (LC-MS m/z: 496.3 [M+1]). The absolute stereochemistry of the title compounds were not ascertained.

Example 76

(E)-2-cyclohexyl-N-(3-(methylsulfonyl)allyl)-4-phenoxypyrimidine-5-carboxamide

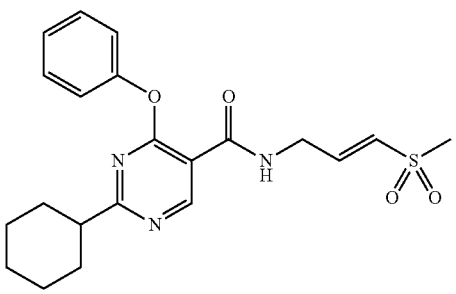 [SMILES: CS(=O)(=O)/C=C/CNC(=O)c1cnc(C2CCCCC2)nc1Oc1ccccc1]

Using cyclohexanecarboxamidine hydrochloride at Step 3 in Procedure A, the title compound was obtained. LC-MS m/z: 416.1 [M+1].

Example 77

(S,E)-2-cyclohexyl-N-(4-(methylsulfonyl)but-3-en-2-yl)-4-phenoxypyrimidine-5-carboxamide

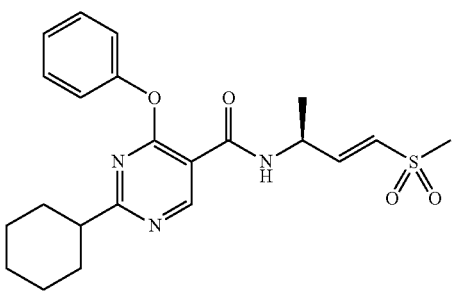 [SMILES: C[C@@H](/C=C/S(C)(=O)=O)NC(=O)c1cnc(C2CCCCC2)nc1Oc1ccccc1]

Using tert-butyl N-[(1S)-1-methyl-2-oxo-ethyl]carbamate/NaH at Step 1 and using cyclohexanecarboxamidine hydrochloride at Step 3 in Procedure A, the title compound was obtained. LC-MS m/z: 430.2 [M+1].

Example 78

N—((S,E)-4-(methylsulfonyl)but-3-en-2-yl)-4-phenoxy-2-(tetrahydrofuran-2-yl)pyrimidine-5-carboxamide

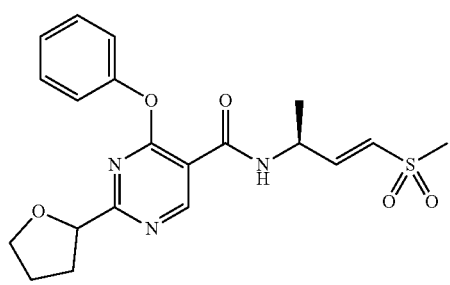 [SMILES: C[C@@H](/C=C/S(C)(=O)=O)NC(=O)c1cnc(C2CCCO2)nc1Oc1ccccc1]

Using tert-butyl N-[(1S)-1-methyl-2-oxo-ethyl]carbamate/NaH at Step 1 and tetrahydrofuran-2-carboxamidine at Step 3 in Procedure A, the title compound was obtained. LC-MS m/z: 418.1 [M+1].

Example 79

N—((S,E)-4-(methylsulfonyl)but-3-en-2-yl)-4-phenoxy-2-(tetrahydrofuran-3-yl)pyrimidine-5-carboxamide

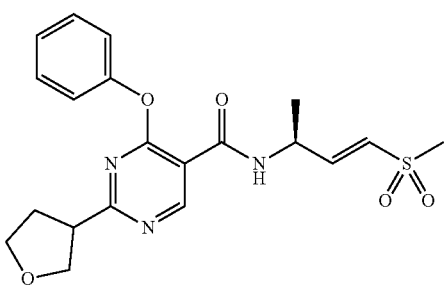 [SMILES: C[C@@H](/C=C/S(C)(=O)=O)NC(=O)c1cnc(C2CCOC2)nc1Oc1ccccc1]

Using tert-butyl N-[(1S)-1-methyl-2-oxo-ethyl]carbamate/NaH at Step 1 and tetrahydrofuran-3-carboxamidine at Step 3 in Procedure A, the title compound was obtained. LC-MS m/z: 418.1 [M+1].

Example 80

(S,E)-N-(4-(methylsulfonyl)but-3-en-2-yl)-4-phenoxy-2-phenylpyrimidine-5-carboxamide

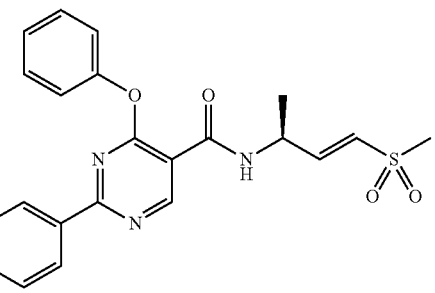

Using tert-butyl N-[(1S)-1-methyl-2-oxo-ethyl]carbamate/NaH at Step 1 and using benzamidine hydrochloride at Step 3 in Procedure A, the title compound was obtained. LC-MS m/z: 424.1 [M+1].

Example 81

(S,E)-N-(4-(methylsulfonyl)but-3-en-2-yl)-4-phenoxy-2-(trifluoromethyl)pyrimidine-5-carboxamide

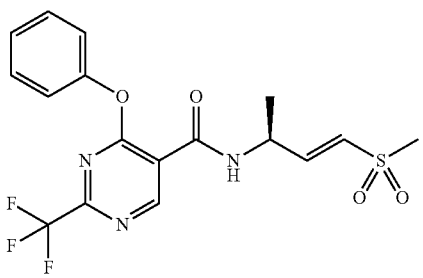 [SMILES: C[C@@H](/C=C/S(C)(=O)=O)NC(=O)c1cnc(C(F)(F)F)nc1Oc1ccccc1]

Starting Step 5 and using ethyl 4-chloro-2-(trifluoromethyl)pyrimidine-5-carboxylate at Step 5 and [(E,1S)-1-methyl-3-methylsulfonyl-allyl]amine 4-methylbenzenesulfonic acid at Step 7 in Procedure A, the title compound was obtained. LC-MS m/z: 416.0 [M+1].

Example 82

(S,E)-N-(1-cyclopropyl-3-(methylsulfonyl)allyl)-4-phenoxy-2-(trifluoromethyl)pyrimidine-5-carboxamide

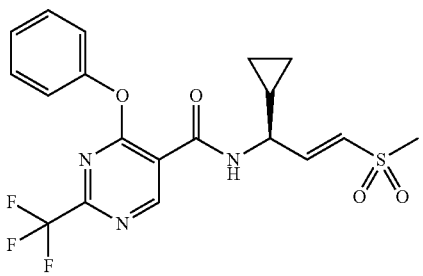 [SMILES: CS(=O)(=O)/C=C/[C@@H](NC(=O)c1cnc(C(F)(F)F)nc1Oc1ccccc1)C1CC1]

Starting Step 5 and using ethyl 4-chloro-2-(trifluoromethyl)pyrimidine-5-carboxylate at Step 5 and [(E,1S)-1-cyclopropyl-3-methylsulfonyl-allyl]amine 4-methylbenzenesulfonic acid at Step 7 in Procedure A, the title compound was obtained. LC-MS m/z: 442.1 [M+1].

Example 83

(S,E)-N-(4-(methylsulfonyl)but-3-en-2-yl)-2-(perfluoroethyl)-4-phenoxypyrimidine-5-carboxamide

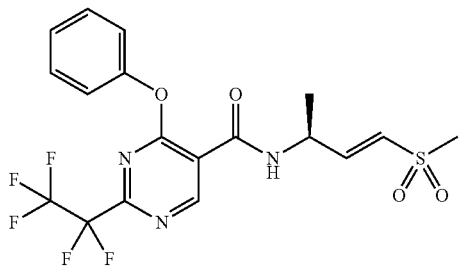 [SMILES: C[C@@H](/C=C/S(C)(=O)=O)NC(=O)c1cnc(C(F)(F)C(F)(F)F)nc1Oc1ccccc1]

Using tert-butyl N-[(1S)-1-methyl-2-oxo-ethyl]carbamate/NaH at Step 1, 2,2,3,3,3-pentafluoropropanamidine at Step 3 in Procedure A, the title compound was obtained. LC-MS m/z: 466.1 [M+1].

Example 84

(S,E)-N-(1-cyclopropyl-3-(methylsulfonyl)allyl)-2-(perfluoroethyl)-4-phenoxypyrimidine-5-carboxamide

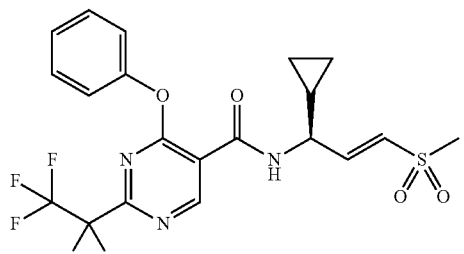

Using tert-butyl N-[(1S)-1-cyclopropyl-2-oxo-ethyl]carbamate/NaH at Step 1, 2,2,3,3,3-pentafluoropropanamidine at Step 3 in Procedure A, the title compound was obtained. LC-MS m/z: 492.1 [M+1].

Example 85

(R,E)-N-(1-methoxy-4-(methylsulfonyl)but-3-en-2-yl)-2-(perfluoroethyl)-4-phenoxypyrimidine-5-carboxamide

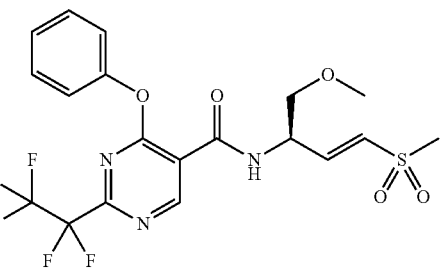

Using tert-butyl N-[(1S)-1-formyl-2-methoxy-ethyl]carbamate/NaH at Step 1 2,2,3,3,3-pentafluoropropanamidine at Step 3 in Procedure A, the title compound was obtained. LC-MS m/z: 496.1 [M+1].

Example 86

(S,E)-2-(1,1-difluoroethyl)-N-(4-(methylsulfonyl)but-3-en-2-yl)-4-phenoxypyrimidine-5-carboxamide

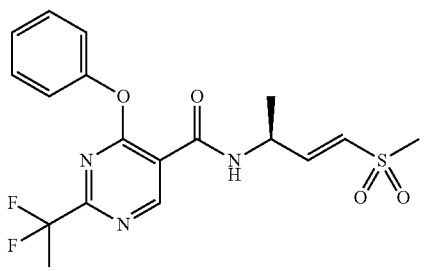

Step 1

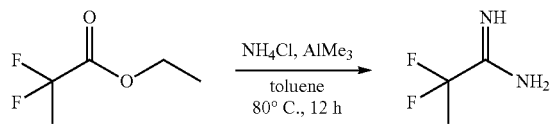

Ammonium chloride (3.87 g, 72.41 mmol) was suspended in toluene (40 mL, 0.362 M) under an argon atmosphere, and the mixture was cooled to 0° C. Triethylaluminium in hexane (41 mL, 2 M) was added dropwise, and the reaction mixture was stirred at 25° C. until no more evolution of gas was observed. After addition of ethyl 2,2-difluoropropanoate (2 g, 14.48 mmol), the mixture was stirred at 80° C. for 12 hours. It was then cooled to 0° C., and methanol (80 mL) were added with consequent stirring for 1 hour at 25° C. After filtration, the solid was washed with methanol for several times and the solution was concentrated under reduced pressure to afford crude 2,2-difluoropropanamidine as a white solid (1.40 g, 89% yield).

Using tert-butyl N-[(1S)-1-methyl-2-oxo-ethyl]carbamate/NaH at Step 1 and 2,2-difluoropropanamidine at Step 3 in Procedure A, the title compound was obtained. LC-MS m/z: 412.1 [M+1].

Example 87

(S,E)-N-(1-cyclopropyl-3-(methylsulfonyl)allyl)-2-(1,1-difluoroethyl)-4-phenoxypyrimidine-5-carboxamide

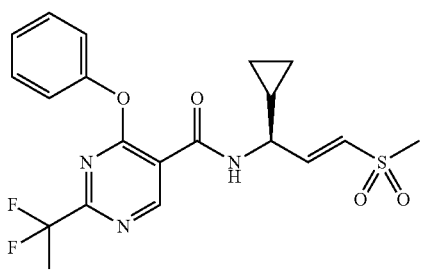

Using tert-butyl N-[(1S)-1-cyclopropyl-2-oxo-ethyl]carbamate/NaH for Step 1 and 2,2-difluoropropanamidine at Step 3 in Procedure A, the title compound was obtained. LC-MS m/z: 438.1 [M+1].

Example 88

(S,E)-N-(1-cyclobutyl-3-(methylsulfonyl)allyl)-2-(1,1-difluoroethyl)-4-phenoxypyrimidine-5-carboxamide

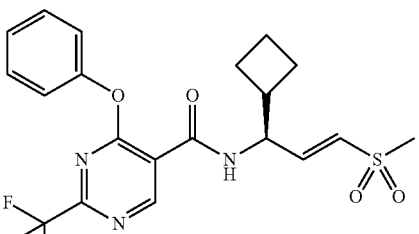

Using tert-butyl N-[(1S)-1-cyclobutyl-2-oxo-ethyl]carbamate/NaH for Step 1 and 2,2-difluoropropanamidine at Step 3 in Procedure A, the title compound was obtained. LC-MS m/z: 452.1 [M+1].

Example 89

(R,E)-2-(1,1-difluoroethyl)-N-(1-methoxy-4-(methylsulfonyl)but-3-en-2-yl)-4-phenoxypyrimidine-5-carboxamide

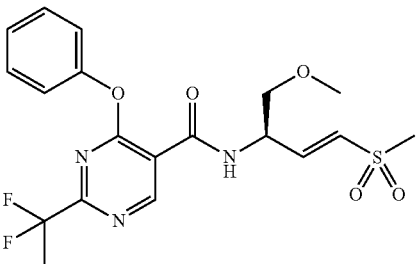

Using tert-butyl N-[(1S)-1-formyl-2-methoxy-ethyl]carbamate/NaH at Step 1 and 2,2-difluoropropanamidine at Step 3 in Procedure A, the title compound was obtained. LC-MS m/z: 442.1 [M+1].

Example 90

(S,E)-N-(5,5-difluoro-1-(methylsulfonyl)pent-1-en-3-yl)-2-(1,1-difluoroethyl)-4-phenoxypyrimidine-5-carboxamide

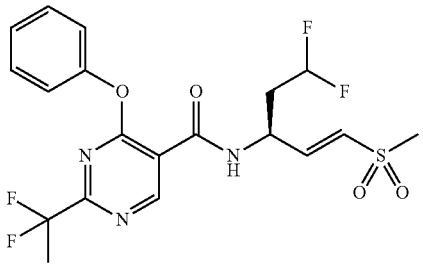 [SMILES: CC(F)(F)c1ncc(C(=O)N[C@H](/C=C/S(C)(=O)=O)CC(F)F)c(Oc2ccccc2)n1]

Using tert-butyl N-[(1S)-3,3-difluoro-1-formyl-propyl]carbamate/NaH at Step 1 and 2,2-difluoropropanamidine at Step 3 in Procedure A, the title compound was obtained. LC-MS m/z: 462.0 [M+1].

Example 91

(S,E)-N-(1-(4,4-difluorocyclohexyl)-3-(methylsulfonyl)allyl)-2-(1,1-difluoroethyl)-4-phenoxypyrimidine-5-carboxamide

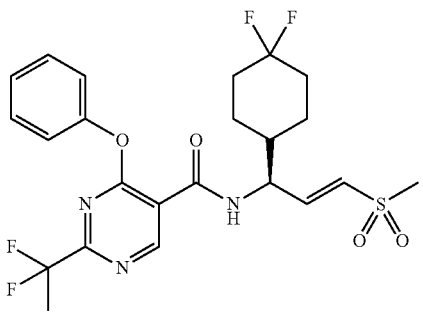 [SMILES: CC(F)(F)c1ncc(C(=O)N[C@H](/C=C/S(C)(=O)=O)C2CCC(F)(F)CC2)c(Oc2ccccc2)n1]

Using tert-butyl N-[(1S)-1-(4,4-difluorocyclohexyl)-2-oxo-ethyl]carbamate/NaH at Step 1 and 2,2-difluoropropanamidine at Step 3 in Procedure A, the title compound was obtained. LC-MS m/z: 516.0 [M+1].

Example 92

(S,E)-2-(1,1-difluoroethyl)-N-(5-(dimethylamino)-1-(methylsulfonyl)-5-oxopent-1-en-3-yl)-4-phenoxypyrimidine-5-carboxamide

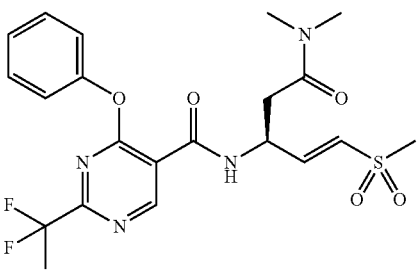 [SMILES: CN(C)C(=O)C[C@@H](/C=C/S(C)(=O)=O)NC(=O)c1cnc(C(C)(F)F)nc1Oc1ccccc1]

Using tert-butyl N-[(1S)-3-(dimethylamino)-1-formyl-3-oxo-propyl]carbamate/Cs$_2$CO$_3$ at Step 1 and 2,2-difluoropropanamidine at Step 3 in Procedure A, the title compound was obtained. LC-MS m/z: 483.0 [M+1].

Example 93

2-(1,1-difluoroethyl)-N-((3R,4S,E)-4-methoxy-1-(methylsulfonyl)pent-1-en-3-yl)-4-phenoxypyrimidine-5-carboxamide

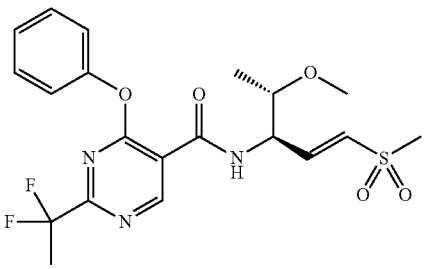 [SMILES: CO[C@@H](C)[C@@H](/C=C/S(C)(=O)=O)NC(=O)c1cnc(C(C)(F)F)nc1Oc1ccccc1]

Using (2S,3S)-2-(tert-butoxycarbonylamino)-3-methoxybutanoic acid at Step 1 to follow the procedure for the compound of Example 28, the title compound was obtained. LC-MS m/z: 456.0 [M+1].

Examples 94 and 95

(S,E)-2-(1,1-difluoroethyl)-4-phenoxy-N-(5,5,5-trifluoro-1-(methylsulfonyl)pent-1-en-3-yl)pyrimidine-5-carboxamide/(R,E)-2-(1,1-difluoroethyl)-4-phenoxy-N-(5,5,5-trifluoro-1-(methylsulfonyl)pent-1-en-3-yl)pyrimidine-5-carboxamide

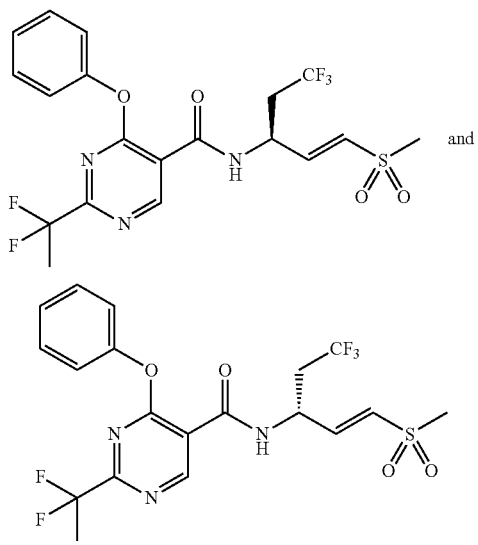

Step 1

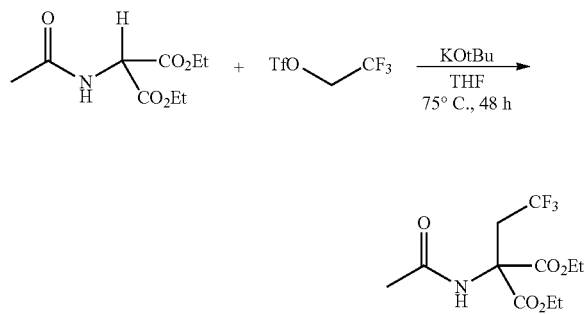

Potassium tert-butoxide (25.8 g, 23.02 mmol) was added dropwise to a mixture of diethyl 2-acetamidopropanedioate (5.0 g, 23.02 mmol) in THF (50 mL, 0.460 M) at 0° C. 2,2,2-trifluoroethyl trifluoromethanesulfonate (10.7 g, 46.04 mmol) was added. The result mixture was stirred at 75° C. for 48 hours. The mixture was poured into saturated aqueous NH$_4$Cl (80 mL) and extracted with EtOAc (2×100 mL). The combined organic layers were washed with brine (100 mL), filtered, concentrated under reduced pressure and purified by flash silica gel chromatography (ISCO®; 20 g SepaFlash® Silica Flash Column, Eluent of 0~70% Ethyl acetate/Petroleum ether gradient at 60 mL/min) to afford diethyl 2-acetamido-2-(2,2,2-trifluoroethyl)propanedioate as a yellow oil (2.0 g, 29% yield).

Step 2

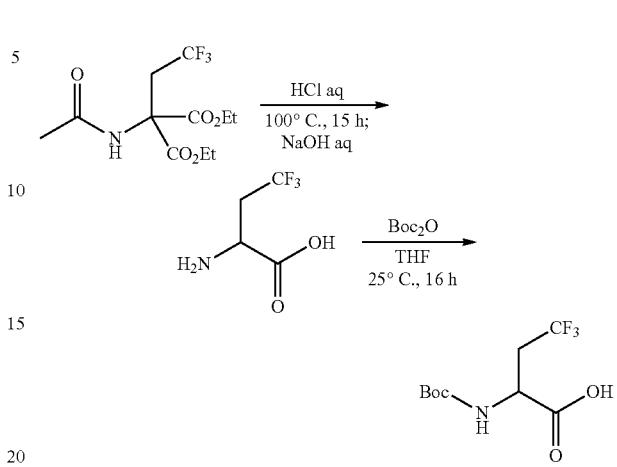

A mixture of diethyl 2-acetamido-2-(2,2,2-trifluoroethyl)propanedioate (2.0 g, 6.68 mmol) in 6N HCl (10 mL) was stirred at 100° C. for 15 hours. The mixture was adjusted to pH=10 with NaOH (aq, 6 M). The mixture was added THF (20 mL) followed by di-tert-butyl decarbonated (1.33 g, 6.11 mmol). The mixture was stirred at rt for 16 hours. The cloudy reaction mixture was neutralized with 1.0 M HCl (pH=4-5) and extracted with EtOAc (2×50 mL). The combined organic layers were dried over Na$_2$SO$_4$ and concentrated to afford crude 2-(tert-butoxycarbonylamino)-4,4,4-trifluoro-butanoic acid as a yellow oil (400 mg).

Step 3

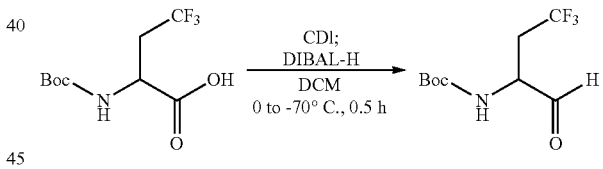

To a solution of 2-(tert-butoxycarbonylamino)-4,4,4-trifluoro-butanoic acid (100 mg, 0.39 mmol) in DCM (2 mL, 0.389 M) was added CDI (69 mg, 0.43 mmol) at 0° C. After stirring at 0° C. for 1 hour, DIBAl-H (0.82 mL, 0.82 mmol, 1 M) was added at −70° C. The reaction was stirred at −70° C. for 0.5 hour. Seignette salt (0.8 mL, sat) and EtOAc (0.8 mL) were added to the reaction dropwise at −70° C. The mixture was extracted with EtOAc (3×10 mL). The combined organic layers were washed with brine (10 mL), dried over Na$_2$SO$_4$, filtered and concentrated under reduced pressure to afford crude tert-butyl N-(3,3,3-trifluoro-1-formyl-propyl)carbamate as a yellow oil (50 mg).

Using tert-butyl N-(3,3,3-trifluoro-1-formyl-propyl)carbamate at Step 1 in Procedure A followed by chiral HPLC separation (column: Phenomenex-Cellulose-2 (250 mm*30 mm*5 um)) and following the subsequent steps separately while using 2,2-difluoropropanamidine at Step 3, the title compounds were obtained separately. Both showed LC-MS m/z: 480.1 [M+1]. The absolute stereochemistry of the title compounds were not ascertained.

Example 96

(R,E)-N-(1-(tert-butoxy)-4-(methylsulfonyl)but-3-en-2-yl)-2-(1,1-difluoroethyl)-4-phenoxypyrimidine-5-carboxamide

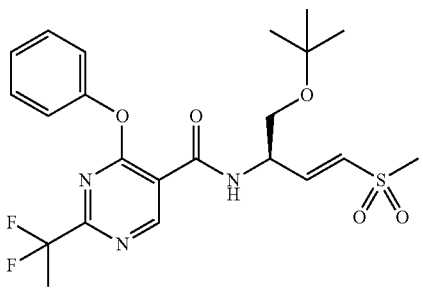 [SMILES: CC(C)(C)OC[C@@H](/C=C/S(C)(=O)=O)NC(=O)c1cnc(C(C)(F)F)nc1Oc1ccccc1]

Step 1

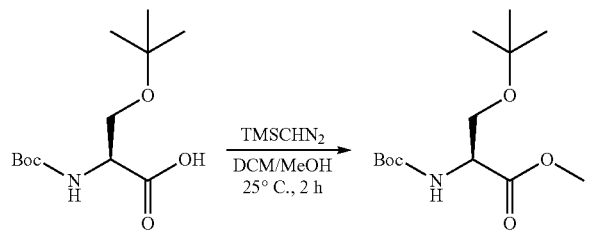 [SMILES: CC(C)(C)OC[C@H](NC(=O)OC(C)(C)C)C(=O)O ; "TMSCHN2" ; COC(=O)[C@H](COC(C)(C)C)NC(=O)OC(C)(C)C]

To a solution of N-(tert-butoxycarbonyl)-O-(tert-butyl)-L-serine (1 g, 3.83 mmol) in DCM (10 mL, 0.348 M) and methanol (1 mL, 0.348 M) was added (trimethylsilyl)diazomethane (3.83 mL, 7.65 mmol, 2 M) under $N_2$ at 0° C. The reaction mixture was stirred at 25° C. for 2 hours. The reaction mixture was quenched by the addition of saturated aqueous AcOH (1 mL) and concentrated under reduced pressure to afford crude methyl (2S)-3-tert-butoxy-2-(tert-butoxycarbonylamino)propanoate as a yellow oil (1.0 g).

Step 2

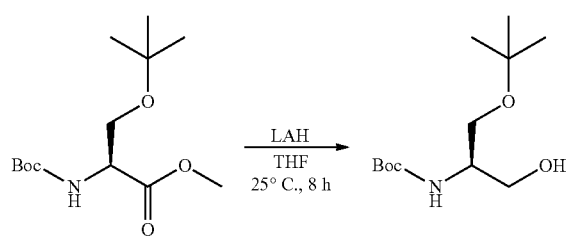 [SMILES: COC(=O)[C@H](COC(C)(C)C)NC(=O)OC(C)(C)C ; "LAH" ; CC(C)(C)OC[C@@H](CO)NC(=O)OC(C)(C)C]

To a solution of methyl (2S)-3-tert-butoxy-2-(tert-butoxycarbonylamino)propanoate (1 g, 3.63 mmol) in THF (10 mL, 0.363 M) was added lithium aluminum hydride solution (0.35 g, 9.08 mmol) at 0° C. The mixture was stirred at 25° C. for 8 hours. The reaction mixture was quenched by $Na_2SO_4 \cdot 10H_2O$, and filtered and concentrated under reduced pressure to give a residue. The residue was purified by column chromatography ($SiO_2$, Petroleum ether/Ethyl acetate=1:0 to 3:1) to give tert-butyl N-[(1R)-1-(tert-butoxymethyl)-2-hydroxy-ethyl]carbamate as a colorless oil (900 mg, 95% yield).

Using tert-butyl N-[(1R)-1-(tert-butoxymethyl)-2-hydroxy-ethyl]carbamate/Dess-Martin Periodinane/DCM to prepare tert-butyl N-[(1S)-1-(tert-butoxymethyl)-2-oxo-ethyl]carbamate for Step 1 and NaH as the base for Step 1 and using 2,2-difluoropropanamidine at Step 3 in Procedure A, the title compound was obtained. LC-MS m/z: 484.1 [M+1].

Example 97

(R,E)-N-(1-cyclopropoxy-4-(methylsulfonyl)but-3-en-2-yl)-2-(1,1-difluoroethyl)-4-phenoxypyrimidine-5-carboxamide

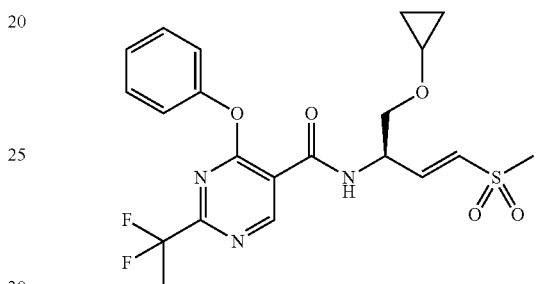

Step 1

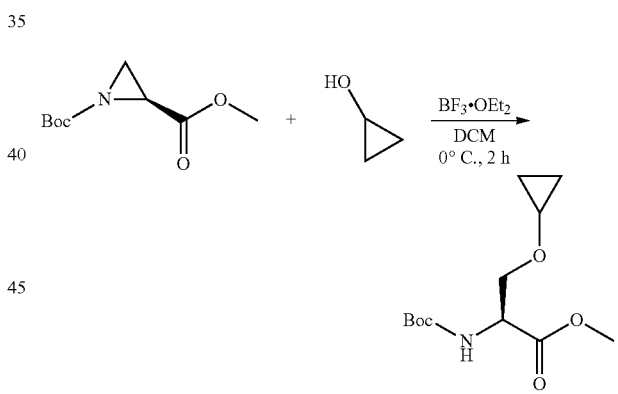

To a solution of 1-(tert-butyl) 2-methyl (S)-aziridine-1,2-dicarboxylate (800 mg, 3.98 mmol) was added boron trifluoride diethyl etherate (84.6 mg, 0.60 mmol) at 0° C. and cyclopropanol (461.8 mg, 7.95 mmol) in DCM (15 mL, 0.265 M). The mixture was stirred at 0° C. for 2 hours under $N_2$. The reaction mixture was diluted with $NaHCO_3$ (50 mL) and extracted with DCM (3×50 mL). The obtained organic layers were dried over $Na_2SO_4$, filtered and concentrated under reduced pressure to give a residue. The residue was purified by flash silica gel chromatography (PE/EA=0/1 to 5/1) to give methyl (2R)-2-(tert-butoxycarbonylamino)-3-(cyclopropoxy)propanoate as a colorless oil (530 mg, 51% yield).

Methyl (2R)-2-(tert-butoxycarbonylamino)-3-(cyclopropoxy)propanoate was converted to tert-butyl N-[(1S)-1-(cyclopropoxymethyl)-2-oxo-ethyl]carbamate via LAH reduction and DMP oxidation as described previously. Using tert-butyl N-[(1S)-1-(cyclopropoxymethyl)-2-oxo-ethyl]carbamate/NaH at Step 1 and 2,2-difluoropropanamidine at Step 3 in Procedure A, the title compound was obtained. LC-MS m/z: 468.1 [M+1].

Example 98

(R,E)-2-(1,1-difluoroethyl)-N-(1-(difluoromethoxy)-4-(methylsulfonyl)but-3-en-2-yl)-4-phenoxypyrimidine-5-carboxamide

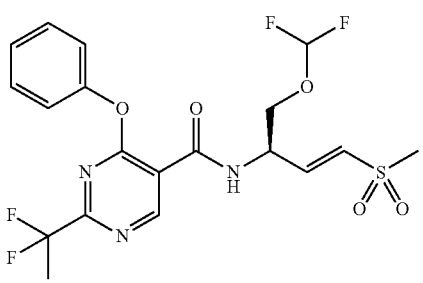 [SMILES: CC(F)(F)c1ncc(C(=O)N[C@H](/C=C/S(C)(=O)=O)COC(F)F)c(Oc2ccccc2)n1]

Step 1

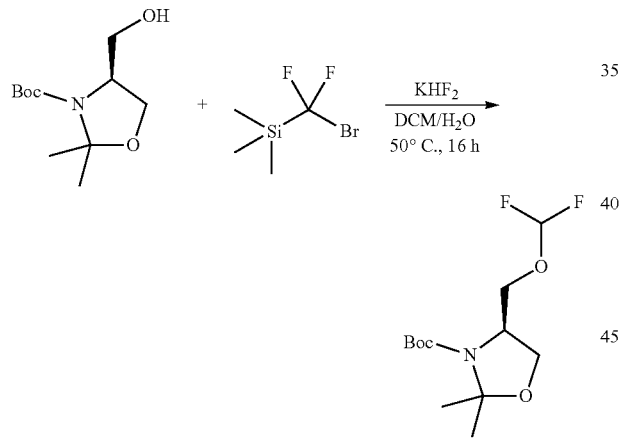

[Bromo(difluoro)methyl]trimethylsilane (4.5 g, 22.01 mmol) was added to a mixture of 3-tert-butyl (S)-4-(hydroxymethyl)-2,2-dimethyloxazolidine-3-carboxylate (2 g, 8.65 mmol) and potassium hydrogenfluoride (3.51 g, 44.97 mmol) in DCM (10 mL, 0.432 M) and water (10 mL, 0.432 M) at 0° C. The mixture was heated at 50° C. for 16 hours. The reaction mixture was poured into water (30 mL) and extracted with DCM (3×30 mL). The combined organic layers were washed with brine (2×20 mL), dried over Na₂SO₄, filtered and concentrated under reduced pressure to give a residue. The residue was purified by flash silica gel chromatography (ISCO®; 20 g SepaFlash® Silica Flash Column, Eluent of 0~5% Ethyl acetate/Petroleum ether gradient at 100 mL/min) to afford tert-butyl (4R)-4-(difluoromethoxymethyl)-2,2-dimethyl-oxazolidine-3-carboxylate as a yellow oil (1.20 g, 49% yield).

Step 2

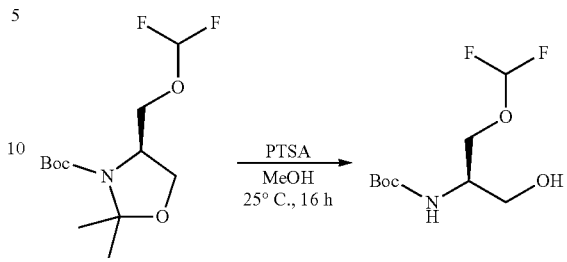

p-Toluenesulfonic acid monohydrate (162.29 mg, 0.85 mmol) was added to tert-butyl (4R)-4-(difluoromethoxymethyl)-2,2-dimethyl-oxazolidine-3-carboxylate (1.2 g, 4.27 mmol) in methanol (20 mL, 0.213 M). The mixture was stirred at 25° C. for 16 hours. The reaction mixture was poured into water (30 mL) and extracted with DCM (3×30 mL). The combined organic layers were washed with brine (2×10 mL), dried over Na₂SO₄, filtered and concentrated under reduced pressure to give a residue. The residue was purified by flash silica gel chromatography (ISCO®; 12 g SepaFlash® Silica Flash Column, Eluent of 0~20% Ethyl acetate/Petroleum ether gradient at 100 mL/min) to afford tert-butyl N-[(1R)-1-(difluoromethoxymethyl)-2-hydroxyethyl]carbamate as a colorless oil (800 mg, 78% yield).

Using N-[(1R)-1-(difluoromethoxymethyl)-2-hydroxyethyl]carbamate/Dess-Martin Periodinane/THF to prepare tert-butyl N-[(1S)-1-(difluoromethoxymethyl)-2-oxo-ethyl]carbamate for Step 1 and NaH as the base for Step 1 and using 2,2-difluoropropanamidine at Step 3 in Procedure A, the title compound was obtained. LC-MS m/z: 478.1 [M+1].

Example 99

(S,E)-2-(1-fluorocyclopropyl)-N-(4-(methylsulfonyl)but-3-en-2-yl)-4-phenoxypyrimidine-5-carboxamide

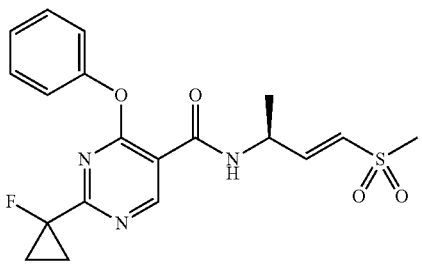 [SMILES: C[C@@H](/C=C/S(C)(=O)=O)NC(=O)c1cnc(C2(F)CC2)nc1Oc1ccccc1]

Using methyl 1-fluorocyclopropanecarboxylate to prepare 1-fluorocyclopropanecarboxamidine as in the procedure for the compound of Example 86 and using tert-butyl N-[(1S)-1-methyl-2-oxo-ethyl]carbamate/NaH at Step 1 and 1-fluorocyclopropanecarboxamidine at Step 3 in Procedure A, the title compound was obtained. LC-MS m/z: 406.1 [M+1].

Example 100

(S,E)-N-(1-cyclopropyl-3-(methylsulfonyl)allyl)-2-(1-fluorocyclopropyl)-4-phenoxypyrimidine-5-carboxamide

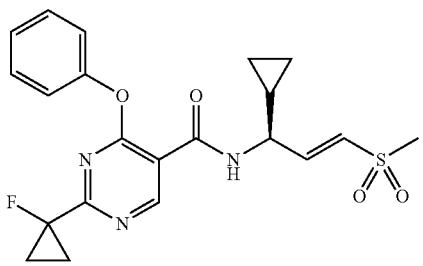 [SMILES: CS(=O)(=O)/C=C/[C@@H](NC(=O)c1cnc(C2(F)CC2)nc1Oc1ccccc1)C1CC1]

Using tert-butyl N-[(1S)-1-cyclopropyl-2-oxo-ethyl]carbamate/NaH at Step 1 and 1-fluorocyclopropanecarboxamidine at Step 3 in Procedure A, the title compound was obtained. LC-MS m/z: 432.1 [M+1].

Example 101

(S,E)-N-(4-(methylsulfonyl)but-3-en-2-yl)-4-phenoxy-2-(1-(trifluoromethyl)cyclopropyl)pyrimidine-5-carboxamide

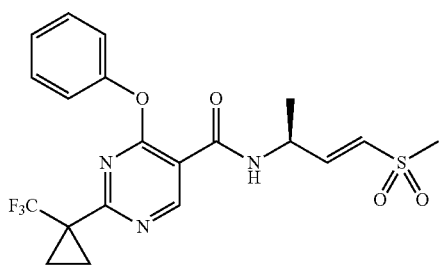 [SMILES: C[C@@H](/C=C/S(C)(=O)=O)NC(=O)c1cnc(C2(C(F)(F)F)CC2)nc1Oc1ccccc1]

Using ethyl 1-(trifluoromethyl)cyclopropanecarboxylate to prepare 1-(trifluoromethyl)cyclopropanecarboxamidine as in the procedure for the compound of Example 86 and using tert-butyl N-[(1S)-1-methyl-2-oxo-ethyl]carbamate/NaH at Step 1 and 1-(trifluoromethyl)cyclopropanecarboxamidine at Step 3 in Procedure A, the title compound was obtained. LC-MS m/z: 456.1 [M+1].

Example 102

(S,E)-N-(1-cyclopropyl-3-(methylsulfonyl)allyl)-4-phenoxy-2-(1-(trifluoromethyl)cyclopropyl)pyrimidine-5-carboxamide

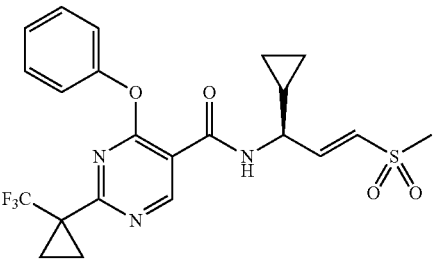 [SMILES: CS(=O)(=O)/C=C/[C@@H](NC(=O)c1cnc(C2(C(F)(F)F)CC2)nc1Oc1ccccc1)C1CC1]

Using tert-butyl N-[(1S)-1-cyclopropyl-2-oxo-ethyl]carbamate/NaH at Step 1 and 1-(trifluoromethyl)cyclopropanecarboxamidine at Step 3 in Procedure A, the title compound was obtained. LC-MS m/z: 482.2 [M+1].

Example 103

(S,E)-2-(3,3-difluorocyclobutyl)-N-(4-(methylsulfonyl)but-3-en-2-yl)-4-phenoxypyrimidine-5-carboxamide

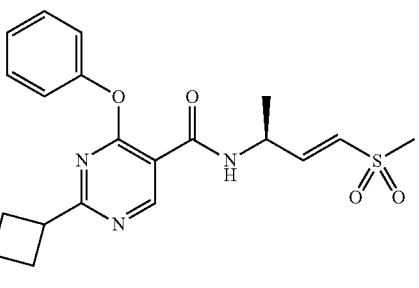

Step 1

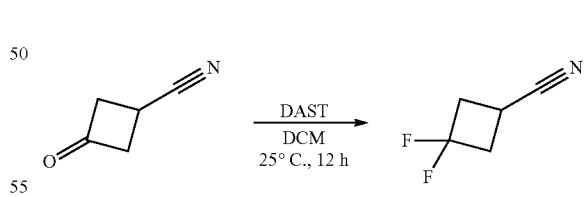

To a solution of 3-oxo-cyclobutanecarbonitrile (2.5 g, 26.29 mmol) in DCM (100 mL, 0.263 M) was added diethylaminosulfur trifluoride (8.5 g, 52.58 mmol) at 0° C., over 0.5 hour. The mixture was stirred at 25° C. for 12 hours under $N_2$. The reaction mixture was concentrated under reduced pressure to give a residue. The residue was diluted with water (20 mL) and the aqueous phase was extracted with DCM (3×30 mL). The combined organic layers were dried over $Na_2SO_4$, filtered and the filtrate was concentrated under reduced pressure to afford crude 3,3-difluorocyclobutanecarbonitrile as a brown oil (3.0 g).

Step 2

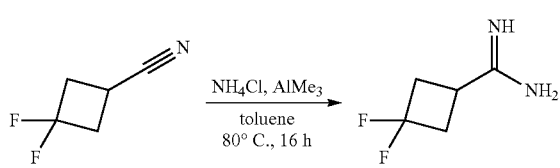

To a solution of ammonium chloride (685 mg, 12.81 mmol) in toluene (15 mL, 0.854 M) was added triethylaluminium (923 mg, 12.81 mmol) at 0° C. The reaction was stirred at 25° C. for 2 hours. 3,3-difluorocyclobutanecarbonitrile (1.5 g, 12.81 mmol) was added dropwise to the mixture. The mixture was stirred at 80° C. for 16 hours. The reaction mixture was cooled to temperature and slowly poured into a slurry of silica gel in DCM (10 mL) and stirred for 10 min. The silica was filtered and washed with MeOH (3×15 mL). The filtrate was concentrated under reduced pressure to afford crude 3,3-difluorocyclobutanecarboxamidine as a light brown solid (1.0 g).

Using tert-butyl N-[(1S)-1-methyl-2-oxo-ethyl]carbamate/NaH at Step 1 and 3,3-difluorocyclobutanecarboxamidine at Step 3 in Procedure A, the title compound was obtained. LC-MS m/z: 438.1 [M+1].

Example 104

(E)-2-cyclopentyl-N-(3-(methylsulfonyl)allyl)-4-(p-tolyloxy)pyrimidine-5-carboxamide

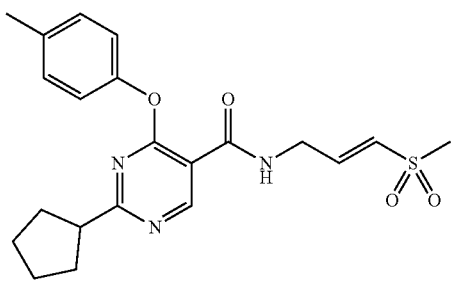

Using p-cresol at Step 5 in Procedure A, the title compound was obtained. LC-MS m/z: 416.1 [M+1].

Example 105

(S,E)-2-cyclopentyl-N-(4-(methylsulfonyl)but-3-en-2-yl)-4-(m-tolyloxy)pyrimidine-5-carboxamide

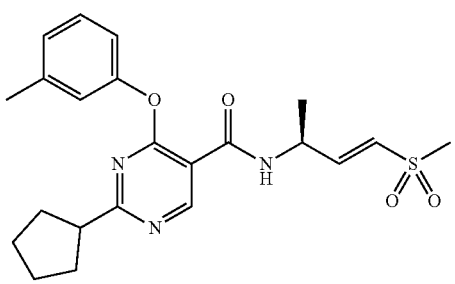

Using tert-butyl N-[(1S)-1-methyl-2-oxo-ethyl]carbamate/NaH at Step 1 and m-cresol at Step 5 in Procedure A, the title compound was obtained. LC-MS m/z: 430.1 [M+1].

Example 106

(S,E)-2-cyclopentyl-N-(4-(methylsulfonyl)but-3-en-2-yl)-4-(o-tolyloxy)pyrimidine-5-carboxamide

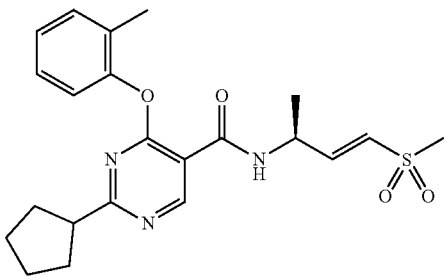 [SMILES: Cc1ccccc1Oc1nc(C2CCCC2)ncc1C(=O)N[C@@H](C)/C=C/S(C)(=O)=O]

Using tert-butyl N-[(1S)-1-methyl-2-oxo-ethyl]carbamate/NaH at Step 1 and o-cresol at Step 5 in Procedure A, the title compound was obtained. LC-MS m/z: 430.2 [M+1].

Example 107

(S,E)-2-cyclopentyl-4-(4-ethylphenoxy)-N-(4-(methylsulfonyl)but-3-en-2-yl)pyrimidine-5-carboxamide

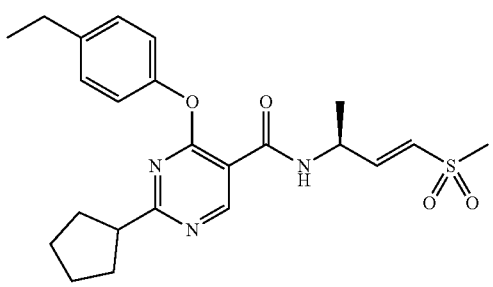 [SMILES: CCc1ccc(Oc2nc(C3CCCC3)ncc2C(=O)N[C@@H](C)/C=C/S(C)(=O)=O)cc1]

Using tert-butyl N-[(1S)-1-methyl-2-oxo-ethyl]carbamate/NaH at Step 1 and 4-ethylphenol at Step 5 in Procedure A, the title compound was obtained. LC-MS m/z: 444.2 [M+1].

Example 108

(S,E)-2-cyclopentyl-4-(3-ethylphenoxy)-N-(4-(methylsulfonyl)but-3-en-2-yl)pyrimidine-5-carboxamide

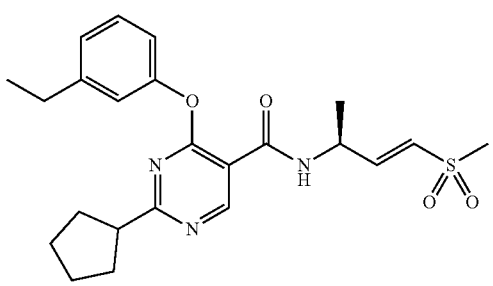 [SMILES: CCc1cccc(Oc2nc(C3CCCC3)ncc2C(=O)N[C@@H](C)/C=C/S(C)(=O)=O)c1]

Using tert-butyl N-[(1S)-1-methyl-2-oxo-ethyl]carbamate/NaH at Step 1 and 3-ethylphenol at Step 5 in Procedure A, the title compound was obtained. LC-MS m/z: 444.2 [M+1].

Example 109

(S,E)-2-cyclopentyl-4-(3,4-dimethylphenoxy)-N-(4-(methylsulfonyl)but-3-en-2-yl)pyrimidine-5-carboxamide

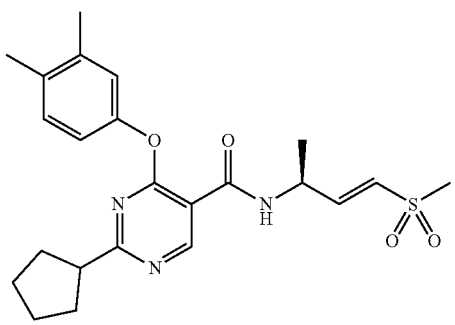

Using tert-butyl N-[(1S)-1-methyl-2-oxo-ethyl]carbamate/NaH at Step 1 and 3,4-dimethylphenol at Step 5 in Procedure A, the title compound was obtained. LC-MS m/z: 444.2 [M+1].

Example 110

(S,E)-2-cyclopentyl-4-(4-fluoro-3-methylphenoxy)-N-(4-(methylsulfonyl)but-3-en-2-yl)pyrimidine-5-carboxamide

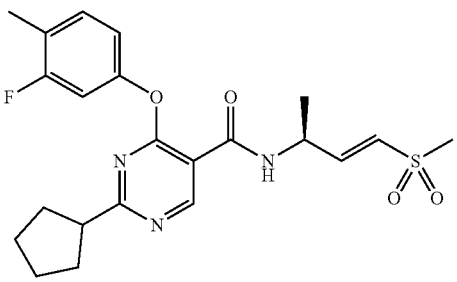

Using tert-butyl N-[(1S)-1-methyl-2-oxo-ethyl]carbamate/NaH at Step 1 and 3-fluoro-4-methylphenol at Step 5 in Procedure A, the title compound was obtained. LC-MS m/z: 448.2 [M+1].

Example 111

(E)-2-cyclopentyl-4-(3-fluorophenoxy)-N-(3-(methylsulfonyl)allyl)pyrimidine-5-carboxamide

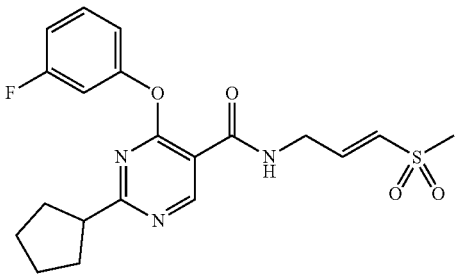 [SMILES: CS(=O)(=O)/C=C/CNC(=O)c1cnc(C2CCCC2)nc1Oc1cccc(F)c1]

Using 3-fluorophenol at Step 5 in Procedure A, the title compound was obtained. LC-MS m/z: 420.1 [M+1].

Example 112

(E)-2-cyclopentyl-4-(4-fluorophenoxy)-N-(3-(methylsulfonyl)allyl)pyrimidine-5-carboxamide

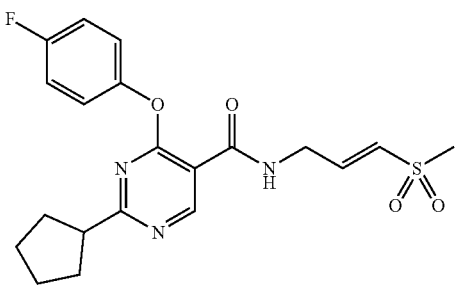 [SMILES: CS(=O)(=O)/C=C/CNC(=O)c1cnc(C2CCCC2)nc1Oc1ccc(F)cc1]

Using 4-fluorophenol at Step 5 in Procedure A, the title compound was obtained. LC-MS m/z: 420.1 [M+1].

Example 113

(S,E)-2-cyclopentyl-4-(4-fluorophenoxy)-N-(4-(methylsulfonyl)but-3-en-2-yl)pyrimidine-5-carboxamide

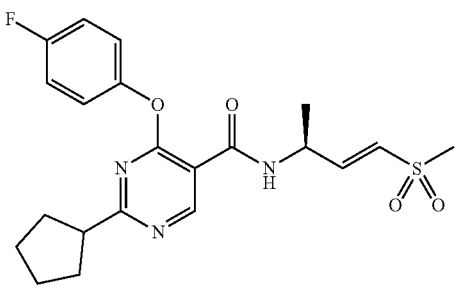 [SMILES: C[C@@H](/C=C/S(C)(=O)=O)NC(=O)c1cnc(C2CCCC2)nc1Oc1ccc(F)cc1]

Using tert-butyl N-[(1S)-1-methyl-2-oxo-ethyl]carbamate/NaH at Step 1 and 4-fluorophenol at Step 5 in Procedure A, the title compound was obtained. LC-MS m/z: 434.1 [M+1].

Example 114

(S,E)-2-cyclopentyl-4-(3-fluorophenoxy)-N-(4-(methylsulfonyl)but-3-en-2-yl)pyrimidine-5-carboxamide

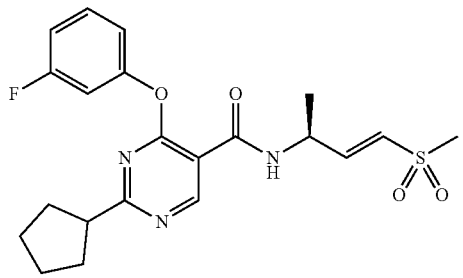 [SMILES: C[C@@H](/C=C/S(C)(=O)=O)NC(=O)c1cnc(C2CCCC2)nc1Oc1cccc(F)c1]

Using tert-butyl N-[(1S)-1-methyl-2-oxo-ethyl]carbamate/NaH at Step 1 and 3-fluorophenol at Step 5 in Procedure A, the title compound was obtained. LC-MS m/z: 434.1 [M+1].

Example 115

(S,E)-2-cyclopentyl-4-(2-fluorophenoxy)-N-(4-(methylsulfonyl)but-3-en-2-yl)pyrimidine-5-carboxamide

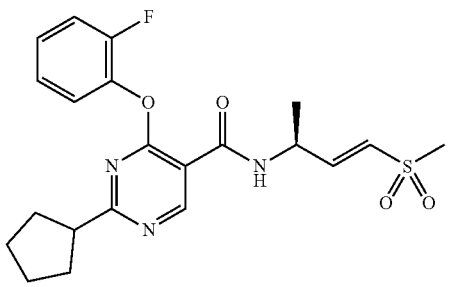 [SMILES: C[C@@H](/C=C/S(C)(=O)=O)NC(=O)c1cnc(C2CCCC2)nc1Oc1ccccc1F]

Using tert-butyl N-[(1S)-1-methyl-2-oxo-ethyl]carbamate/NaH at Step 1 and 2-fluorophenol at Step 5 in Procedure A, the title compound was obtained. LC-MS m/z: 434.1 [M+1].

Example 116

(S,E)-2-cyclopentyl-4-(3,5-difluorophenoxy)-N-(4-(methylsulfonyl)but-3-en-2-yl)pyrimidine-5-carboxamide

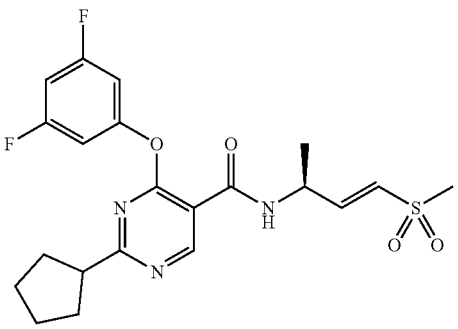 [SMILES: C[C@@H](/C=C/S(C)(=O)=O)NC(=O)c1cnc(C2CCCC2)nc1Oc1cc(F)cc(F)c1]

Using tert-butyl N-[(1S)-1-methyl-2-oxo-ethyl]carbamate/NaH at Step 1 and 3,5-difluorophenol at Step 5 in Procedure A, the title compound was obtained. LC-MS m/z: 452.1 [M+1].

Example 117

(E)-4-(3-chlorophenoxy)-2-cyclopentyl-N-(3-(methylsulfonyl)allyl)pyrimidine-5-carboxamide

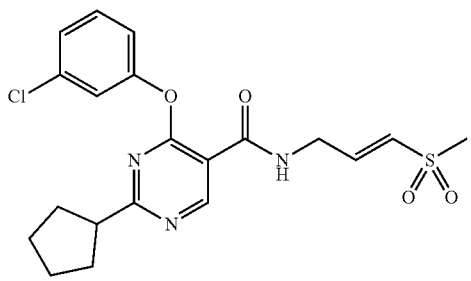 [SMILES: CS(=O)(=O)/C=C/CNC(=O)c1cnc(C2CCCC2)nc1Oc1cccc(Cl)c1]

Using 3-chlorophenol at Step 5 in Procedure A, the title compound was obtained. LC-MS m/z: 436.1 [M+1].

Example 118

(S,E)-4-(3-chlorophenoxy)-2-cyclopentyl-N-(4-(methylsulfonyl)but-3-en-2-yl)pyrimidine-5-carboxamide

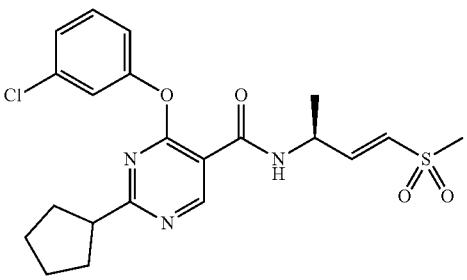 [SMILES: C[C@@H](/C=C/S(C)(=O)=O)NC(=O)c1cnc(C2CCCC2)nc1Oc1cccc(Cl)c1]

Using tert-butyl N-[(1S)-1-methyl-2-oxo-ethyl]carbamate/NaH at Step 1 and 3-chlorophenol at Step 5 in Procedure A, the title compound was obtained. LC-MS m/z: 450.1 [M+1].

Example 119

(S,E)-4-(2-chlorophenoxy)-2-cyclopentyl-N-(4-(methylsulfonyl)but-3-en-2-yl)pyrimidine-5-carboxamide

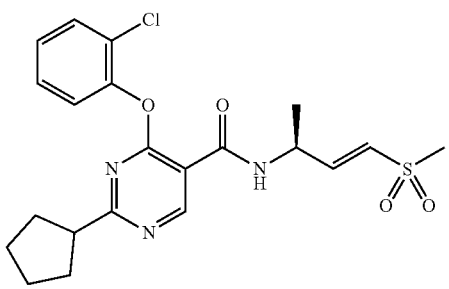 [SMILES: C[C@@H](/C=C/S(C)(=O)=O)NC(=O)c1cnc(C2CCCC2)nc1Oc1ccccc1Cl]

Using tert-butyl N-[(1S)-1-methyl-2-oxo-ethyl]carbamate/NaH at Step 1 and 2-chlorophenol at Step 5 in Procedure A, the title compound was obtained. LC-MS m/z: 450.1 [M+1].

Example 120

(E)-4-(4-chlorophenoxy)-2-cyclopentyl-N-(3-(methylsulfonyl)allyl)pyrimidine-5-carboxamide

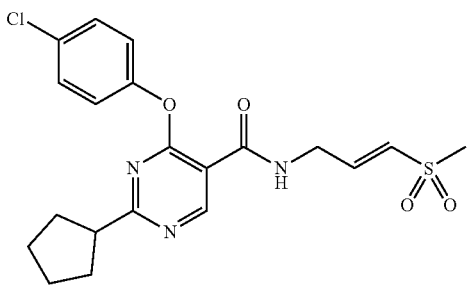 [SMILES: CS(=O)(=O)/C=C/CNC(=O)c1cnc(C2CCCC2)nc1Oc1ccc(Cl)cc1]

Using 4-chlorophenol at Step 5 in Procedure A, the title compound was obtained. LC-MS m/z: 436.1 [M+1].

Example 121

(S,E)-4-(4-chlorophenoxy)-2-cyclopentyl-N-(4-(methylsulfonyl)but-3-en-2-yl)pyrimidine-5-carboxamide

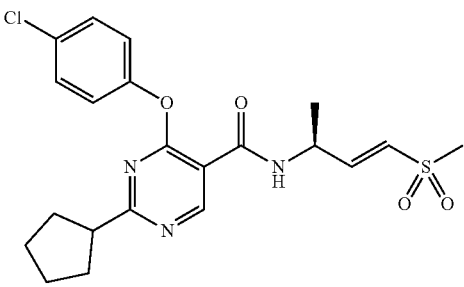 [SMILES: C[C@@H](/C=C/S(C)(=O)=O)NC(=O)c1cnc(C2CCCC2)nc1Oc1ccc(Cl)cc1]

Using tert-butyl N-[(1S)-1-methyl-2-oxo-ethyl]carbamate/NaH at Step 1 and 4-chlorophenol at Step 5 in Procedure A, the title compound was obtained. LC-MS m/z: 450.1 [M+1].

Example 122

(S,E)-4-(3-chloro-5-fluorophenoxy)-2-cyclopentyl-N-(4-(methylsulfonyl)but-3-en-2-yl)pyrimidine-5-carboxamide

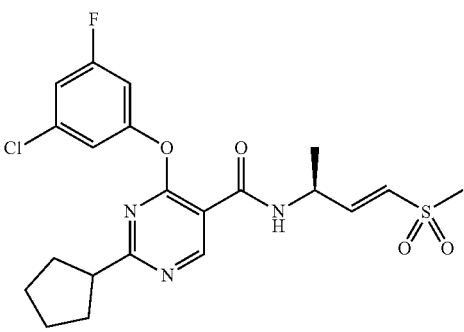 [SMILES: C[C@@H](/C=C/S(C)(=O)=O)NC(=O)c1cnc(C2CCCC2)nc1Oc1cc(F)cc(Cl)c1]

Using tert-butyl N-[(1S)-1-methyl-2-oxo-ethyl]carbamate/NaH at Step 1 and 3-chloro-5-fluorophenol at Step 5 in Procedure A, the title compound was obtained. LC-MS m/z: 468.1 [M+1].

Example 123

(S,E)-2-cyclopentyl-4-(3,5-dichlorophenoxy)-N-(4-(methylsulfonyl)but-3-en-2-yl)pyrimidine-5-carboxamide

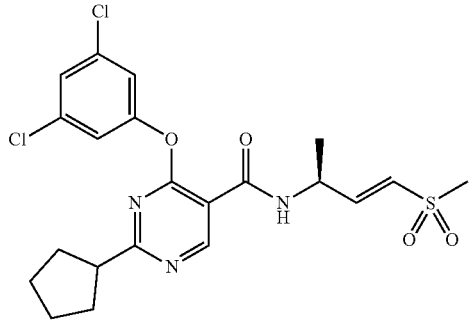

Using tert-butyl N-[(1S)-1-methyl-2-oxo-ethyl]carbamate/NaH at Step 1 and 3,5-dichlorophenol at Step 5 in Procedure A, the title compound was obtained. LC-MS m/z: 484.1 [M+1].

Example 124

(S,E)-4-(4-cyanophenoxy)-2-cyclopentyl-N-(4-(methylsulfonyl)but-3-en-2-yl)pyrimidine-5-carboxamide

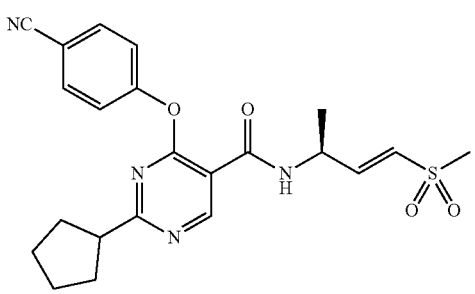 [SMILES: C[C@@H](/C=C/S(C)(=O)=O)NC(=O)c1cnc(C2CCCC2)nc1Oc1ccc(C#N)cc1]

Using tert-butyl N-[(1S)-1-methyl-2-oxo-ethyl]carbamate/NaH at Step 1 and 4-hydroxybenzonitrile at Step 5 in Procedure A, the title compound was obtained. LC-MS m/z: 441.2 [M+1].

Example 125

(S,E)-2-cyclopentyl-N-(4-(methylsulfonyl)but-3-en-2-yl)-4-(pyridin-3-yloxy)pyrimidine-5-carboxamide

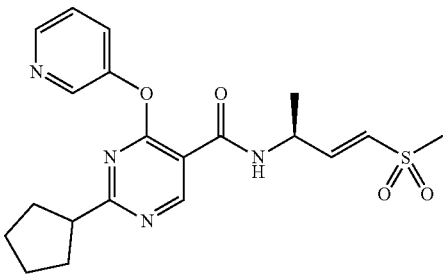 [SMILES: C[C@@H](/C=C/S(C)(=O)=O)NC(=O)c1cnc(C2CCCC2)nc1Oc1cccnc1]

Using tert-butyl N-[(1S)-1-methyl-2-oxo-ethyl]carbamate/NaH at Step 1 and 3-hydroxypyridine at Step 5 in Procedure A, the title compound was obtained. LC-MS m/z: 417.1 [M+1].

Example 126

(S,E)-2-cyclopentyl-N-(4-(methylsulfonyl)but-3-en-2-yl)-4-(pyridin-2-yloxy)pyrimidine-5-carboxamide

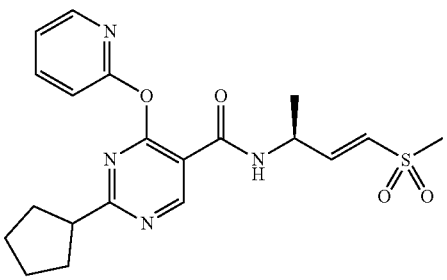 [SMILES: C[C@@H](/C=C/S(C)(=O)=O)NC(=O)c1cnc(C2CCCC2)nc1Oc1ccccn1]

Using tert-butyl N-[(1S)-1-methyl-2-oxo-ethyl]carbamate/NaH at Step 1 and pyridine-2-ol at Step 5 in Procedure A, the title compound was obtained. LC-MS m/z: 417.2 [M+1].

Example 127

(S,E)-4-cyclobutoxy-2-cyclopentyl-N-(4-(methylsulfonyl)but-3-en-2-yl)pyrimidine-5-carboxamide

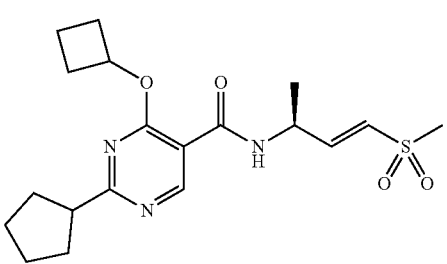 [SMILES: C[C@@H](/C=C/S(C)(=O)=O)NC(=O)c1cnc(C2CCCC2)nc1OC1CCC1]

Using tert-butyl N-[(1S)-1-methyl-2-oxo-ethyl]carbamate/NaH at Step 1 and cyclobutanol/potassium tert-butoxide/

Example 128

(S,E)-4-(cycloheptyloxy)-2-cyclopentyl-N-(4-(methylsulfonyl)but-3-en-2-yl)pyrimidine-5-carboxamide

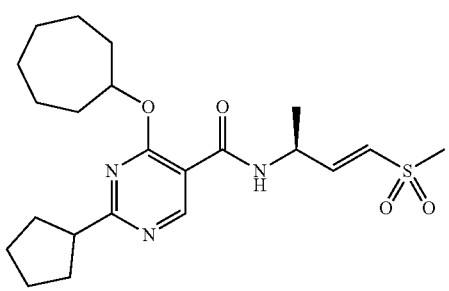 [SMILES: C[C@@H](/C=C/S(C)(=O)=O)NC(=O)c1cnc(C2CCCC2)nc1OC1CCCCCC1]

Using tert-butyl N-[(1S)-1-methyl-2-oxo-ethyl]carbamate/NaH at Step 1 and cycloheptanol/tBuOK/THF at Step 5 in Procedure A, the title compound was obtained. LC-MS m/z: 436.2 [M+1].

Examples 129 and 130

2-cyclopentyl-4-[(1S,2R)-2-hydroxycyclohexoxy]-N—[(E,1S)-1-methyl-3-methylsulfonyl-allyl]pyrimidine-5-carboxamide (Example 129)

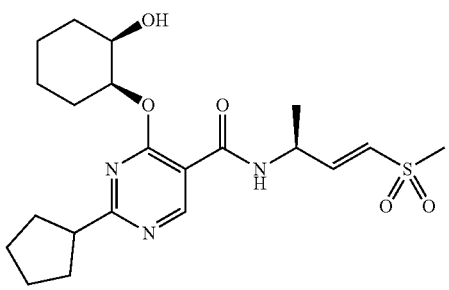 [SMILES: C[C@@H](/C=C/S(C)(=O)=O)NC(=O)c1cnc(C2CCCC2)nc1O[C@H]1CCCC[C@H]1O]

2-cyclopentyl-4-[(1R,2S)-2-hydroxycyclohexoxy]-N—[(E,1S)-1-methyl-3-methylsulfonyl-allyl]pyrimidine-5-carboxamide (Example 130)

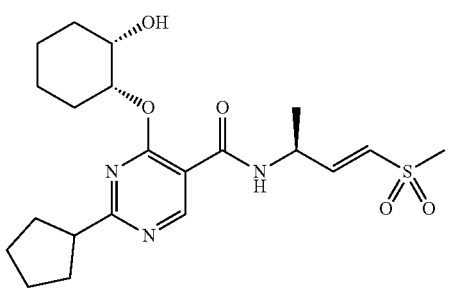 [SMILES: C[C@@H](/C=C/S(C)(=O)=O)NC(=O)c1cnc(C2CCCC2)nc1O[C@@H]1CCCC[C@@H]1O]

Using tert-butyl N-[(1S)-1-methyl-2-oxo-ethyl]carbamate/NaH at Step 1 and rac-(1R,2S)-cyclohexane-1,2-diol/NaH/THF at Step 5 in Procedure A, the mixture of the title compounds was obtained. The mixture was separated by Prep-HPLC (neutral condition) to afford Peak 1 (Compound of Example 129) (LC-MS m/z: 438.2 [M+1]) and Peak 2 (Compound of Example 130) LC-MS m/z: 438.2 [M+1]).

Examples 131 and 132

2-cyclopentyl-4-[(1S,2S)-2-hydroxycyclohexoxy]-N—[(E,1S)-1-methyl-3-methylsulfonyl-allyl]pyrimidine-5-carboxamide (Example 131)

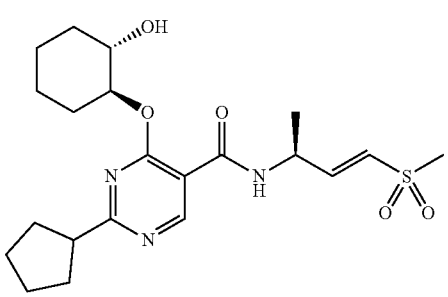 [SMILES: C[C@@H](/C=C/S(C)(=O)=O)NC(=O)c1cnc(C2CCCC2)nc1O[C@H]1CCCC[C@@H]1O]

2-cyclopentyl-4-[(1R,2R)-2-hydroxycyclohexoxy]-N—[(E,1S)-1-methyl-3-methylsulfonyl-allyl]pyrimidine-5-carboxamide (Example 132)

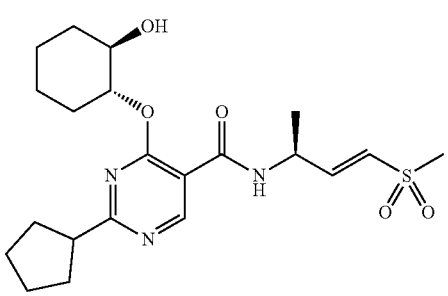 [SMILES: C[C@@H](/C=C/S(C)(=O)=O)NC(=O)c1cnc(C2CCCC2)nc1O[C@@H]1CCCC[C@H]1O]

Using tert-butyl N-[(1S)-1-methyl-2-oxo-ethyl]carbamate/NaH at Step 1 and rac-(1S,2S)-cyclohexane-1,2-diol/NaH/THF at Step 5 in Procedure A, the mixture of the title compounds was obtained. The mixture was separated by Prep-HPLC (neutral condition) to afford Peak 1 (LC-MS m/z: 438.2 [M+1]) and Peak 2 (LC-MS m/z: 438.2 [M+1]).

Example 133

(S,E)-2-cyclopentyl-N-(4-(methylsulfonyl)but-3-en-2-yl)-4-((tetrahydro-2H-pyran-4-yl)oxy)pyrimidine-5-carboxamide

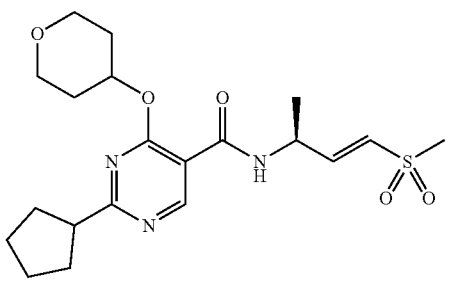

Using tert-butyl N-[(1S)-1-methyl-2-oxo-ethyl]carbamate/NaH at Step 1 and tetrahydro-2H-pyran-4-ol/NaH/DMF at Step 5 in Procedure A, the title compound was obtained. LC-MS m/z: 424.2 [M+1].

Example 134

2-cyclopentyl-N—((S,E)-4-(methylsulfonyl)but-3-en-2-yl)-4-(((S)-tetrahydro-2H-pyran-3-yl)oxy)pyrimidine-5-carboxamide

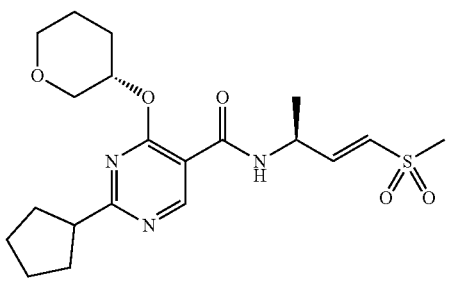

Using tert-butyl N-[(1S)-1-methyl-2-oxo-ethyl]carbamate/NaH at Step 1 and (3S)-tetrahydropyran-3-ol/LiHMDS/THF at Step 5 in Procedure A, the title compound was obtained. LC-MS m/z: 424.2 [M+1].

Example 135

(S,E)-2-cyclopentyl-4-(4-hydroxyphenoxy)-N-(4-(methylsulfonyl)but-3-en-2-yl)pyrimidine-5-carboxamide

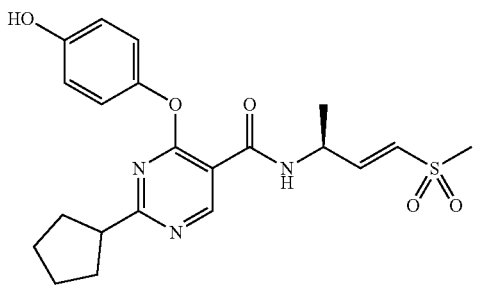

Using tert-butyl N-[(1S)-1-methyl-2-oxo-ethyl]carbamate/NaH at Step 1 and hydroquinone at Step 5 in Procedure A, the title compound was obtained. LC-MS m/z: 432.2 [M+1].

Example 136

(S,E)-2-cyclopentyl-4-(3-hydroxyphenoxy)-N-(4-(methylsulfonyl)but-3-en-2-yl)pyrimidine-5-carboxamide

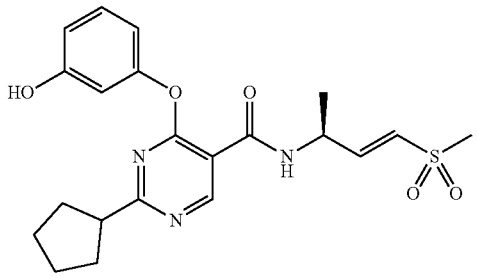 [SMILES: C[C@@H](/C=C/S(C)(=O)=O)NC(=O)c1cnc(C2CCCC2)nc1Oc1cccc(O)c1]

Using tert-butyl N-[(1S)-1-methyl-2-oxo-ethyl]carbamate/NaH at Step 1 and resorcinol at Step 5 in Procedure A, the title compound was obtained. LC-MS m/z: 432.2 [M+1].

Example 137

(S,E)-2-cyclopentyl-4-(2-hydroxyphenoxy)-N-(4-(methylsulfonyl)but-3-en-2-yl)pyrimidine-5-carboxamide

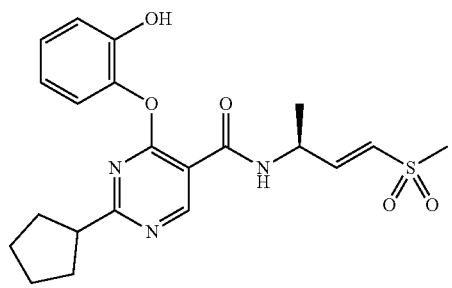 [SMILES: C[C@@H](/C=C/S(C)(=O)=O)NC(=O)c1cnc(C2CCCC2)nc1Oc1ccccc1O]

Using tert-butyl N-[(1S)-1-methyl-2-oxo-ethyl]carbamate/NaH at Step 1 and catechol at Step 5 in Procedure A, the title compound was obtained. LC-MS m/z: 432.2 [M+1].

Example 138

(S,E)-4-(3-aminophenoxy)-2-cyclopentyl-N-(4-(methylsulfonyl)but-3-en-2-yl)pyrimidine-5-carboxamide

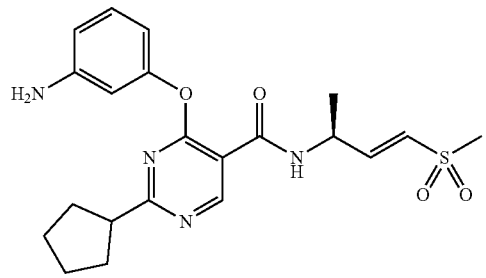 [SMILES: C[C@@H](/C=C/S(C)(=O)=O)NC(=O)c1cnc(C2CCCC2)nc1Oc1cccc(N)c1]

Using tert-butyl N-[(1S)-1-methyl-2-oxo-ethyl]carbamate/NaH at Step 1 and tert-Butyl 3-hydroxyphenylcarbamate at Step 5 in Procedure A, tert-butyl N-[3-[2-cyclopentyl-5-[[(E,1S)-1-methyl-3-methylsulfonyl-allyl]carbamoyl]pyrimidin-4-yl]oxyphenyl]carbamate was obtained as a yellow solid.

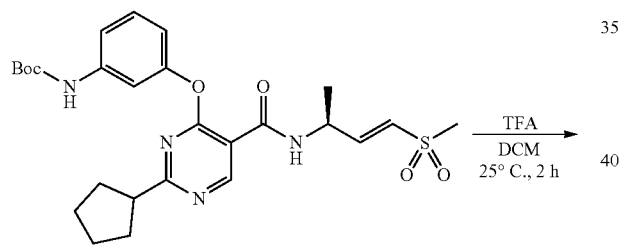

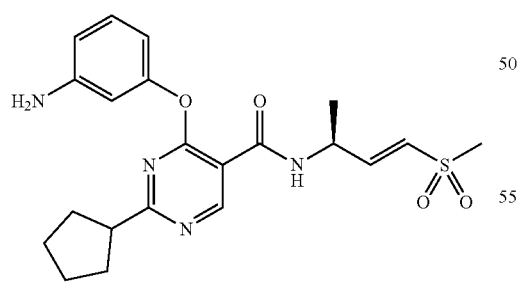

To a solution of tert-butyl N-[3-[2-cyclopentyl-5-[[(E,1S)-1-methyl-3-methylsulfonyl-allyl]carbamoyl]pyrimidin-4-yl]oxyphenyl]carbamate (50 mg, 0.094 mmol) in DCM (2 mL) was added TFA (0.4 mL) at 0° C. The mixture was stirred at 25° C. for 2 hours. The reaction mixture was concentrated under reduced pressure to give a residue. The residue was dissolved in MeCN (1 mL), and the resulting solution was purified by prep-HPLC to afford the title compound as a yellow solid (17.8 mg). LC-MS m/z: 431.2 [M+1].

Example 139

(S,E)-2-cyclopentyl-N-(4-(methylsulfonyl)but-3-en-2-yl)-4-(naphthalen-1-yloxy)pyrimidine-5-carboxamide

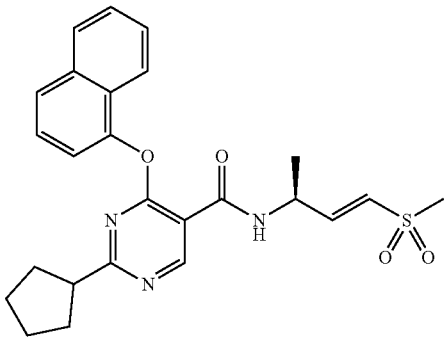 [SMILES: C[C@@H](/C=C/S(C)(=O)=O)NC(=O)c1cnc(C2CCCC2)nc1Oc1cccc2ccccc12]

Using tert-butyl N-[(1S)-1-methyl-2-oxo-ethyl]carbamate/NaH at Step 1 and naphthalen-1-ol at Step 3 in Procedure A, the title compound was obtained. LC-MS m/z: 466.2 [M+1].

Example 140

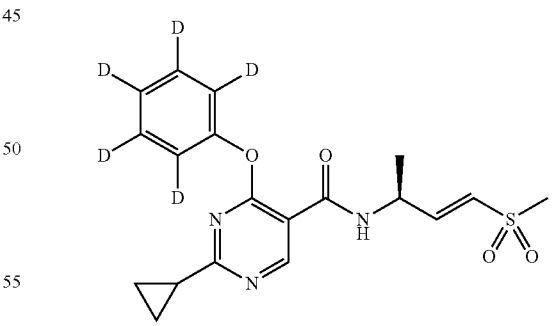

Using tert-butyl N-[(1S)-1-methyl-2-oxo-ethyl]carbamate/NaH at Step 1, cyclopropanecarboxamidine at Step 3 and 1,2,3,4,5-pentadeuterio-6-deuteriooxy-benzene at Step 5 in Procedure A, the title compound was obtained. LC-MS m/z: 393.2 [M+1].

Example 141

(S,E)-2-cyclopropyl-N-(4-(methylsulfonyl)but-3-en-2-yl)-4-(spiro[3.3]heptan-2-yloxy)pyrimidine-5-carboxamide

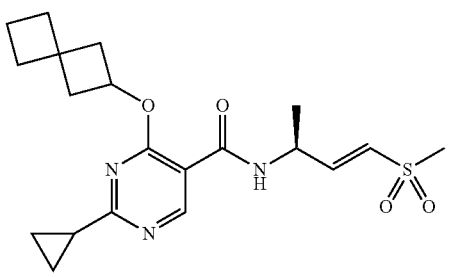 [SMILES: C[C@@H](/C=C/S(C)(=O)=O)NC(=O)c1cnc(C2CC2)nc1OC1CC2(CCC2)C1]

Using tert-butyl N-[(1S)-1-methyl-2-oxo-ethyl]carbamate/NaH at Step 1, cyclopropanecarboxamidine at Step 3 and spiro[3.3]heptan-2-ol/LiHMDS/THF at Step 5 in Procedure A, the title compound was obtained. LC-MS m/z: 406.2 [M+1].

Example 142

(S,E)-2-cyclopropyl-N-(4-(methylsulfonyl)but-3-en-2-yl)-4-(spiro[2.3]hexan-5-yloxy)pyrimidine-5-carboxamide

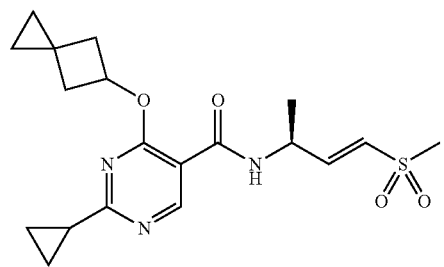 [SMILES: C[C@@H](/C=C/S(C)(=O)=O)NC(=O)c1cnc(C2CC2)nc1OC1CC2(CC2)C1]

Using tert-butyl N-[(1S)-1-methyl-2-oxo-ethyl]carbamate/NaH at Step 1, cyclopropanecarboxamidine at Step 3 and spiro[2.3]hexan-5-ol/LiHMDS/THF at Step 5 in Procedure A, the title compound was obtained. LC-MS m/z: 392.0 [M+1].

Example 143

(S,E)-4-(bicyclo[2.2.1]heptan-1-yloxy)-2-cyclopropyl-N-(4-(methylsulfonyl)but-3-en-2-yl)pyrimidine-5-carboxamide

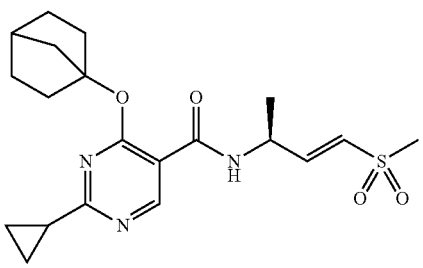 [SMILES: C[C@@H](/C=C/S(C)(=O)=O)NC(=O)c1cnc(C2CC2)nc1OC12CCC(CC1)C2]

Using tert-butyl N-[(1S)-1-methyl-2-oxo-ethyl]carbamate/NaH at Step 1, cyclopropanecarboxamidine at Step 3 and norbornan-1-ol/LiHMDS/THF at Step 5 in Procedure A, the title compound was obtained. LC-MS m/z: 406.2 [M+1].

Example 144

(S,E)-4-(cyclopentyloxy)-2-cyclopropyl-N-(4-(methylsulfonyl)but-3-en-2-yl)pyrimidine-5-carboxamide

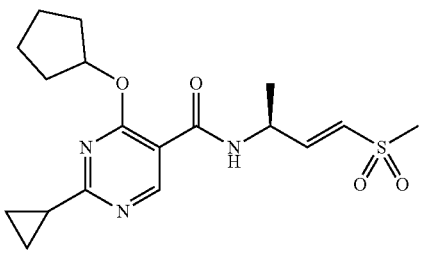 [SMILES: C[C@@H](/C=C/S(C)(=O)=O)NC(=O)c1cnc(C2CC2)nc1OC1CCCC1]

Using tert-butyl N-[(1S)-1-methyl-2-oxo-ethyl]carbamate/NaH at Step 1, cyclopropanecarboxamidine at Step 3 and cyclopentanol/LiHMDS/THF at Step 5 in Procedure A, the title compound was obtained. LC-MS m/z: 380.2 [M+1].

Example 145

4-(((1R,3s,5S)-bicyclo[3.1.0]hexan-3-yl)oxy)-2-(tert-butyl)-N—((E)-3-(methylsulfonyl)allyl)pyrimidine-5-carboxamide

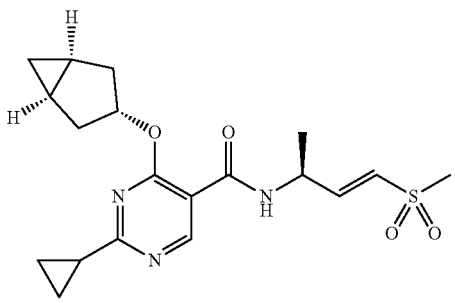 [SMILES: C[C@@H](/C=C/S(C)(=O)=O)NC(=O)c1cnc(C2CC2)nc1O[C@H]1C[C@@H]2C[C@@H]2C1]

Using tert-butyl N-[(1S)-1-methyl-2-oxo-ethyl]carbamate/NaH at Step 1, cyclopropanecarboxamidine at Step 3 and (1S,5R)-bicyclo[3.1.0]hexan-3-ol/LiHMDS/THF at Step 5 in Procedure A, the title compound was obtained. LC-MS m/z: 378.0 [M+1].

Example 146

2-cyclopropyl-4-((3,3-difluorocyclopentyl)oxy)-N—((S,E)-4-(methylsulfonyl)but-3-en-2-yl)pyrimidine-5-carboxamide

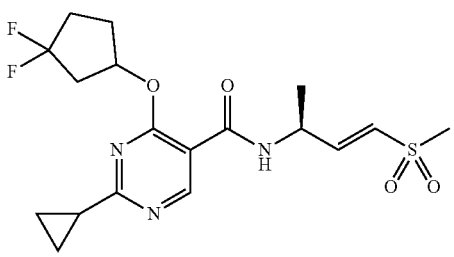 [SMILES: C[C@@H](/C=C/S(C)(=O)=O)NC(=O)c1cnc(C2CC2)nc1OC1CCC(F)(F)C1]

Using tert-butyl N-[(1S)-1-methyl-2-oxo-ethyl]carbamate/NaH at Step 1, cyclopropanecarboxamidine at Step 3 and 3,3-difluorocyclopentanol/LiHMDS/THF at Step 5 in Procedure A, the title compound was obtained. LC-MS m/z: 416.0 [M+1].

Examples 147 and 148

2-cyclopropyl-4-(((S)-2,2-difluorocyclopentyl)oxy)-N—((S,E)-4-(methylsulfonyl)but-3-en-2-yl)pyrimidine-5-carboxamide/2-cyclopropyl-4-(((R)-2,2-difluorocyclopentyl)oxy)-N—((S,E)-4-(methylsulfonyl)but-3-en-2-yl)pyrimidine-5-carboxamide

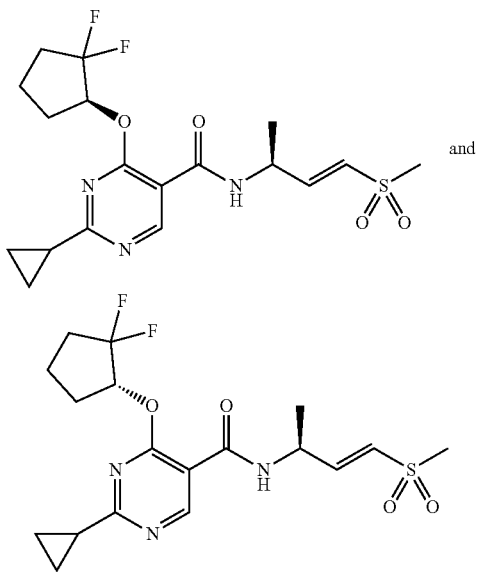

Using tert-butyl N-[(1S)-1-methyl-2-oxo-ethyl]carbamate/NaH at Step 1, cyclopropanecarboxamidine at Step 3 and 2,2-difluorocyclopentanol/LiHMDS/THF at Step 5 in Procedure A, the mixture of the title compounds was obtained. The mixture was separated by Prep-HPLC (reverse phase, H₂O/MeCN=5 to 95%) to afford Peak 1 (LC-MS m/z: 416.0 [M+1]) and Peak 2 (LC-MS m/z: 416.0 [M+1]). The absolute stereochemistry of these compounds were not ascertained.

Example 149

2-cyclopropyl-4-(((1R,2R)-2-fluorocyclohexyl)oxy)-N—((S,E)-4-(methylsulfonyl)but-3-en-2-yl)pyrimidine-5-carboxamide; or 2-cyclopropyl-4-(((1S,2S)-2-fluorocyclohexyl)oxy)-N—((S,E)-4-(methylsulfonyl)but-3-en-2-yl)pyrimidine-5-carboxamide

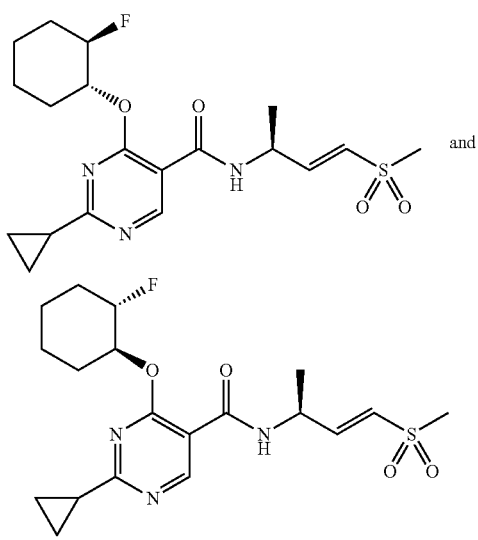

Using tert-butyl N-[(1S)-1-methyl-2-oxo-ethyl]carbamate/NaH at Step 1, cyclopropanecarboxamidine at Step 3 and rac-(1R,2R)-2-fluorocyclohexanol/LiHMDS/THF at Step 5 in Procedure A, the title compound was obtained. LC-MS m/z: 412.0 [M+1]. The absolute stereochemistry of these compounds were not ascertained.

Example 150

(S,E)-2-cyclopropyl-4-(cyclopropylmethoxy)-N-(4-(methylsulfonyl)but-3-en-2-yl)pyrimidine-5-carboxamide

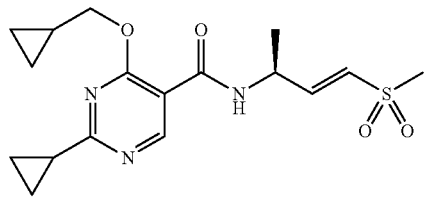 [SMILES: C[C@@H](/C=C/S(C)(=O)=O)NC(=O)c1cnc(C2CC2)nc1OCC1CC1]

Using tert-butyl N-[(1S)-1-methyl-2-oxo-ethyl]carbamate/NaH at Step 1, cyclopropanecarboxamidine at Step 3 and cyclopropanemethanol/LiHMDS/THF at Step 5 in Procedure A, the title compound was obtained. LC-MS m/z: 366.0 [M+1].

Example 151

4-((1r,3S)-3-chlorocyclobutoxy)-2-cyclopropyl-N—((S,E)-4-(methylsulfonyl)but-3-en-2-yl)pyrimidine-5-carboxamide

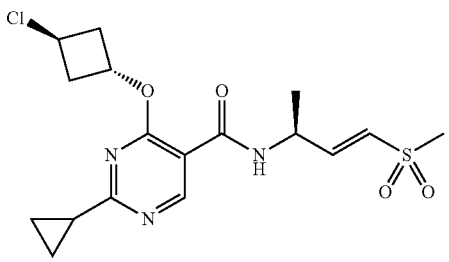 [SMILES: C[C@@H](/C=C/S(C)(=O)=O)NC(=O)c1cnc(C2CC2)nc1O[C@H]1C[C@H](Cl)C1]

Using tert-butyl N-[(1S)-1-methyl-2-oxo-ethyl]carbamate/NaH at Step 1, cyclopropanecarboxamidine at Step 3 and 3-chlorocyclobutanol/LiHMDS/THF at Step 5 in Procedure A, the title compound was obtained. LC-MS m/z: 400.2 [M+1].

Example 152

(S,E)-2-(tert-butyl)-N-(4-(methylsulfonyl)but-3-en-2-yl)-4-(phenoxy-d5)pyrimidine-5-carboxamide

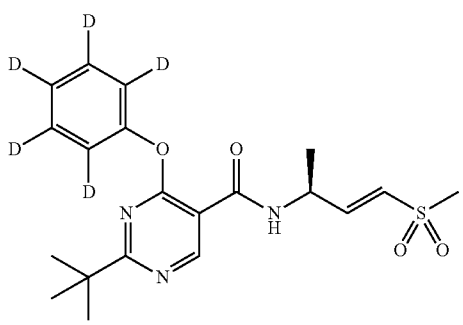 [SMILES: [2H]c1c([2H])c([2H])c(Oc2nc(C(C)(C)C)ncc2C(=O)N[C@@H](C)/C=C/S(C)(=O)=O)c([2H])c1[2H]]

Using tert-butyl N-[(1S)-1-methyl-2-oxo-ethyl]carbamate/NaH at Step 1, 2,2-dimethylpropanamidine hydrochloride at Step 3 and 1,2,3,4,5-pentadeuterio-6-deuteriooxybenzene at Step 5 in Procedure A, the title compound was obtained. LC-MS m/z: 409.2 [M+1].

Example 153

(S,E)-2-(tert-butyl)-4-(cyclopentyloxy)-N-(4-(methylsulfonyl)but-3-en-2-yl)pyrimidine-5-carboxamide

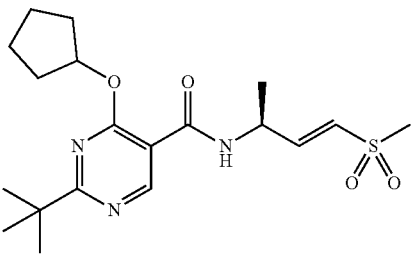 [SMILES: C[C@@H](/C=C/S(C)(=O)=O)NC(=O)c1cnc(C(C)(C)C)nc1OC1CCCC1]

Using tert-butyl N-[(1S)-1-methyl-2-oxo-ethyl]carbamate/NaH at Step 1, 2,2-dimethylpropanamidine hydrochloride at Step 3 and cyclopentanol/LiHMDS/THF at Step 5 in Procedure A, the title compound was obtained. LC-MS m/z: 396.0 [M+1].

Example 154

(S,E)-2-(tert-butyl)-4-(cyclohexyloxy)-N-(4-(methylsulfonyl)but-3-en-2-yl)pyrimidine-5-carboxamide

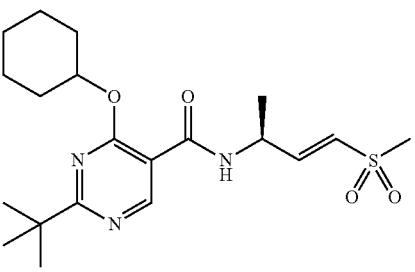 [SMILES: C[C@@H](/C=C/S(C)(=O)=O)NC(=O)c1cnc(C(C)(C)C)nc1OC1CCCCC1]

Using tert-butyl N-[(1S)-1-methyl-2-oxo-ethyl]carbamate/NaH at Step 1, 2,2-dimethylpropanamidine hydrochloride at Step 3 and cyclohexanol/LiHMDS/THF at Step 5 in Procedure A, the title compound was obtained. LC-MS m/z: 410.2 [M+1].

Example 155

(S,E)-2-(tert-butyl)-4-((4,4-difluorocyclohexyl)oxy)-N-(4-(methylsulfonyl)but-3-en-2-yl)pyrimidine-5-carboxamide

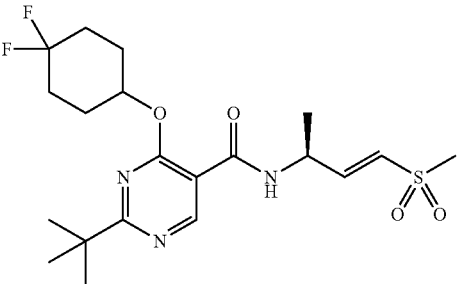 [SMILES: C[C@@H](/C=C/S(C)(=O)=O)NC(=O)c1cnc(C(C)(C)C)nc1OC1CCC(F)(F)CC1]

Using tert-butyl N-[(1S)-1-methyl-2-oxo-ethyl]carbamate/NaH at Step 1, 2,2-dimethylpropanamidine hydrochloride at Step 3 and 4,4-difluorocyclohexanol/LiHMDS/THF at Step 5 in Procedure A, the title compound was obtained. LC-MS m/z: 446.2 [M+1].

Example 156

(S,E)-2-(tert-butyl)-4-(3,3-difluorocyclobutoxy)-N-(4-(methylsulfonyl)but-3-en-2-yl)pyrimidine-5-carboxamide

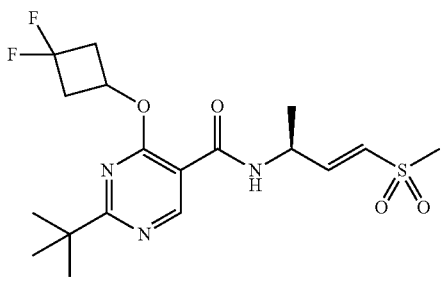 [SMILES: C[C@@H](/C=C/S(C)(=O)=O)NC(=O)c1cnc(C(C)(C)C)nc1OC1CC(F)(F)C1]

Using tert-butyl N-[(1S)-1-methyl-2-oxo-ethyl]carbamate/NaH at Step 1, 2,2-dimethylpropanamidine hydrochloride at Step 3 and 3,3-difluorocyclobutan-1-ol/LiHMDS/THF at Step 5 in Procedure A, the title compound was obtained. LC-MS m/z: 418.2 [M+1].

Example 157

4-[[(1S,5R)-3-bicyclo[3.1.0]hexanyl]oxy]-2-tert-butyl-N—[(E,1S)-1-methyl-3-methylsulfonyl-allyl]pyrimidine-5-carboxamide

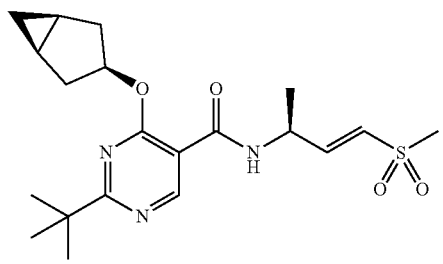 [SMILES: C[C@@H](/C=C/S(C)(=O)=O)NC(=O)c1cnc(C(C)(C)C)nc1O[C@@H]1C[C@@H]2C[C@@H]2C1]

Using tert-butyl N-[(1S)-1-methyl-2-oxo-ethyl]carbamate/NaH at Step 1, 2,2-dimethylpropanamidine hydrochloride at Step 3 and (1S,5R)-bicyclo[3.1.0]hexan-3-ol/LiHMDS/THF at Step 5 in Procedure A, the title compound was obtained. LC-MS m/z: 408.2 [M+1].

Example 158

4-(((1R,3r,5S)-bicyclo[3.1.0]hexan-3-yl)oxy)-N—((S,E)-1-cyclopropyl-3-(methylsulfonyl)allyl)-2-(1,1-difluoroethyl)pyrimidine-5-carboxamide

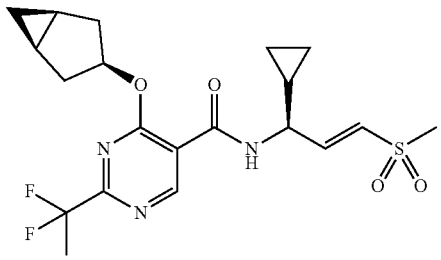 [SMILES: CC(F)(F)c1ncc(C(=O)N[C@H](/C=C/S(C)(=O)=O)C2CC2)c(O[C@@H]2C[C@@H]3C[C@@H]3C2)n1]

Using tert-butyl N-[(1S)-1-cyclopropyl-2-oxo-ethyl]carbamate/NaH at Step 1, 2,2-difluoropropanamidine at Step 3 and (1R,3r,5S)-bicyclo[3.1.0]hexan-3-ol/NaH/DMF at Step 5 in Procedure A, the title compound was obtained. LC-MS m/z: 442.2 [M+1].

Example 159

4-(((1R,3s,5S)-bicyclo[3.1.0]hexan-3-yl)oxy)-2-(tert-butyl)-N—((E)-3-(methylsulfonyl)allyl)pyrimidine-5-carboxamide

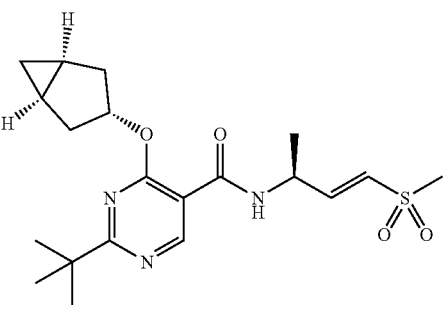 [SMILES: C[C@@H](/C=C/S(C)(=O)=O)NC(=O)c1cnc(C(C)(C)C)nc1O[C@H]1C[C@@H]2C[C@@H]2C1]

Using tert-butyl N-[(1S)-1-methyl-2-oxo-ethyl]carbamate/NaH at Step 1, 2,2-dimethylpropanamidine hydrochloride at Step 3 and (1R,3s,5S)-bicyclo[3.1.0]hexan-3-ol/LiHMDS/THF at Step 5 in Procedure A, the title compound was obtained. LC-MS m/z: 394.2 [M+1].

Example 160

4-(((1R,3s,5S)-bicyclo[3.1.0]hexan-3-yl)oxy)-2-(tert-butyl)-N—((S,E)-1-cyclopropyl-3-(methylsulfonyl)allyl)pyrimidine-5-carboxamide

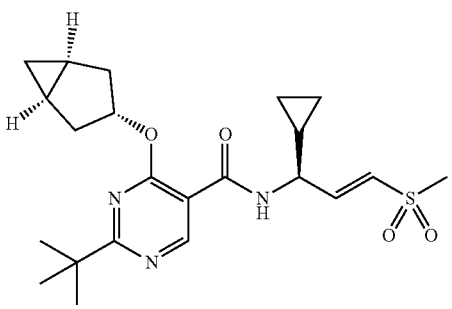 [SMILES: CC(C)(C)c1ncc(C(=O)N[C@H](/C=C/S(C)(=O)=O)C2CC2)c(O[C@H]2C[C@@H]3C[C@@H]3C2)n1]

Using tert-butyl N-[(1S)-1-cyclopropyl-2-oxo-ethyl]carbamate/NaH at Step 1, 2,2-dimethylpropanamidine hydrochloride at Step 3 and (1R,3s,5S)-bicyclo[3.1.0]hexan-3-ol/LiHMDS/THF at Step 5 in Procedure A, the title compound was obtained. LC-MS m/z: 434.2 [M+1].

Example 161

(S,E)-2-(tert-butyl)-4-((1-cyanocyclopentyl)oxy)-N-(4-(methylsulfonyl)but-3-en-2-yl)pyrimidine-5-carboxamide

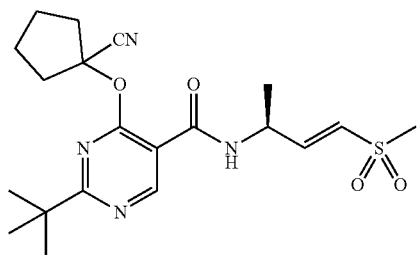 [SMILES: C[C@@H](/C=C/S(C)(=O)=O)NC(=O)c1cnc(C(C)(C)C)nc1OC1(C#N)CCCC1]

Using tert-butyl N-[(1S)-1-methyl-2-oxo-ethyl]carbamate/NaH at Step 1, 2,2-dimethylpropanamidine hydrochloride at Step 3 and 1-hydroxycyclopentane-1-carbonitrile/LiHMDS/THF at Step 5 in Procedure A, the title compound was obtained. LC-MS m/z: 421.0 [M+1].

Example 162

(S,E)-2-cyclopentyl-4-methyl-N-(4-(methylsulfonyl)but-3-en-2-yl)-6-phenoxypyrimidine-5-carboxamide

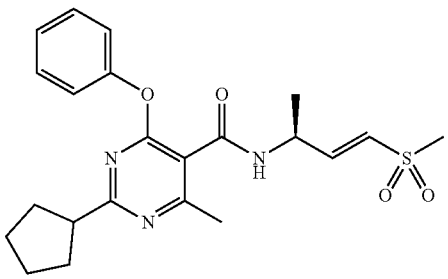 [SMILES: Cc1nc(C2CCCC2)nc(Oc2ccccc2)c1C(=O)N[C@@H](C)/C=C/S(C)(=O)=O]

Using tert-butyl N-[(1S)-1-methyl-2-oxo-ethyl]carbamate/NaH at Step 1 and ethyl (2Z)-2-(ethoxymethylene)-3-oxo-butanoate at Step 3 in Procedure A, the title compound was obtained. LC-MS m/z: 430.2 [M+1].

Example 163

(S,E)-5-cyano-6-cyclopentyl-N-(4-(methylsulfonyl)but-3-en-2-yl)-2-phenoxynicotinamide

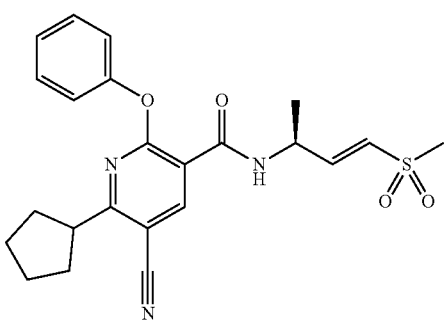 [SMILES: C[C@@H](/C=C/S(C)(=O)=O)NC(=O)c1cc(C#N)c(C2CCCC2)nc1Oc1ccccc1]

Using tert-butyl N-[(1S)-1-methyl-2-oxo-ethyl]carbamate/NaH at Step 1 and (E)-3-amino-3-cyclopentyl-prop-2-enenitrile at Step 3 in Procedure A, the title compound was obtained. LC-MS m/z: 440.2 [M+1].

Example 164

(S,E)-2-(cyclopentylamino)-N-(4-(methylsulfonyl)but-3-en-2-yl)-4-phenoxypyrimidine-5-carboxamide

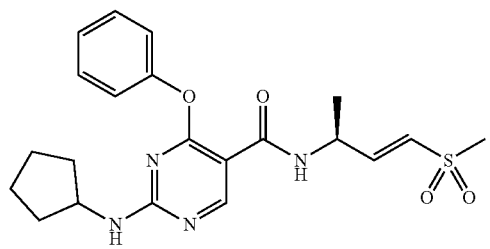 [SMILES: C[C@@H](/C=C/S(C)(=O)=O)NC(=O)c1cnc(NC2CCCC2)nc1Oc1ccccc1]

Procedure B

Step 1

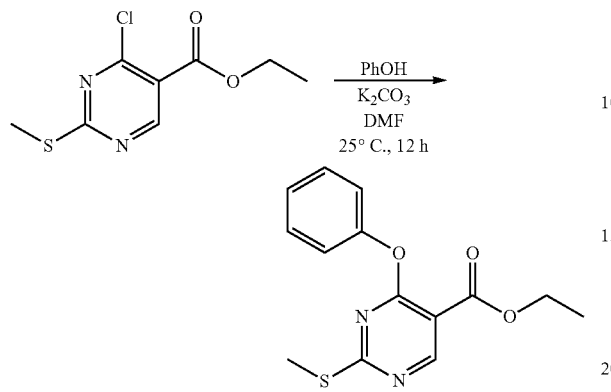

To a solution of ethyl 4-chloro-2-(methylthio)pyrimidine-5-carboxylate (1 g, 4.32 mmol) and phenol (0.50 g, 5.31 mmol) in DMF (10 mL, 0.432 M) was added K₂CO₃ (900 mg), and then stirred at 25° C. for 12 hours. After cooling to room temperature, the reaction mixture was concentrated under reduced pressure to give a residue. The residue was purified by Prep-TLC (SiO₂, Petroleum ether/Ethyl acetate=2/1) to afford ethyl 2-methylsulfanyl-4-phenoxy-pyrimidine-5-carboxylate as a brown oil (800 mg, 64% yield).

Step 2

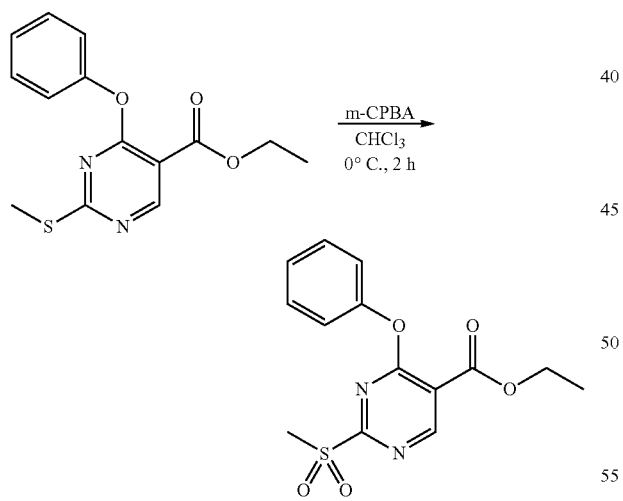

To a solution of ethyl 2-methylsulfanyl-4-phenoxy-pyrimidine-5-carboxylate (300 mg, 1.03 mmol) in chloroform (5 mL, 0.207 M) was added 3-chloroperbenzoic acid (250 mg, 1.23 mmol) in one portion, and stirred at 0° C. for 2 hours. The mixture was diluted with DCM (15 mL) and washed with NaHCO₃ (3×10 mL). The combined organic layers were washed with brine (20 mL), dried over Na₂SO₄, filtered and concentrated under reduced pressure to afford crude ethyl 2-methylsulfonyl-4-phenoxy-pyrimidine-5-carboxylate as a white solid (300 mg).

Step 3

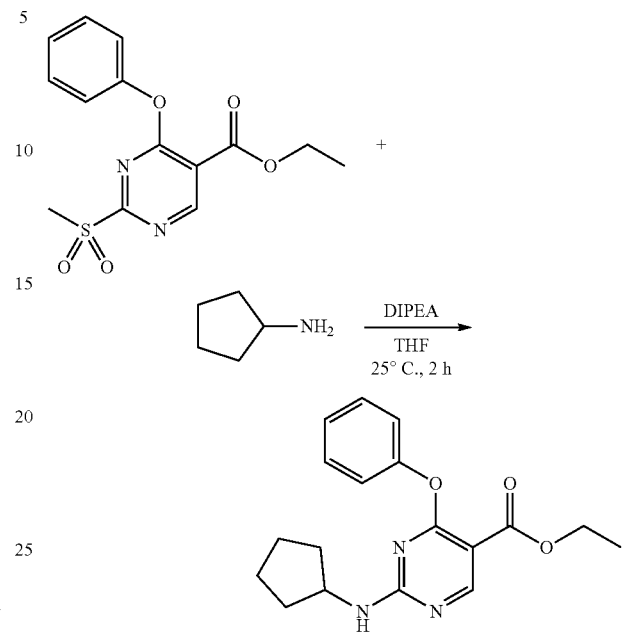

To a solution of ethyl 2-methylsulfonyl-4-phenoxy-pyrimidine-5-carboxylate (300 mg, 0.9307 mmol) and cyclopentylamine (150 mg, 1.76 mmol) in THF (5 mL, 0.186 M) was added DIPEA (400 mg), then stirred at 25° C. for 2 hours. The reaction mixture was concentrated under reduced pressure to give a residue. The residue was purified by Prep-TLC (SiO₂, Petroleum ether/Ethyl acetate=2/1) to afford ethyl 2-(cyclopentylamino)-4-phenoxy-pyrimidine-5-carboxylate as a colorless oil (100 mg, 33% yield).

Following Step 6 and 7 in Procedure A and using [(E,1S)-1-methyl-3-methylsulfonyl-allyl]amine 4-methylbenzenesulfonic acid, the title compound was obtained. LC-MS m/z: 431.1 [M+1].

Example 165

(S,E)-2-(cyclopentyloxy)-N-(4-(methylsulfonyl)but-3-en-2-yl)-4-phenoxypyrimidine-5-carboxamide

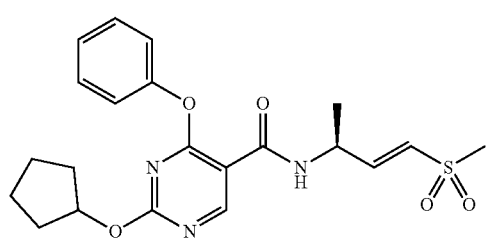 [SMILES: C[C@@H](/C=C/S(C)(=O)=O)NC(=O)c1cnc(OC2CCCC2)nc1Oc1ccccc1]

Using cyclopentanol/LiHMDS at Step 3 in Procedure B, the title compound was obtained. LC-MS m/z: 432.2 [M+1].

Example 166

(S,E)-2-(7-azabicyclo[2.2.1]heptan-7-yl)-N-(4-(methylsulfonyl)but-3-en-2-yl)-4-phenoxypyrimidine-5-carboxamide

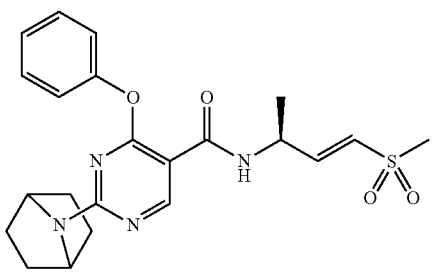 [SMILES: C[C@@H](/C=C/S(C)(=O)=O)NC(=O)c1cnc(N2C3CCC2CC3)nc1Oc1ccccc1]

Using 7-azabicyclo[2.2.1]heptane hydrochloride at Step 3 in Procedure B, the title compound was obtained. LC-MS m/z: 443.2 [M+1].

Example 167

(E)-N-(3-(methylsulfonyl)allyl)-4-phenoxy-2-(pyrrolidin-1-yl)pyrimidine-5-carboxamide

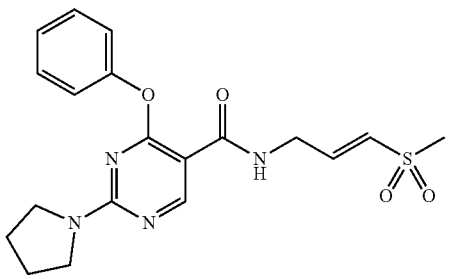

Procedure C

Step 1

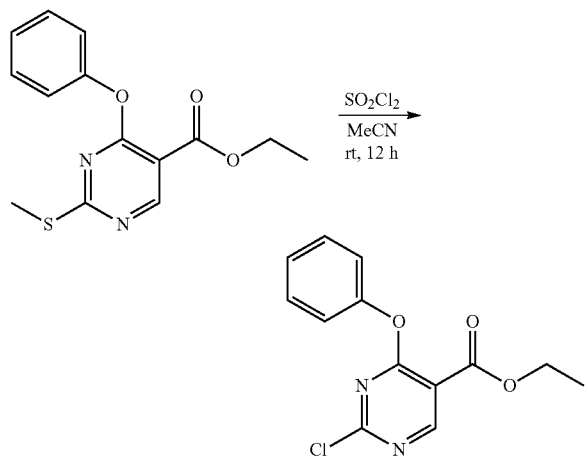

To the mixture of ethyl 2-methylsulfanyl-4-phenoxy-pyrimidine-5-carboxylate (30 g, 103.33 mmol) in MeCN (200 mL, 0.517 M) was added DCM (200 mL) and SO$_2$Cl$_2$ (125 mL) at 0° C. The resulting mixture was allowed to warm to room temperature and stirred for 12 hours. The reaction mixture was poured into ice saturated NaHCO$_3$ solution (100 mL). The aqueous phase was extracted with EtOAc (3×150 mL). The combined organic layers were dried over anhydrous Na$_2$SO$_4$, filtered and concentrated under reduced pressure to give a residue. The residue was purified by flash column (petroleum ether:ethyl acetate=1:0 to 5:1) to afford ethyl 2-chloro-4-phenoxy-pyrimidine-5-carboxylate as a white solid (13.0 g, 45% yield).

Step 2

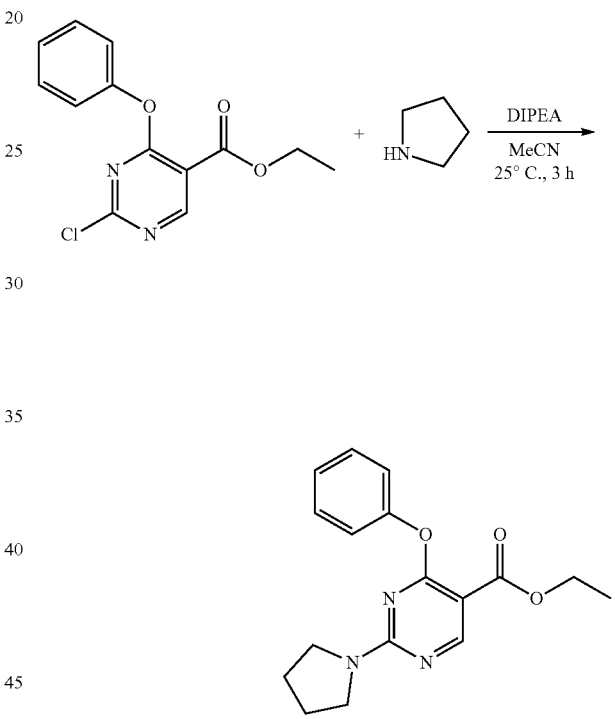

To a solution of ethyl 2-chloro-4-phenoxy-pyrimidine-5-carboxylate (400 mg, 1.44 mmol) and pyrrolidine (112 mg, 1.59 mmol) in MeCN (7 mL, 0.205 M) was added DIPEA (694 mg, 5.37 mmol). The mixture was stirred at 25° C. for 3 hours. The reaction mixture was partitioned between EtOAc (10 mL) and brine (10 mL). The organic layer was dried over Na$_2$SO$_4$, filtered and concentrated under reduced pressure to give a residue. The residue was purified by prep-HPLC to afford ethyl 4-phenoxy-2-pyrrolidin-1-yl-pyrimidine-5-carboxylate as a white solid (130 mg, 29% yield).

Following Step 6 and 7 in Procedure A, the title compound was obtained. LC-MS m/z: 403.1 [M+1].

Example 168

(S,E)-N-(4-(methylsulfonyl)but-3-en-2-yl)-4-phenoxy-2-(pyrrolidin-1-yl)pyrimidine-5-carboxamide

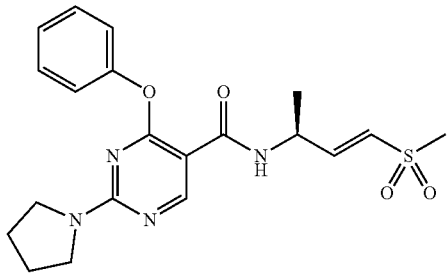 [SMILES: C[C@@H](/C=C/S(C)(=O)=O)NC(=O)c1cnc(N2CCCC2)nc1Oc1ccccc1]

Using [(E,1S)-1-methyl-3-methylsulfonyl-allyl]amine 4-methylbenzenesulfonic acid at the last step in Procedure C, the title compound was obtained. LC-MS m/z: 417.2 [M+1].

Example 169

(S,E)-2-(3-methoxyazetidin-1-yl)-N-(4-(methylsulfonyl)but-3-en-2-yl)-4-phenoxypyrimidine-5-carboxamide

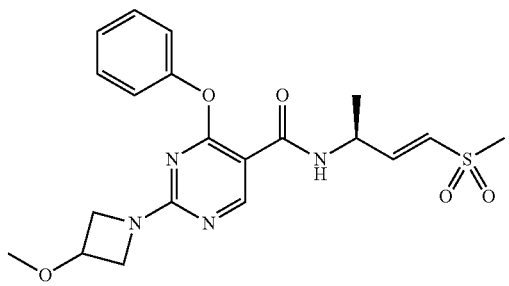

Using 3-methoxyazetidine at Step 2 and [(E,1S)-1-methyl-3-methylsulfonyl-allyl]amine 4-methylbenzenesulfonic acid at the last step in Procedure C, the title compound was obtained. LC-MS m/z: 433.2 [M+1].

Example 170

(S,E)-N-(4-(methylsulfonyl)but-3-en-2-yl)-4-phenoxy-2-(2-azaspiro[3.3]heptan-2-yl)pyrimidine-5-carboxamide

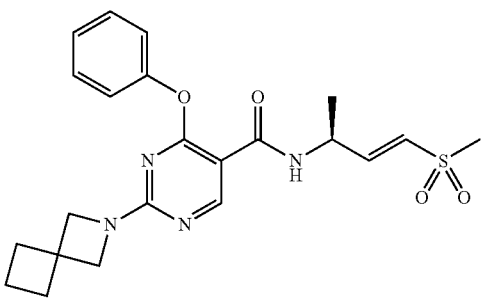 [SMILES: C[C@@H](/C=C/S(C)(=O)=O)NC(=O)c1cnc(N2CC3(CCC3)C2)nc1Oc1ccccc1]

Using 2-azaspiro[3.3]heptane at Step 2 and [(E,1S)-1-methyl-3-methylsulfonyl-allyl]amine 4-methylbenzenesulfonic acid at the last step in Procedure C, the title compound was obtained. LC-MS m/z: 443.2 [M+1].

Example 171

2-((2R,5S)-2,5-dimethylpyrrolidin-1-yl)-N—((S,E)-4-(methylsulfonyl)but-3-en-2-yl)-4-phenoxypyrimidine-5-carboxamide

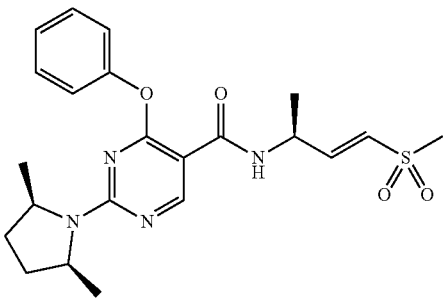 [SMILES: C[C@@H]1CC[C@H](C)N1c1ncc(C(=O)N[C@@H](C)/C=C/S(C)(=O)=O)c(Oc2ccccc2)n1]

Using (2R,5S)-2,5-dimethylpyrrolidine hydrochloride at Step 2 and [(E,1S)-1-methyl-3-methylsulfonyl-allyl]amine 4-methylbenzenesulfonic acid at the last step in Procedure C, the title compound was obtained. LC-MS m/z: 445.0 [M+1].

Example 172

2-((2R,5S)-2,5-dimethylpyrrolidin-1-yl)-N—((S,E)-4-(methylsulfonyl)but-3-en-2-yl)-4-phenoxypyrimidine-5-carboxamide

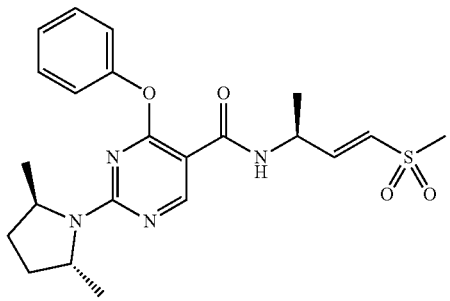 [SMILES: C[C@@H]1CC[C@@H](C)N1c1ncc(C(=O)N[C@@H](C)/C=C/S(C)(=O)=O)c(Oc2ccccc2)n1]

Using (2R,5R)-2,5-dimethylpyrrolidine hydrochloride at Step 2 and [(E,1S)-1-methyl-3-methylsulfonyl-allyl]amine 4-methylbenzenesulfonic acid at the last step in Procedure C, the title compound was obtained. LC-MS m/z: 445.2 [M+1].

Example 173

(S,E)-2-(3,3-difluoropyrrolidin-1-yl)-N-(4-(methylsulfonyl)but-3-en-2-yl)-4-phenoxypyrimidine-5-carboxamide

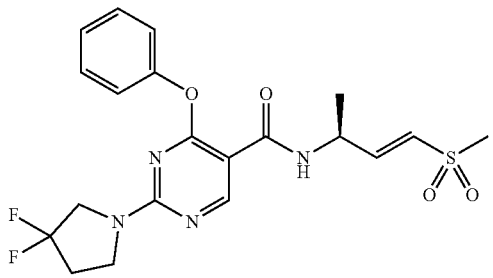 [SMILES: C[C@@H](/C=C/S(C)(=O)=O)NC(=O)c1cnc(N2CCC(F)(F)C2)nc1Oc1ccccc1]

Using 3,3-difluoropyrrolidine hydrochloride/LiHMDS at Step 2 and [(E,1S)-1-methyl-3-methylsulfonyl-allyl]amine 4-methylbenzenesulfonic acid at the last step in Procedure C, the title compound was obtained. LC-MS m/z: 453.0 [M+1].

Example 174

(S,E)-2-(2,2-dimethylpyrrolidin-1-yl)-N-(4-(methylsulfonyl)but-3-en-2-yl)-4-phenoxypyrimidine-5-carboxamide

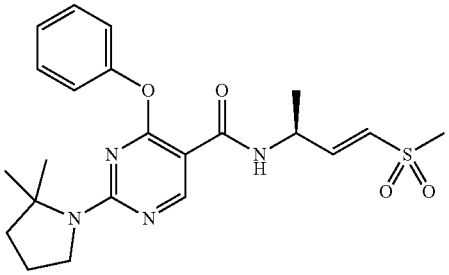

Using 2,2-dimethylpyrrolidine at Step 2 and [(E,1S)-1-methyl-3-methylsulfonyl-allyl]amine 4-methylbenzenesulfonic acid at the last step in Procedure C, the title compound was obtained. LC-MS m/z: 445.2 [M+1].

Example 175

2-((S)-2-methylpyrrolidin-1-yl)-N—((S,E)-4-(methylsulfonyl)but-3-en-2-yl)-4-phenoxypyrimidine-5-carboxamide

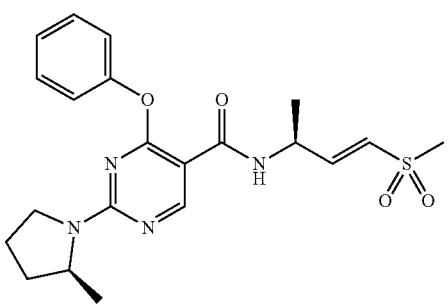 [SMILES: C[C@@H](/C=C/S(C)(=O)=O)NC(=O)c1cnc(N2CCC[C@@H]2C)nc1Oc1ccccc1]

Using (S)-2-methylpyrrolidine at Step 2 and [(E,1S)-1-methyl-3-methylsulfonyl-allyl]amine 4-methylbenzenesulfonic acid at the last step in Procedure C, the title compound was obtained. LC-MS m/z: 431.2 [M+1].

Example 176

2-((R)-2-methylpyrrolidin-1-yl)-N—((S,E)-4-(methylsulfonyl)but-3-en-2-yl)-4-phenoxypyrimidine-5-carboxamide

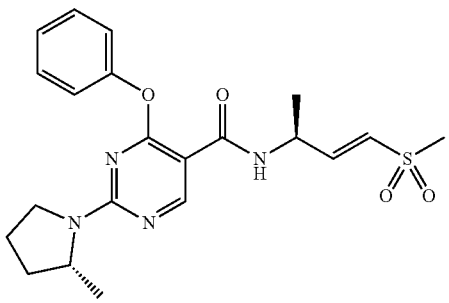 [SMILES: C[C@@H]1CCCN1c1ncc(C(=O)N[C@@H](C)/C=C/S(C)(=O)=O)c(Oc2ccccc2)n1]

Using (R)-2-methylpyrrolidine at Step 2 and [(E,1S)-1-methyl-3-methylsulfonyl-allyl]amine 4-methylbenzenesulfonic acid at the last step in Procedure C, the title compound was obtained. LC-MS m/z: 431.2 [M+1].

Example 177

(S,E)-N-(1-cyclopropyl-3-(methylsulfonyl)allyl)-2-(dimethylamino)-4-phenoxypyrimidine-5-carboxamide

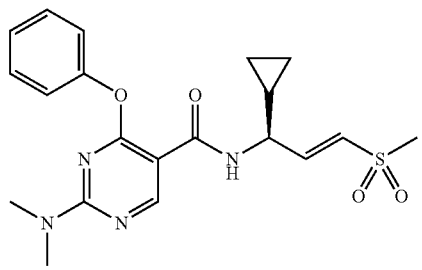

Using dimethylamine hydrochloride at Step 2 and [(E, 1S)-1-cyclopropyl-3-methylsulfonyl-allyl]amine 4-methylbenzenesulfonic acid at the last step in Procedure C, the title compound was obtained. LC-MS m/z: 417.1 [M+1].

Example 178

(S,E)-N-(1-cyclopropyl-3-(methylsulfonyl)allyl)-2-(methylamino)-4-phenoxypyrimidine-5-carboxamide

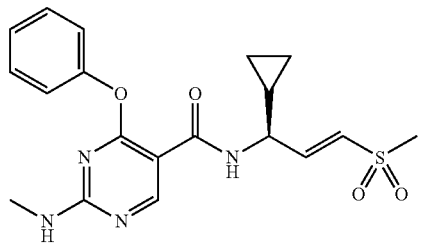 [SMILES: CNc1ncc(C(=O)N[C@H](/C=C/S(C)(=O)=O)C2CC2)c(Oc2ccccc2)n1]

Using methylamine hydrochloride at Step 2 and [(E,1S)-1-cyclopropyl-3-methylsulfonyl-allyl]amine 4-methylbenzenesulfonic acid at the last step in Procedure C, the title compound was obtained. LC-MS m/z: 403.1 [M+1].

Example 179

(S,E)-N-(1-cyclopropyl-3-(methylsulfonyl)allyl)-2-(diethylamino)-4-phenoxypyrimidine-5-carboxamide

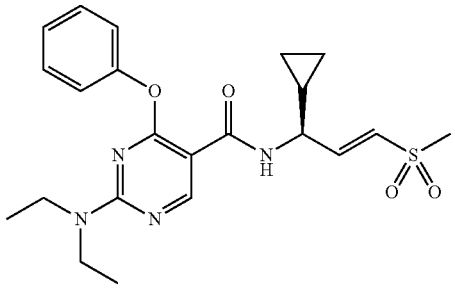 [SMILES: CCN(CC)c1ncc(C(=O)N[C@H](/C=C/S(C)(=O)=O)C2CC2)c(Oc2ccccc2)n1]

Using diethylamine at Step 2 and [(E,1S)-1-cyclopropyl-3-methylsulfonyl-allyl]amine 4-methylbenzenesulfonic acid at the last step in Procedure C, the title compound was obtained. LC-MS m/z: 445.2 [M+1].

Example 180

(S,E)-2-(cyclopropyl(methyl)amino)-N-(1-cyclopropyl-3-(methylsulfonyl)allyl)-4-phenoxypyrimidine-5-carboxamide

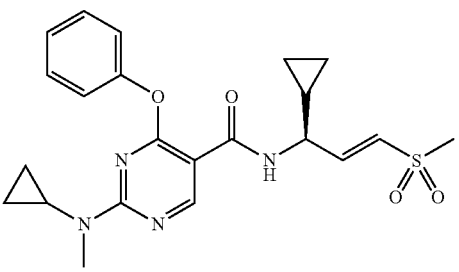 [SMILES: CN(c1ncc(C(=O)N[C@H](/C=C/S(C)(=O)=O)C2CC2)c(Oc2ccccc2)n1)C1CC1]

Using N-methylcyclopropanamine hydrochloride at Step 2 and [(E,1S)-1-cyclopropyl-3-methylsulfonyl-allyl]amine 4-methylbenzenesulfonic acid at the last step in Procedure C, the title compound was obtained. LC-MS m/z: 443.3 [M+1].

Example 181

(S,E)-2-(azetidin-1-yl)-N-(1-cyclopropyl-3-(methylsulfonyl)allyl)-4-phenoxypyrimidine-5-carboxamide

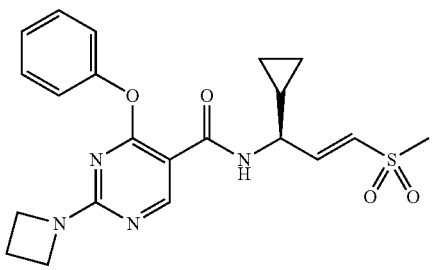 [SMILES: CS(=O)(=O)/C=C/[C@@H](NC(=O)c1cnc(N2CCC2)nc1Oc1ccccc1)C1CC1]

Using azetidine hydrochloride at Step 2 and [(E,1S)-1-cyclopropyl-3-methylsulfonyl-allyl]amine 4-methylbenzenesulfonic acid at the last step in Procedure C, the title compound was obtained. LC-MS m/z: 429.3 [M+1].

Example 182

(S,E)-N-(1-cyclopropyl-3-(methylsulfonyl)allyl)-2-(3-fluoroazetidin-1-yl)-4-phenoxypyrimidine-5-carboxamide

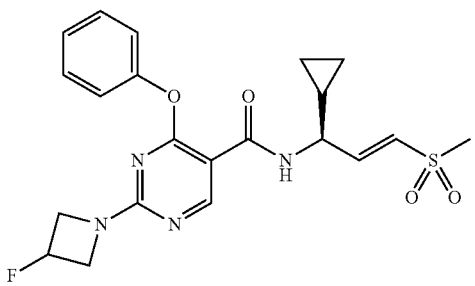 [SMILES: CS(=O)(=O)/C=C/[C@@H](NC(=O)c1cnc(N2CC(F)C2)nc1Oc1ccccc1)C1CC1]

Using 3-fluoroazetidine hydrochloride at Step 2 and [(E, 1S)-1-cyclopropyl-3-methylsulfonyl-allyl]amine 4-methylbenzenesulfonic acid at the last step in Procedure C, the title compound was obtained. LC-MS m/z: 447.2 [M+1].

Example 183

(S,E)-N-(1-cyclopropyl-3-(methylsulfonyl)allyl)-2-(3,3-difluoroazetidin-1-yl)-4-phenoxypyrimidine-5-carboxamide

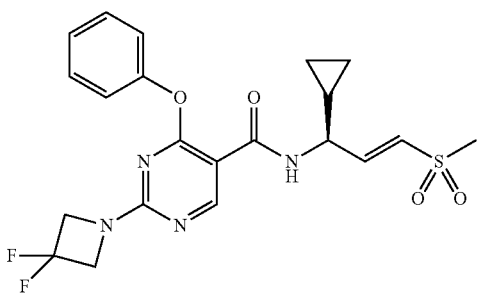 [SMILES: CS(=O)(=O)/C=C/[C@@H](NC(=O)c1cnc(N2CC(F)(F)C2)nc1Oc1ccccc1)C1CC1]

Using 3,3-difluoroazetidine hydrochloride at Step 2 and [(E,1S)-1-cyclopropyl-3-methylsulfonyl-allyl]amine 4-methylbenzenesulfonic acid at the last step in Procedure C, the title compound was obtained. LC-MS m/z: 465.2 [M+1].

Example 184

(S,E)-N-(1-cyclopropyl-3-(methylsulfonyl)allyl)-2-(methyl(2,2,2-trifluoroethyl)amino)-4-phenoxypyrimidine-5-carboxamide

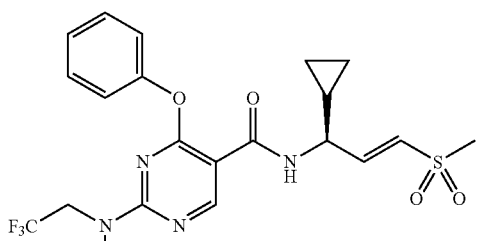

Using 2,2,2-trifluoro-N-methyl-ethanamine hydrochloride at Step 2 and [(E,1S)-1-cyclopropyl-3-methylsulfonyl-allyl]amine 4-methylbenzenesulfonic acid at the last step in Procedure C, the title compound was obtained. LC-MS m/z: 485.2 [M+1].

Example 185

(S,E)-N-(1-cyclopropyl-3-(methylsulfonyl)allyl)-2-(ethyl(methyl)amino)-4-phenoxypyrimidine-5-carboxamide

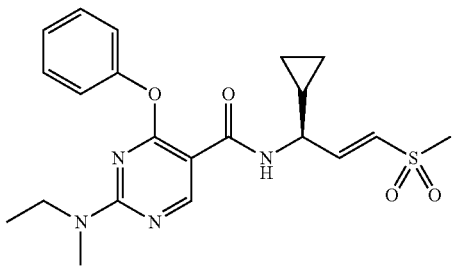 [SMILES: CCN(C)c1ncc(C(=O)N[C@H](/C=C/S(C)(=O)=O)C2CC2)c(Oc2ccccc2)n1]

Using N-ethylmethylamine at Step 2 and [(E,1S)-1-cyclopropyl-3-methylsulfonyl-allyl]amine 4-methylbenzenesulfonic acid at the last step in Procedure C, the title compound was obtained. LC-MS m/z: 431.2 [M+1].

Example 186

(S,E)-N-(1-cyclopropyl-3-(methylsulfonyl)allyl)-2-(isopropyl(methyl)amino)-4-phenoxypyrimidine-5-carboxamide

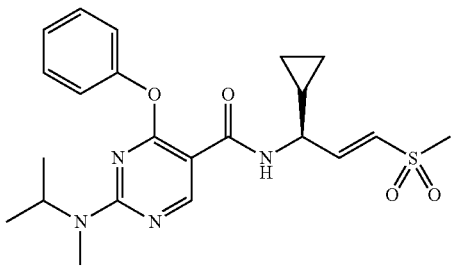 [SMILES: CC(C)N(C)c1ncc(C(=O)N[C@H](/C=C/S(C)(=O)=O)C2CC2)c(Oc2ccccc2)n1]

Using N-methylisopropylamine at Step 2 and [(E,1S)-1-cyclopropyl-3-methylsulfonyl-allyl]amine 4-methylbenzenesulfonic acid at the last step in Procedure C, the title compound was obtained. LC-MS m/z: 445.1 [M+1].

Example 187

(E)-2-cyclopentyl-N-methyl-N-(3-(methylsulfonyl)allyl)-4-phenoxypyrimidine-5-carboxamide

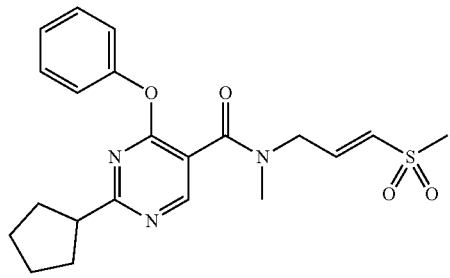 [SMILES: CN(C/C=C/S(C)(=O)=O)C(=O)c1cnc(C2CCCC2)nc1Oc1ccccc1]

Step 1

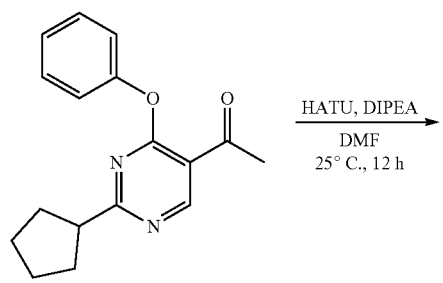

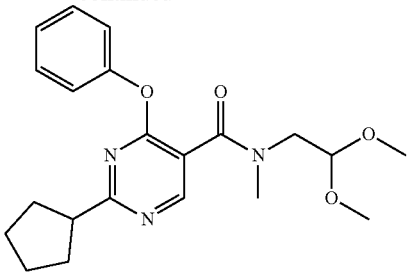

To a solution of 2-cyclopentyl-4-phenoxy-pyrimidine-5-carboxylic acid (500 mg, 1.76 mmol) in DMF (2 mL, 0.879 M) was added methylaminoacetaldehyde dimethyl acetal (220 mg, 1.85 mmol), HATU (1.0 g), and DIPEA (0.91 mL). The mixture was stirred at 25° C. for 12 hours under N$_2$. The reaction mixture was diluted with water (5 mL) and extracted with EtOAc (3×10 mL). The combined organic layers were washed with brine (8 mL), dried over Na$_2$SO$_4$, filtered and concentrated under reduced pressure to give a residue. The residue was purified by flash column chromatography (Biotage using a 12 g Agela flash silica gel column, eluted with 0% to 15% ethyl acetate in petroleum ether) to afford 2-cyclopentyl-N-(2,2-dimethoxyethyl)-N-methyl-4-phenoxy-pyrimidine-5-carboxamide as a white solid (600 mg, 89% yield).

Step 2

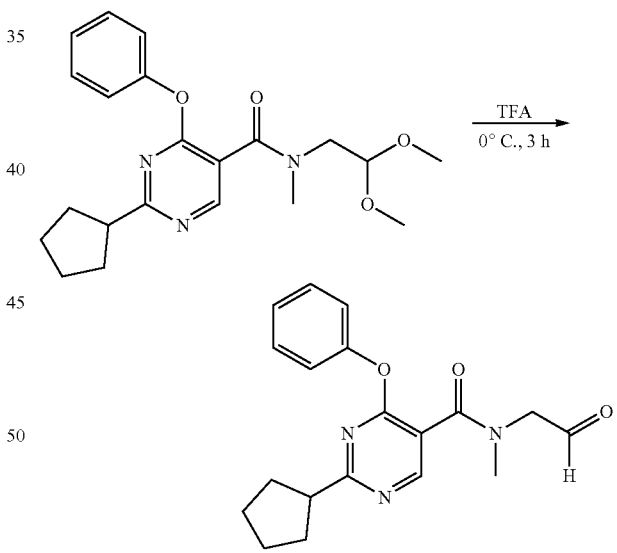

2-cyclopentyl-N-(2,2-dimethoxyethyl)-N-methyl-4-phenoxy-pyrimidine-5-carboxamide (210 mg, 0.55 mmol) was added in TFA (25 mL). The mixture was stirred at 0° C. for 3 hours under N$_2$. The reaction mixture was concentrated under reduced pressure to give a residue. The residue was diluted with water (20 mL) and the aqueous phase was extracted with EtOAc (3×30 mL). The combined organic layers were dried over anhydrous Na$_2$SO$_4$, filtered and the filtrate was concentrated under reduced pressure to afford crude 2-cyclopentyl-N-methyl-N-(2-oxoethyl)-4-phenoxy-pyrimidine-5-carboxamide (210 mg).

Following Step 1 using 2-cyclopentyl-N-methyl-N-(2-oxoethyl)-4-phenoxy-pyrimidine-5-carboxamide in Procedure A, the title compound was obtained. LC-MS m/z: 416.1 [M+1].

Example 188

(2-cyclopropyl-4-phenoxypyrimidin-5-yl)(3-((methylsulfonyl)methylene)azetidin-1-yl)methanone

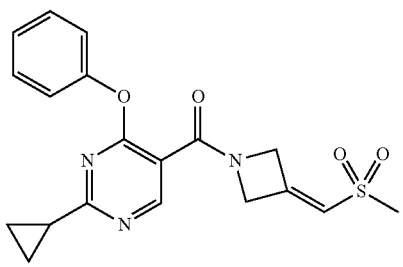 [SMILES: CS(=O)(=O)C=C1CN(C(=O)c2cnc(C3CC3)nc2Oc2ccccc2)C1]

Using 2-cyclopropyl-4-phenoxy-pyrimidine-5-carboxylic acid/3-azetidinone at Step 1 of the procedure for the compound of Example 187, 1-(2-cyclopropyl-4-phenoxy-pyrimidine-5-carbonyl)183zetidine-3-one was obtained. Following Step 1 of Procedure A using ⁿBuLi as the base, the title compound was obtained. LC-MS m/z: 386.0 [M+1].

Example 189

(2-(tert-butyl)-4-phenoxypyrimidin-5-yl)(3-((methylsulfonyl)methylene)azetidin-1-yl)methanone

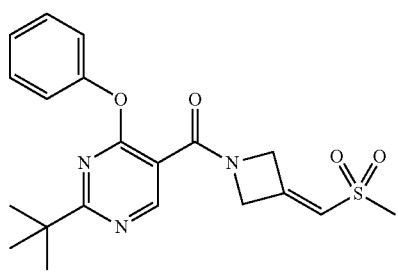 [SMILES: CC(C)(C)c1ncc(C(=O)N2CC(=CS(C)(=O)=O)C2)c(Oc2ccccc2)n1]

Using 2-tert-butyl-4-phenoxy-pyrimidine-5-carboxylic acid and following the procedure for the compound of Example 188, the title compound was obtained. LC-MS m/z: 402.0 [M+1].

Example 190

1-(1-(2-(tert-butyl)-4-phenoxypyrimidine-5-carbonyl)azetidin-3-ylidene)propan-2-one

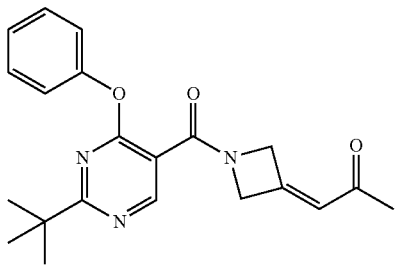

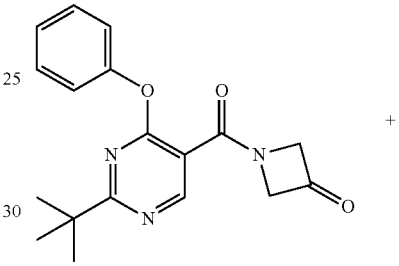

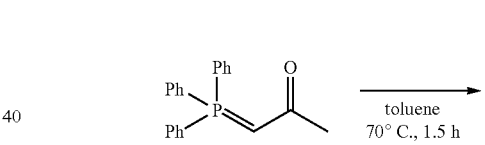

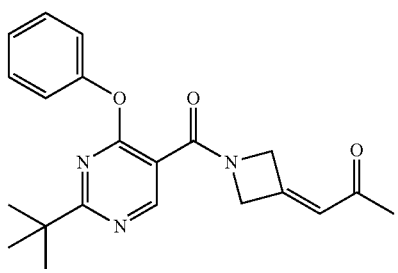 [SMILES: CC(=O)C=C1CN(C(=O)c2cnc(C(C)(C)C)nc2Oc2ccccc2)C1]

The mixture of 1-(2-tert-butyl-4-phenoxy-pyrimidine-5-carbonyl)azetidin-3-one (63 mg, 0.19 mmol) and 1-(triphenyl-λ5-phosphaneylidene)propan-2-one (108 mg, 0.34 mmol) in toluene (3 mL, 0.065 M) was heated at 70° C. for 1.5 hours. The mixture was concentrated and directly purified by prep-HPLC (reverse phase, MeCN/H$_2$O (0.1% FA): 5-95%) to afford the title compound as a white solid (2.8 mg, 4%). LC-MS m/z: 366.2 [M+1].

Example 191 methyl 2-(1-(2-(tert-butyl)-4-phenoxypyrimidine-5-carbonyl)azetidin-3-ylidene)acetate

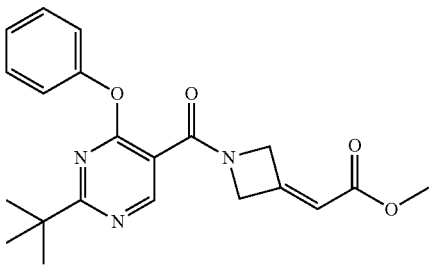 [SMILES: COC(=O)C=C1CN(C(=O)c2cnc(C(C)(C)C)nc2Oc2ccccc2)C1]

Using methyl (triphenylphosphoranylidene)acetate as the starting material to follow the procedure for the compound of Example 190, the title compound was obtained. LC-MS m/z: 382.2 [M+1].

Examples 192 and 193

(S,E)-N-(1-(3,3-difluorocyclobutyl)-3-(methylsulfonyl)allyl)-2-(1,1-difluoroethyl)-4-phenoxypyrimidine-5-carboxamide/(R,E)-N-(1-(3,3-difluorocyclobutyl)-3-(methylsulfonyl)allyl)-2-(1,1-difluoroethyl)-4-phenoxypyrimidine-5-carboxamide

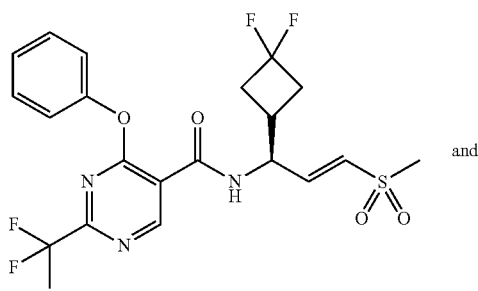

and

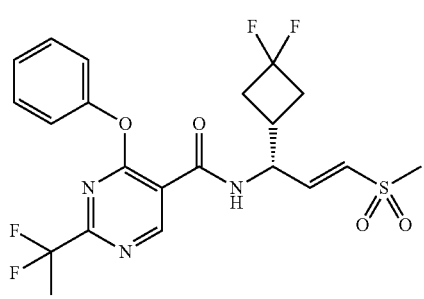

Step 1

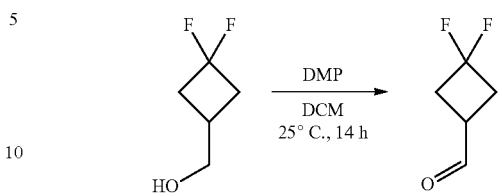

To a solution of (3,3-difluorocyclobutyl)methanol (1 g, 8.19 mmol) in DCM (30 mL, 0.273 M) was added Dess-Martin periodinane (4.86 g, 11.47 mmol) at 25° C. and the mixture was stirred for 14 hours. The mixture was filtered and the filter cake was rinsed with DCM (3×5 mL). Then the combined filtrates were washed with saturated $Na_2S_2O_3$ solution (3×30 mL), saturated $NaHCO_3$ solution (3×30 mL) and brine (20 mL). The combined organic phase was dried over anhydrous $Na_2SO_4$, filtered to afford crude 3,3-difluorocyclobutanecarbaldehyde (983 mg).

Step 2

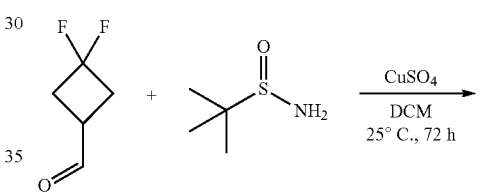

To a mixture of 3,3-difluorocyclobutanecarbaldehyde (713 mg, 5.94 mmol) and 2-methylpropane-2-sulfinamide (600 mg, 4.95 mmol) in DCM (10 mL, 0.495 M) was added cupric sulfate (1.98 g, 12.38 mmol). The mixture was stirred for 72 hours at 25° C. The reaction mixture was filtered through a pad of Celite and the filter cake was washed with EtOAc (2×10 mL). The combined filtrates were concentrated to dryness to give a residue. The residue was purified by flash chromatography (Biotage using a 20 g Agela flash silica gel column, eluted with 10% to 15% ethyl acetate in petroleum ether) to afford (Z)—N-((3,3-difluorocyclobutyl)methylene)-2-methylpropane-2-sulfinamide as a light yellow oil (770 mg, 70% yield).

Step 3

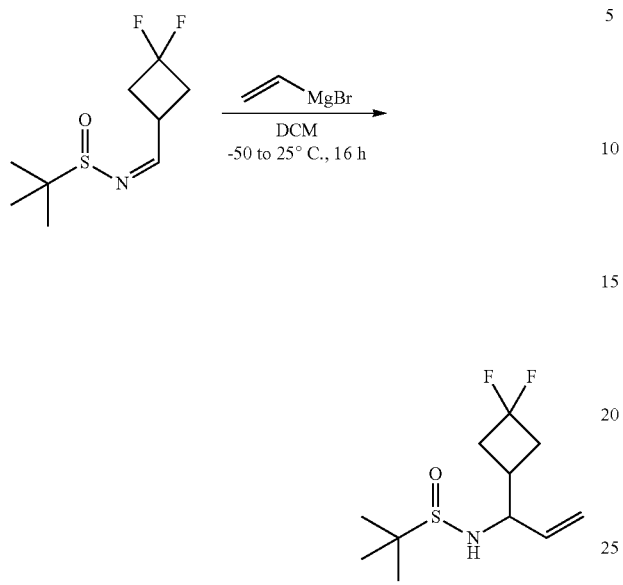

To a solution of (Z)—N-((3,3-difluorocyclobutyl)methylene)-2-methylpropane-2-sulfinamide (1 g, 4.48 mmol) in DCM (20 mL, 0.224 M) at −50° C. was added a vinylmagnesium bromide (13.4 mL, 13.44 mmol, 1 M in THF). The solution was allowed to warm to 25° C., over 16 hours. The mixture was diluted with DCM (30 mL) and slowly quenched with water (10 mL). The mixture was then washed successively with saturated NaHCO$_3$ (2×10 mL) and brine (2×10 mL). The organic phase was dried over Na$_2$SO$_4$, filtered, and concentrated to afford crude N-(1-(3,3-difluorocyclobutyl)allyl)-2-methylpropane-2-sulfinamide as a 1:1 mixture of isomers (800 mg).

Step 4

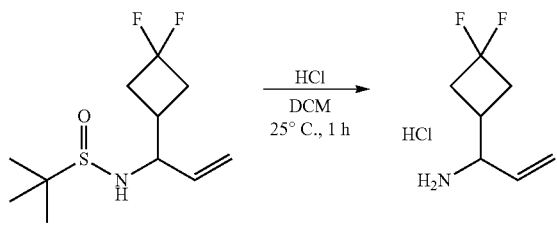

N-(1-(3,3-difluorocyclobutyl)allyl)-2-methylpropane-2-sulfinamide (300 mg, 1.19 mmol) in HCl/MeOH (10 mL) was stirred at 25° C. for 1 hour under N$_2$. The reaction mixture was concentrated under reduced pressure to afford crude 1-(3,3-difluorocyclobutyl)prop-2-en-1-amine HCl salt as a light yellow oil (180 mg).

Step 5

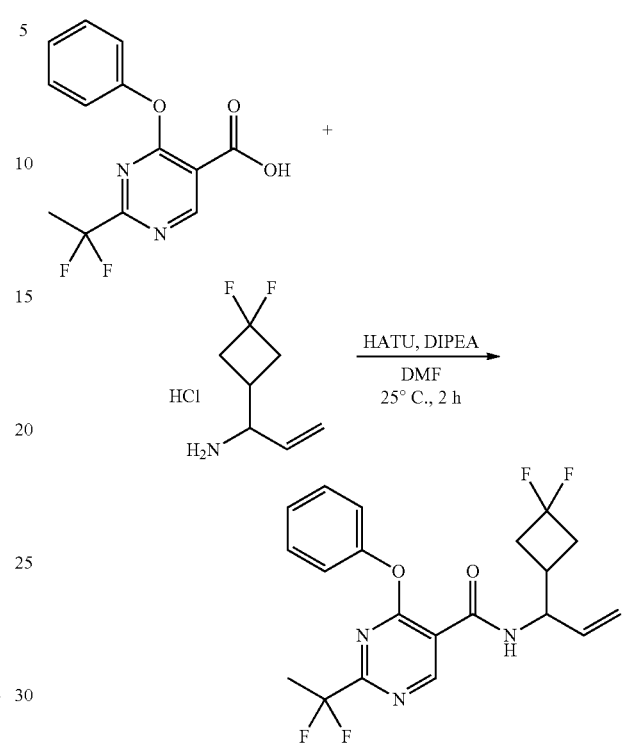

To a solution of 1-(3,3-difluorocyclobutyl)prop-2-en-1-amine HCl salt (50 mg, 0.34 mmol) in DMF (2 mL, 0.170 M) was added 2-(1,1-difluoroethyl)-4-phenoxy-pyrimidine-5-carboxylic acid (95.2 mg, 0.34 mmol), HATU (194 mg, 0.51 mmol) and N,N-diisopropylethylamine (0.15 mL, 0.85 mmol). The mixture was stirred at 25° C. for 2 hours under N$_2$. The reaction mixture was diluted with water (30 mL) and extracted with EtOAc (3×10 mL). The combined organic layers were washed with brine (5 mL), dried over Na$_2$SO$_4$, filtered and concentrated under reduced pressure to give a residue. The residue was purified by flash column chromatography (Biotage using a 12 g Agela flash silica gel column, eluted with 15% to 17% ethyl acetate in petroleum ether) to afford N-[1-(3,3-difluorocyclobutyl)allyl]-2-(1,1-difluoroethyl)-4-phenoxy-pyrimidine-5-carboxamide as a white solid (100 mg, 72% yield).

Step 6

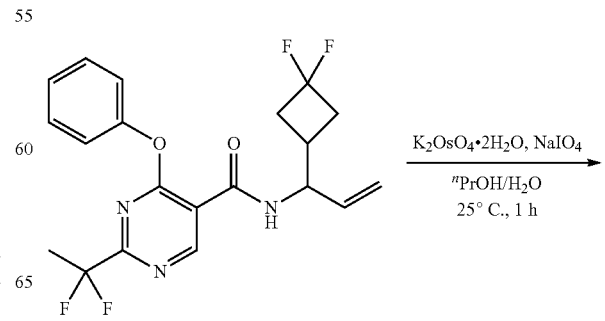

-continued

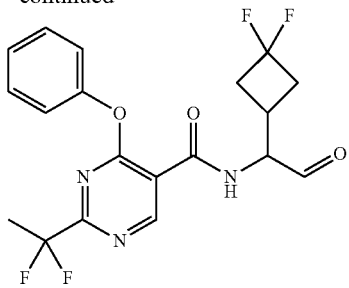

To a solution of N-[1-(3,3-difluorocyclobutyl)allyl]-2-(1,1-difluoroethyl)-4-phenoxy-pyrimidine-5-carboxamide (90 mg, 0.22 mmol) in 1-propanol (2 mL, 0.055 M) and water (2 mL, 0.055 M) was added potassium osmate(VI) dihydrate (6.8 mg, 0.022 mmol) and sodium periodate (94.9 mg, 0.44 mmol). The mixture was stirred at 25° C. for 1 hour under $N_2$. The reaction mixture was concentrated under reduced pressure to remove solvent to afford crude N-[1-(3,3-difluorocyclobutyl)-2-oxo-ethyl]-2-(1,1-difluoroethyl)-4-phenoxy-pyrimidine-5-carboxamide as a yellow solid (90 mg).

Step 7

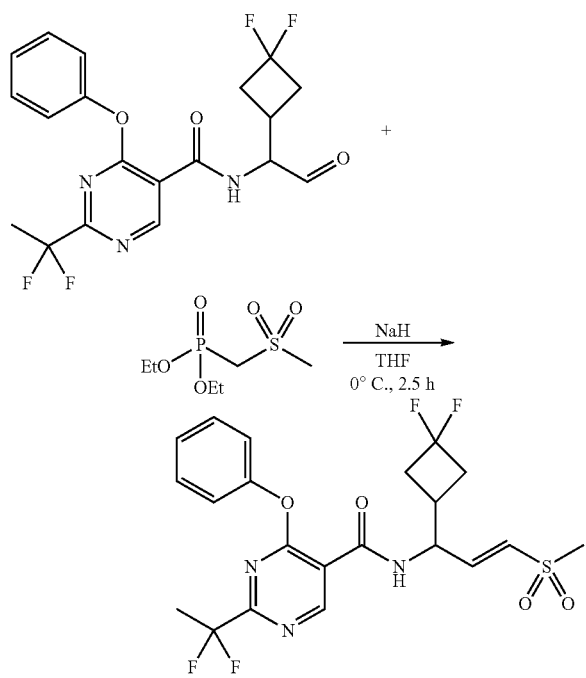

To a solution of diethyl ((methylsulfonyl)methyl)phosphonate (92.3 mg, 0.40 mmol) in THF (5 mL, 0.052 M) was added sodium hydride (11.7 mg, 0.29 mmol) at 0° C. The mixture was stirred at 0° C. for 1 hour. Then a solution of N-[1-(3,3-difluorocyclobutyl)-2-oxo-ethyl]-2-(1,1-difluoroethyl)-4-phenoxy-pyrimidine-5-carboxamide (150 mg, 0.36 mmol) in THF (2 mL, 0.052 M) was added dropwise at 0° C. After stirred at the temperature for 2.5 hours, the reaction mixture was poured into ice saturated $NH_4Cl$ solution (15 mL). The aqueous phase was extracted with EtOAc (3×20 mL). The combined organic phase was dried over anhydrous $Na_2SO_4$, filtered and concentrated under reduced pressure to give a residue. The residue was purified by prep-HPLC (Waters Xbridge BEH C18 100*30 mm*10 uM, water ($NH_4HCO_3$)/MeCN=35-55% B, flow rate=25 mL/min) to afford the mixture of the title compounds (50 mg, 28% yield). The mixture was separated by chiral SFC (column: Daicel ChiralPak AD (250 mm*30 mm*10 um), Neutral Methanol) to afford Peak 1 (LC-MS m/z: 488.1 [M+1]) and Peak 2 (LC-MS m/z: 488.1 [M+1]). The absolute stereochemistry of the title compounds were not ascertained.

Examples 194 and 195

(S,E)-N-(1-cyclopropyl-3-(methylsulfonyl)allyl-1-d)-2-(1,1-difluoroethyl)-4-phenoxypyrimidine-5-carboxamide/(R,E)-N-(1-cyclopropyl-3-(methylsulfonyl)allyl-1-d)-2-(1,1-difluoroethyl)-4-phenoxypyrimidine-5-carboxamide

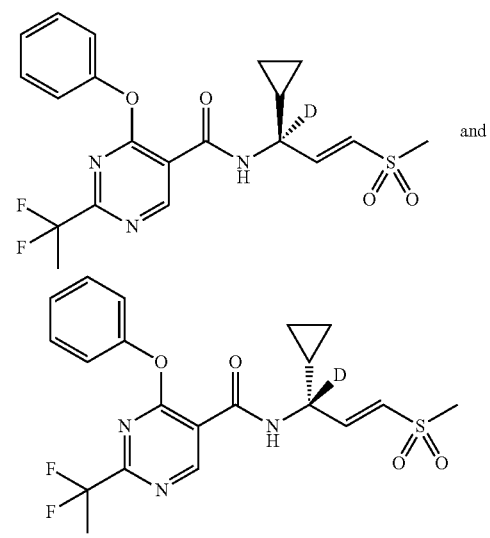

Step 1

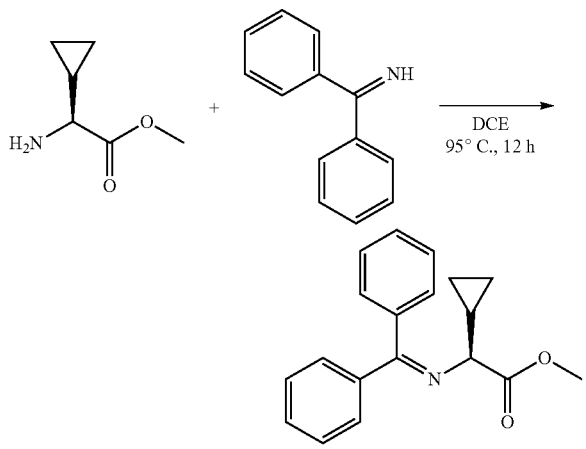

To a solution of methyl (S)-2-amino-2-cyclopropylacetate (0.8 g, 6.19 mmol) in DCE (20 mL, 0.310 M) was added di(phenyl)methanimine (1.12 g, 6.19 mmol) under $N_2$ at 25°

C. The reaction mixture was stirred at 95° C. for 12 hours. The mixture was concentrated under reduced pressure and the residue was purity by flash column chromatography (PE:EA=2:1, Rf=0.8, UV=254 nm) to give methyl (2S)-2-(benzhydrylideneamino)-2-cyclopropyl-acetate as a yellow oil (0.82 g, 45% yield).

Step 2

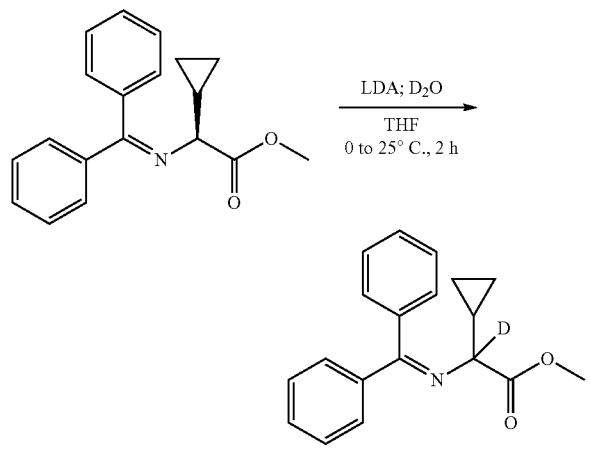

To a solution of methyl (2S)-2-(benzhydrylideneamino)-2-cyclopropyl-acetate (300 mg, 1.02 mmol) in THF (10 mL, 0.102 M) and was added lithium diisopropylamide solution (1.02 mL, 2.05 mmol, 2 M) at 0° C. for 2 hours. D$_2$O (20 mL) was added to the mixture and it was allowed to warm to 25° C. under N$_2$. The reaction mixture was stirred at 25° C. for 1 hour. The reaction mixture was poured into water (5 mL) and extracted with EtOAc (3×10 mL). The combined organic layers were washed with brine (2×10 mL), dried over Na$_2$SO$_4$, filtered and concentrated under reduced pressure to afford crude methyl 2-(benzhydrylideneamino)-2-cyclopropyl-2-deuterio-acetate as a yellow oil (100 mg).

Step 3

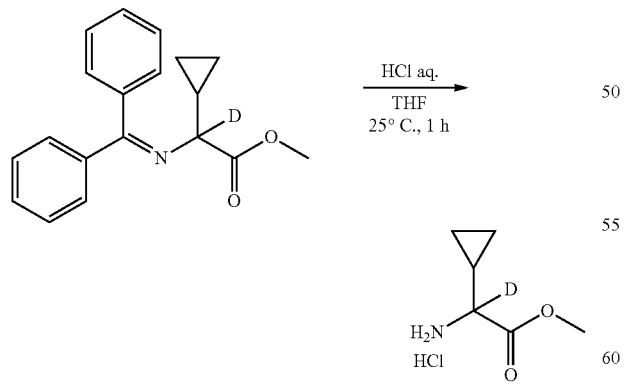

To a solution of methyl 2-(benzhydrylideneamino)-2-cyclopropyl-2-deuterio-acetate (100 mg, 0.34 mmol) in THF (5 mL, 0.068 M) and was added 2N HCl (2 mL) at 0° C. under N$_2$. The reaction mixture was stirred at 25° C. for 1 hour. The reaction mixture was concentrated under reduced pressure and poured into H$_2$O (5 mL) and extracted with EtOAc (3×10 mL). Then aqueous solution was filtered and concentrated under reduced pressure to afford crude methyl 2-amino-2-cyclopropyl-2-deuterio-acetate hydrochloride as a colorless oil (25 mg).

Step 4

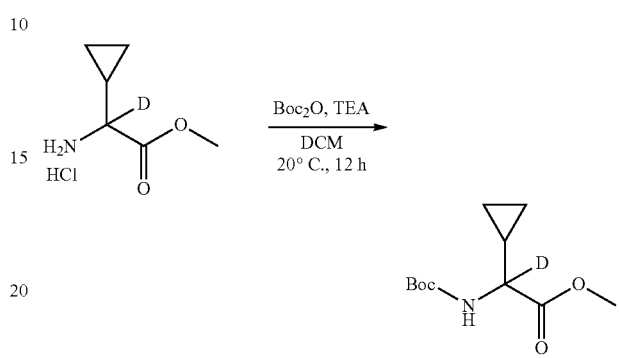

To a mixture of methyl 2-amino-2-cyclopropyl-2-deuterio-acetate hydrochloride (300 mg, 1.80 mmol) in DCM (10 mL, 0.180 M) was added di-tert-butyl dicarbonate (0.47 g, 2.161 mmol) and triethylamine (1.82 g, 18.01 mmol) at 20° C. The mixture was stirred at 20° C. for 12 hours. The mixture was diluted with water (5 mL) and extracted with DCM (3×10 mL). The combined organic layers were washed with brine (10 mL), dried over Na$_2$SO$_4$, filtered and concentrated under reduced pressure to give a residue. The residue was purified by prep-TLC (PE:EtOAc=1:1) to afford methyl 2-(tert-butoxycarbonylamino)-2-cyclopropyl-2-deuterio-acetate as a colorless oil (0.35 g, 84% yield).

Methyl 2-(tert-butoxycarbonylamino)-2-cyclopropyl-2-deuterio-acetate was converted to tert-butyl N-(1-cyclopropyl-1-deuterio-2-oxo-ethyl)carbamate via LAH reduction and DMP oxidation as described previously. Using tert-butyl N-(1-cyclopropyl-1-deuterio-2-oxo-ethyl)carbamate at Step 1 and 2,2-difluoropropanamidine at Step 3 in Procedure A, the mixture of the title compounds was obtained. The mixture was separated by chiral SFC to afford Peak 1 (LC-MS m/z: 439.2 [M+1]) and Peak 2 (LC-MS m/z: 439.2 [M+1]). The absolute stereochemistry of the title compounds were not ascertained.

Example 196

(S,E)-4-(cyclohexyloxy)-2-cyclopentyl-N-(4-(methylsulfonyl)but-3-en-2-yl)pyrimidine-5-carboxamide

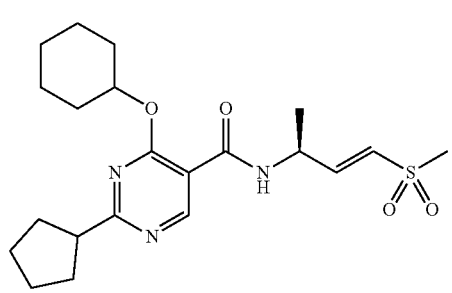 [SMILES: C[C@@H](/C=C/S(C)(=O)=O)NC(=O)c1cnc(C2CCCC2)nc1OC1CCCCC1]

Step 1

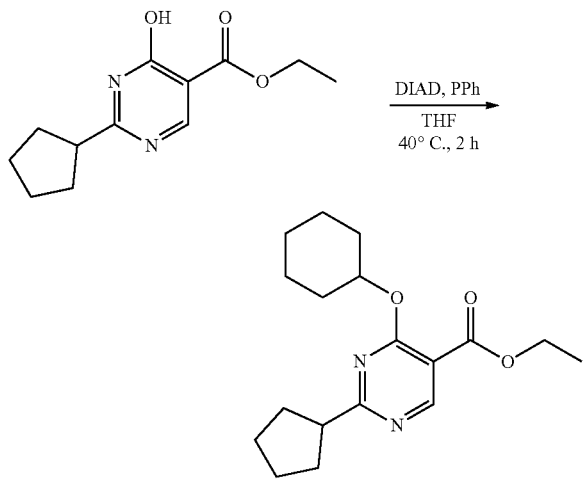

To a solution of ethyl 2-cyclopentyl-4-hydroxy-pyrimidine-5-carboxylate (0.300 g, 1.27 mmol) in THF (6 mL, 0.212 M) at 0° C. was added PPh₃ (0.4 g) and cyclohexanol (0.127 g, 1.27 mmol). Then DIAD (0.308 g) was added dropwise. The mixture was stirred at 40° C. for 2 hours. The reaction was diluted with water (5 mL) and extracted with EtOAc (3×5 mL). The combined organic layers were dried over anhydrous $Na_2SO_4$, filtered and the filtrate was concentrated under reduced pressure to give a residue. The residue was purified by Prep-TLC (Petroleum ether/Ethyl acetate=10/1, Rf (product)=0.5) to afford ethyl 4-(cyclohexoxy)-2-cyclopentyl-pyrimidine-5-carboxylate as a yellow oil (0.1 g, 25% yield).

Following Step 6 with ethyl 4-(cyclohexoxy)-2-cyclopentyl-pyrimidine-5-carboxylate and Step 7 with [(E,1S)-1-methyl-3-methylsulfonyl-allyl]amine 4-methylbenzenesulfonic acid in Procedure A, the title compound was obtained. LC-MS m/z: 422.1 [M+1].

Example 197

(S,E)-2-cyclopentyl-4-(cyclopentyloxy)-N-(4-(methylsulfonyl)but-3-en-2-yl)pyrimidine-5-carboxamide

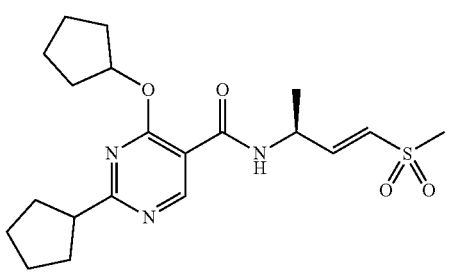 [SMILES: C[C@@H](/C=C/S(C)(=O)=O)NC(=O)c1cnc(C2CCCC2)nc1OC1CCCC1]

Using cyclopentanol at Step 1 in the procedure for the compound of Example 196, the title compound was obtained. LC-MS m/z: 408.2 [M+1].

Example 198

(E)-4-cyclopentyl-2-(cyclopentyloxy)-N-(3-(methylsulfonyl)allyl)benzamide

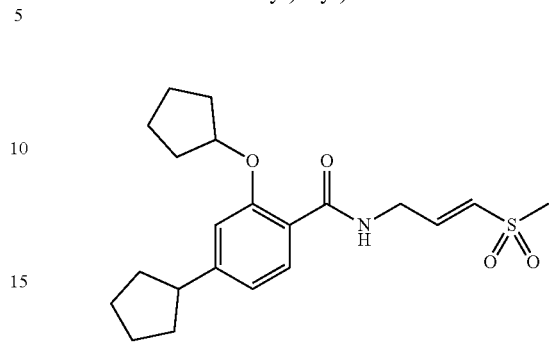

Using cyclopentanol and methyl 4-cyclopentyl-2-hydroxy-benzoate at Step 1 and [(E,1S)-1-methyl-3-methylsulfonyl-allyl]amine 4-methylbenzenesulfonic acid at the last step in the procedure for the compound of Example 196, the title compound was obtained. LC-MS m/z: 392.2 [M+1].

Example 199

(S,E)-6-cyclopentyl-N-(4-(methylsulfonyl)but-3-en-2-yl)-4-phenoxynicotinamide

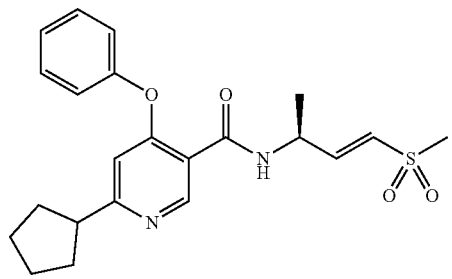 [SMILES: C[C@@H](/C=C/S(C)(=O)=O)NC(=O)c1cnc(C2CCCC2)cc1Oc1ccccc1]

Procedure D

Step 1

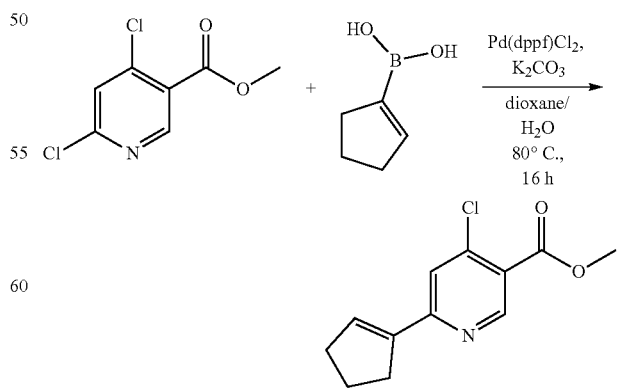

Pd(dppf)Cl₂ (702 mg, 0.97 mmol) was added to the mixture of methyl 4,6-dichloronicotinate (2 g, 9.71 mmol), cyclopenten-1-ylboronic acid (978 mg, 8.74 mmol) and K₂CO₃ (2.68 g, 19.42 mmol) in 1,4-dioxane (25 mL, 0.324 M) and water (5 mL, 0.324 M). The resulting mixture was stirred at 80° C. for 16 hours under N₂. The reaction mixture was poured into water (50 mL) and extracted with EtOAc (3×50 mL). The combined organic layers were washed with brine (2×40 mL), dried over Na₂SO₄, filtered and concentrated under reduced pressure to give a residue. The residue was purified by flash silica gel chromatography (ISCO®; 40 g SepaFlash® Silica Flash Column, Eluent of 0-4% Ethyl acetate/Petroleum ether gradient at 100 mL/min) to afford methyl 4-chloro-6-(cyclopenten-1-yl)pyridine-3-carboxylate as a yellow oil (1.5 g, 65% yield).

Using methyl 4-chloro-6-(cyclopenten-1-yl)pyridine-3-carboxylate to follow Step 5 in Procedure A, methyl 6-(cyclopenten-1-yl)-4-phenoxy-pyridine-3-carboxylate was obtained.

Step 2

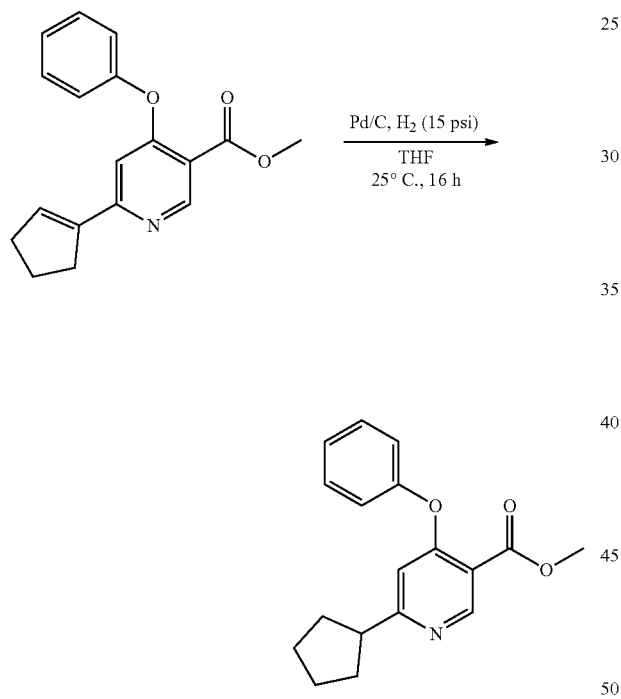

Pd/C (200 mg) was added to methyl 6-(cyclopenten-1-yl)-4-phenoxy-pyridine-3-carboxylate (310 mg, 1.05 mmol) in THF (7 mL, 0.150 M). The resulting mixture was stirred at 25° C. for 16 hours under H₂ (15 psi). The reaction mixture was filtered and the filtrate was concentrated to afford crude methyl 6-cyclopentyl-4-phenoxy-pyridine-3-carboxylate as a yellow oil (310 mg).

Following Step 6 with methyl 6-cyclopentyl-4-phenoxy-pyridine-3-carboxylate and Step 7 with [(E,1S)-1-cyclopropyl-3-methylsulfonyl-allyl]amine 4-methylbenzenesulfonic acid in Procedure A, the title compound was obtained. LC-MS m/z: 415.0 [M+1].

Example 200

(S,E)-6-(cyclopent-1-en-1-yl)-N-(4-(methylsulfonyl)but-3-en-2-yl)-4-phenoxynicotinamide

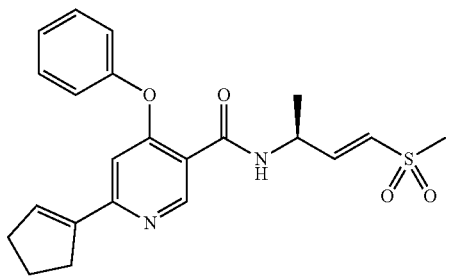 [SMILES: C[C@@H](/C=C/S(C)(=O)=O)NC(=O)c1cnc(C2=CCCC2)cc1Oc1ccccc1]

Following Step 6 with methyl 6-(cyclopenten-1-yl)-4-phenoxy-pyridine-3-carboxylate and Step 7 with [(E,1S)-1-cyclopropyl-3-methylsulfonyl-allyl]amine 4-methylbenzenesulfonic acid in Procedure A, the title compound was obtained. LC-MS m/z: 413.1 [M+1].

Example 201

(S,E)-6-cyclopentyl-N-(4-(methylsulfonyl)but-3-en-2-yl)-2-phenoxynicotinamide

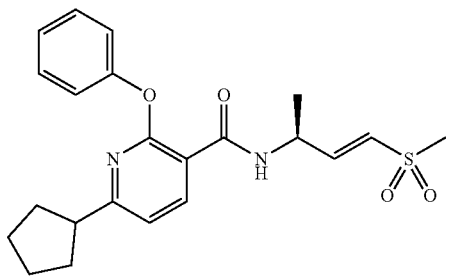

Using ethyl 2,6-dichloropyridine-3-carboxylate at Step 1 in Procedure D, the title compound was obtained. LC-MS m/z: 415.2 [M+1].

Example 202

(S,E)-6-(cyclopent-1-en-1-yl)-N-(4-(methylsulfonyl)but-3-en-2-yl)-2-phenoxynicotinamide

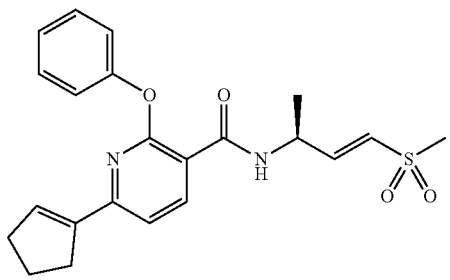 [SMILES: C[C@@H](/C=C/S(C)(=O)=O)NC(=O)c1ccc(C2=CCCC2)nc1Oc1ccccc1]

Following Step 6 with ethyl 6-cyclopentyl-2-phenoxy-pyridine-3-carboxylate and Step 7 with [(E,1S)-1-cyclopropyl-3-methylsulfonyl-allyl]amine 4-methylbenzenesulfonic acid in Procedure A, the title compound was obtained. LC-MS m/z: 413.2 [M+1].

Example 203

(S,E)-5-cyclopentyl-N-(4-(methylsulfonyl)but-3-en-2-yl)quinoline-8-carboxamide

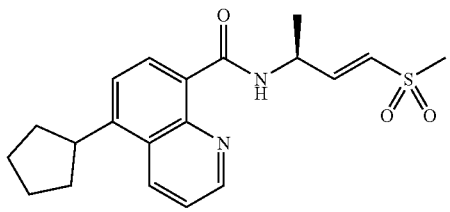 [SMILES: C[C@@H](/C=C/S(C)(=O)=O)NC(=O)c1ccc(C2CCCC2)c2cccnc12]

Using ethyl 5-bromoquinoline-8-carboxylate as the starting material and following Step 1 and Step 2 of Procedure D, methyl 5-cyclopentyl-1,2,3,4-tetrahydroquinoline-8-carboxylate was obtained.

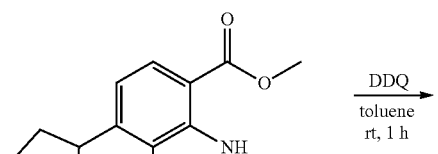

To a solution of methyl 5-cyclopentyl-1,2,3,4-tetrahydroquinoline-8-carboxylate (149 mg, 0.575 mmol) in toluene (6 mL, 0.096 M) was added 2,3-dichloro-5,6-dicyano-p-benzoquinone (313 mg, 1.38 mmol) at RT. The reaction was stirred at this temperature for 1 hour. The reaction mixture was concentrated in reduced pressure and purified via normal phase column chromatography using Biotage Isolera (0-10% MeOH/DCM) to afford methyl 5-cyclopentylquinoline-8-carboxylate as a dark solid (140 mg, 95% yield).

Following Step 6 and 7 in Procedure A and using [(E,1S)-1-methyl-3-methylsulfonyl-allyl]amine 4-methylbenzenesulfonic acid, the title compound was obtained. LC-MS m/z: 373.2 [M+1].

Example 204

(S,E)-6-cyclopropyl-5-methyl-N-(4-(methylsulfonyl)but-3-en-2-yl)-4-phenoxynicotinamide

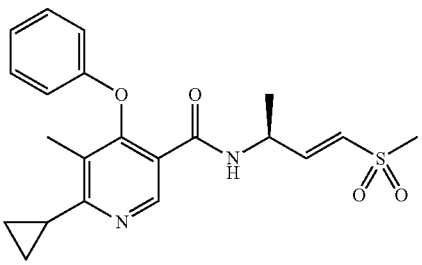 [SMILES: Cc1c(C2CC2)ncc(C(=O)N[C@@H](C)/C=C/S(C)(=O)=O)c1Oc1ccccc1]

Using ethyl 4,6-dichloro-5-methylnicotinate/cyclopropylboronic acid/potassium phosphate (tribasic) at Step 1, skipping Step 2 and following the subsequent steps in Procedure D, the title compound was obtained. LC-MS m/z: 401.2 [M+1].

Example 205

(S,E)-6-cyclopropyl-5-fluoro-N-(4-(methylsulfonyl)but-3-en-2-yl)-4-phenoxynicotinamide

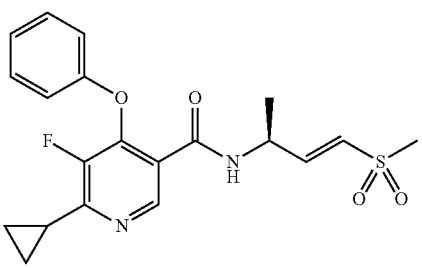 [SMILES: C[C@@H](/C=C/S(C)(=O)=O)NC(=O)c1cnc(C2CC2)c(F)c1Oc1ccccc1]

Using ethyl 4,6-dichloro-5-fluoronicotinate/cyclopropylboronic acid/potassium phosphate (tribasic) at Step 1, skipping Step 2 and following the subsequent steps in Procedure D, the title compound was obtained. LC-MS m/z: 405.0 [M+1].

Example 206

(R,E)-6-(cyclopent-1-en-1-yl)-5-fluoro-N-(4-(methylsulfonyl)but-3-en-2-yl)-2-phenoxynicotinamide

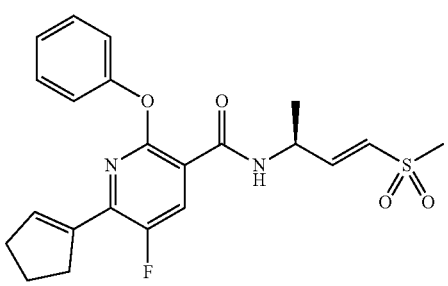 [SMILES: C[C@@H](/C=C/S(C)(=O)=O)NC(=O)c1cc(F)c(C2=CCCC2)nc1Oc1ccccc1]

Using methyl 2,6-dichloro-5-fluoro-pyridine-3-carboxylate at Step 1, skipping Step 2 and following the subsequent steps in Procedure D, the title compound was obtained. LC-MS m/z: 401.2 [M+1].

Example 207

(S,E)-5-(cyclopent-1-en-1-yl)-N-(4-(methylsulfonyl)but-3-en-2-yl)-3-phenoxypyrazine-2-carboxamide

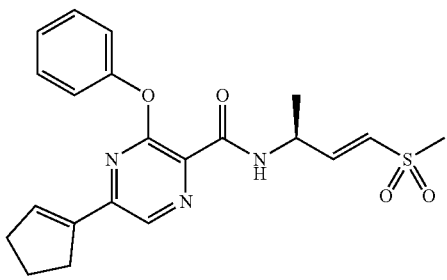 [SMILES: C[C@@H](/C=C/S(C)(=O)=O)NC(=O)c1ncc(C2=CCCC2)nc1Oc1ccccc1]

Using methyl 3,5-dichloropyrazine-2-carboxylate at Step 1, skipping Step 2 and following the subsequent steps in Procedure D, the title compound was obtained. LC-MS m/z: 414.2 [M+1].

Example 208

(S,E)-5-cyclopentyl-N-(4-(methylsulfonyl)but-3-en-2-yl)-3-phenoxypyrazine-2-carboxamide

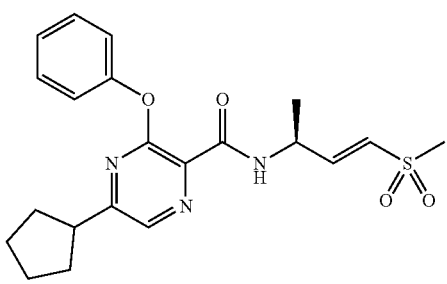

Using methyl 3,5-dichloropyrazine-2-carboxylate at Step 1 to follow Procedure D, the title compound was obtained. LC-MS m/z: 416.2 [M+1].

Example 209

(E)-N-(3-(methylsulfonyl)allyl)-4-phenoxy-2-(1H-pyrazol-5-yl)pyrimidine-5-carboxamide

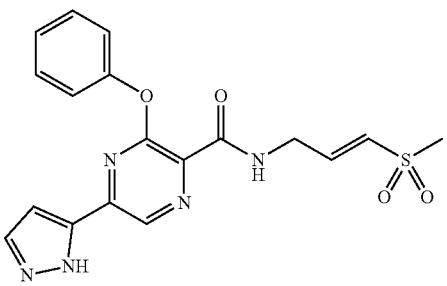 [SMILES: CS(=O)(=O)/C=C/CNC(=O)c1ncc(-c2ccn[nH]2)nc1Oc1ccccc1]

Step 1

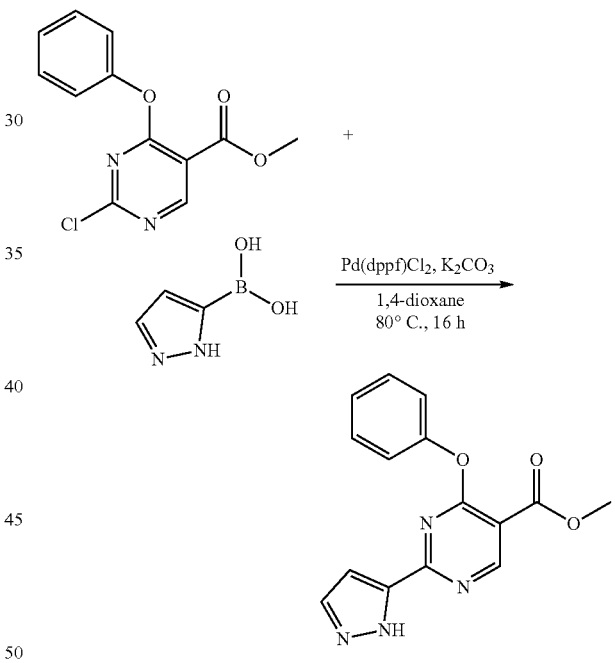

To a solution of methyl 2-chloro-4-phenoxy-pyrimidine-5-carboxylate (100 mg, 0.38 mmol), 1H-pyrazol-5-ylboronic acid (50.7 mg, 0.45 mmol), potassium carbonate (78.33 mg, 0.57 mmol) in 1,4-dioxane (3 mL, 0.105 M) and water (0.600 mL, 0.105 M) was added Pd(dppf)Cl$_2$ (15 mg) under N$_2$. The mixture was stirred at 80° C. for 16 hours. The mixture was added EtOAc (5 ml) and water (5 ml). The aqueous phase was extracted with EtOAc (2×5 ml). The organic phase was washed with brine (2×5 ml) and dried with anhydrous Na$_2$SO$_4$. The mixture was concentrated. The residue was purified by prep-HPLC(TFA) to afford methyl 4-phenoxy-2-(1H-pyrazol-5-yl)pyrimidine-5-carboxylate as a yellow solid (26 mg, 23% yield).

Following Step 6 and 7 in Procedure A, the title compound was obtained. LC-MS m/z: 400.1 [M+1].

Example 210

(R,E)-2-(2-fluorophenyl)-N-(4-(methylsulfonyl)but-3-en-2-yl)-4-phenoxypyrimidine-5-carboxamide

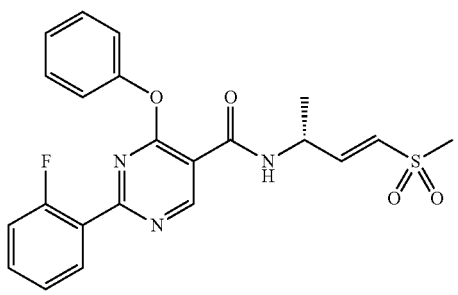 [SMILES: C[C@H](/C=C/S(C)(=O)=O)NC(=O)c1cnc(-c2ccccc2F)nc1Oc1ccccc1]

Using 2-fluorophenylboronic acid at Step 1 of the procedure for the compound of Example 209 and using [(E,1R)-1-methyl-3-methylsulfonyl-allyl]amine 4-methylbenzenesulfonic acid at the last step, the title compound was obtained. LC-MS m/z: 442.0 [M+1].

Example 211

(S,E)-2-(5,6-dihydro-2H-pyran-3-yl)-N-(4-(methylsulfonyl)but-3-en-2-yl)-4-phenoxypyrimidine-5-carboxamide

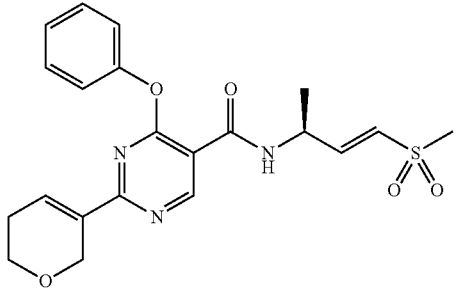 [SMILES: C[C@@H](/C=C/S(C)(=O)=O)NC(=O)c1cnc(C2=CCCOC2)nc1Oc1ccccc1]

Using 2-(5,6-dihydro-2h-pyran-3-yl)-4,4,5,5-tetramethyl-1,3,2-dioxaborolane at Step 1 of the procedure for the compound of Example 209 and using [(E,1S)-1-methyl-3-methylsulfonyl-allyl]amine 4-methylbenzenesulfonic acid at the last step, the title compound was obtained. LC-MS m/z: 430.2 [M+1].

Example 212

N—((S,E)-4-(methylsulfonyl)but-3-en-2-yl)-4-phenoxy-2-(tetrahydro-2H-pyran-3-yl)pyrimidine-5-carboxamide

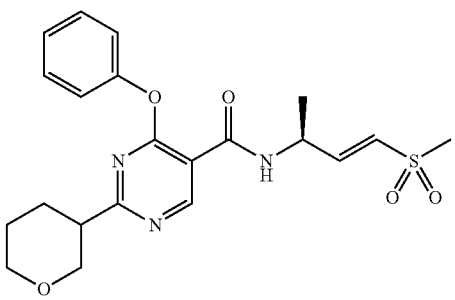 [SMILES: C[C@@H](/C=C/S(C)(=O)=O)NC(=O)c1cnc(C2CCCOC2)nc1Oc1ccccc1]

Using 2-(5,6-dihydro-2h-pyran-3-yl)-4,4,5,5-tetramethyl-1,3,2-dioxaborolane at Step 1 of the procedure for the compound of Example 209, following Step 2 in Procedure D (hydrogenation) and using [(E,1S)-1-methyl-3-methylsulfonyl-allyl]amine 4-methylbenzenesulfonic acid at the last step, the title compound was obtained. LC-MS m/z: 432.0 [M+1].

Example 213

(S,E)-2-(2-methylprop-1-en-1-yl)-N-(4-(methylsulfonyl)but-3-en-2-yl)-4-phenoxypyrimidine-5-carboxamide

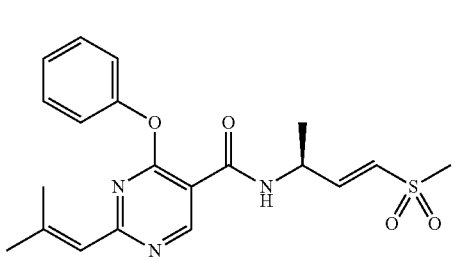 [SMILES: CC(C)=Cc1ncc(C(=O)N[C@@H](C)/C=C/S(C)(=O)=O)c(Oc2ccccc2)n1]

Using 4,4,5,5-tetramethyl-2-(2-methylprop-1-enyl)-1,3,2-dioxaborolane at Step 1 of the procedure for the compound of Example 209 and using [(E,1S)-1-methyl-3-methylsulfonyl-allyl]amine 4-methylbenzenesulfonic acid at the last step, the title compound was obtained. LC-MS m/z: 402.1 [M+1].

Example 214

(S,E)-2-isobutyl-N-(4-(methylsulfonyl)but-3-en-2-yl)-4-phenoxypyrimidine-5-carboxamide

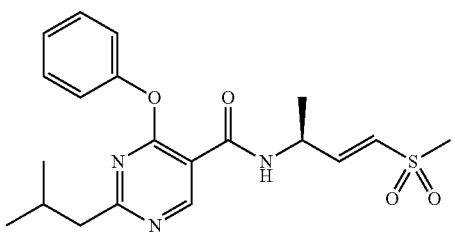 [SMILES: CC(C)Cc1ncc(C(=O)N[C@@H](C)/C=C/S(C)(=O)=O)c(Oc2ccccc2)n1]

Using 4,4,5,5-tetramethyl-2-(2-methylprop-1-enyl)-1,3,2-dioxaborolane at Step 1 of the procedure for the compound of Example 209, following Step 2 in Procedure D (hydrogenation) and using [(E,1S)-1-methyl-3-methylsulfonyl-allyl]amine 4-methylbenzenesulfonic acid at the last step, the title compound was obtained. LC-MS m/z: 404.2 [M+1].

Example 215

Rac-2-((1R,3S)-3-methylcyclopentyl)-N—((S,E)-4-(methylsulfonyl)but-3-en-2-yl)-4-phenoxypyrimidine-5-carboxamide

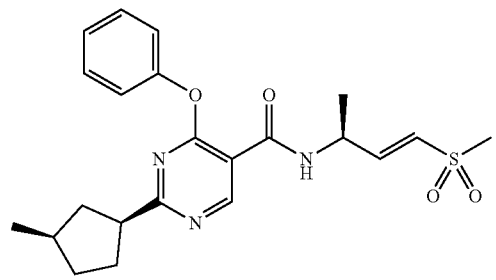

Step 1

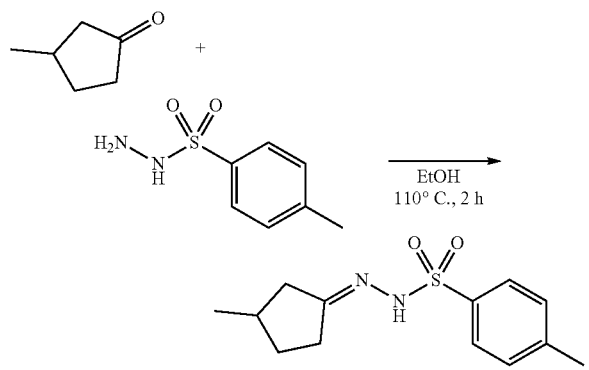

To a solution of 3-methylcyclopentanone (500 mg, 5.10 mmol) in ethanol (10 mL, 0.51 M) was added p-toluenesulfonyl hydrazide (948.8 mg, 5.10 mmol) and then the mixture was stirred at 110° C. for 2 hours. The reaction mixture was concentrated under reduced pressure to give a residue. The residue was triturated with MTBE and DCM to afford 4-methyl-N—[(Z)-(3-methylcyclopentylidene)amino]benzenesulfonamide as a white solid (900 mg, 66% yield).

Step 2

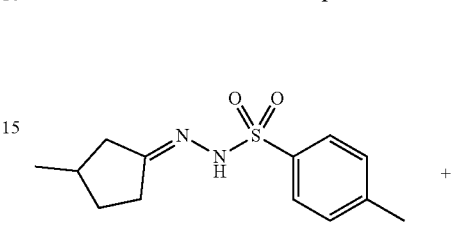

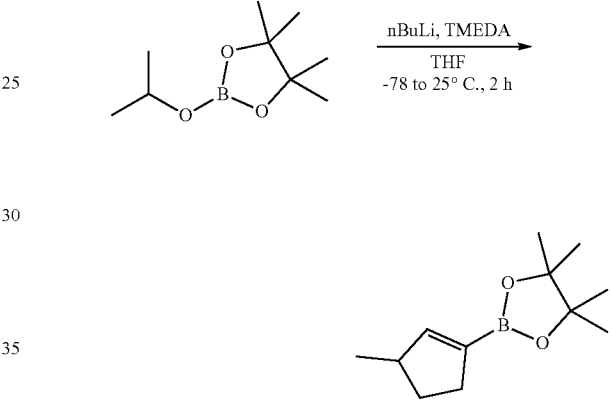

To a solution of 4-methyl-N—[(Z)-(3-methylcyclopentylidene)amino]benzenesulfonamide (5.0 g, 18.77 mmol) in THF (60 mL, 0.313 M) was added N,N,N',N'-tetramethylethylenediamine (60 mL, 389.85 mmol, 0.7550 g/ml) and the mixture was cooled to −78° C. and then n-butyllithium solution (34.54 mL, 86.35 mmol, 2.5 M) was added dropwise at −78° C. The mixture was stirred at −78° C. for 1 hour, then allowed to warm to 25° C. After stirring for 1.5 hours, the mixture was cooled to −78° C. and was added 2-isopropoxy-4,4,5,5-tetramethyl-1,3,2-dioxaborolane (15.4 g, 82.60 mmol) dropwise at −78° C. The mixture was stirred at −78° C. for 1 hour then at 25° C. for 2 hours. The reaction mixture was quenched by saturated aqueous·$NH_4Cl$ (200 mL) and extracted with EtOAc (4×50 mL). The combined organic layers were washed with brine (200 mL), dried over $Na_2SO_4$, filtered and concentrated under reduced pressure to give a residue. The residue was purified by column chromatography ($SiO_2$, Petroleum ether/Ethyl acetate=1:0 to 1:1) to afford 4,4,5,5-tetramethyl-2-(3-methylcyclopenten-1-yl)-1,3,2-dioxaborolane as a yellow oil (1.0 g, 26% yield).

Using 4,4,5,5-tetramethyl-2-(3-methylcyclopenten-1-yl)-1,3,2-dioxaborolane at Step 1 of the procedure for the compound of Example 209, following Step 2 in Procedure D (hydrogenation) and using [(E,1S)-1-methyl-3-methylsulfonyl-allyl]amine 4-methylbenzenesulfonic acid at the last step, the title compound was obtained. LC-MS m/z: 430.2 [M+1].

Example 216

(S,E)-2-(1-hydroxycyclopentyl)-N-(4-(methylsulfonyl)but-3-en-2-yl)-4-phenoxypyrimidine-5-carboxamide

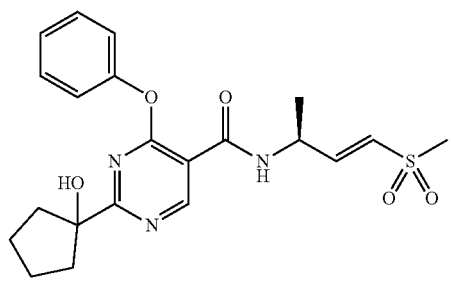 [SMILES: C[C@@H](/C=C/S(C)(=O)=O)NC(=O)c1cnc(C2(O)CCCC2)nc1Oc1ccccc1]

Using cyclopenten-1-ylboronic acid at Step 1 of the procedure for the compound of Example 209, ethyl 2-(cyclopenten-1-yl)-4-phenoxy-pyrimidine-5-carboxylate was obtained as a white solid.

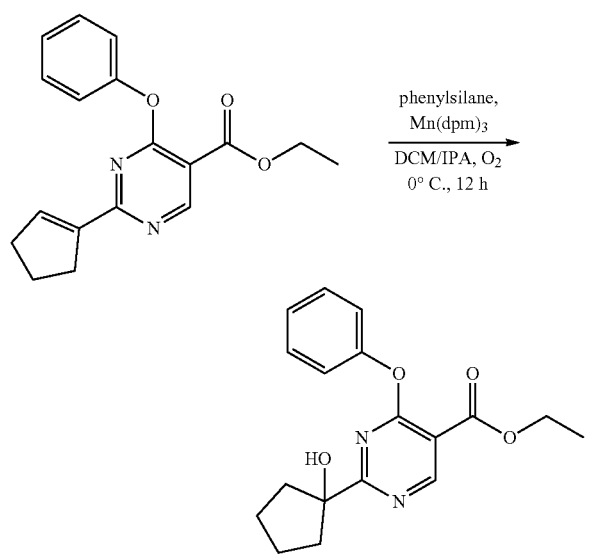

To a solution of ethyl 2-(cyclopenten-1-yl)-4-phenoxy-pyrimidine-5-carboxylate (600 mg, 1.93 mmol) in DCM (6 mL, 0.242 M) and IPA (2 mL, 0.242 M) was added phenylsilane (209.2 mg, 1.93 mmol) and Mn(dpm)₃ (84 mg) at 0° C. The air was removed from the flask. The reaction mixture was stirred under an atmosphere of oxygen for 12 h. The reaction mixture was filtered through a pad of celite, and concentrated under reduced pressure to give a residue. The residue was purified by column chromatography (SiO₂, Petroleum ether/Ethyl acetate=1/0 to 10/1) to afford ethyl 2-(1-hydroxycyclopentyl)-4-phenoxy-pyrimidine-5-carboxylate as a white solid (300 mg, 47% yield).

Following Step 6 with ethyl 2-(1-hydroxycyclopentyl)-4-phenoxy-pyrimidine-5-carboxylate and Step 7 with [(E,1S)-1-methyl-3-methylsulfonyl-allyl]amine 4-methylbenzenesulfonic acid in Procedure A, the title compound was obtained. LC-MS m/z: 432.1 [M+1].

Example 217

(S,E)-2-(1-fluorocyclopentyl)-N-(4-(methylsulfonyl)but-3-en-2-yl)-4-phenoxypyrimidine-5-carboxamide

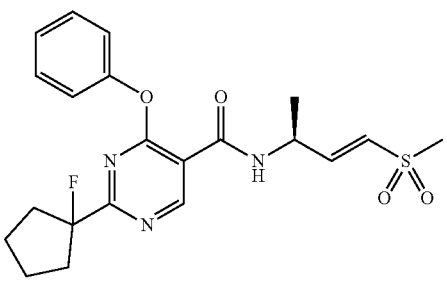 [SMILES: C[C@@H](/C=C/S(C)(=O)=O)NC(=O)c1cnc(C2(F)CCCC2)nc1Oc1ccccc1]

Step 1

To a solution of ethyl 2-(1-hydroxycyclopentyl)-4-phenoxy-pyrimidine-5-carboxylate (200 mg, 0.61 mmol) in DCM (5 mL, 0.122 M) was added diethylaminosulfur trifluoride (147.3 mg, 0.91 mmol) at 0° C. The mixture was stirred at 0° C. for 0.5 hour. The reaction mixture was diluted with water (5 mL) and extracted with DCM (3×5 mL). The combined organic layers were dried over anhydrous Na₂SO₄, filtered and the filtrate was concentrated under reduced pressure to give a residue. The residue was purified by prep-TLC (Petroleum ether/Ethyl acetate=10/1, Rf (product)=0.4) to afford ethyl 2-(1-fluorocyclopentyl)-4-phenoxy-pyrimidine-5-carboxylate as a white solid (80 mg, 40% yield).

Following Step 6 with ethyl 2-(1-fluorocyclopentyl)-4-phenoxy-pyrimidine-5-carboxylate and Step 7 with [(E,1S)-1-methyl-3-methylsulfonyl-allyl]amine 4-methylbenzenesulfonic acid in Procedure A, the title compound was obtained. LC-MS m/z: 434.2 [M+1].

Example 218

(S,E)-2-(2-hydroxypropan-2-yl)-N-(4-(methylsulfonyl)but-3-en-2-yl)-4-phenoxypyrimidine-5-carboxamide

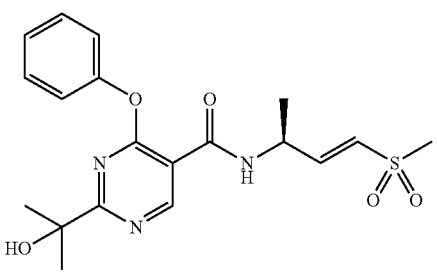 [SMILES: C[C@@H](/C=C/S(C)(=O)=O)NC(=O)c1cnc(C(C)(C)O)nc1Oc1ccccc1]

Using 2-isopropenyl-4,4,5,5-tetramethyl-1,3,2-dioxaborolane as the starting material to follow the procedure for the compound of Example 216, the title compound was obtained. LC-MS m/z: 406.2 [M+1].

Example 219

(S,E)-2-(2-fluoropropan-2-yl)-N-(4-(methylsulfonyl)but-3-en-2-yl)-4-phenoxypyrimidine-5-carboxamide

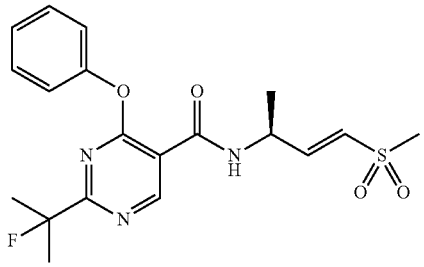 [SMILES: C[C@@H](/C=C/S(C)(=O)=O)NC(=O)c1cnc(C(C)(C)F)nc1Oc1ccccc1]

Using ethyl 2-(1-hydroxy-1-methyl-ethyl)-4-phenoxy-pyrimidine-5-carboxylate as the starting material to follow the procedure for the compound of Example 217, the title compound was obtained. LC-MS m/z: 408.1 [M+1].

Example 220

(S,E)-N-(1-cyclopropyl-3-(methylsulfonyl)allyl)-2-(2-fluoropropan-2-yl)-4-phenoxypyrimidine-5-carboxamide

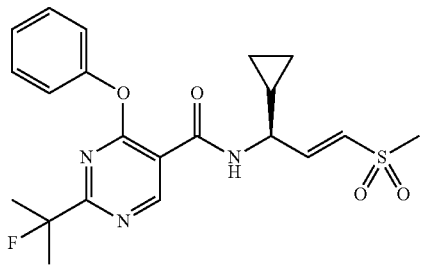 [SMILES: CC(C)(F)c1ncc(C(=O)N[C@H](/C=C/S(C)(=O)=O)C2CC2)c(Oc2ccccc2)n1]

Following Step 7 with 2-(2-fluoropropan-2-yl)-4-phenoxypyrimidine-5-carboxylic acid/[(E,1S)-1-cyclopropyl-3-methylsulfonyl-allyl]amine 4-methylbenzenesulfonic acid in Procedure A, the title compound was obtained. LC-MS m/z: 434.1 [M+1].

Example 221

(S,E)-2-(2-methoxypropan-2-yl)-N-(4-(methylsulfonyl)but-3-en-2-yl)-4-phenoxypyrimidine-5-carboxamide

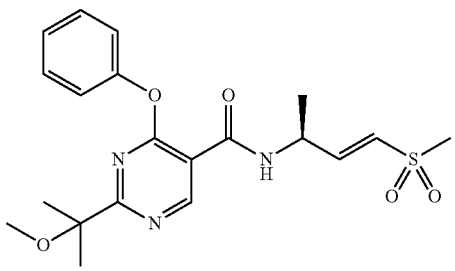

Step 1

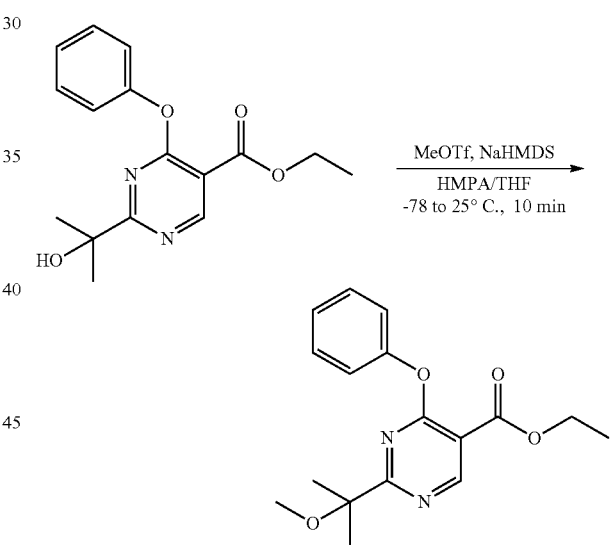

To the mixture of ethyl 2-(1-hydroxy-1-methyl-ethyl)-4-phenoxy-pyrimidine-5-carboxylate (50 mg, 0.17 mmol) in THF (3 mL, 0.028 M) was added a solution of NaHMDS (0.2 mL, 1M) and hexamethylphosphoramide (59.3 mg, 0.33 mmol) in THF (3 mL, 0.028 M) at −78° C. The mixture was stirred at −78° C. for 5 minutes. Then the mixture was added methyl trifluoromethanesulfonate (54.3 mg, 0.33 mmol) at −78° C. and the resulting mixture was stirred at 25° C. for 10 minutes. The reaction mixture was quenched by NH$_4$Cl (5 mL) and the aqueous phase was extracted with EtOAc (3×10 mL). The combined organic layers were dried over anhydrous Na$_2$SO$_4$, filtered and the filtrate was concentrated under reduced pressure to give a residue. The residue was purified by Prep-TLC (SiO$_2$, Petroleum ether/Ethyl acetate=3/1) to give ethyl 2-(1-methoxy-1-methyl-ethyl)-4-phenoxy-pyrimidine-5-carboxylate as a white solid (40 mg, 76% yield).

Following Step 6 with ethyl 2-(1-methoxy-1-methyl-ethyl)-4-phenoxy-pyrimidine-5-carboxylate and Step 7 with [(E,1S)-1-methyl-3-methylsulfonyl-allyl]amine 4-methylbenzenesulfonic acid in Procedure A, the title compound was obtained. LC-MS m/z: 420.1 [M+1].

Example 222

(S,E)-2-(bicyclo[1.1.1]pentan-1-yl)-N-(4-(methylsulfonyl)but-3-en-2-yl)-4-phenoxypyrimidine-5-carboxamide

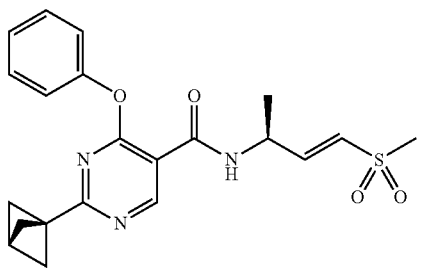

Step 1

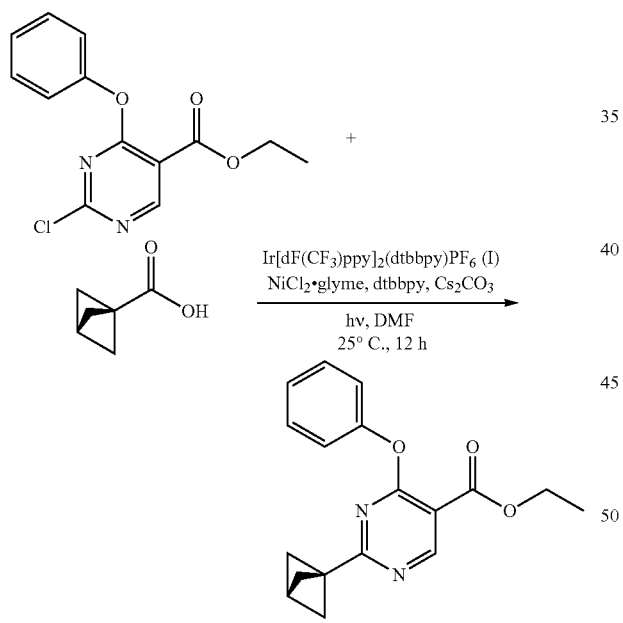

To the mixture of ethyl 2-chloro-4-phenoxy-pyrimidine-5-carboxylate (300 mg, 1.08 mmol), bicyclo[1.1.1]pentane-1-carboxylic acid (120.7 mg, 1.08 mmol) in DMF (2 mL, 0.179 M) was added Ir[dF(CF$_3$)ppy]$_2$(dtbbpy)PF$_6$ (I) (10 mg, 10.0 μmol), NiCl$_2$·glyme (36 mg), dtbbpy (60 mg), Cs$_2$CO$_3$ (1.15 g). The reaction mixture was degassed by bubbling nitrogen stream for 15 minutes at 0° C. The reaction mixture was then stirred and irradiated with two 34 W blue LEDs (vials approximately 6 cm away from the light source) with a fan placed above for cooling. The reaction was stirred at 25° C. for 12 hours. The reaction mixture was added with water (5 mL) and the aqueous phase was extracted with EtOAc (3×10 mL). The combined organic layers were dried over anhydrous Na$_2$SO$_4$, filtered and concentrated under reduced pressure to give a residue. The residue was purified by Prep-TLC (SiO$_2$, Petroleum ether/ Ethyl acetate=3/1) to afford ethyl 2-(1-bicyclo[1.1.1]pentanyl)-4-phenoxy-pyrimidine-5-carboxylate as a red oil (20 mg, 6.0% yield).

Following Step 6 with ethyl 2-(1-bicyclo[1.1.1]pentanyl)-4-phenoxy-pyrimidine-5-carboxylate and Step 7 with [(E, 1S)-1-methyl-3-methylsulfonyl-allyl]amine 4-methylbenzenesulfonic acid in Procedure A, the title compound was obtained. LC-MS m/z: 414.1 [M+1].

Example 223

(S,E)-2-(cyclopropyldifluoromethyl)-N-(4-(methylsulfonyl)but-3-en-2-yl)-4-phenoxypyrimidine-5-carboxamide

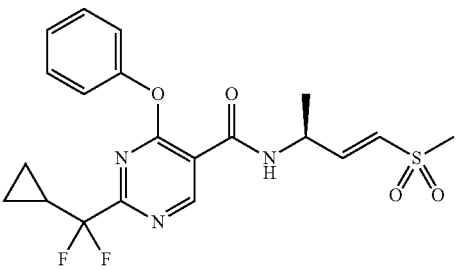 [SMILES: C[C@@H](/C=C/S(C)(=O)=O)NC(=O)c1cnc(C(F)(F)C2CC2)nc1Oc1ccccc1]

Step 1

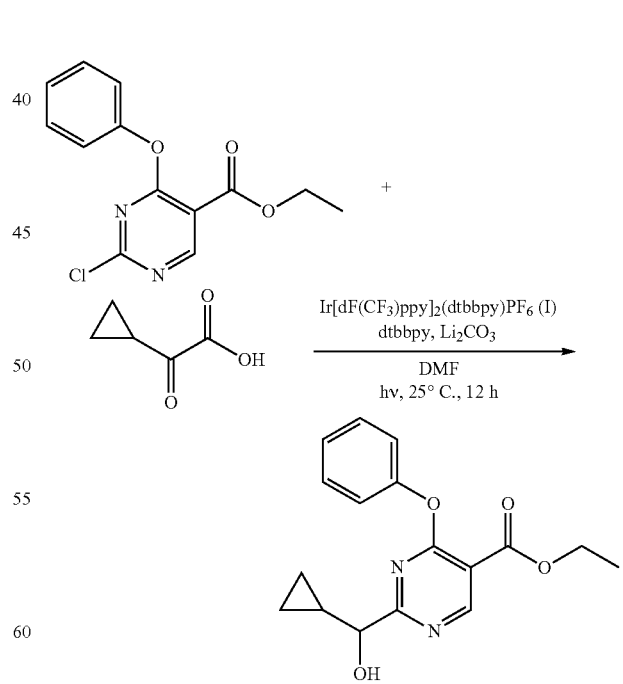

To the mixture of ethyl 2-chloro-4-phenoxy-pyrimidine-5-carboxylate (150 mg, 0.54 mmol) in DMF (2 mL, 0.179 M) was added 2-cyclopropyl-2-oxo-acetic acid (122.8 mg, 1.08 mmol), Ir[dF(CH$_3$)ppy]$_2$(dtbbpy)PF$_6$ (I) (3.5 mg, 10.0 mol), NiCl₂·glyme (12 mg), dtbbpy (14 mg), Li₂CO₃ (230 mg). The reaction mixture was degassed by bubbling nitrogen stream for 15 minutes at 0° C. The reaction mixture was then stirred and irradiated with two 34 W blue LEDs (vials approximately 6 cm away from the light source) with a fan placed above for cooling. The mixture was stirred for 12 hours at 25° C. The mixture was added with H₂O (5 mL) and the aqueous phase was extracted with EtOAc (3×10 mL). The combined organic layers were dried over anhydrous Na₂SO₄, filtered and concentrated under reduced pressure to give a residue. The residue was purified by prep-TLC (SiO₂, Petroleum ether/Ethyl acetate=5/1, Rf=0.35) to give ethyl 2-[cyclopropyl(hydroxy)methyl]-4-phenoxy-pyrimidine-5-carboxylate as a yellow oil (30 mg, 18% yield).

Step 2

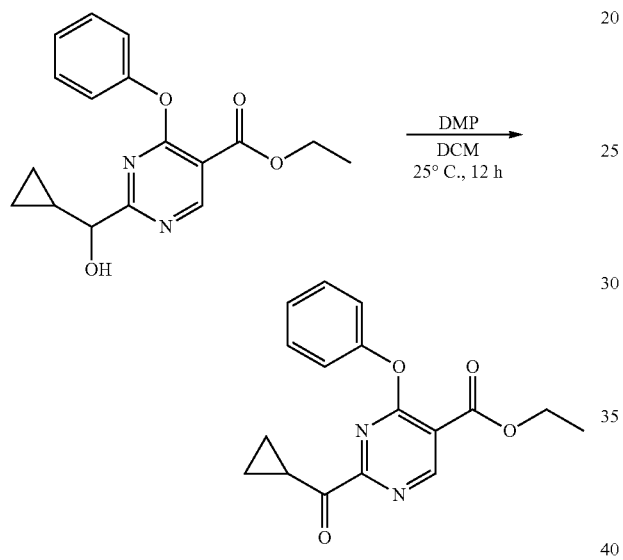

To the mixture of ethyl 2-[cyclopropyl(hydroxy)methyl]-4-phenoxy-pyrimidine-5-carboxylate (20 mg, 0.064 mmol) in DCM (3 mL, 0.0212 M) was added Dess-Martin periodinane (17.5 mg). The mixture was stirred at 25° C. for 12 hours. The reaction mixture was added with Na₂S₂O₃·aq (2 mL) and the aqueous phase was extracted with EtOAc (3×10 mL). The combined organic layers were dried over anhydrous Na₂SO₄, filtered and concentrated under reduced pressure to afford crude ethyl 2-(cyclopropanecarbonyl)-4-phenoxy-pyrimidine-5-carboxylate as a yellow oil (10 mg).

Step 3

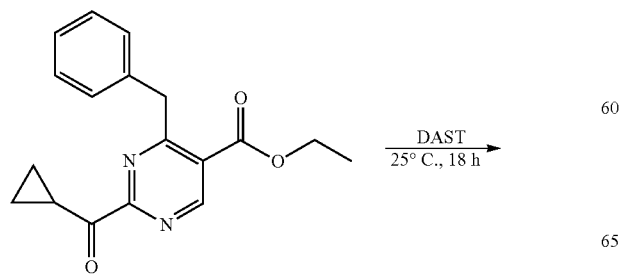

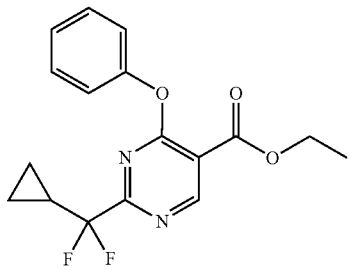

The mixture of ethyl 2-(cyclopropanecarbonyl)-4-phenoxy-pyrimidine-5-carboxylate (140 mg, 0.45 mmol) in DAST (2 mL) was stirred at 25° C. for 18 hours. The reaction mixture was quenched by addition of Na₂S₂O₃·aq (2 mL) at 25° C., and then diluted with H₂O (2 mL) and extracted with EtOAc (3×3 mL). The combined organic layers were washed with brine (3 mL), dried over anhydrous Na₂SO₄, filtered and concentrated under reduced pressure to give a residue. The residue was purified by prep-TLC (SiO₂, Petroleum ether/Ethyl acetate=3/1) to give ethyl 2-[cyclopropyl(difluoro)methyl]-4-phenoxy-pyrimidine-5-carboxylate as a yellow oil (130 mg, 87% yield).

Following Step 6 with ethyl 2-[cyclopropyl(difluoro)methyl]-4-phenoxy-pyrimidine-5-carboxylate and Step 7 with [(E,1S)-1-methyl-3-methylsulfonyl-allyl]amine 4-methylbenzenesulfonic acid in Procedure A, the title compound was obtained. LC-MS m/z: 438.1 [M+1].

Example 224

(S,E)-N-(1-cyclopropyl-3-(methylsulfonyl)allyl)-2-(cyclopropyldifluoromethyl)-4-phenoxypyrimidine-5-carboxamide

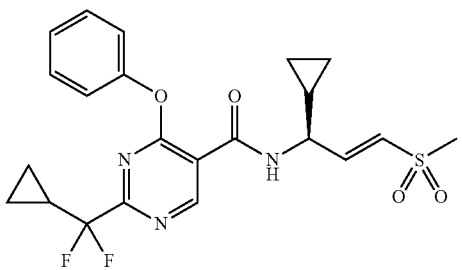 [SMILES: CS(=O)(=O)/C=C/[C@@H](NC(=O)c1cnc(C(F)(F)C2CC2)nc1Oc1ccccc1)C1CC1]

Following Step 6 with ethyl 2-[cyclopropyl(difluoro)methyl]-4-phenoxy-pyrimidine-5-carboxylate and Step 7 with [(E,1S)-1-cyclopropyl-3-methylsulfonyl-allyl]amine 4-methylbenzenesulfonic acid in Procedure A, the title compound was obtained. LC-MS m/z: 464.1 [M+1].

Example 225

(S,E)-N-(1-cyclobutyl-3-(methylsulfonyl)allyl)-2-(cyclopropyldifluoromethyl)-4-phenoxypyrimidine-5-carboxamide

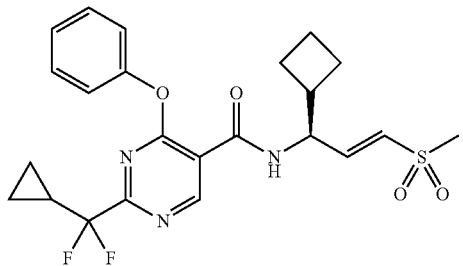 [SMILES: CS(=O)(=O)/C=C/[C@@H](NC(=O)c1cnc(C(F)(F)C2CC2)nc1Oc1ccccc1)C1CCC1]

Following Step 6 with ethyl 2-[cyclopropyl(difluoro)methyl]-4-phenoxy-pyrimidine-5-carboxylate and Step 7 with [(E,1S)-1-cyclobutyl-3-methylsulfonyl-allyl]amine 4-methylbenzenesulfonic acid in Procedure A, the title compound was obtained. LC-MS m/z: 478.1 [M+1].

Example 226

(S,E)-2-(cyclopropyldifluoromethyl)-N-(1-methoxy-4-(methylsulfonyl)but-3-en-2-yl)-4-phenoxypyrimidine-5-carboxamide

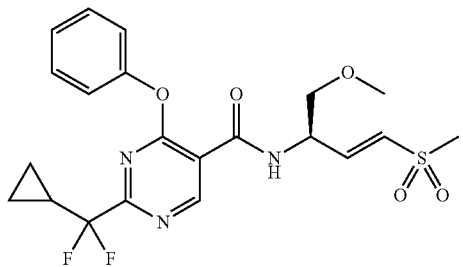 [SMILES: COC[C@@H](/C=C/S(C)(=O)=O)NC(=O)c1cnc(C(F)(F)C2CC2)nc1Oc1ccccc1]

Following Step 6 with ethyl 2-[cyclopropyl(difluoro)methyl]-4-phenoxy-pyrimidine-5-carboxylate and Step 7 with (E,2R)-1-methoxy-4-methylsulfonyl-but-3-en-2-amine 4-methylbenzenesulfonic acid in Procedure A, the title compound was obtained. LC-MS m/z: 468.1 [M+1].

Examples 227 and 228

(S,E)-2-(cyclopropyldifluoromethyl)-N-(1-(3,3-difluorocyclobutyl)-3-(methylsulfonyl)allyl)-4-phenoxypyrimidine-5-carboxamide/(R,E)-2-(cyclopropyldifluoromethyl)-N-(1-(3,3-difluorocyclobutyl)-3-(methylsulfonyl)allyl)-4-phenoxypyrimidine-5-carboxamide

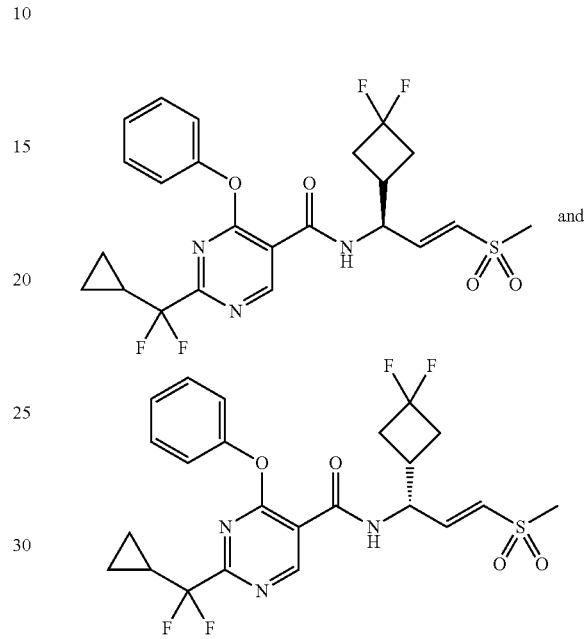

Using 2-[cyclopropyl(difluoro)methyl]-4-phenoxy-pyrimidine-5-carboxylic acid at Step 5 to follow the procedure for the compounds of Example 192/193, the mixture of title compounds was obtained. The mixture was separated by chiral SFC (column: Daicel ChiralPak AD (250 mm*30 mm, 10 um)) to afford Peak 1 (LC-MS m/z: 514.2 [M+1]) and Peak 2 (LC-MS m/z: 514.1 [M+1]). The absolute stereochemistry of the title compounds were not ascertained.

Example 229

(S,E)-N-(1-cyclopropyl-3-(methylsulfonyl)allyl)-2-(cyclopropyldifluoromethyl)-4-(phenoxy-d5)pyrimidine-5-carboxamide

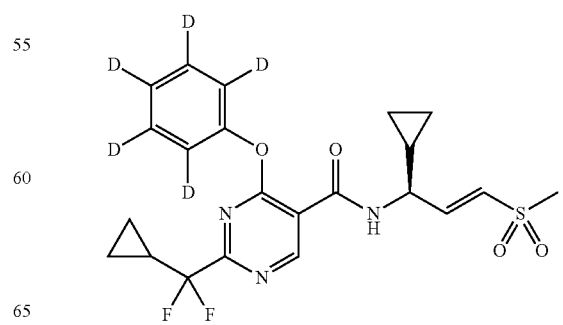

215

Step 1

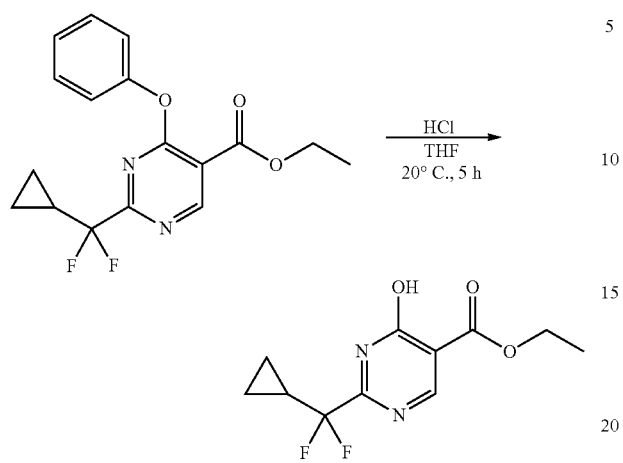

A solution of ethyl 2-[cyclopropyl(difluoro)methyl]-4-phenoxy-pyrimidine-5-carboxylate (500 mg, 1.50 mmol) in THF (5 mL, 0.299 M) and HCl (6 N, 5 mL) was stirred at 20° C. for 5 hours. The reaction mixture was poured into water (30 mL) and extracted with DCM:isopropyl alcohol=3:1 (3×30 mL). The combined organic layers were washed with brine (3×30 mL), dried over $Na_2SO_4$, filtered and concentrated under reduced pressure to give a residue. The residue was purified by prep-HPLC (column: Phenomenex Luna 80*30 mm*3 um; mobile phase: water (TFA)-MeCN; B %: 10%-45%, 8 min) to afford ethyl 2-[cyclopropyl(difluoro)methyl]-4-hydroxy-pyrimidine-5-carboxylate as a white solid (210 mg, 54% yield).

Following Step 4 in Procedure A with ethyl 2-[cyclopropyl(difluoro)methyl]-4-hydroxy-pyrimidine-5-carboxylate, Step 5 with phen-d5-ol and subsequent steps while using [(E,1S)-1-cyclopropyl-3-methylsulfonyl-allyl]amine 4-methylbenzenesulfonic acid at the last step, the title compound was obtained. LC-MS m/z: 469.3 [M+1].

Example 230

(S,E)-N-(1-cyclopropyl-3-(methylsulfonyl)allyl)-2-(1,1-difluoropropyl)-4-phenoxypyrimidine-5-carboxamide

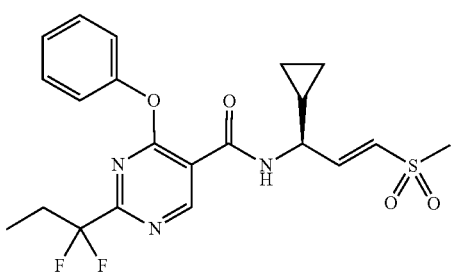 [SMILES: CCC(F)(F)c1ncc(C(=O)N[C@H](/C=C/S(C)(=O)=O)C2CC2)c(Oc2ccccc2)n1]

Using 2-oxobutanoic acid at Step 1 of the procedure for the compound of Example 223 and following the subsequent steps while using [(E,1S)-1-cyclopropyl-3-methylsulfonyl-allyl]amine 4-methylbenzenesulfonic acid at the last step, the title compound was obtained. LC-MS m/z: 452.2 [M+1].

216

Example 231

(S,E)-N-(1-cyclopropyl-3-(methylsulfonyl)allyl)-6-(1,1-difluoroethyl)-4-phenoxynicotinamide

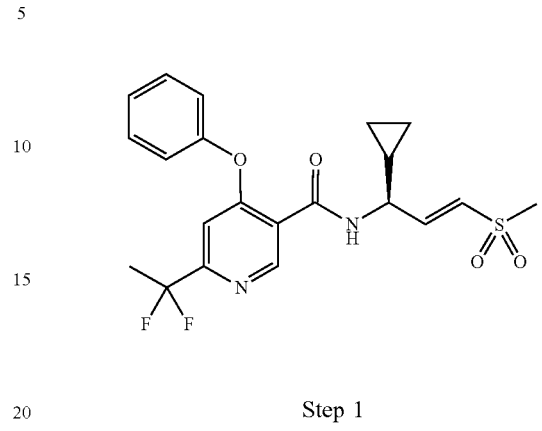

Step 1

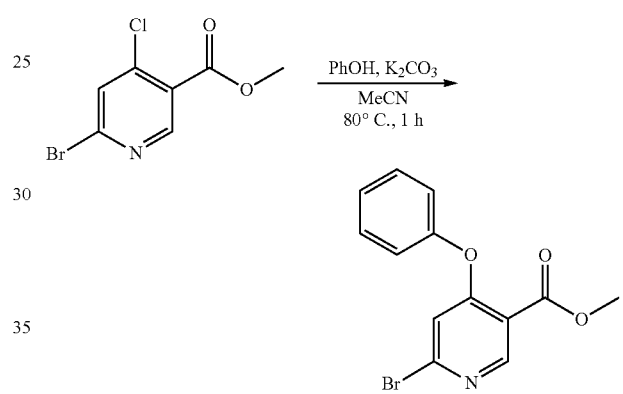

To a solution of methyl 6-bromo-4-chloro-pyridine-3-carboxylate (90 mg, 0.36 mmol) in MeCN (2 mL, 0.095 M) was added phenol (27 mg, 0.29 mmol) and potassium carbonate (149 mg, 1.08 mmol). The mixture was stirred at 80° C. for 1 hour under $N_2$. The reaction mixture was concentrated under reduced pressure to give a residue. The residue was diluted with brine (10 mL) and the aqueous phase was extracted with EtOAc (5×5 mL). The combined organic layers were dried over anhydrous $Na_2SO_4$, filtered and the filtrate was concentrated under reduced pressure to give a residue. The residue was purified by prep-TLC ($SiO_2$, Petroleum ether/Ethyl acetate=3/1) to afford methyl 6-bromo-4-phenoxy-pyridine-3-carboxylate as a white solid (80 mg, 72% yield).

Step 2

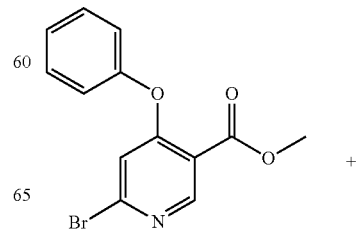 +

-continued

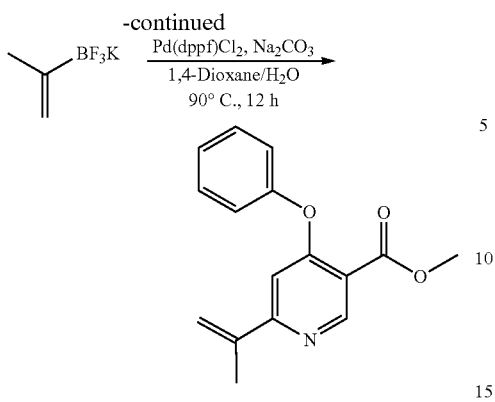

To a solution of methyl 6-bromo-4-phenoxy-pyridine-3-carboxylate (610 mg, 1.98 mmol) in 1,4-dioxane (40 mL, 0.048 M) and water (1 mL, 0.048 M) was added trifluoro(prop-1-en-2-yl)-λ4-borane potassium salt (293 mg, 1.98 mmol), sodium carbonate (629.48 mg, 5.9391 mmol) and Pd(dppf)Cl₂ (143 mg, 0.20 mmol). The mixture was heated at 90° C. for 12 hours under N₂. After cooling to room temperature, the reaction mixture was concentrated under reduced pressure to give a residue. The residue was diluted with brine (20 mL) and the aqueous phase was extracted with EtOAc (3×30 mL). The combined organic layers were dried over anhydrous Na₂SO₄, filtered and concentrated under reduced pressure to give a residue. The residue was purified by flash column chromatography (Biotage using a 40 g Agela flash silica gel column, eluted with 0% to 17% ethyl acetate in petroleum ether) to afford methyl 6-isopropenyl-4-phenoxy-pyridine-3-carboxylate as a light yellow solid (320 mg, 60% yield).

Step 3

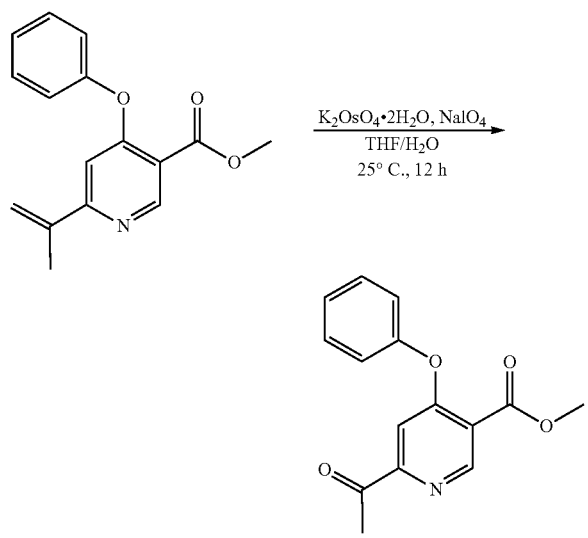

To a solution of methyl 6-isopropenyl-4-phenoxy-pyridine-3-carboxylate (26 mg, 0.097 mmol) in THF (2 mL, 0.032 M) and water (1 mL, 0.032 M) was added potassium osmate (VI) dihydrate (3.0 mg, 0.0097 mmol) and sodium periodate (104 mg, 0.48 mmol). The mixture was stirred at 25° C. for 12 hours under N₂. The reaction mixture was concentrated under reduced pressure to afford crude methyl 6-acetyl-4-phenoxy-pyridine-3-carboxylate as a yellow oil (0.30 g).

Using methyl 6-acetyl-4-phenoxy-pyridine-3-carboxylate to follow Step 3 of the procedure for the compound of Example 223 and the subsequent the steps while using [(E,1S)-1-cyclopropyl-3-methylsulfonyl-allyl]amine 4-methylbenzenesulfonic acid at the last step, the title compound was obtained. LC-MS m/z: 437.1 [M+1].

Example 232

(S,E)-6-(1,1-difluoroethyl)-N-(4-(methylsulfonyl)but-3-en-2-yl)-2-phenoxynicotinamide

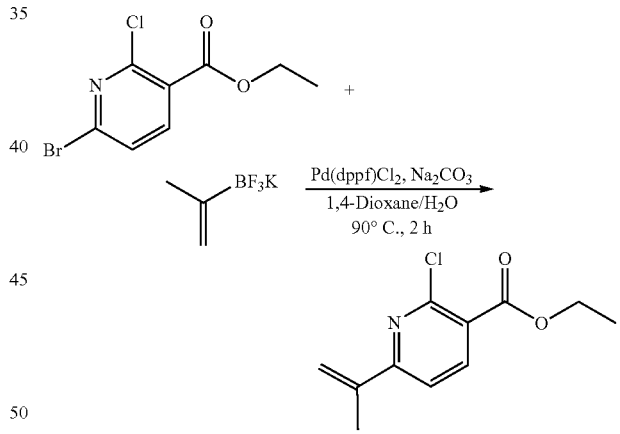

Step 1

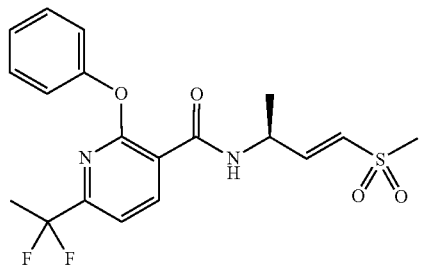 [SMILES: C[C@@H](/C=C/S(C)(=O)=O)NC(=O)c1ccc(C(C)(F)F)nc1Oc1ccccc1]

To a solution of ethyl 6-bromo-2-chloro-pyridine-3-carboxylate (900 mg, 3.40 mmol) in 1,4-dioxane (10 mL, 0.28 M) and water (2 mL, 0.28 M) was added trifluoro(prop-1-en-2-yl)-λ4-borane potassium salt (503.5 mg, 3.40 mmol), Na₂CO₃ (1.08 g) and Pd(dppf)Cl₂ (210 mg). The mixture was stirred at 90° C. for 2 hours under N₂. The reaction mixture was quenched by addition of water (20 mL) at 20° C. and extracted with EtOAc (3×15 mL). The combined organic layers were washed with brine (30 mL), dried over Na₂SO₄, filtered and concentrated under reduced pressure to give a residue. The residue was purified by column chromatography (silica gel eluted with petroleum ether/ethyl acetate=100:1 to 10:1) to afford ethyl 2-chloro-6-isopropenyl-pyridine-3-carboxylate as a colorless oil (690 mg, 90% yield).

Step 2

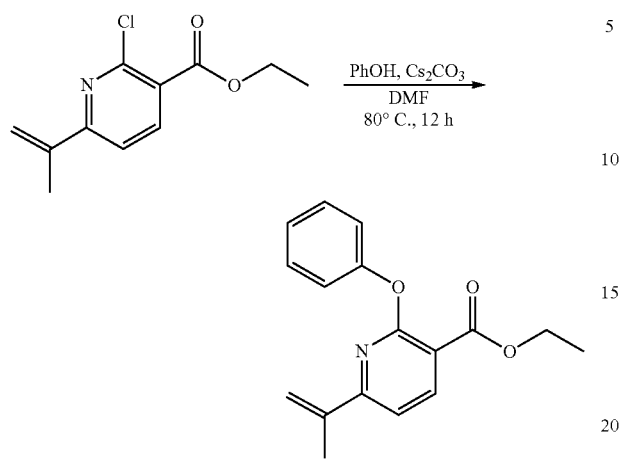

To a solution of phenol (316.5 mg, 3.36 mmol) in DMF (10 mL, 0.306 M) was added $Cs_2CO_3$ (1.2 g) and ethyl 2-chloro-6-isopropenyl-pyridine-3-carboxylate (690 mg, 3.06 mmol). The mixture was heated at 80° C. for 12 hours under $N_2$. The reaction mixture was quenched by addition water (30 mL) at 20° C. and extracted with EtOAc (3×10 mL). The combined organic layers were washed with brine (20 mL), dried over $Na_2SO_4$, filtered and concentrated under reduced pressure to give a residue. The residue was purified by column chromatography (silica gel eluted with petroleum ether/ethyl acetate=100:1 to 10:1) to afford ethyl 6-isopropenyl-2-phenoxy-pyridine-3-carboxylate as a colorless oil (670 mg, 77% yield).

Using ethyl 6-isopropenyl-2-phenoxy-pyridine-3-carboxylate to follow the procedure for the compound of Example 231 from Step 3 and using [(E,1S)-1-methyl-3-methylsulfonyl-allyl]amine 4-methylbenzenesulfonic acid at the last step, the title compound was obtained. LC-MS m/z: 411.1 [M+1].

Example 233

(S,E)-N-(1-cyclopropyl-3-(methylsulfonyl)allyl)-6-(1,1-difluoroethyl)-2-phenoxynicotinamide

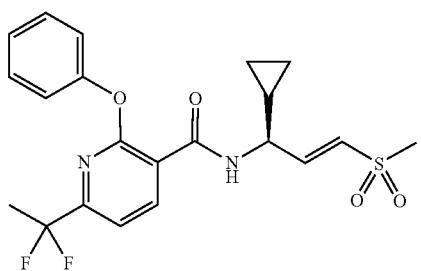 [SMILES: CC(F)(F)c1ccc(C(=O)N[C@H](/C=C/S(C)(=O)=O)C2CC2)c(Oc2ccccc2)n1]

Following the procedure for the compound of Example 232 and using [(E,1S)-1-cyclopropyl-3-methylsulfonyl-allyl]amine 4-methylbenzenesulfonic acid at the last step, the title compound was obtained. LC-MS m/z: 437.1 [M+1].

Example 234

(S,E)-N-(1-cyclopropyl-3-(methylsulfonyl)allyl)-6-(cyclopropyldifluoromethyl)-2-phenoxynicotinamide

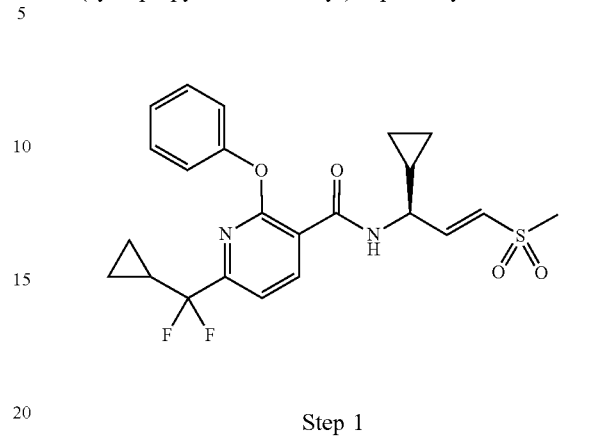

Step 1

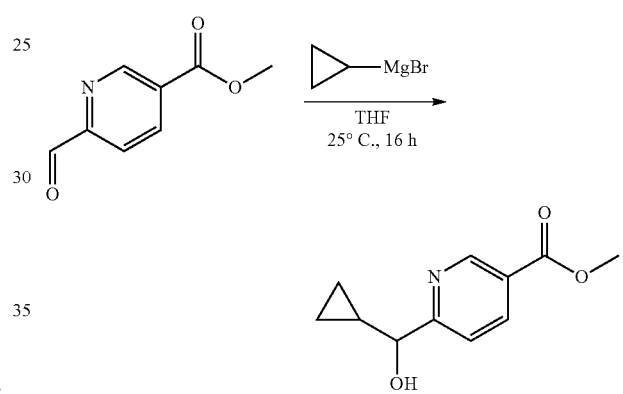

Bromo(cyclopropyl)magnesium (20.0 mL, 19.98 mmol, 1M) was added to methyl 6-formylpyridine-3-carboxylate (3 g, 18.17 mmol) in THF (50 mL, 0.363 M) at 0° C. The resulting mixture was stirred at 25° C. for 16 hours. The reaction mixture was poured into saturated aqueous·$NH_4Cl$ (100 mL) and extracted with EtOAc (3×100 mL). The combined organic layers were washed with brine (2×100 mL), dried over $Na_2SO_4$, filtered and concentrated under reduced pressure to give a residue. The residue was purified by flash silica gel chromatography (ISCO®; 40 g SepaFlash® Silica Flash Column, Eluent of 0~15% Ethyl acetate/ Petroleum ether gradient at 100 mL/min) to afford methyl 6-[cyclopropyl(hydroxy)methyl]pyridine-3-carboxylate as a yellow oil (1.5 g, 40% yield).

Step 2

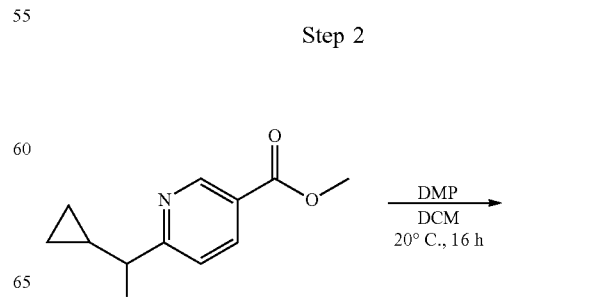

-continued

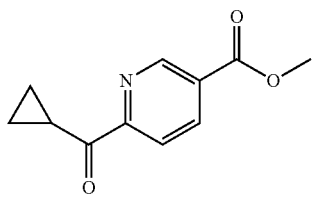

DMP (300 mg) was added to methyl 6-[cyclopropyl(hydroxy)methyl]pyridine-3-carboxylate (1.4 g, 6.76 mmol) in DCM (30 mL, 0.225 M) at 0° C. The mixture was stirred at 20° C. for 16 hours. The reaction was quenched by addition of the saturated aq·Na$_2$S$_2$O$_3$ (40 mL), and the solution was extracted with DCM (3×40 mL). The combined organic layers were washed brine (40 mL) and aq·NaHCO$_3$ (20 mL), dried over Na$_2$SO$_4$, filtered and concentrated to give a residue. The residue was purified by flash silica gel chromatography (ISCO®; 12 g SepaFlash® Silica Flash Column, Eluent of 0~5% Ethyl acetate/Petroleum ether gradient at 100 mL/min) to afford methyl 6-(cyclopropanecarbonyl)pyridine-3-carboxylate as a white solid (1.35 g, 97% yield).

Step 3

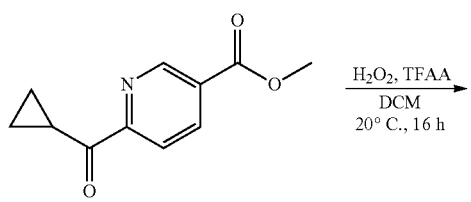

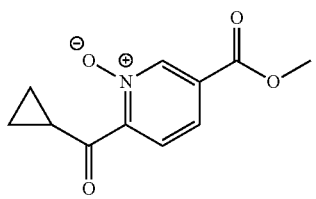

To the mixture of methyl 6-(cyclopropanecarbonyl)pyridine-3-carboxylate (650 mg, 3.17 mmol) in DCM (25 mL, 0.127 M) was added hydrogen peroxide urea (1.04 g, 11.09 mmol). The mixture was cooled to 0° C., then trifluoroacetic anhydride (1.66 g, 7.92 mmol) was added dropwise. The resulting mixture was stirred at 20° C. for 16 hours. The reaction mixture was poured into saturated aqueous NaHCO$_3$ (50 mL) and extracted with DCM (3×50 mL). The combined organic layers were washed with brine (2×50 mL), dried over Na$_2$SO$_4$, filtered and concentrated under reduced pressure to afford crude methyl 6-(cyclopropanecarbonyl)-1-oxido-pyridin-1-ium-3-carboxylate as a yellow oil (700 mg).

Step 4

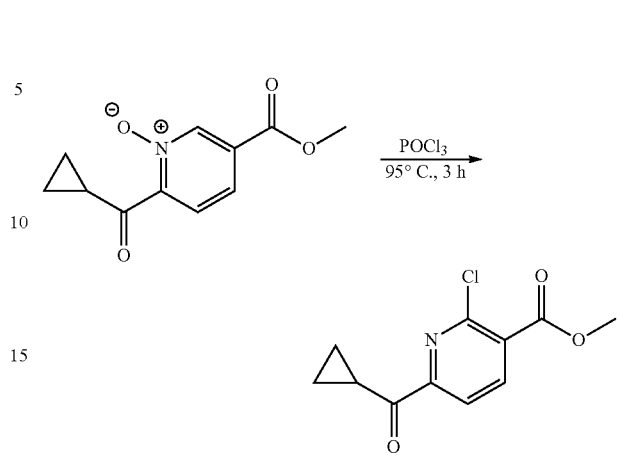

Methyl 6-(cyclopropanecarbonyl)-1-oxido-pyridin-1-ium-3-carboxylate (700 mg, 3.16 mmol) in POCl$_3$ (5 mL) was heated at 95° C. for 3 hours. The reaction mixture was poured into water (30 mL) and extracted with DCM (3×30 mL). The combined organic layers were washed with brine (2×30 mL), dried over Na$_2$SO$_4$, filtered and concentrated under reduced pressure to give a residue. The residue was purified by flash silica gel chromatography (ISCO®; SepaFlash® Silica Flash Column, Eluent of 0~100% Ethyl acetate/Petroleum ether gradient) to afford methyl 2-chloro-6-(cyclopropanecarbonyl)pyridine-3-carboxylate as a yellow oil (270 mg, 36% yield).

Step 5

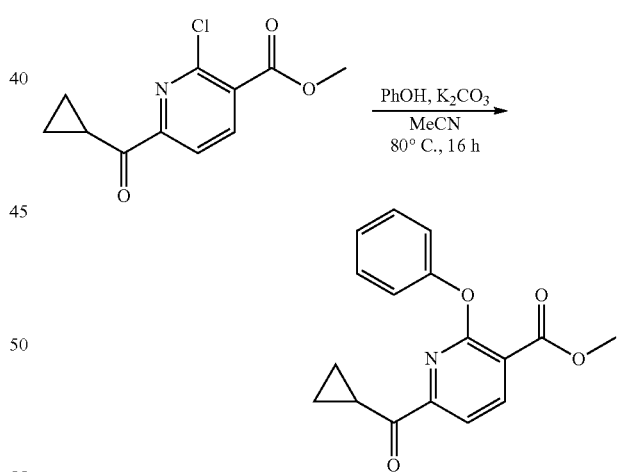

A mixture of methyl 2-chloro-6-(cyclopropanecarbonyl)pyridine-3-carboxylate (270 mg, 1.13 mmol), phenol (127 mg, 1.35 mmol) and K$_2$CO$_3$ (389 mg, 2.82 mmol) in MeCN (5 mL, 0.225 M). The mixture was stirred at 80° C. for 16 hours. The mixture was filtered and the filtrate was concentrated under reduced pressure to give a residue. The residue was purified by prep-TLC (SiO$_2$, PE:EtOAc=5:1) to afford methyl 6-(cyclopropanecarbonyl)-2-phenoxy-pyridine-3-carboxylate as a yellow oil (270 mg, 81% yield).

Using methyl 6-(cyclopropanecarbonyl)-2-phenoxy-pyridine-3-carboxylate to follow Step 3 of the procedure for the compound of Example 223 and the subsequent steps while using [(E,1S)-1-cyclopropyl-3-methylsulfonyl-allyl]amine 4-methylbenzenesulfonic acid at the last step, the title compound was obtained. LC-MS m/z: 463.1 [M+1].

Example 235

(S,E)-N-(1-cyclopropyl-3-(methylsulfonyl)allyl)-6-(1,1-difluoroethyl)-5-fluoro-2-phenoxynicotinamide

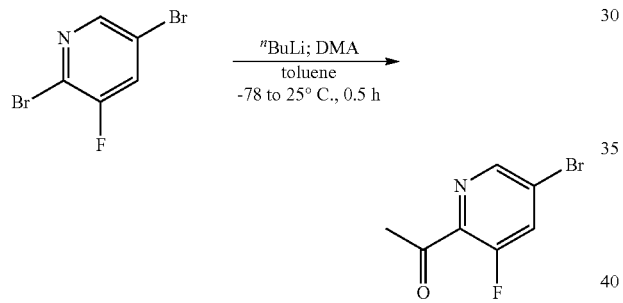

Step 1

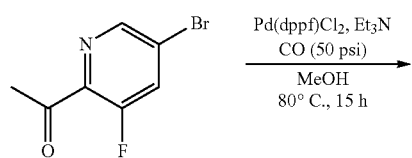

To the mixture of 2,5-dibromo-3-fluoro-pyridine (1 g, 3.92 mmol) in toluene (10 mL, 0.392 M) was added n-BuLi (2.5 M, 1.73 mL) at −78° C. and then stirred for 10 minutes. The mixture was added N,N-dimethylacetamide (0.34 g, 3.92 mmol) and the resulting mixture was stirred at 25° C. for 0.5 hour. The reaction mixture was added with water (5 mL) and the aqueous phase was extracted with EtOAc (3×10 mL). The combined organic layers were dried over anhydrous Na₂SO₄, filtered and concentrated under reduced pressure to give a residue. The residue was purified by flash column (petroleum ether:ethyl acetate=1:0 to 10:1) to afford 1-(5-bromo-3-fluoro-2-pyridyl)ethenone as a white solid (520 mg, 61% yield).

Step 2

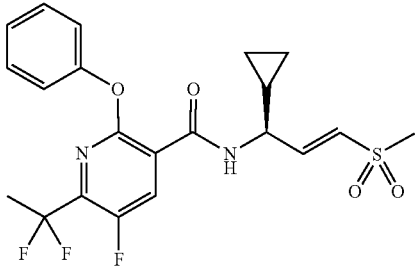 [SMILES: CC(F)(F)c1nc(Oc2ccccc2)c(C(=O)N[C@H](/C=C/S(C)(=O)=O)C2CC2)cc1F]

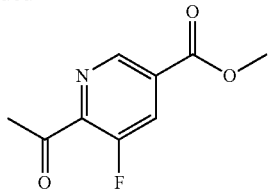

To a mixture of triethylamine (92.8 mg, 0.92 mmol) and 1-(5-bromo-3-fluoro-2-pyridyl)ethanone (100 mg, 0.46 mmol) in methanol (2 mL, 0.229 M) was added Pd(dppf)Cl₂ (45 mg) at 20° C. The mixture was purged with CO and stirred at 80° C. under CO (50 psi) for 15 hours. The mixture was filtered and the filtrate was concentrated under reduced pressure. The residue was purified by prep-TLC (PE:EtOAc=3:1, Rf=0.3) to afford methyl 6-acetyl-5-fluoro-pyridine-3-carboxylate as a white solid (90 mg, 100% yield).

Step 3

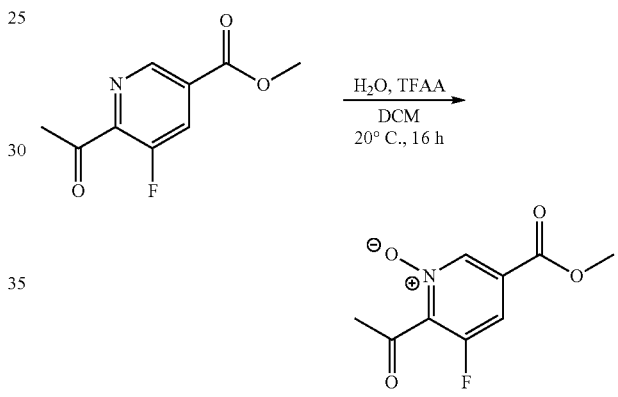

To the mixture of methyl 6-acetyl-5-fluoro-pyridine-3-carboxylate (800 mg, 4.058 mmol) in DCM (10 mL, 0.406 M) was added hydrogen peroxide urea (1.34 g, 14.20 mmol). The mixture was cooled to 0° C., then trifluoroacetic anhydride (2.13 g, 10.14 mmol) was added dropwise into the mixture. The resulting mixture was stirred at 20° C. for 16 hours. The reaction mixture was poured into saturated aqueous NaHCO₃ (5 mL) and extracted with DCM (3×5 mL). The combined organic layers were washed with brine (2×5 mL), dried over Na₂SO₄, filtered and concentrated under reduced pressure to afford crude methyl 6-acetyl-5-fluoro-1-oxido-pyridin-1-ium-3-carboxylate as a yellow oil (470 mg).

Step 4

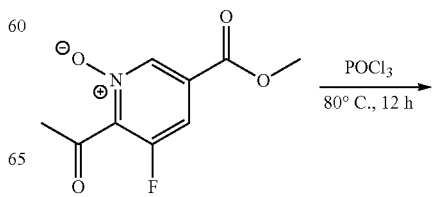

225
-continued

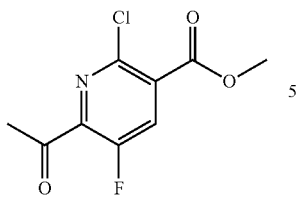

Methyl 6-acetyl-5-fluoro-1-oxido-pyridin-1-ium-3-carboxylate (400 mg, 1.88 mmol) in POCl₃ (5 mL) was heated 80° C. for 12 hours. The reaction mixture was concentrated under reduced pressure to give a residue. The residue was purified by flash column chromatography (petroleum ether: ethyl acetate=1:0 to 3:1) to afford methyl 6-acetyl-2-chloro-5-fluoro-pyridine-3-carboxylate as a yellow oil (210 mg, 48% yield).

Step 5

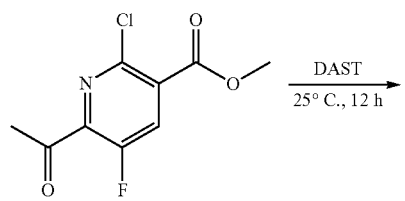

Methyl 6-acetyl-2-chloro-5-fluoro-pyridine-3-carboxylate (200 mg, 0.864 mmol) in DAST (2 mL) was stirred at 25° C. for 12 hours. The reaction mixture was quenched by addition of aqueous Na₂S₂O₃ (2 mL) at 25° C. and diluted with water (2 mL) and extracted with EtOAc (3×3 mL). The combined organic layers were washed with brine (3 mL), dried over, filtered and concentrated under reduced pressure to give a residue. The residue was purified by prep-TLC (SiO₂, Petroleum ether/Ethyl acetate=3/1) to give methyl 2-chloro-6-(1,1-difluoroethyl)-5-fluoro-pyridine-3-carboxylate as a yellow oil (140 mg, 64% yield).

Following Procedure A from Step 5 and using methyl 2-chloro-6-(1,1-difluoroethyl)-5-fluoro-pyridine-3-carboxylate at Step 5 and [(E,1S)-1-cyclopropyl-3-methylsulfonyl-allyl]amine 4-methylbenzenesulfonic acid at Step 7, the title compound was obtained. LC-MS m/z: 455.2 [M+1].

226
Example 236

(S,E)-N-(1-cyclopropyl-3-(methylsulfonyl)allyl)-6-(cyclopropyldifluoromethyl)-5-fluoro-2-phenoxynicotinamide

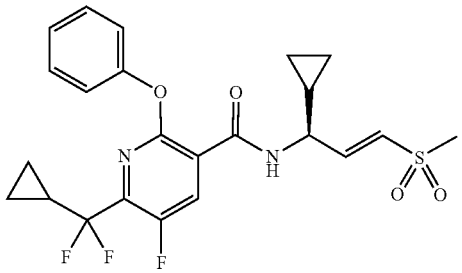 [SMILES: CS(=O)(=O)/C=C/[C@@H](NC(=O)c1cc(F)c(C(F)(F)C2CC2)nc1Oc1ccccc1)C1CC1]

Methyl 2-chloro-6-[cyclopropyl(difluoro)methyl]-5-fluoro-pyridine-3-carboxylate was prepared by following the procedure from Step 1 to Step 5 for the compound of Example 235 and using N-methoxy-N-methylcyclopropanecarboxamide instead of DMA at Step 1.

Step 1

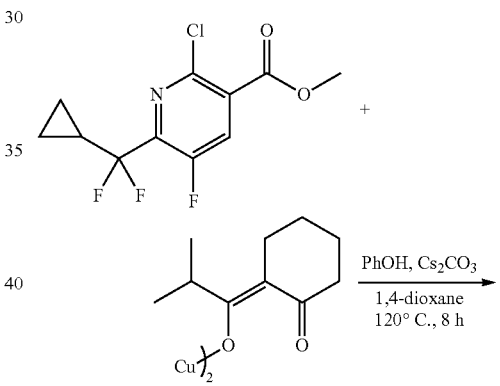

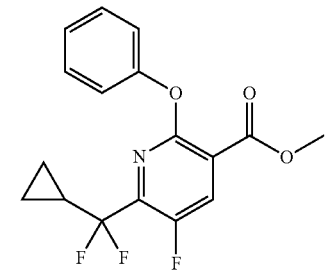

To the mixture of methyl 2-chloro-6-[cyclopropyl(difluoro)methyl]-5-fluoro-pyridine-3-carboxylate (100 mg, 0.358 mmol) and phenol (33.7 mg, 0.358 mmol) in 1,4-dioxane (2 mL, 0.179 M) was added bis[(1Z)-2-methyl-1-(2-oxocyclohexylidene)propoxy]copper (14.23 mg, 0.0358 mmol) and cesium carbonate (233 mg, 0.715 mmol). The mixture was stirred at 120° C. for 8 hours. The reaction mixture was added with water (5 mL) and extracted with DCM (3×3 mL). The combined organic layers were dried over anhydrous Na₂SO₄, filtered and concentrated under reduced pressure to give a residue. The residue was purified by prep-TLC (SiO₂, Petroleum ether/Ethyl acetate=3/1) to afford methyl 6-[cyclopropyl(difluoro)methyl]-5-fluoro-2-phenoxy-pyridine-3-carboxylate as a yellow oil (80 mg, 66% yield).

Following Procedure A from Step 6 and using [(E,1S)-1-cyclopropyl-3-methylsulfonyl-allyl]amine 4-methylbenzenesulfonic acid at Step 7, the title compound was obtained. LC-MS m/z: 481.2 [M+1].

Example 237

(S,E)-N-(1-cyclopropyl-3-(methylsulfonyl)allyl)-7,7-difluoro-2-phenoxy-6,7-dihydro-5H-cyclopenta[b]pyridine-3-carboxamide

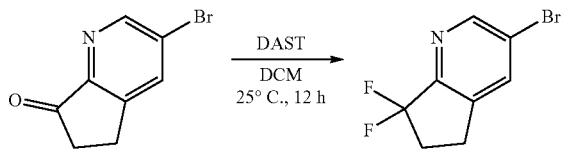

Step 1

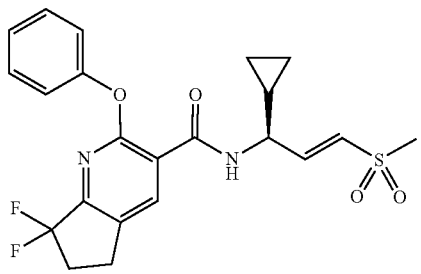 [SMILES: CS(=O)(=O)/C=C/[C@@H](NC(=O)c1cc2c(nc1Oc1ccccc1)C(F)(F)CC2)C1CC1]

The mixture of 3-bromo-5,6-dihydrocyclopenta[b]pyridin-7-one (900 mg, 4.24 mmol) in DAST (6 mL) and DCM (3 mL) was stirred at 25° C. for 12 hours. The reaction mixture was quenched by addition of water (3 mL) dropwise at 0° C., and then diluted with water (5 mL) and extracted with DCM (4×10 mL). The combined organic layers were washed with brine (10 mL), dried over anhydrous Na₂SO₄, filtered and concentrated under reduced pressure to give a residue. The residue was purified by flash column (SiO₂, petroleum ether:ethyl acetate=1:0 to 3:1) to afford 3-bromo-5,6-dihydrocyclopenta[b]pyridin-7-one as a brown solid (900 mg, 61% yield).

Step 2

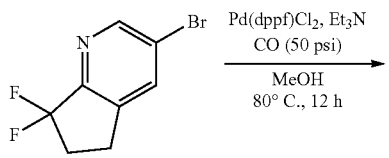

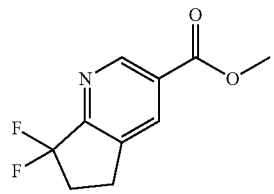

To a mixture of 3-bromo-7,7-difluoro-5,6-dihydrocyclopenta[b]pyridine (600 mg, 2.56 mmol) in methanol (15 mL, 0.171 M) was added Pd(dppf)Cl₂ (186 mg, 0.26 mmol) and TEA (778 mg) at 20° C. The mixture was purged CO and stirred at 80° C. under CO (50 psi) for 12 hours. The mixture was filtered and the filtrate was concentrated under reduced pressure. The residue was purified by silica gel column (PE:EtOAc=3:1, Rf=0.3) to afford methyl 7,7-difluoro-5,6-dihydrocyclopenta[b]pyridine-3-carboxylate as a gray solid (460 mg, 84% yield).

Step 3

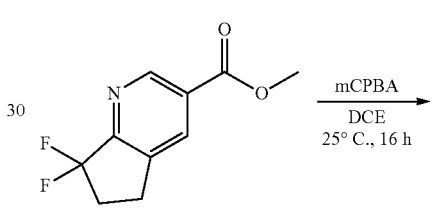

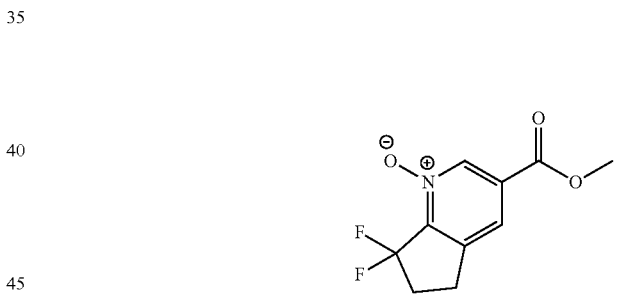

To a solution of methyl 7,7-difluoro-5,6-dihydrocyclopenta[b]pyridine-3-carboxylate (300 mg, 1.41 mmol) in DCE (6 mL, 0.235 M) was added 3-chloroperbenzoic acid (1.2 g, 7.04 mmol). The mixture was stirred at 25° C. for 16 hours. The reaction mixture was added with aq·Na₂S₂O₃ (5 mL) and the aqueous phase was extracted with EtOAc (3×10 mL). The combined organic layers were dried over anhydrous Na₂SO₄, filtered and concentrated under reduced pressure to give a residue. The residue was purified by flash column (petroleum ether:ethyl acetate=1:0 to 3:1, Rf=0.3) to afford methyl 7,7-difluoro-1-oxido-5,6-dihydrocyclopenta[b]pyridin-1-ium-3-carboxylate as a colorless oil (130 mg, 40% yield).

Using methyl 7,7-difluoro-1-oxido-5,6-dihydrocyclopenta[b]pyridin-1-ium-3-carboxylate to follow Step 4 in Procedure A and following the subsequent steps while using [(E,1S)-1-methyl-3-methylsulfonyl-allyl]amine 4-methylbenzenesulfonic acid at the last step, the title compound was obtained. LC-MS m/z: 449.2 [M+1].

Example 238

(S,E)-N-(4-(methylsulfonyl)but-3-en-2-yl)-4-phenoxy-2-(tetrahydro-2H-pyran-4-yl)pyrimidine-5-carboxamide

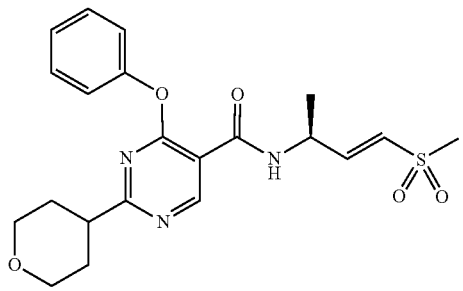 [SMILES: C[C@@H](/C=C/S(C)(=O)=O)NC(=O)c1cnc(C2CCOCC2)nc1Oc1ccccc1]

Step 1

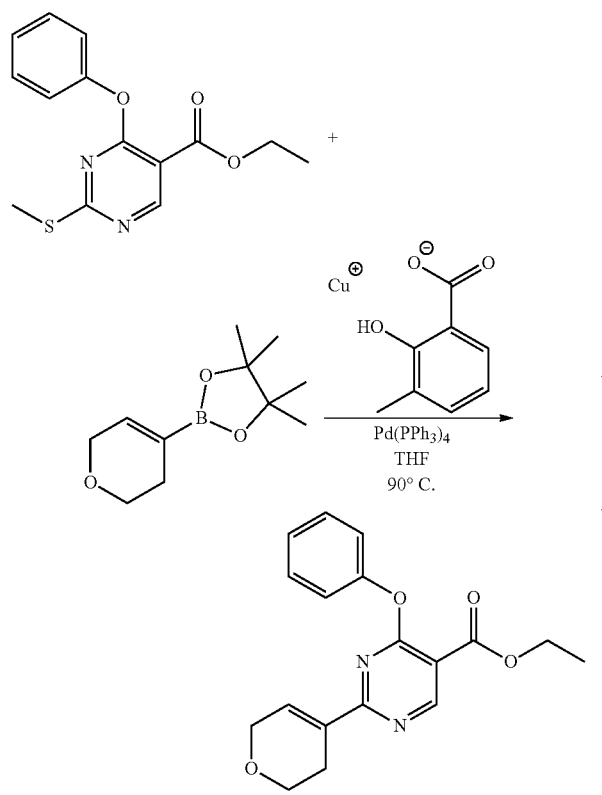

To a solution of 2-(3,6-dihydro-2H-pyran-4-yl)-4,4,5,5-tetramethyl-1,3,2-dioxaborolane (362 mg, 1.72 mmol), ethyl 2-methylsulfanyl-4-phenoxy-pyrimidine-5-carboxylate (500 mg, 1.72 mmol) and cuprous 2-hydroxy-3-methylbenzoate (555 mg, 2.58 mmol) in THF (4 mL, 0.431 M) was added Pd(PPh$_3$)$_4$ (199 mg). The reaction mixture was concentrated under reduced pressure to give a residue. The residue was purified by flash column chromatography (Biotage using a 4 g Agela flash silica gel column, eluted with 0% to 15% ethyl acetate in petroleum ether to afford ethyl 2-(3,6-dihydro-2H-pyran-4-yl)-4-phenoxy-pyrimidine-5-carboxylate as a yellow oil (130 mg, 23% yield).

Following Step 2 (hydrogenation) of the procedure for the compound of Example 199, then Step 6 and 7 in Procedure A using [(E,1S)-1-methyl-3-methylsulfonyl-allyl]amine 4-methylbenzenesulfonic acid, the title compound was obtained. LC-MS m/z: 432.2 [M+1].

Example 239

(S,E)-4-cyclohexyl-2-cyclopentyl-N-(4-(methylsulfonyl)but-3-en-2-yl)pyrimidine-5-carboxamide

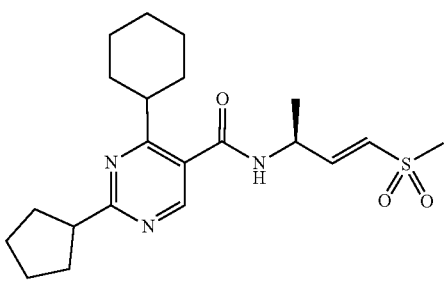 [SMILES: C[C@@H](/C=C/S(C)(=O)=O)NC(=O)c1cnc(C2CCCC2)nc1C1CCCCC1]

Step 1

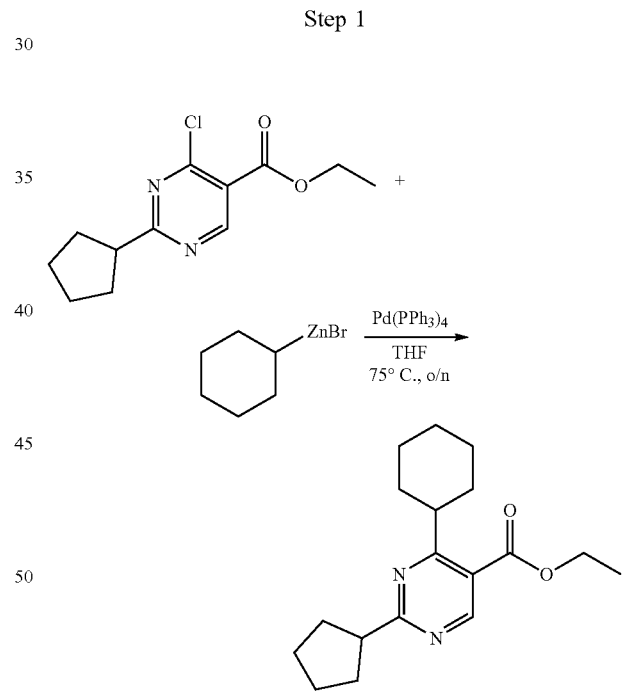

To a solution of ethyl 4-chloro-2-cyclopentyl-pyrimidine-5-carboxylate (50 mg, 0.196 mmol) in THF (2 mL, 0.098 M) was added tetrakis(triphenylphosphine) (11 mg) and cyclohexylzinc bromide (0.47 mL, 0.236 mmol). The reaction was stirred at 75° C. overnight. The reaction mixture was filtered through a pad of celite, washed with EtOAc, and concentrated in reduced pressure. The residue was purified via normal phase column chromatography using Biotage Isolera (0-100% EtOAc/hexanes) to afford ethyl 4-cyclohexyl-2-cyclopentyl-pyrimidine-5-carboxylate as a colorless oil (56 mg, 94% yield).

Following Step 6 with ethyl 4-cyclohexyl-2-cyclopentyl-pyrimidine-5-carboxylate and Step 7 with [(E,1S)-1-methyl-3-methylsulfonyl-allyl]amine 4-methylbenzenesulfonic acid in Procedure A, the title compound was obtained. LC-MS m/z: 406.2 [M+1].

Example 240

(S,E)-2-(cyclohexylmethyl)-N-(4-(methylsulfonyl)but-3-en-2-yl)-4-phenoxypyrimidine-5-carboxamide

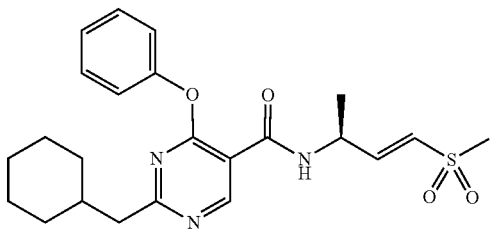 [SMILES: C[C@@H](/C=C/S(C)(=O)=O)NC(=O)c1cnc(CC2CCCCC2)nc1Oc1ccccc1]

Step 1

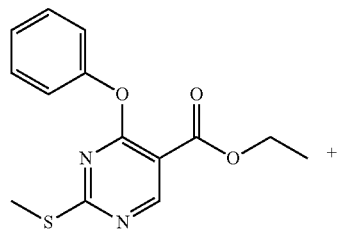

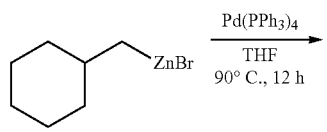

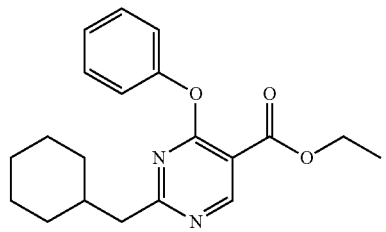

To a solution of ethyl 2-methylsulfanyl-4-phenoxy-pyrimidine-5-carboxylate (300 mg, 1.03 mmol) in THF (10 mL, 0.103 M) was added Pd(PPh₃)₄ (240 mg) and cyclohexylmethylzinc bromide (2.26 g, 9.30 mmol) (2.5 M, 13.4 mL) under N₂. The mixture was stirred at 90° C. for 12 hours. The reaction mixture was added with water (10 mL) and the aqueous phase was extracted with EtOAc (3×20 mL). The combined organic layers were dried over anhydrous Na₂SO₄, filtered and the filtrate was concentrated under reduced pressure to give a residue. The residue was purified by flash column (petroleum ether:ethyl acetate=1:0 to 5:1) to afford ethyl 2-(cyclohexylmethyl)-4-phenoxy-pyrimidine-5-carboxylate as a yellow oil (210 mg, 60% yield).

Following Step 6 with ethyl 2-(cyclohexylmethyl)-4-phenoxy-pyrimidine-5-carboxylate and Step 7 with [(E,1S)-1-methyl-3-methylsulfonyl-allyl]amine 4-methylbenzenesulfonic acid in Procedure A, the title compound was obtained. LC-MS m/z: 444.2 [M+1].

Example 241

(E)-N-(3-(methylsulfonyl)allyl)-2-(methylthio)-4-phenoxypyrimidine-5-carboxamide

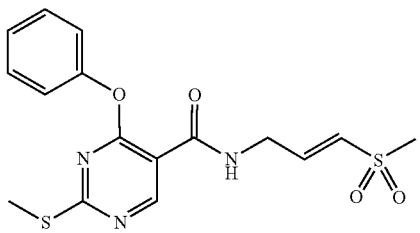 [SMILES: CSc1ncc(C(=O)NC/C=C/S(C)(=O)=O)c(Oc2ccccc2)n1]

Following Step 6 and 7 in Procedure A and using ethyl 2-methylsulfanyl-4-phenoxy-pyrimidine-5-carboxylate, the title compound was obtained. LC-MS m/z: 380.1 [M+1].

Example 242

(S,E)-N-(4-(methylsulfonyl)but-3-en-2-yl)-2-phenoxyquinoline-3-carboxamide

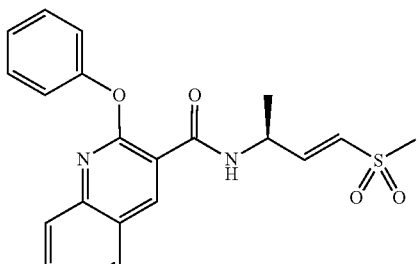

Following Step 5 with methyl 2-chloroquinoline-3-carboxylate, Step 6 and Step 7 with [(E,1S)-1-methyl-3-methylsulfonyl-allyl]amine 4-methylbenzenesulfonic acid in Procedure A, the title compound was obtained. LC-MS m/z: 397.0 [M+1].

Example 243

(S,E)-N-(4-(methylsulfonyl)but-3-en-2-yl)-2-phenoxy-6,7-dihydro-5H-cyclopenta[b]pyridine-3-carboxamide

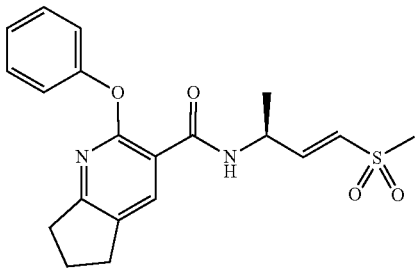 [SMILES: C[C@@H](/C=C/S(C)(=O)=O)NC(=O)c1cc2c(nc1Oc1ccccc1)CCC2]

Following Step 5 with methyl 2-chloro-6,7-dihydro-5H-cyclopenta[b]pyridine-3-carboxylate, Step 6 and Step 7 with [(E,1S)-1-methyl-3-methylsulfonyl-allyl]amine 4-methylbenzenesulfonic acid in Procedure A, the title compound was obtained. LC-MS m/z: 387.0 [M+1].

Example 244

(S,E)-N-(1-cyclopropyl-3-(methylsulfonyl)allyl)-2-methoxy-4-phenoxypyrimidine-5-carboxamide

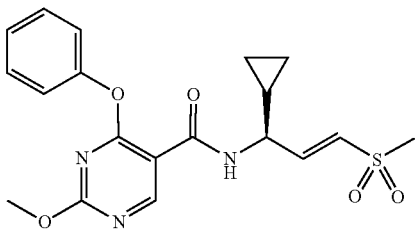 [SMILES: COc1ncc(C(=O)N[C@H](/C=C/S(C)(=O)=O)C2CC2)c(Oc2ccccc2)n1]

Following Step 5 with ethyl 4-chloro-2-methoxy-pyrimidine-5-carboxylate, Step 6 and Step 7 with [(E,1S)-1-cyclopropyl-3-methylsulfonyl-allyl]amine 4-methylbenzenesulfonic acid in Procedure A, the title compound was obtained. LC-MS m/z: 404.1 [M+1].

Example 245

(S,E)-2-cyclopropoxy-N-(1-cyclopropyl-3-(methylsulfonyl)allyl)-4-phenoxypyrimidine-5-carboxamide

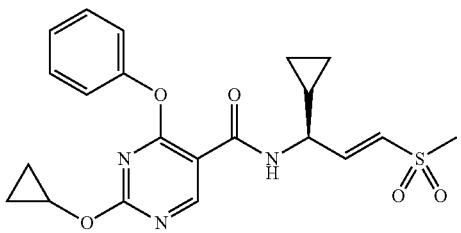

Step 1

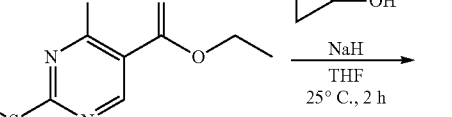

To a solution of cyclopropanol (109.7 mg, 1.89 mmol) in THF (18 mL, 0.073 M) was added sodium hydride (75.6 mg, 1.89 mmol, 60%) at 0° C. The mixture was stirred at 25° C. for 30 minutes. Then ethyl 4-chloro-2-methylsulfonyl-pyrimidine-5-carboxylate (500 mg, 1.89 mmol) in THF (8 mL, 0.073 M) was added into the mixture. The mixture was stirred at 25° C. for 2 hours under N$_2$. The reaction mixture was concentrated under reduced pressure to give a residue. The residue was diluted with H$_2$O (20 mL) and the aqueous phase was extracted with EtOAc (3×15 mL). The combined organic layers were dried over Na$_2$SO$_4$, filtered and concentrated under reduced pressure to give a residue. The residue was purified by flash column chromatography (Biotage using a 40 g Agela flash silica gel column, eluted with 0% to 7% ethyl acetate in petroleum ether) to afford ethyl 4-chloro-2-(cyclopropoxy)pyrimidine-5-carboxylate as a white solid (80 mg, 17% yield).

Following Step 5 with ethyl 4-chloro-2-(cyclopropoxy)pyrimidine-5-carboxylate, Step 6 and Step 7 with [(E,1S)-1-cyclopropyl-3-methylsulfonyl-allyl]amine 4-methylbenzenesulfonic acid in Procedure A, the title compound was obtained. LC-MS m/z: 430.1 [M+1].

Example 246

(S,E)-N-(1-cyclopropyl-3-(methylsulfonyl)allyl)-4-phenoxy-2-(2,2,2-trifluoroethoxy)pyrimidine-5-carboxamide

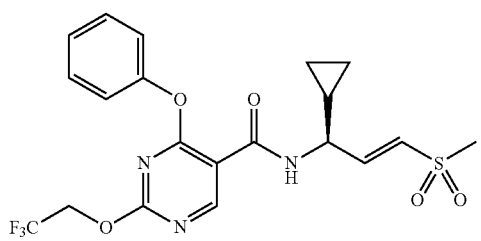 [SMILES: CS(=O)(=O)/C=C/[C@@H](NC(=O)c1cnc(OCC(F)(F)F)nc1Oc1ccccc1)C1CC1]

Using 2,2,2-trifluoroethanol at Step 1 to follow the procedure for the compound of Example 245, the title compound was obtained. LC-MS m/z: 472.1 [M+1].

Example 247

(S,E)-N-(4-(methylsulfonyl)but-3-en-2-yl)-3-oxo-6-phenoxy-2,3-dihydro-1H-indene-5-carboxamide

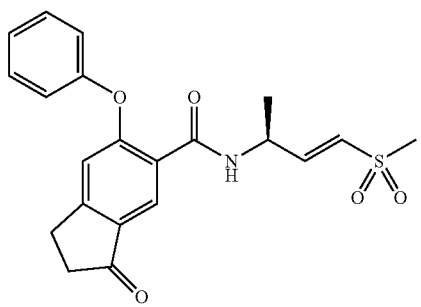 [SMILES: C[C@@H](/C=C/S(C)(=O)=O)NC(=O)c1cc2c(cc1Oc1ccccc1)CCC2=O]

Following Step 5 with methyl 6-fluoro-3-oxo-indane-5-carboxylate, Step 6 and Step 7 with [(E,1S)-1-methyl-3-methylsulfonyl-allyl]amine 4-methylbenzenesulfonic acid in Procedure A, the title compound was obtained. LC-MS m/z: 400.0 [M+1].

Example 248

(S,E)-2,2-dimethyl-N-(4-(methylsulfonyl)but-3-en-2-yl)-3-oxo-6-phenoxy-2,3-dihydro-1H-indene-5-carboxamide

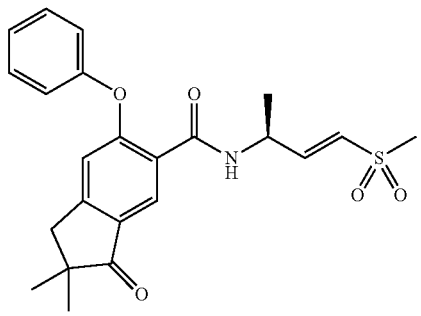 [SMILES: C[C@@H](/C=C/S(C)(=O)=O)NC(=O)c1cc2c(cc1Oc1ccccc1)CC(C)(C)C2=O]

Step 1

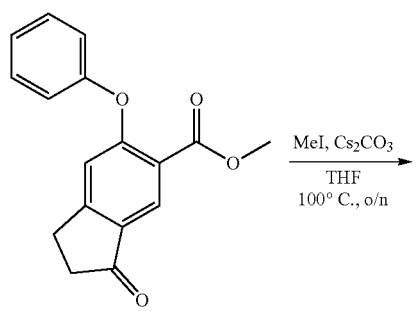

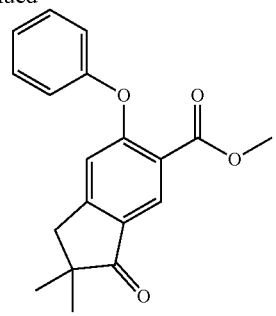

A mixture of iodomethane (1.1 g, 7.86 mmol), methyl 3-oxo-6-phenoxy-indane-5-carboxylate (222 mg, 0.79 mmol) and cesium carbonate (1.2 g, 3.53 mmol) in THF (3 mL) was heated in a sealed vial at 100° C. for 60 hours. The mixture was diluted with saturated aqueous $NH_4Cl$ and extracted with DCM. Combined organic layers were dried over anhydrous $Na_2SO_4$ and concentrated under reduced pressure to give a residue. The residue was purified by flash chromatography (Biotage, $SiO_2$, EtOAc/heptanes=0-100%) to afford methyl 2,2-dimethyl-3-oxo-6-phenoxy-indane-5-carboxylate (72 mg, 30% yield).

Following Step 6 with methyl 2,2-dimethyl-3-oxo-6-phenoxy-indane-5-carboxylate and Step 7 with [(E,1S)-1-methyl-3-methylsulfonyl-allyl]amine 4-methylbenzenesulfonic acid in Procedure A, the title compound was obtained. LC-MS m/z: 428.0 [M+1].

Example 249

2,2-dimethyl-6-(3-((methylsulfonyl)methylene)azetidine-1-carbonyl)-5-phenoxy-2,3-dihydro-1H-inden-1-one

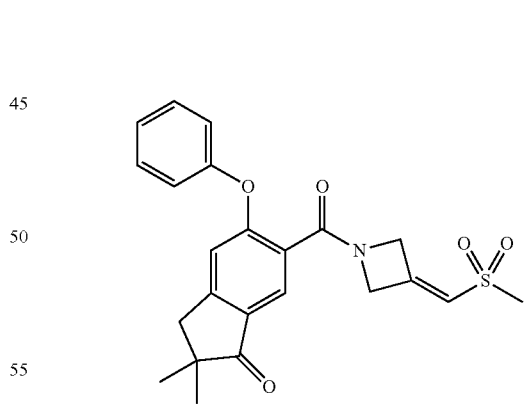

Following Step 6 with methyl 2,2-dimethyl-3-oxo-6-phenoxy-indane-5-carboxylate and Step 7 with 3-(methylsulfonylmethylene)azetidine 4-methylbenzenesulfonic acid in Procedure A, the title compound was obtained. LC-MS m/z: 426.0 [M+1].

Example 250

(S,E)-N-(1-cyclopropyl-3-(methylsulfonyl)allyl)-1-methyl-6-phenoxy-1H-pyrrolo[2,3-b]pyridine-5-carboxamide

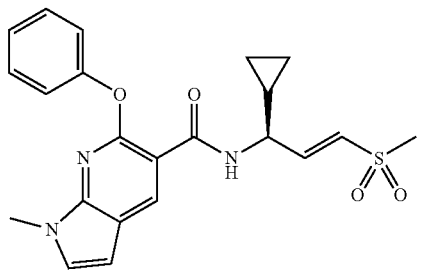 [SMILES: Cn1ccc2cc(C(=O)N[C@H](/C=C/S(C)(=O)=O)C3CC3)c(Oc3ccccc3)nc21]

Step 1

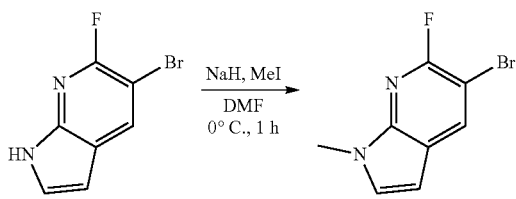

To a solution of 5-bromo-6-fluoro-1H-pyrrolo[2,3-b]pyridine (500 mg, 2.33 mmol) in DMF (3 mL, 0.775 M) was added sodium hydride (112 mg, 2.79 mmol, 60%) under $N_2$. The mixture was cooled to 0° C. and iodomethane (363 mg, 2.56 mmol) was added and the mixture was stirred for 1 hour at 0° C. The reaction was quenched with ice cold water (100 mL) and extracted with ethyl acetate (3×100 mL). The combined organic layers were dried over $Na_2SO_4$ and concentrated under reduced pressure to afford crude 5-bromo-6-fluoro-1-methyl-pyrrolo[2,3-b]pyridine (400 mg).

Step 2

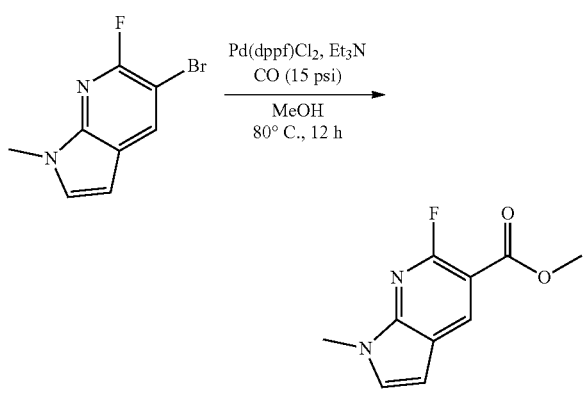

To a solution of 5-bromo-6-fluoro-1-methyl-pyrrolo[2,3-b]pyridine (200 mg, 0.87 mmol) in methanol (7.5 mL, 0.116 M) were added Pd(dppf)Cl$_2$ (63 mg, 0.087 mmol) and triethylamine (0.37 mL, 2.62 mmol). The mixture was stirred at 80° C. under CO (15 psi) for 12 hours. The mixture was concentrated under reduced pressure and purified by silica gel column (100-200 mush, PE/EA=10/1) to afford methyl 6-fluoro-1-methyl-pyrrolo[2,3-b]pyridine-5-carboxylate as a white solid (90 mg).

Using methyl 6-fluoro-1-methyl-pyrrolo[2,3-b]pyridine-5-carboxylate at Step 5 in Procedure A and following Step 6 and 7 with [(E,1S)-1-cyclopropyl-3-methylsulfonyl-allyl] amine 4-methylbenzenesulfonic acid, the title compound was obtained. LC-MS m/z: 426.1 [M+1].

Example 251

(S,E)-N-(1-cyclopropyl-3-(methylsulfonyl)allyl)-3-methyl-5-phenoxy-3H-imidazo[4,5-b]pyridine-6-carboxamide

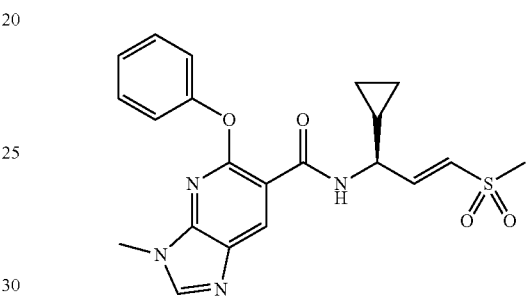

Using 6-bromo-5-chloro-3-methyl-3H-imidazo[4,5-b]pyridine to follow the procedure for the compound of Example 250 from Step 2, the title compound was obtained. LC-MS m/z: 401.2 [M+1].

Example 252

(S,E)-N-(1-cyclopropyl-3-(methylsulfonyl)allyl)-1-methyl-6-phenoxy-1H-pyrazolo[3,4-b]pyridine-5-carboxamide

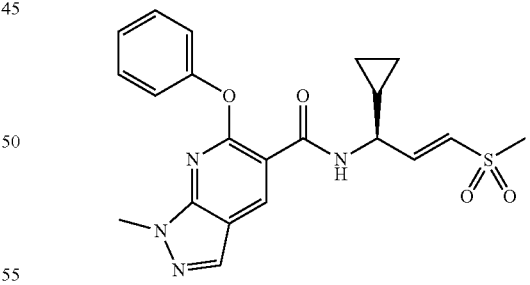

Step 1

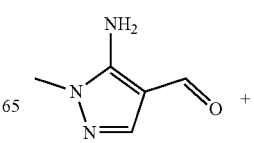

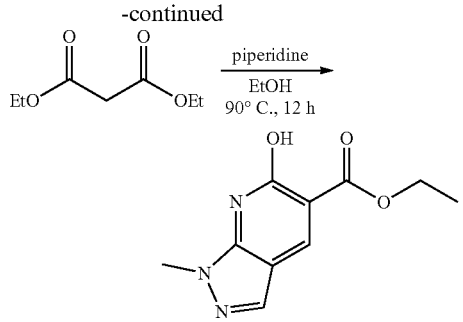

To a solution of 5-amino-1-methyl-pyrazole-4-carbaldehyde (5 g, 39.96 mmol) in ethanol (50 mL, 0.799 M) was added diethyl malonate (12.8 g, 79.92 mmol) and piperidine (6.8 g, 79.92 mmol). The mixture was stirred at 90° C. for 12 hours under $N_2$. The reaction mixture was concentrated under reduced pressure to give a residue. The residue was purified by flash column chromatography (Biotage using a 40 g Agela flash silica gel column, eluted with 0% to 35% ethyl acetate in petroleum ether) to afford ethyl 1-methyl-6-oxo-7H-pyrazolo[3,4-b]pyridine-5-carboxylate as a white solid (1.0 g, 11% yield).

Using ethyl 1-methyl-6-oxo-7H-pyrazolo[3,4-b]pyridine-5-carboxylate at Step 4 in Procedure A and following Step 5, 6 and 7 while using [(E,1S)-1-cyclopropyl-3-methylsulfonyl-allyl]amine 4-methylbenzenesulfonic acid, the title compound was obtained. LC-MS m/z: 427.2 [M+1].

Example 253

(S,E)-6-(tert-butyl)-N-(4-(methylsulfonyl)but-3-en-2-yl)-4-phenoxynicotinamide

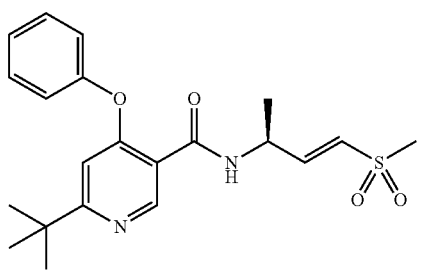 [SMILES: C[C@@H](/C=C/S(C)(=O)=O)NC(=O)c1cnc(C(C)(C)C)cc1Oc1ccccc1]

Following Step 5 with ethyl 6-tert-butyl-4-chloro-pyridine-3-carboxylate, Step 6 then Step 7 with [(E,1S)-1-methyl-3-methylsulfonyl-allyl]amine 4-methylbenzenesulfonic acid in Procedure A, the title compound was obtained. LC-MS m/z: 403.2 [M+1].

Example 255

(S,E)-4-amino-2-cyclopentyl-N-(4-(methylsulfonyl)but-3-en-2-yl)-6-phenoxypyrimidine-5-carboxamide

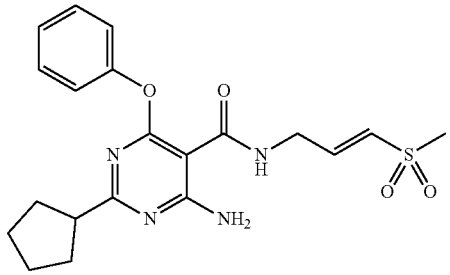 [SMILES: CS(=O)(=O)/C=C/CNC(=O)c1c(N)nc(C2CCCC2)nc1Oc1ccccc1]

Step 1

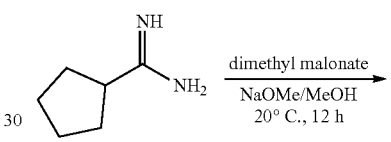

To the mixture of cyclopentanecarboxamidine (5 g, 44.58 mmol) in methanol (60 mL, 0.743 M) was added a solution of NaOMe (5 M, 26.67 mL) in MeOH (20 mL) at 0° C. The resulting mixture was stirred at 0° C. for 15 minutes, then dimethyl malonate (5.9 g, 44.58 mmol) in MeOH (10 mL) was added into the mixture. The mixture was allowed to warm to rt and stirred for 12 hours. The reaction mixture was concentrated under reduced pressure to give a residue. The residue was added water (15 mL) and adjusted to pH 3-4 with 2N HCl. The solid was collected by filtration, rinsed with water (3×5 mL) and dried under reduced pressure to afford 2-cyclopentylpyrimidine-4,6-diol as a white solid (4.10 g, 51% yield).

Step 2

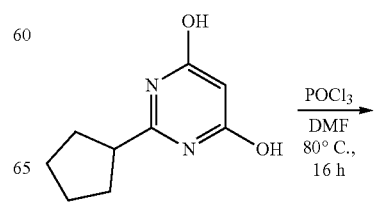

-continued

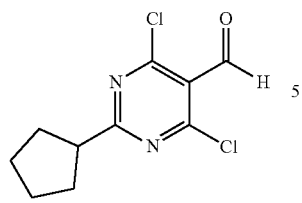

Under ice cooling DMF (3 mL) was added dropwise to POCl₃ (25 mL), and the mixture was stirred at 0° C. for 1 hour. 2-cyclopentylpyrimidine-4,6-diol (3.0 g, 16.65 mmol) was added to the reaction mixture, and the mixture was stirred at room temperature for 1 hour and heated at 80° C. for 16 hours. The reaction mixture was concentrated under reduced pressure. Water (20 mL) was added and the aqueous phase was extracted with EtOAc (3×30 mL). The combined organic layers were dried over anhydrous Na₂SO₄, filtered and the filtrate was concentrated under reduced pressure to give a residue. The residue was purified by prep-TLC (SiO2, Petroleum ether/Ethyl acetate=10/1) to afford 4,6-dichloro-2-cyclopentyl-pyrimidine-5-carbaldehyde as a white solid (280 mg, 6.9% yield).

Step 3

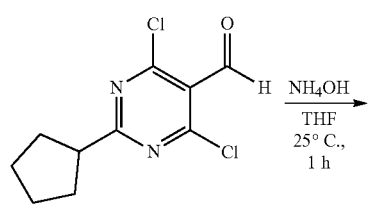

To the mixture of 4,6-dichloro-2-cyclopentyl-pyrimidine-5-carbaldehyde (150 mg, 0.61 mmol) in THF (2 mL, 0.306 M) was added ammonium hydroxide (172 mg, 4.90 mmol) at 0° C. The mixture was stirred at 25° C. for 1 hour. The reaction mixture was added with water (5 mL) and the aqueous phase was extracted with EtOAc (3×10 mL). The combined organic layers were dried over anhydrous Na₂SO₄, filtered and the filtrate was concentrated under reduced pressure to give a residue. The residue was purified by flash column (petroleum ether:ethyl acetate=1:0 to 5:1) to afford 4-amino-6-chloro-2-cyclopentyl-pyrimidine-5-carbaldehyde as a white solid (150 mg).

Step 4

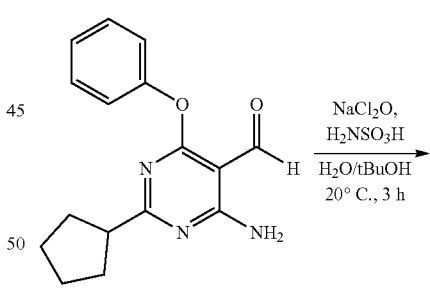

To the mixture of 4-amino-6-chloro-2-cyclopentyl-pyrimidine-5-carbaldehyde (100 mg, 0.44 mmol) in DMF (2 mL, 0.223 M) was added phenol (125 mg, 1.33 mmol) and K₂CO₃ (122 mg). The mixture was stirred at 80° C. for 12 hours. The reaction mixture was added with water (5 mL) and the aqueous phase was extracted with EtOAc (3×10 mL). The combined organic layers were dried over anhydrous Na₂SO₄, filtered and the filtrate was concentrated under reduced pressure to give a residue. The residue was purified by prep-TLC (SiO2, Petroleum ether/Ethyl acetate=5/1, Rf=0.4) to give 4-amino-2-cyclopentyl-6-phenoxy-pyrimidine-5-carbaldehyde as a white solid (30 mg, 24% yield).

Step 5

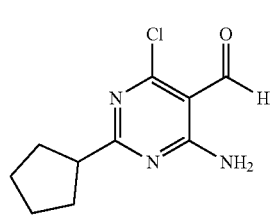

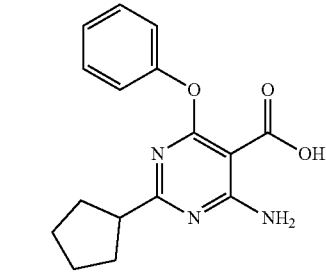

To the mixture of 4-amino-2-cyclopentyl-6-phenoxy-pyrimidine-5-carbaldehyde (60 mg, 0.21 mmol) in water (1 mL, 0.071 M) and tert-butanol (2 mL, 0.071 M) was added sulfamic acid (21.6 mg, 0.22 mmol). A solution of NaCl₂O (24 mg) in water (0.2 mL) was added to the mixture at 0° C. Then the mixture was stirred at 20° C. for 3 hours. The reaction mixture was added with water (5 mL) and the aqueous phase was extracted with EtOAc (3×10 mL). The combined organic layers were dried over anhydrous Na₂SO₄, filtered and the filtrate was concentrated under reduced pressure to afford crude product 4-amino-2-cyclopentyl-6-phenoxy-pyrimidine-5-carboxylic acid as a white solid (30 mg).

Following Step 7 in Procedure A, the title compound was obtained. LC-MS m/z: 431.2 [M+1].

Example 256

(S,E)-4-acetamido-2-cyclopentyl-N-(4-(methylsulfonyl)but-3-en-2-yl)-6-phenoxypyrimidine-5-carboxamide

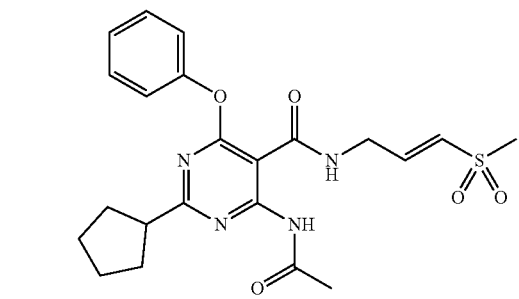

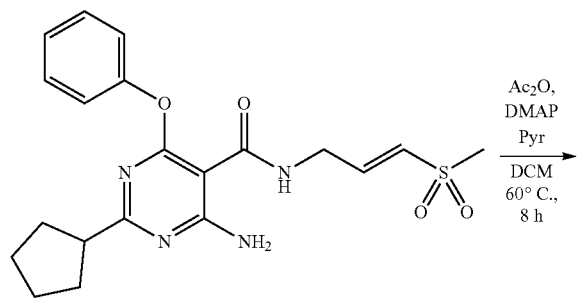

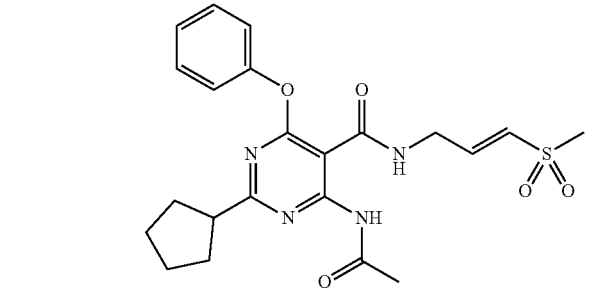 [SMILES: CC(=O)Nc1nc(C2CCCC2)nc(Oc2ccccc2)c1C(=O)NC/C=C/S(C)(=O)=O]

A mixture of 4-amino-2-cyclopentyl-N—[(E,1S)-1-methyl-3-methylsulfonyl-allyl]-6-phenoxy-pyrimidine-5-carboxamide (5.5 mg, 0.0128 mmol), pyridine (1.5 mg, 0.0192 mmol) and 4-(dimethylamino)pyridine (0.16 mg, 0.001 mmol) in acetic anhydride (1 mL) and DCM (1 mL) was heated at 60° C. for 8 hours. The mixture was directly purified by prep-HPLC to afford the title compound (4 mg). LC-MS m/z: 473.2 [M+1].

Example 259

(S,E)-4'-cyclopropyl-N-(4-(methylsulfonyl)but-3-en-2-yl)-3'H-spiro[cyclopentane-1,2'-furo[3,2-c]pyridine]-7'-carboxamide

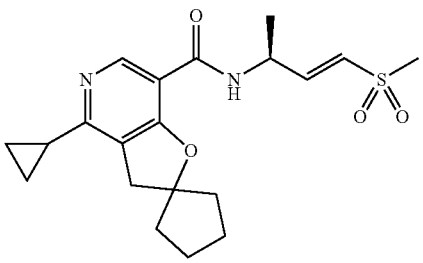 [SMILES: C[C@@H](/C=C/S(C)(=O)=O)NC(=O)c1cnc(C2CC2)c2c1OC1(CCCC1)C2]

Step 1

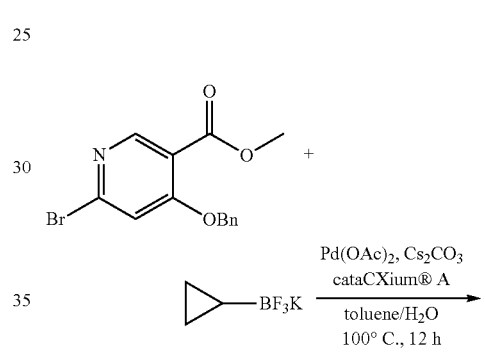

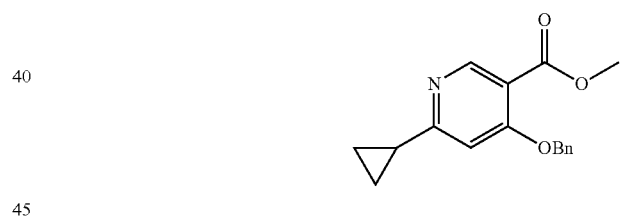

A mixture of methyl 4-benzyloxy-6-chloro-pyridine-3-carboxylate (850 mg, 3.06 mmol), potassium cyclopropyl-trifluoroborate (544 mg, 3.67 mmol), bis(1-adamantyl)-butyl-phosphane (220 mg, 0.61 mmol), cesium carbonate (3.0 g, 9.18 mmol) and palladium(II) acetate (69.3 mg, 0.31 mmol) in toluene (36 mL, 0.077 M) and water (4 mL, 0.077 M) was purged with N₂ 3 times, and then the reaction mixture was stirred at 100° C. for 12 hours under N₂. After cooling to room temperature, the reaction mixture was concentrated under reduced pressure to give a residue. The residue was diluted with water (30 mL) and the aqueous phase was extracted with EtOAc (3×30 mL). The combined organic layers were dried over anhydrous Na₂SO₄, filtered and concentrated under reduced pressure to give a residue. The residue was purified by flash column chromatograpy (Biotage using a 20 g Agela flash silica gel column, eluted with 20% to 25% ethyl acetate in petroleum ether) to afford methyl 4-benzyloxy-6-cyclopropyl-pyridine-3-carboxylate as a light yellow solid (700 mg, 81% yield).

Step 2

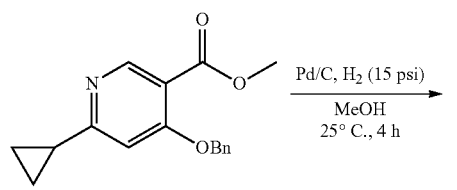

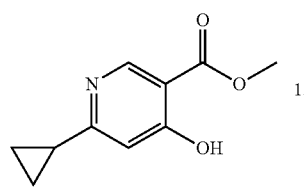

To a solution of methyl 4-benzyloxy-6-cyclopropyl-pyridine-3-carboxylate (500 mg, 1.76 mmol) in methanol (10 mL, 0.177 M) was added Pd/C (10%, 100 mg) under N$_2$. The suspension was purged with H$_2$ 3 times. The mixture was stirred under H$_2$ (15 Psi) at 25° C. for 4 hours. The reaction mixture was filtered through a Celite pad, washed with MeOH (2×6 mL), and the filtrate was concentrated to give crude methyl 6-cyclopropyl-4-hydroxy-pyridine-3-carboxylate as light yellow solid (300 mg).

Step 3

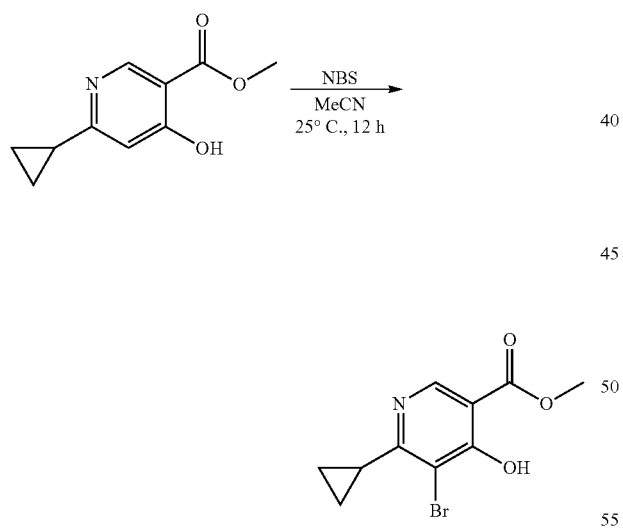

To a solution of methyl 6-cyclopropyl-4-hydroxy-pyridine-3-carboxylate (1.8 g, 9.31 mmol) in MeCN (60 mL, 0.155 M) was added N-bromosuccinimide (2.3 g, 13.04 mmol). The mixture was stirred at 25° C. for 12 hours under N$_2$. The residue was purified by flash column chromatography (Biotage using a 40 g Agela flash silica gel column, eluted with 15% to 20% ethyl acetate in petroleum ether) to afford methyl 5-bromo-6-cyclopropyl-4-hydroxy-pyridine-3-carboxylate as a white solid (2.0 g, 79% yield).

Step 4

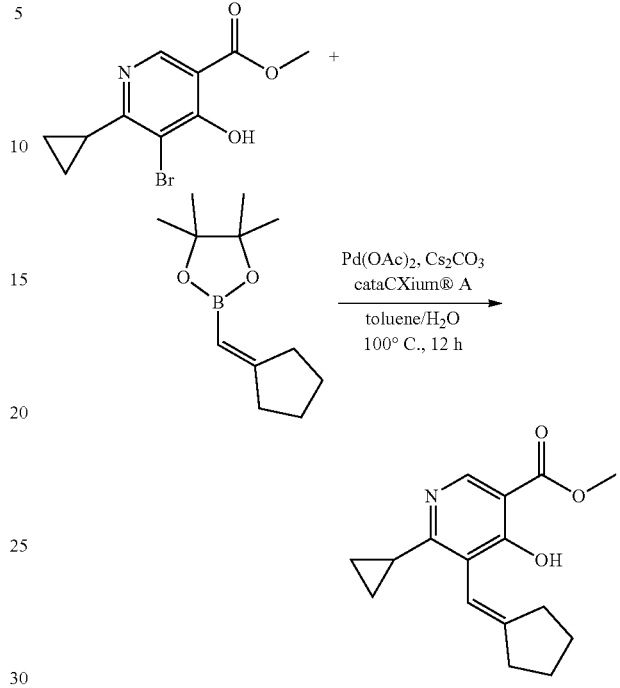

A mixture of methyl 5-bromo-6-cyclopropyl-4-hydroxy-pyridine-3-carboxylate (1 g, 3.68 mmol), 2-(cyclopentylidenemethyl)-4,4,5,5-tetramethyl-1,3,2-dioxaborolane (2.3 g, 11.03 mmol), bis(1-adamantyl)-butyl-phosphane (264 mg, 0.74 mmol), cesium carbonate (3.6 g, 11.03 mmol) and palladium(II) acetate (83.3 mg, 0.37 mmol) in toluene (27 mL, 0.123 M) and water (3 mL, 0.123 M) was degassed and purged with N$_2$ 3 times, and then the reaction mixture was stirred at 100° C. for 12 hours under N$_2$ atmosphere. After cooling to room temperature, the reaction mixture was concentrated under reduced pressure to give a residue. The residue was diluted with H$_2$O (20 mL) and the aqueous phase was extracted with EtOAc (3×40 mL). The combined organic layers were dried over anhydrous Na$_2$SO$_4$, filtered and concentrated under reduced pressure to give a residue. The residue was purified by flash column chromatography to afford methyl 5-(cyclopentylidenemethyl)-6-cyclopropyl-4-hydroxy-pyridine-3-carboxylate as a light yellow oil (250 mg, 25% yield).

Step 5

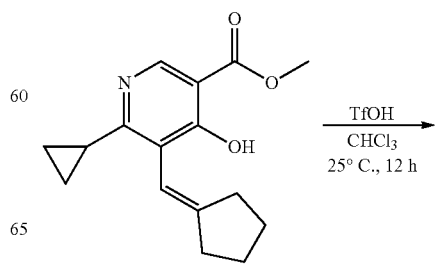

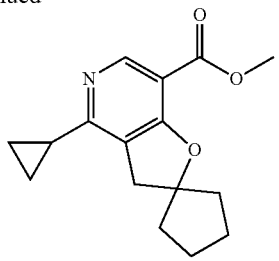

To a solution of methyl 5-(cyclopentylidenemethyl)-6-cyclopropyl-4-hydroxy-pyridine-3-carboxylate (150 mg, 0.55 mmol) in chloroform (5 mL, 0.110 M) was added trifluoromethanesulfonic acid (0.70 mL, 0.55 mmol). The mixture was stirred at 25° C. for 12 hours under $N_2$. The reaction mixture was added saturated aqueous $NaHCO_3$ to adjust pH to ~7, then diluted with water (4 mL) and extracted with DCM (3×10 mL). The combined organic layers were washed with brine (10 mL), dried over $Na_2SO_4$, filtered and concentrated under reduced pressure to give a residue. The residue was purified by prep-HPLC (HCl) to afford methyl 4-cyclopropylspiro[3H-furo[3,2-c]pyridine-2,1'-cyclopentane]-7-carboxylate as a yellow solid (80 mg, 53% yield).

Following Step 6 with methyl 4-cyclopropylspiro[3H-furo[3,2-c]pyridine-2,1'-cyclopentane]-7-carboxylate and Step 7 with [(E,1S)-1-methyl-3-methylsulfonyl-allyl]amine 4-methylbenzenesulfonic acid in Procedure A, the title compound was obtained. LC-MS m/z: 391.1 [M+1].

Example 260

(S,E)-N-(4-(methylsulfonyl)but-3-en-2-yl)-4-phenoxy-2-(2,2,2-trifluoroethyl)pyrimidine-5-carboxamide

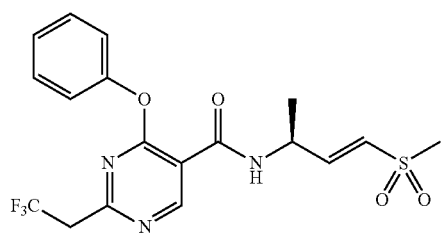 [SMILES: C[C@@H](/C=C/S(C)(=O)=O)NC(=O)c1cnc(CC(F)(F)F)nc1Oc1ccccc1]

Step 1

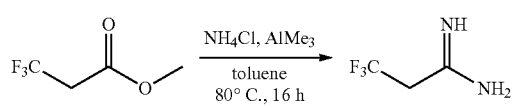

To a solution of ammonium chloride (4.7 g, 87.98 mmol) in toluene (50 mL, 0.352 M) was added trimethylaluminum (44 mL, 87.98 mmol, 0.8100 g/ml) at 0° C. The reaction was stirred at 25° C. until no more evolution of gas was observed. Then methyl 3,3,3-trifluoropropanoate (2.5 g, 17.60 mmol) was added dropwise in the mixture. The mixture was stirred at 80° C. for 16 hours under $N_2$. After the mixture was cooled down to 0° C., methanol (30 mL) was added with consequent stirring for 1 hour at 25° C. After filtration, the solid was washed with methanol for several times and the solution was evaporated to dryness under reduced pressure to afford crude 3,3,3-trifluoropropanamidine as a yellow oil (1.0 g).

Step 2

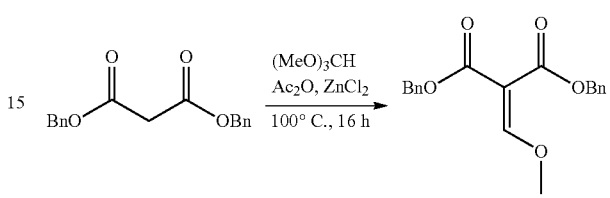

A mixture of dibenzyl malonate (25 g, 87.93 mmol), trimethyl orthoformate (10.3 g, 96.73 mmol), acetic anhydride (18.0 g, 175.86 mmol) and $ZnCl_2$ (4.40 mL, 8.79 mmol, 2M) was heated at 100° C. for 16 hours. The reaction mixture was concentrated under reduced pressure and directly purified by flash silica gel chromatography (ISCO®; 220 g SepaFlash® Silica Flash Column, Eluent of 0~30% Ethyl acetate/Petroleum ether gradient at 120 mL/min) to afford dibenzyl 2-(methoxymethylene)propanedioate as a yellow oil (13.0 g, 45% yield).

Using 3,3,3-trifluoropropanamidine and dibenzyl 2-(methoxymethylene)propanedioate as the starting materials and following Step 3,4 and 5 in Procedure A, benzyl 4-phenoxy-2-(2,2,2-trifluoroethyl)pyrimidine-5-carboxylate was obtained.

Step 3

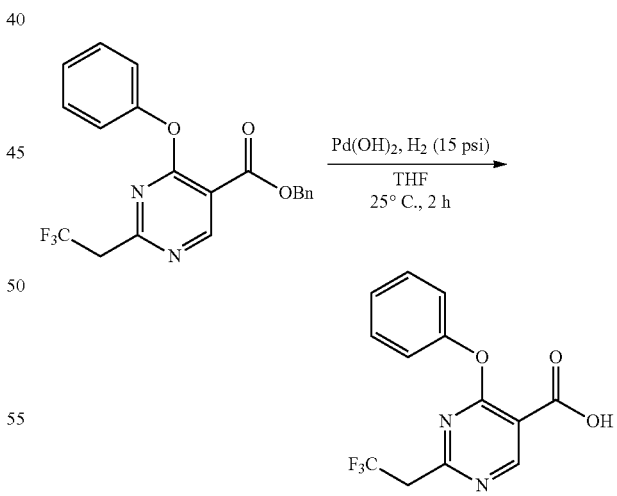

Benzyl 4-phenoxy-2-(2,2,2-trifluoroethyl)pyrimidine-5-carboxylate (100 mg, 0.26 mmol) was added to the mixture of dry $Pd(OH)_2$ (20 mg) in THF (4 mL, 0.0644 M). The mixture was stirred at 25° C. for 2 hours under $H_2$ (15 psi). The mixture was filtered, concentrated under reduced pressure and purified by prep-TLC ($SiO_2$, EtOAc) to afford 4-phenoxy-2-(2,2,2-trifluoroethyl)pyrimidine-5-carboxylic acid as a yellow oil (70 mg, 91% yield).

Following Step 7 in Procedure A with 4-phenoxy-2-(2,2,2-trifluoroethyl)pyrimidine-5-carboxylic acid and [(E,1S)-1-methyl-3-methylsulfonyl-allyl]amine 4-methylbenzenesulfonic acid, the title compound was obtained. LC-MS m/z: 430.1 [M+1].

Example 261

(S,E)-N-(1-cyclopropyl-3-(methylsulfonyl)allyl)-4-phenoxy-2-(2,2,2-trifluoroethyl)pyrimidine-5-carboxamide

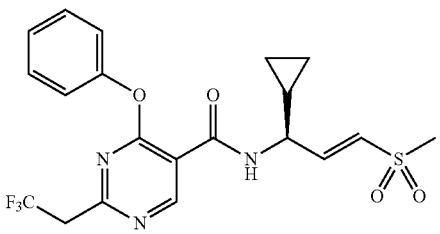 [SMILES: CS(=O)(=O)/C=C/[C@@H](NC(=O)c1cnc(CC(F)(F)F)nc1Oc1ccccc1)C1CC1]

Following Step 7 in Procedure A with 4-phenoxy-2-(2,2,2-trifluoroethyl)pyrimidine-5-carboxylic acid and [(E,1S)-1-cyclopropyl-3-methylsulfonyl-allyl]amine 4-methylbenzenesulfonic acid, the title compound was obtained. LC-MS m/z: 456.1 [M+1].

Example 262

(S,E)-6-cyclopentyl-5-methyl-N-(4-(methylsulfonyl)but-3-en-2-yl)-2-phenoxynicotinamide

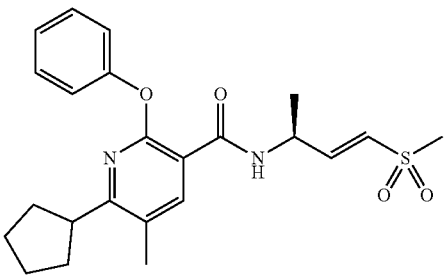

Step 1

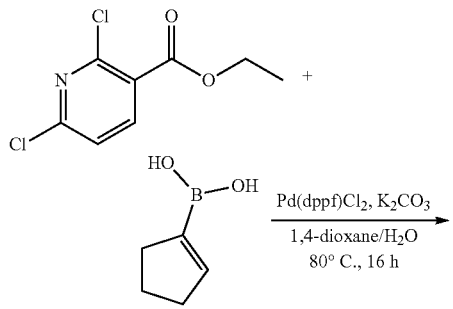

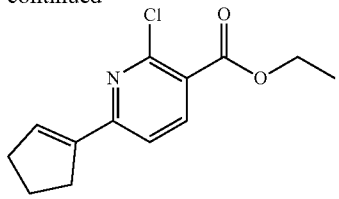

Pd(dppf)Cl$_2$ (3.29 g, 4.54 mmol) was added to the mixture of ethyl 2,6-dichloropyridine-3-carboxylate (10 g, 45.44 mmol), cyclopenten-1-ylboronic acid (4.069 g, 36.36 mmol) and K$_2$CO$_3$ (12.543 g, 90.89 mmol) in 1,4-dioxane (100 mL, 0.379 M) and water (20 mL, 0.379 M). The mixture was stirred at 80° C. for 16 hours under N$_2$. The reaction mixture was poured into water (100 mL) and extracted with EtOAc (3×100 mL). The combined organic layers were washed with brine (2×80 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0~3% Ethyl acetate/Petroleum ether gradient at 100 mL/min) to afford ethyl 2-chloro-6-(cyclopenten-1-yl)pyridine-3-carboxylate as a yellow oil (7.7 g, 67% yield).

Step 2

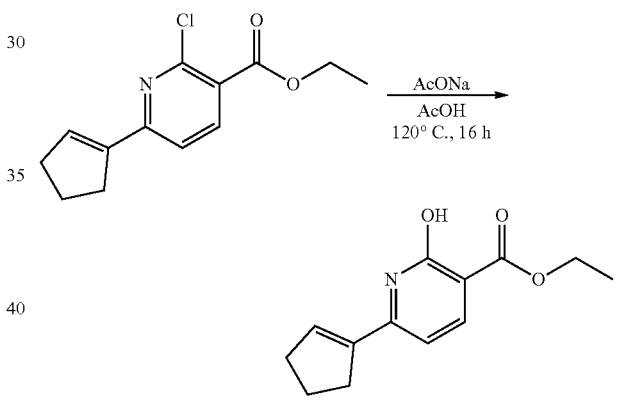

AcONa (3.0 g, 36.71 mmol) was added to ethyl 2-chloro-6-(cyclopenten-1-yl)pyridine-3-carboxylate (7.7 g, 30.59 mmol) in acetic acid (18 mL, 1.700 M). The mixture was stirred at 120° C. for 16 hours. The mixture was concentrated under reduced pressure to give a residue. The residue was purified by flash silica gel chromatography (ISCO®; 80 g SepaFlash® Silica Flash Column, Eluent of 0~35% Ethyl acetate/Petroleum ether gradient at 100 mL/min) to afford ethyl 6-(cyclopenten-1-yl)-2-hydroxy-pyridine-3-carboxylate as a yellow oil (5.0 g, 70% yield).

Step 3

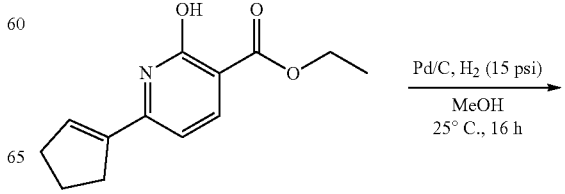

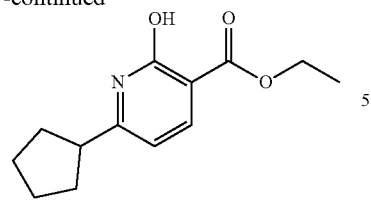

Ethyl 6-(cyclopenten-1-yl)-2-hydroxy-pyridine-3-carboxylate (5 g, 21.44 mmol) was added to Pd/C (2.5 g) in methanol (100 mL, 0.214 M). The mixture was stirred at 25° C. for 16 hours under H$_2$ (15 psi). The mixture was filtered and concentrated under reduced pressure to afford crude ethyl 6-cyclopentyl-2-hydroxy-pyridine-3-carboxylate as a yellow solid (5.0 g).

Step 4

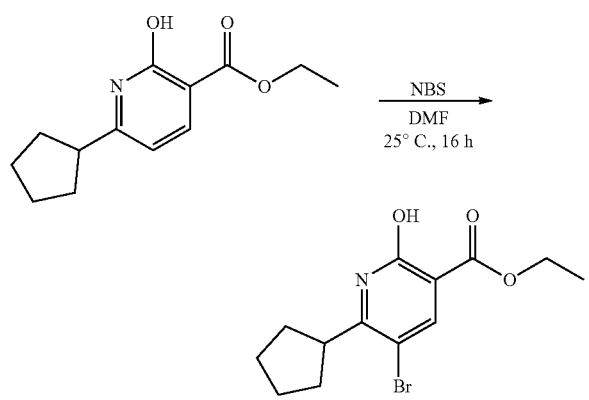

N-bromosuccinimide (1.9 g, 10.63 mmol) was added to ethyl 6-cyclopentyl-2-hydroxy-pyridine-3-carboxylate (2.5 g, 10.63 mmol) in DMF (50 mL, 0.213 M). The mixture was stirred at 25° C. for 16 hours. The reaction mixture was poured into water (80 mL) and extracted with EtOAc (3×80 mL). The combined organic layers were washed with brine (2×70 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~30% Ethyl acetate/Petroleum ether gradient at 100 mL/min) to afford ethyl 5-bromo-6-cyclopentyl-2-hydroxy-pyridine-3-carboxylate as a yellow solid (1.8 g, 54% yield)

Step 5

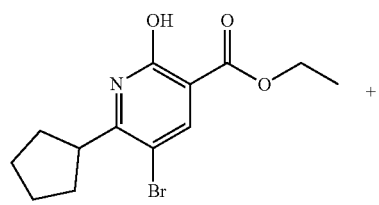 +

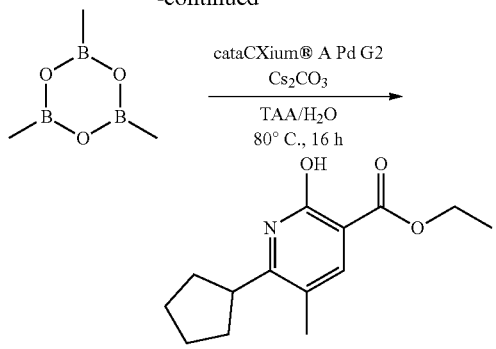

CataCXium® A Pd G2 (128 mg, 0.19 mmol) was added to the mixture of ethyl 5-bromo-6-cyclopentyl-2-hydroxy-pyridine-3-carboxylate (600 mg, 1.91 mmol), trimethylboroxine (623 mg, 2.48 mmol) and Cs$_2$CO$_3$ (1.25 g, 3.82 mmol) in t-amyl alcohol (12 mL) and water (3 mL, 0.637 M). The mixture was stirred at 80° C. for 16 hours under N$_2$. The reaction mixture was poured into water (30 mL) and extracted with EtOAc (3×30 mL). The combined organic layers were washed with brine (2×20 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0~25% Ethyl acetate/Petroleum ether gradient at 100 mL/min) to afford ethyl 6-cyclopentyl-2-hydroxy-5-methyl-pyridine-3-carboxylate as a yellow oil (80 mg, 17% yield).

Step 6

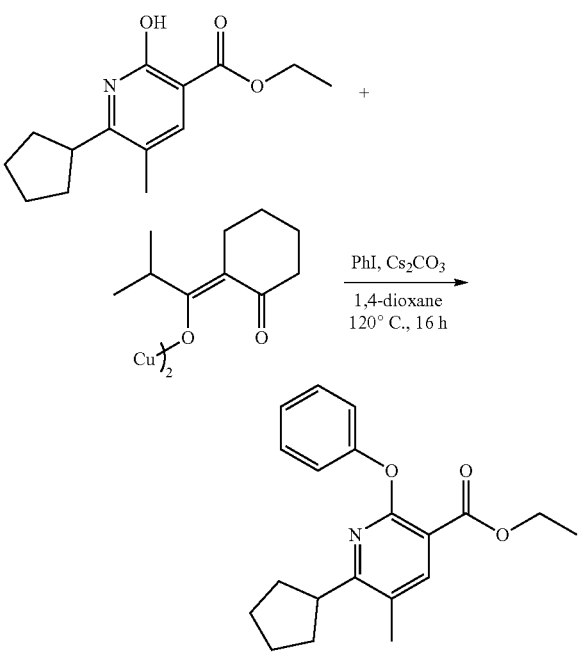

Bis[(1Z)-2-methyl-1-(2-oxocyclohexylidene)propoxy] copper (22.4 mg, 0.056 mmol) was added to the mixture of ethyl 6-cyclopentyl-2-hydroxy-5-methyl-pyridine-3-carboxylate (140 mg, 0.56 mmol), iodobenzene (137 mg, 0.67 mmol) and Cs$_2$CO$_3$ (366 mg, 1.12 mmol) in 1,4-dioxane (1 mL, 0.562 M). The mixture was heated at 120° C. for 16 hours. The reaction mixture was poured into water (15 mL) and extracted with EtOAc (3×15 mL). The combined organic layers were washed with brine (2×10 mL), dried over Na₂SO₄, filtered and concentrated under reduced pressure to give a residue. The residue was purified by flash silica gel chromatography (ISCO®; 4 g SepaFlash® Silica Flash Column, Eluent of 0~5% Ethyl acetate/Petroleum ether gradient at 100 mL/min) followed by prep-HPLC (column: Waters Xbridge Prep OBD C18 150*40 mm*10 um; mobile phase: water (NH₄HCO₃)-MeCN; B %: 60%-90%, 8 min) to afford ethyl 6-cyclopentyl-5-methyl-2-phenoxy-pyridine-3-carboxylate as a yellow oil (20 mg, 11% yield).

Following Step 6 with ethyl 6-cyclopentyl-5-methyl-2-phenoxy-pyridine-3-carboxylate and Step 7 with [(E,1S)-1-methyl-3-methylsulfonyl-allyl]amine 4-methylbenzenesulfonic acid, the title compound was obtained. LC-MS m/z: 429.2 [M+1].

Example 263

(S)-2-(1,1-difluoroethyl)-N-(5-(dimethylamino)-5-oxopent-3-yn-2-yl)-4-phenoxypyrimidine-5-carboxamide

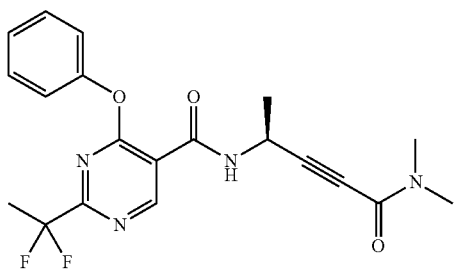 [SMILES: C[C@@H](C#CC(=O)N(C)C)NC(=O)c1cnc(C(C)(F)F)nc1Oc1ccccc1]

Step 1

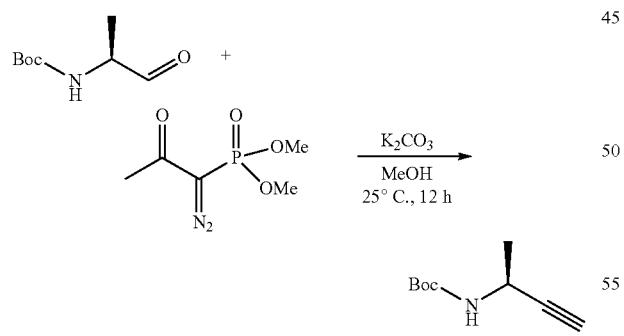

To a solution of Boc-L-alanine aldehyde (2.3 g, 13.23 mmol) in methanol (25 mL, 0.531 M) was added potassium carbonate (5.5 g, 39.836 mmol) and dimethyl (1-diazo-2-oxopropyl)phosphonate (2.8 g, 14.61 mmol) at 25° C. The mixture was stirred at 25° C. for 12 hours. The reaction mixture was filtered and concentrated under reduced pressure to give a residue. The residue was purified by flash silica gel chromatography (ISCO®; 12 g SepaFlash® Silica Flash Column, Eluent of 0~5% Ethyl acetate/Petroleum ether gradient at 40 mL/min) to afford tert-butyl N-[(1S)-1-methylprop-2-ynyl]carbamate as a white solid (1.0 g, 45% yield).

Step 2

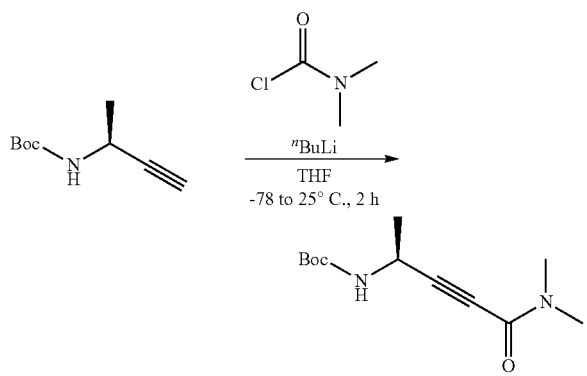

To a mixture of tert-butyl N-[(1S)-1-methylprop-2-ynyl]carbamate (0.5 g, 2.95 mmol) in THF (10 mL, 0.296M) at −70° C. was added dropwise n-butyllithium solution (1.54 mL, 3.84 mmol, 2.5 M). The resulting mixture is stirred for 1 hour at −70° C. before adding dimethylcarbamyl chloride (0.35 mL, 3.84 mmol, 1.168 g/ml) at −70° C. The mixture was stirred under N₂ at −78° C. for 1 hour. Then the mixture was stirred under N₂ at 25° C. for 2 hours. The reaction mixture was poured into ice saturated NH₄Cl solution (10 mL). The aqueous phase was extracted with dichloromethane (3×20 mL). The combined organic phase was dried over anhydrous Na₂SO₄, filtered and concentrated under reduced pressure to give a residue. The residue was purified by flash column chromatography (SiO₂, PE:EA=20:1) to afford tert-butyl N-[(1S)-4-(dimethylamino)-1-methyl-4-oxo-but-2-ynyl]carbamate as a yellow oil (0.35 g, 30% yield).

PTSA/tert-butyl N-[(1S)-4-(dimethylamino)-1-methyl-4-oxo-but-2-ynyl]carbamate was used to obtain (4S)-4-amino-N,N-dimethyl-pent-2-ynamide 4-methylbenzenesulfonic acid. Following Step 7 in Procedure A with 2-(1,1-difluoroethyl)-4-phenoxy-pyrimidine-5-carboxylic acid and (4S)-4-amino-N,N-dimethyl-pent-2-ynamide 4-methylbenzenesulfonic acid, the title compound was obtained. LC-MS m/z: 403.2 [M+1].

Example 264

2-(1-(2-cyclopropyl-4-phenoxypyrimidine-5-carbonyl)azetidin-3-ylidene)acetonitrile

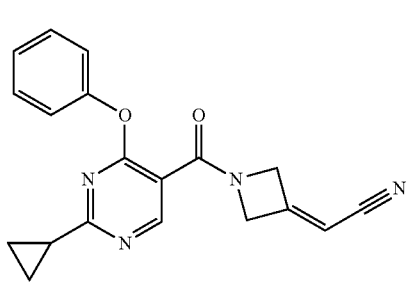 [SMILES: N#CC=C1CN(C(=O)c2cnc(C3CC3)nc2Oc2ccccc2)C1]

Step 1

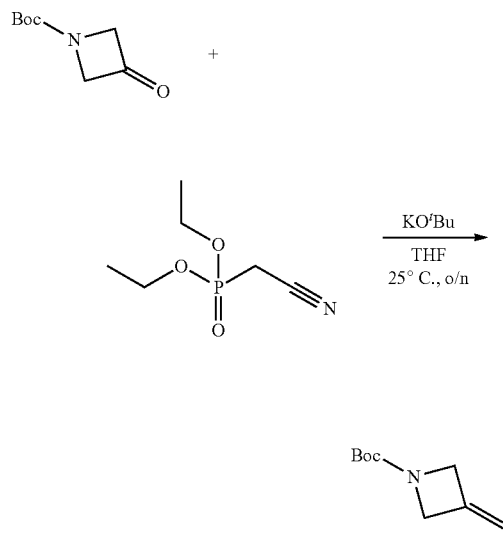

Potassium tert-butoxide (5.14 mL, 5.14 mmol) was added to a mixture of diethyl cyanomethylphosphonate (911 mg, 5.14 mmol) in THF (20 mL, 0.234 M) at 0° C. The mixture was warm to room temperature and cooled back to 0° C. The mixture was added t-butyl 3-oxoazetidine-1-carboxylate (800 mg, 4.67 mmol) in THF (2 ml) dropwise. The resulting mixture was stirred at 25° C. overnight. The mixture was diluted with water (20 ml) and extracted with EtOAc (3×15 mL). The combined organic layers were washed with brine (2×10 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0~5% Ethyl acetate/Petroleum ether gradient at 45 mL/min) to afford tert-butyl 3-(cyanomethylene)azetidine-1-carboxylate as a white solid (350 mg, 39% yield).

Step 2

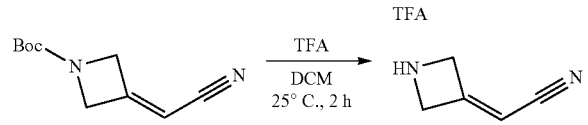 [SMILES: CC(C)(C)OC(=O)N1CC(=CC#N)C1 ; N#CC=C1CNC1 ; "TFA"]

To a solution of tert-butyl 3-(cyanomethylene)azetidine-1-carboxylate (100 mg, 0.515 mmol) in DCM (1 mL, 0.412 M) was added trifluoroacetic acid (0.25 mL, 0.412 M). The reaction was stirred at room temperature for 2 hours. The mixture was concentrated under reduced pressure to dryness to afford crude 2-(azetidin-3-ylidene)acetonitrile TFA salt (48 mg).

Following Step 7 in Procedure A and using 2-cyclopropyl-4-phenoxy-pyrimidine-5-carboxylic acid and 2-(azetidin-3-ylidene)acetonitrile TFA salt, the title compound was obtained. LC-MS m/z: 333.0 [M+1].

Example 265

2-(1-(2-cyclopropyl-4-phenoxypyrimidine-5-carbonyl)-2-methylazetidin-3-ylidene)acetonitrile

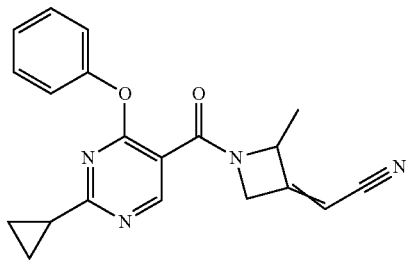 [SMILES: CC1C(=CC#N)CN1C(=O)c1cnc(C2CC2)nc1Oc1ccccc1]

Using tert-butyl 2-methyl-3-oxo-azetidine-1-carboxylate at Step 1 and following the procedure for the compound of Example 264, the title compound was obtained as a mixture of racemic olefin isomers (E/Z=undetermined). LC-MS m/z: 347.2 [M+1].

Example 266

(E)-N-(3-cyanoallyl)-2-cyclopropyl-4-phenoxypyrimidine-5-carboxamide

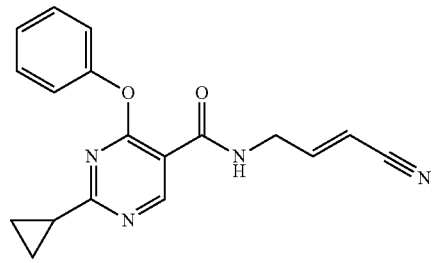 [SMILES: N#C/C=C/CNC(=O)c1cnc(C2CC2)nc1Oc1ccccc1]

Using N-Boc-2-aminoacetaldehyde/K$_2$CO$_3$ at Step 1 and following the procedure for the compound of Example 264, the title compound was obtained. LC-MS m/z: 321.0 [M+1].

Example 267

(Z)—N-(3-cyanoallyl)-2-cyclopropyl-4-phenoxypyrimidine-5-carboxamide

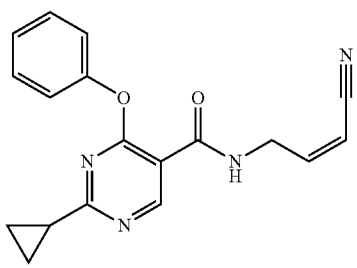 [SMILES: N#C/C=C\CNC(=O)c1cnc(C2CC2)nc1Oc1ccccc1]

Following the procedure for the compound of Example 266 and using the minor olefin isomer (3.5:1) tert-butyl N—[(Z)-3-cyanoallyl]carbamate after the first step, the title compound was obtained. LC-MS m/z: 321.0 [M+1].

Example 268

N-(2-cyanoallyl)-2-cyclopentyl-4-phenoxypyrimidine-5-carboxamide

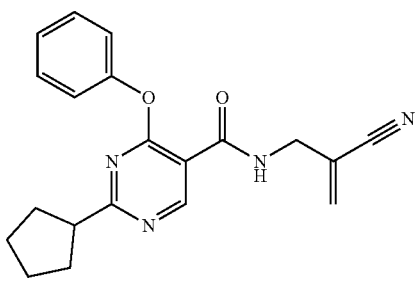 [SMILES: C=C(C#N)CNC(=O)c1cnc(C2CCCC2)nc1Oc1ccccc1]

Step 1

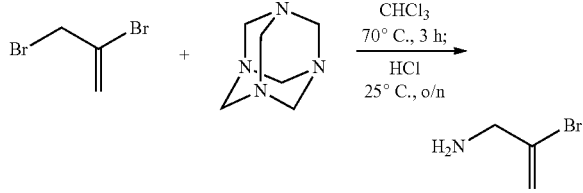

To a solution of hexamethylene tetramine (21 g, 180.12 mmol) in chloroform (210 mL, 0.858 M) in two-necked flask under 70° C. was dropwise added 2,3-dibromopropene (36 g, 180.12 mmol). After the addition is complete, the reaction mixture was stirred at 70° C. for 3 hours and allowed to stand overnight at 25° C. Then, the mixture was cooled in an ice bath and the salt was collected by filtration to give the crude solid (~50 g). The solid was dissolved in a warm solution prepared from water (60 mL), ethanol (300 mL) and concentrated HCl (72 mL). The reaction mixture was allowed to stand at 25° C. overnight and the white solid was removed by filtration. When the reaction mixture was concentrated to 30 mL, the solid was removed again by filtration, then the mother liquid was concentrated and dried to afford crude 2-bromoprop-2-en-1-amine hydrochloride salt as a white solid (30 g).

Step 2

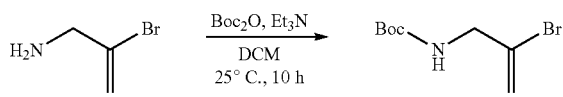

To a solution of 2-bromoprop-2-en-1-amine hydrochloride salt (30 g, 173.96 mmol) in DCM (300 mL, 0.580 M) was added di-tert-butyl dicarbonate (45.6 g, 208.76 mmol) and triethylamine (35.2 g, 347.93 mmol). The mixture was stirred at 25° C. for 10 hours. The mixture was diluted with H$_2$O (100 mL) and extracted with DCM (100 mL). The extract was washed with brine (50 mL), dried over Na$_2$SO$_4$ and filtered. The filtrate was concentrated under reduced pressure and purified by flash column chromatography (PE: EtOAc=5:1) to afford tert-butyl N-(2-bromoallyl)carbamate as a white solid (33 g, 80% yield).

Step 3

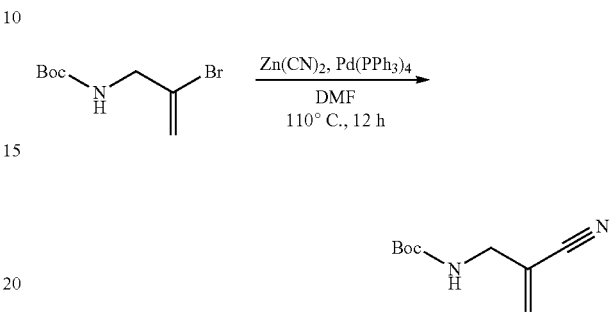

To a solution of tert-butyl N-(2-bromoallyl)carbamate (33 g, 139.77 mmol) in DMF (350 mL, 0.399 M) was added zinc cyanide (24.6 g, 209.65 mmol) and tetrakis(triphenylphosphine) (8.08 g, 6.99 mmol) under N$_2$. The mixture was stirred at 110° C. for 12 hours. The reaction mixture was quenched with water (1 L) and extracted with EtOAc (2×200 mL). The combined organic layer was washed with brine (1 L) and dried over Na$_2$SO$_4$. filtered and concentrated under reduced pressure to give a residue. The residue was purified by flash column chromatography (SiO$_2$, Petroleum ether/Ethyl acetate=10/1 to 5/1) to afford tert-butyl N-(2-cyanoallyl)carbamate as a white solid (29 g).

Step 4

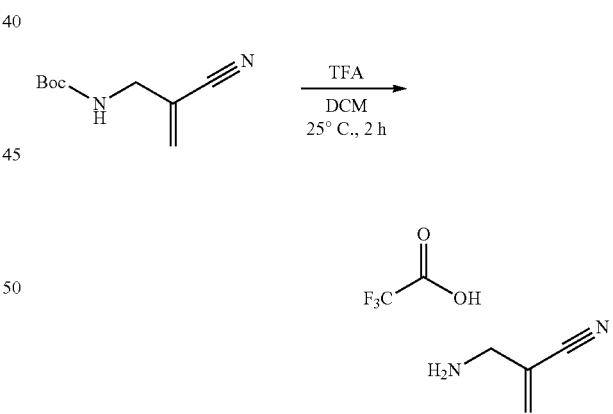

To a solution of tert-butyl N-(2-cyanoallyl)carbamate (2.0 g, 10.98 mmol) was added TFA (7 ml) in DCM (21 mL, 0.523 M). The mixture was stirred at 25° C. for 2 hours. The reaction mixture was concentrated under reduced pressure to afford crude 2-(aminomethyl)prop-2-enenitrile; 2,2,2-trifluoroacetic acid as a yellow oil (2.5 g).

Following Step 7 in Procedure A with 2-cyclopentyl-4-phenoxy-pyrimidine-5-carboxylic acid and 2-(aminomethyl)prop-2-enenitrile; 2,2,2-trifluoroacetic acid, the title compound was obtained. LC-MS m/z: 349.2 [M+1].

Example 269

N-(2-cyanoallyl)-2-cyclopropyl-4-phenoxypyrimidine-5-carboxamide

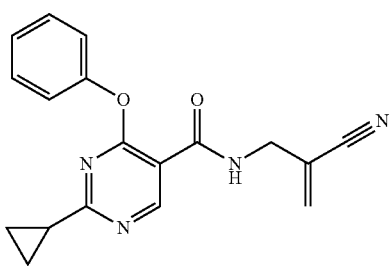 [SMILES: C=C(C#N)CNC(=O)c1cnc(C2CC2)nc1Oc1ccccc1]

Following Step 7 in Procedure A with 2-cyclopropyl-4-phenoxy-pyrimidine-5-carboxylic acid and 2-(aminomethyl)prop-2-enenitrile; 2,2,2-trifluoroacetic acid, the title compound was obtained. LC-MS m/z: 321.0 [M+1].

Example 270

2-(tert-butyl)-N-(2-cyanoallyl)-4-phenoxypyrimidine-5-carboxamide

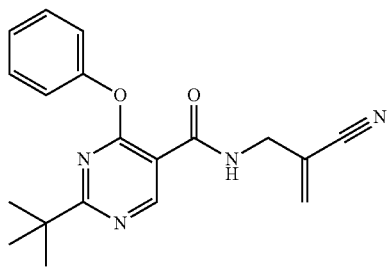 [SMILES: C=C(C#N)CNC(=O)c1cnc(C(C)(C)C)nc1Oc1ccccc1]

Following Step 7 in Procedure A with 2-tert-butyl-4-phenoxy-pyrimidine-5-carboxylic acid and 2-(aminomethyl)prop-2-enenitrile; 2,2,2-trifluoroacetic acid, the title compound was obtained. LC-MS m/z: 337.2 [M+1].

Example 271

N-(2-cyanoallyl)-2-(1,1-difluoroethyl)-4-phenoxypyrimidine-5-carboxamide

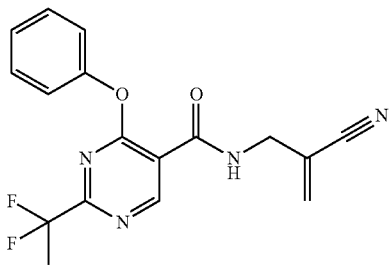 [SMILES: C=C(C#N)CNC(=O)c1cnc(C(C)(F)F)nc1Oc1ccccc1]

Following Step 7 in Procedure A with 2-(1,1-difluoroethyl)-4-phenoxy-pyrimidine-5-carboxylic acid and 2-(aminomethyl)prop-2-enenitrile; 2,2,2-trifluoroacetic acid, the title compound was obtained. LC-MS m/z: 345.0 [M+1].

Example 272

N-(2-cyanoallyl)-2-(cyclopropyldifluoromethyl)-4-phenoxypyrimidine-5-carboxamide

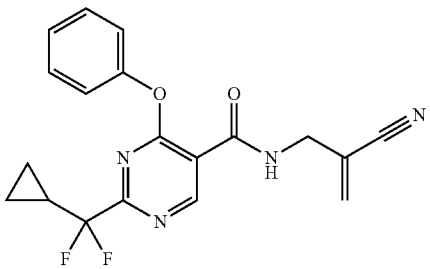 [SMILES: C=C(C#N)CNC(=O)c1cnc(C(F)(F)C2CC2)nc1Oc1ccccc1]

Following Step 7 in Procedure A with 2-[cyclopropyl(difluoro)methyl]-4-phenoxy-pyrimidine-5-carboxylic acid and 2-(aminomethyl)prop-2-enenitrile 2,2,2-trifluoroacetic acid, the title compound was obtained. LC-MS m/z: 371.0 [M+1].

Examples 273 and 274

(S)—N-(3-cyanobut-3-en-2-yl)-2-(1,1-difluoroethyl)-4-phenoxypyrimidine-5-carboxamide/(R)—N-(3-cyanobut-3-en-2-yl)-2-(1,1-difluoroethyl)-4-phenoxypyrimidine-5-carboxamide

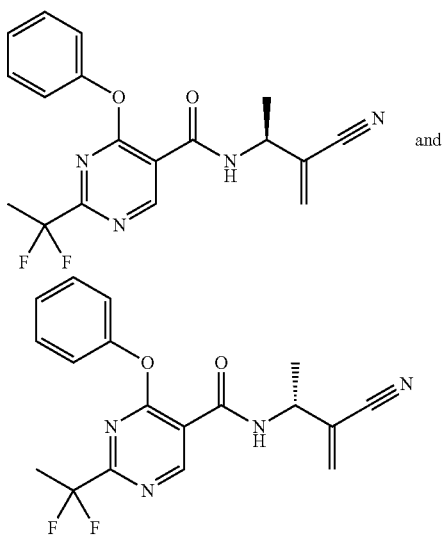

Step 1

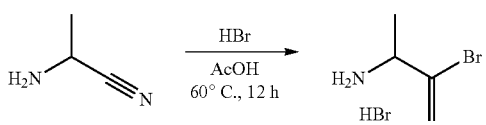

Tert-butyl but-3-yn-2-ylcarbamate (500 mg, 2.95 mmol) was added in HBr/AcOH (5 mL, 1 M) at 25° C. The mixture was warmed to 60° C. and stirred for 12 hours under $N_2$. The mixture was concentrated under reduced pressure to give crude 3-bromobut-3-en-2-amine HBr salt as a brown oil (440 mg).

Using 3-bromobut-3-en-2-amine HBr salt at Step 2 of the procedure for the compound of Example 268 and following the subsequent steps while using 2-(1,1-difluoroethyl)-4-phenoxy-pyrimidine-5-carboxylic acid at the last step, the mixture of the title compounds was obtained. The mixture was separated by chiral SFC (column: (S,S)-WHELK-O1) to afford to afford Peak 1 (LC-MS m/z: 359.2 [M+1]) and Peak 2 (LC-MS m/z: 359.2 [M+1]). The absolute stereochemistry of the title compounds were not ascertained.

Examples 275 and 276

(S)—N-(3-cyanobut-3-en-2-yl)-2-(cyclopropyldifluoromethyl)-4-phenoxypyrimidine-5-carboxamide/ (R)—N-(3-cyanobut-3-en-2-yl)-2-(cyclopropyldifluoromethyl)-4-phenoxypyrimidine-5-carboxamide

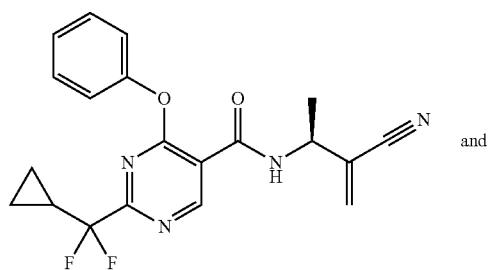

Following the procedure for the compounds of Example 273/274 while using 2-[cyclopropyl(difluoro)methyl]-4-phenoxy-pyrimidine-5-carboxylic acid at the last step, the mixture of the title compounds was obtained. The mixture was separated by chiral SFC (column: (S,S)-WHELK-O1) to afford to afford Peak 1 (LC-MS m/z: 385.2 [M+1]) and Peak 2 (LC-MS m/z: 385.2 [M+1]). The absolute stereochemistry of the title compounds were not ascertained.

Examples 278 and 279

(S)—N-(2-cyano-1-cyclopropylallyl)-2-(1,1-difluoroethyl)-4-phenoxypyrimidine-5-carboxamide/(R)—N-(2-cyano-1-cyclopropylallyl)-2-(1,1-difluoroethyl)-4-phenoxypyrimidine-5-carboxamide

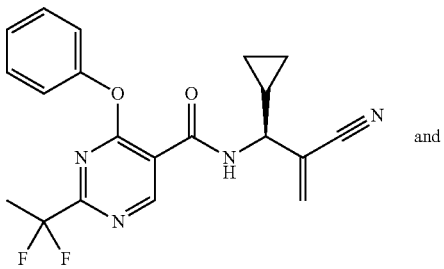

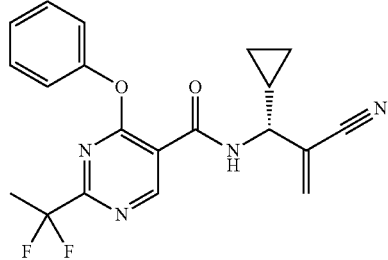

Step 1

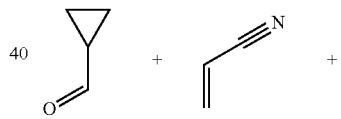

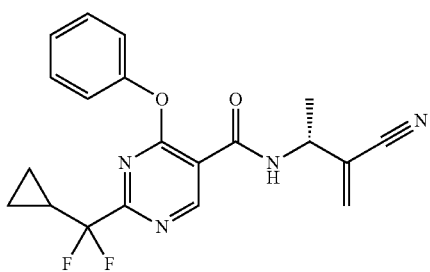

To a solution of cyclopropanecarboxaldehyde (9.3 g, 132 mmol) and 1,4-diazabicyclo[2.2.2]octane (7.4 g, 66 mmol) and 2,6-ditert-butyl-4-methyl-phenol (72.7 mg, 0.33 mmol) in water (1.45 mL, 89.98 M) was added acrylonitrile (8.4 g, 158 mmol). The mixture was stirred at 50° C. for 12 hours under $N_2$. The reaction mixture was diluted with EtOAc (50 mL). The organic phase was washed three times with HCl aq. (5%, 200 mL), once with water (50 mL), once with aqueous $NaHCO_3$ (10%, 2×50 mL). The combined organic layers were dried over $Na_2SO_4$, filtered and concentrated under reduced pressure to afford crude 2-[cyclopropyl(hydroxy)methyl]prop-2-enenitrile as a light yellow oil (16 g).

Step 2

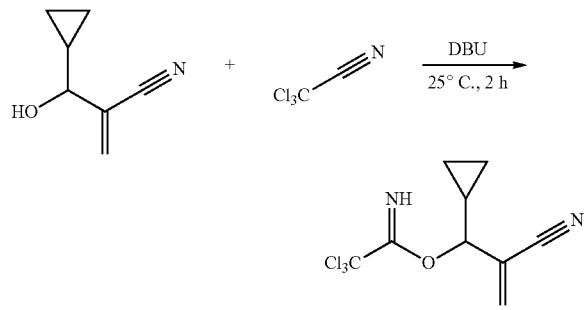

1,8-Diazabicyclo[5.4.0]undec-7-ene (3.89 mL, 25.99 mmol) was added to a mixture of 2-[cyclopropyl(hydroxy)methyl]prop-2-enenitrile (16 g, 130 mmol) and trichloroacetonitrile (93.8 g, 650 mmol) at 0° C. The mixture was allowed to warm to room temperature and stirred at 25° C. for 2 hours under $N_2$. The reaction mixture was concentrated under reduced pressure to afford crude (2-cyano-1-cyclopropyl-allyl) 2,2,2-trichloroethanimidate as a yellow oil (15 g).

Step 3

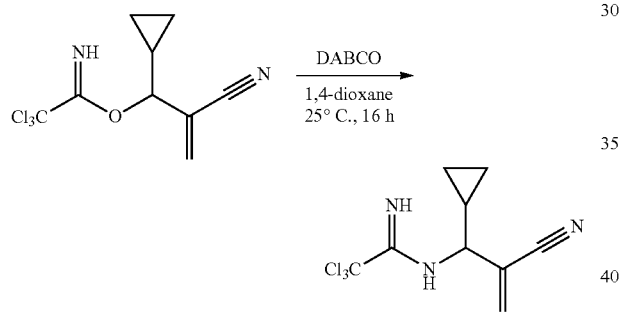

To a solution of (2-cyano-1-cyclopropyl-allyl) 2,2,2-trichloroethanimidate (12 g, 44.85 mmol) in 1,4-dioxane (100 mL, 0.449 M) was added 1,4-diazabicyclo[2.2.2]octane (503 mg, 4.49 mmol). The mixture was stirred at 25° C. for 16 hours under N2. The reaction mixture was concentrated under reduced pressure to give a residue. The residue was diluted with HCl (50 mL, 1M) and the aqueous phase was extracted with EtOAc (3×300 mL). The combined organic layers were dried over anhydrous $Na_2SO_4$, filtered and concentrated under reduced pressure to give a residue. The residue was purified by prep-TLC ($SiO_2$, Petroleum ether/Ethyl acetate=3/1) to afford 2,2,2-trichloro-N-(2-cyano-1-cyclopropyl-allyl)acetamide as a white solid (8.0 g, 67% yield).

Step 4

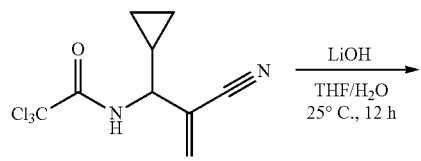

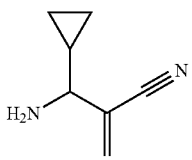

To a solution of 2,2,2-trichloro-N-(2-cyano-1-cyclopropyl-allyl)acetamide (500 mg, 1.87 mmol) in THF (5 mL, 0.187 M) and water (5 mL, 0.187 M) was added lithium hydride hydrate (157 mg, 3.74 mmol). The mixture was stirred at 25° C. for 12 hours under $N_2$. The reaction mixture was concentrated under reduced pressure to give a residue. The residue was directly purified by flash column chromatography (Biotage using a 40 g Agela flash silica gel column, eluted with 0% to 10% Methanol in DCM (10% TEA)) to afford 2-[amino(cyclopropyl)methyl]prop-2-enenitrile as a yellow oil (77 mg, 34% yield).

Using 2-[amino(cyclopropyl)methyl]prop-2-enenitrile and 2-(1,1-difluoroethyl)-4-phenoxy-pyrimidine-5-carboxylic acid to follow Step 7 in Procedure A, the mixture of the title compounds were obtained. The mixture was separated by chiral SFC (column: (S,S)-WHELK-O1 (250 mm*30 mm*5 um), mobile phase $CO_2$/EtOH, gradient 23% B, flow rate: 70 mL/min) to afford to afford Peak 1 (LC-MS m/z: 385.2 [M+1]) and Peak 2 (LC-MS m/z: 385.3 [M+1]). The absolute stereochemistry of the title compounds were not ascertained.

Example 280

(E)-4-cyclopentyl-2-ethoxy-N-(3-(methylsulfonyl)allyl)benzamide

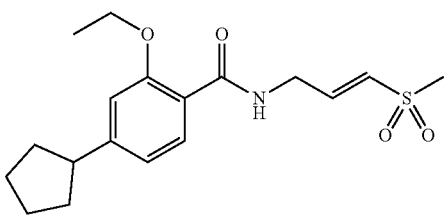 [SMILES: CCOc1cc(C2CCCC2)ccc1C(=O)NC/C=C/S(C)(=O)=O]

Step 1

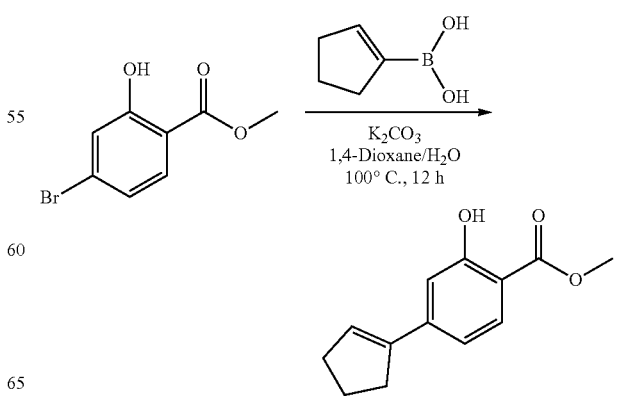

To a solution methyl 4-bromo-2-hydroxy-benzoate (3 g, 12.99 mmol) and cyclopenten-1-ylboronic acid (1.7 g, 15.58 mmol) in water (3 mL, 0.394 M) and 1,4-dioxane (30 mL, 0.394 M) was added potassium carbonate (5.4 g, 38.95 mmol) and Pd(dppf)Cl$_2$·DCM (1.05 g, 1.30 mmol). The mixture was stirred at 100° C. for 12 hours under N$_2$. The aqueous phase was adjusted to around pH=5-6 by progressively adding 2 M HCl. The reaction mixture was poured into water (40 mL) and extracted with EtOAc (3×50 mL). The combined organic layers were washed with brine (2×60 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 0~6% Ethyl acetate/Petroleum ether gradient@80 mL/min) to afford methyl 4-(cyclopenten-1-yl)-2-hydroxy-benzoate as a yellow solid (1.7 g, 60% yield).

Step 2

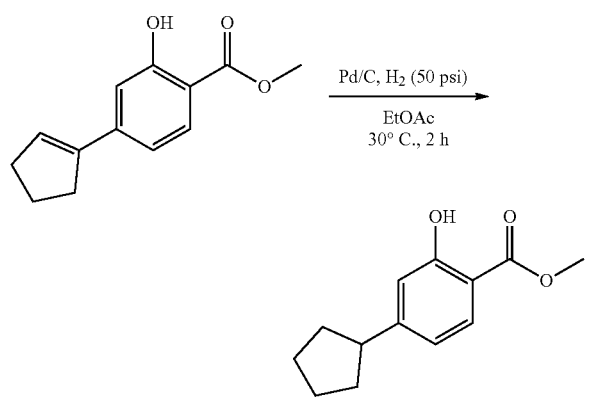

To a solution of methyl 4-(cyclopenten-1-yl)-2-hydroxy-benzoate (1.7 g, 7.79 mmol) in ethyl acetate (30 mL, 0.2596 M) was added Pd/C (0.8 g, 5% purity). The mixture was stirred at 30° C. for 2 hours under H$_2$ (50 psi). The mixture was filtered through a Celite pad and concentrated under reduced pressure to afford methyl 4-cyclopentyl-2-hydroxy-benzoate as a yellow oil (1.6 g, 93% yield).

Step 3

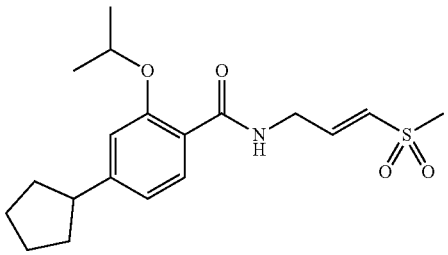 [SMILES: CC(C)Oc1cc(C2CCCC2)ccc1C(=O)NC/C=C/S(C)(=O)=O]

To a solution of methyl 4-cyclopentyl-2-hydroxy-benzoate (150 mg, 0.68 mmol) in DMF (2 mL, 0.341 M) was added iodoethane (637 mg, 4.09 mmol) and Cs$_2$CO$_3$ (444 mg, 1.36 mmol). The mixture was stirred at 25° C. for 12 hours. The reaction mixture was poured into water (15 mL) and extracted with EtOAc (3×15 mL). The combined organic layers were washed with brine (10 mL), dried over Na$_2$SO$_4$, filtered and concentrated under reduced pressure to afford crude methyl 4-cyclopentyl-2-ethoxy-benzoate (150 mg) as a white solid.

Following Step 6 with methyl 4-cyclopentyl-2-ethoxy-benzoate and Step 7 with [(E)-3-methylsulfonylallyl]amine 4-methylbenzenesulfonic acid in Procedure A, the title compound was obtained. LC-MS m/z: 352.2 [M+1].

Example 281

(E)-4-cyclopentyl-2-isopropoxy-N-(3-(methylsulfonyl)allyl)benzamide

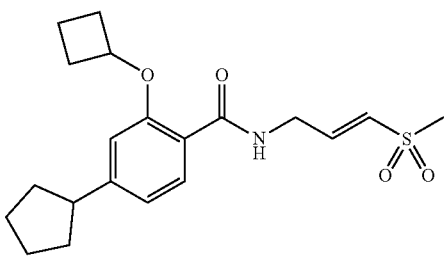 [SMILES: CS(=O)(=O)/C=C/CNC(=O)c1ccc(C2CCCC2)cc1OC1CCC1]

Using 2-iodopropane at Step 3 of the procedure for the compound of Example 280, the title compound was obtained. LC-MS m/z: 366.2 [M+1].

Example 282

(E)-2-cyclobutoxy-4-cyclopentyl-N-(3-(methylsulfonyl)allyl)benzamide

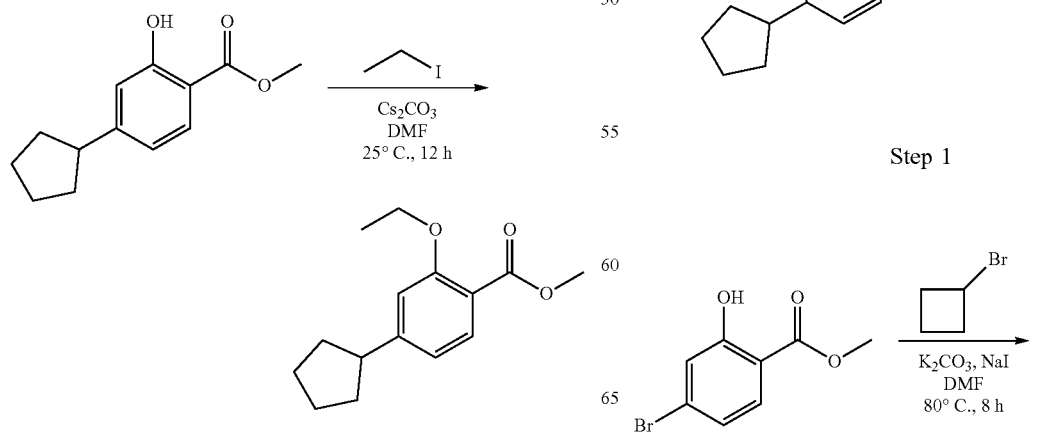

Step 1

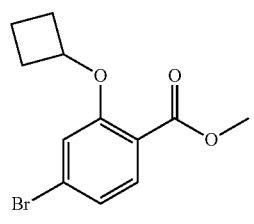

A solution of methyl 4-bromo-2-hydroxy-benzoate (200 mg, 0.87 mmol) in DMF (4 mL, 0.22 M) was added bromocyclobutane (140 mg, 1.04 mmol), sodium iodide (13.0 mg, 0.087 mmol). The mixture was stirred at 80° C. for 8 hours under $N_2$. The mixture was extracted with EtOAc (3×25 mL). The combined organic layers were washed with brine, dried over $Na_2SO_4$, filtered and concentrated under reduced pressure to give a residue. The residue was purified by flash silica gel chromatography (ISCO®; 0.5 g Sepa-Flash® Silica Flash Column, Eluent of 0 to 50% Ethyl acetate/Petroleum ether gradient @45 mL/min) to afford methyl 4-bromo-2-(cyclobutoxy)benzoate as a yellow oil (280 mg).

Step 2

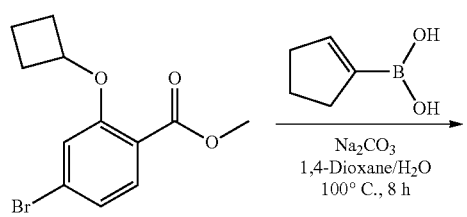

A solution of sodium carbonate (96.6 mg, 0.91 mmol), cyclopenten-1-ylboronic acid (76.5 mg, 0.68 mmol), methyl 4-bromo-2-(cyclobutoxy)benzoate (130 mg, 0.46 mmol) in 1,4-dioxane (2.6 mL, 0.16 M) and water (0.26 mL, 0.16 M) was added Pd(pddf)Cl₂ (33.4 mg, 0.0456 mmol). The mixture was stirred at 100° C. for 8 hours. The mixture was extracted with EtOAC (3×30 mL) and water (30 mL). The organic layers were concentrated under reduced pressure. The residue was purified by prep-TLC (SiO₂, PE:EtOAc=1:1) to afford methyl 2-(cyclobutoxy)-4-(cyclopenten-1-yl)benzoate as a white solid (45 mg, 36% yield).

Step 3

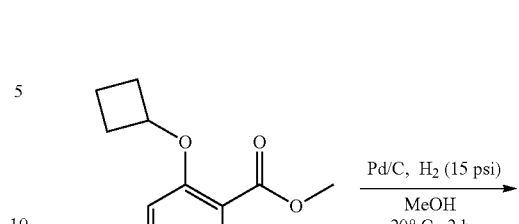

A solution of methyl 2-(cyclobutoxy)-4-(cyclopenten-1-yl)benzoate (45 mg, 0.165 mmol) in methanol (5 mL, 0.033 M) was added 10% Pd/C (5 mg). The mixture was stirred at 20° C. for 2 hours under $H_2$ (15 psi). The mixture was filtered and concentrated under reduced pressure to afford crude methyl 2-(cyclobutoxy)-4-cyclopentyl-benzoate as a yellow solid (70 mg).

Following Step 6 with methyl 2-(cyclobutoxy)-4-cyclopentyl-benzoate and Step 7 with [(E)-3-methylsulfonylallyl]amine 4-methylbenzenesulfonic acid in Procedure A, the title compound was obtained. LC-MS m/z: 378.1 [M+1].

Example 283

(E)-4-cyclopentyl-2-cyclopropoxy-N-(3-(methylsulfonyl)allyl)benzamide

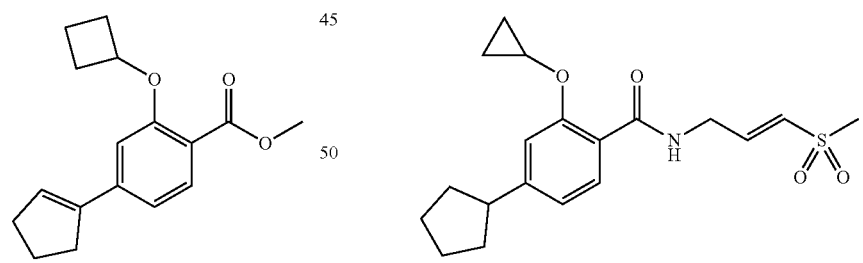

Step 1

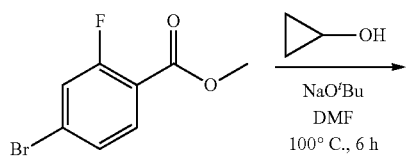

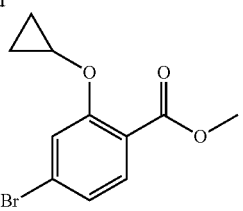

To a solution of methyl 4-bromo-2-fluorobenzoate (1.0 g, 4.29 mmol) in DMF (10 mL, 0.429 M) was added cyclopropanol (498 mg, 8.58 mmol) and sodium tert-butoxide (619 mg, 6.44 mmol) at 25° C. The mixture was stirred at 100° C. for 6 hours under N$_2$. The reaction mixture was poured into water (50 mL) and extracted with EtOAc (3×50 mL). The combined organic layers were washed with brine (2×300 mL), dried over Na$_2$SO$_4$, filtered and concentrated under reduced pressure to give a residue. The residue was purified by flash silica gel chromatography (Silica Flash Column 12 g, Eluent of 0~15% Ethyl acetate/Petroleum ether gradient at 40 mL/min) to afford methyl 4-bromo-2-(cyclopropoxy)benzoate as a yellow oil (320 mg, 28% yield).

Starting from Step 2 of the procedure for the compound of Example 282 and using methyl 4-bromo-2-(cyclopropoxy)benzoate, the title compound was obtained. LC-MS m/z: 364.1 [M+1].

Example 284

(S,E)-5-cyclopentyl-N-(4-(methylsulfonyl)but-3-en-2-yl)-3-phenoxypicolinamide

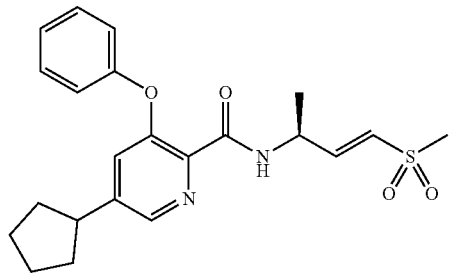 [SMILES: C[C@@H](/C=C/S(C)(=O)=O)NC(=O)c1ncc(C2CCCC2)cc1Oc1ccccc1]

Step 1

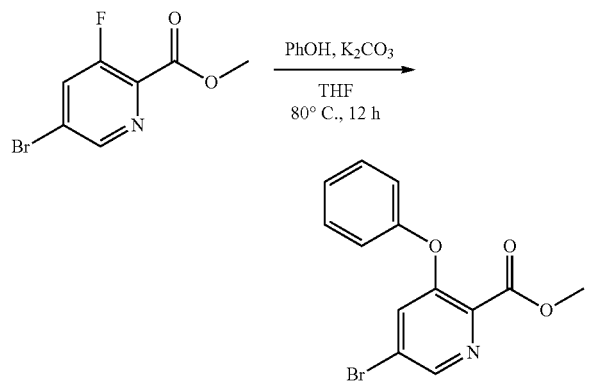

A mixture of methyl 5-bromo-3-chloro-pyridine-2-carboxylate (5 g, 19.96 mmol), potassium carbonate (4.1 g, 29.94 mmol) and phenol (1.97 g, 20.96 mmol) in THF (50 mL, 0.399 M) was heated at 80° C. for 12 hours. The reaction mixture was diluted with water (30 mL) and extracted with EtOAc (2×30 mL). The organic layers were dried over MgSO$_4$, filtered and concentrated under reduced pressure to give a residue. The residue was purified by flash silica gel column (PE:EA=100%-90%) to afford methyl 5-bromo-3-phenoxy-pyridine-2-carboxylate (2.0 g, 33% yield).

Following the procedure for the compound of Example 282 from Step 2 and using methyl 4-bromo-2-(cyclopropoxy)benzoate at Step 2 and [(E,1S)-1-methyl-3-methylsulfonyl-allyl]amine 4-methylbenzenesulfonic acid at the last step, the title compound was obtained. LC-MS m/z: 415.1 [M+1].

Example 285

(E)-4-cyclopentyl-N-(3-(methylsulfonyl)allyl)-2-phenoxybenzamide

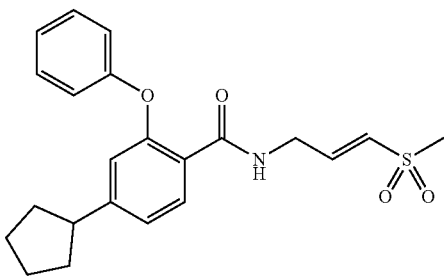 [SMILES: CS(=O)(=O)/C=C/CNC(=O)c1ccc(C2CCCC2)cc1Oc1ccccc1]

Step 1

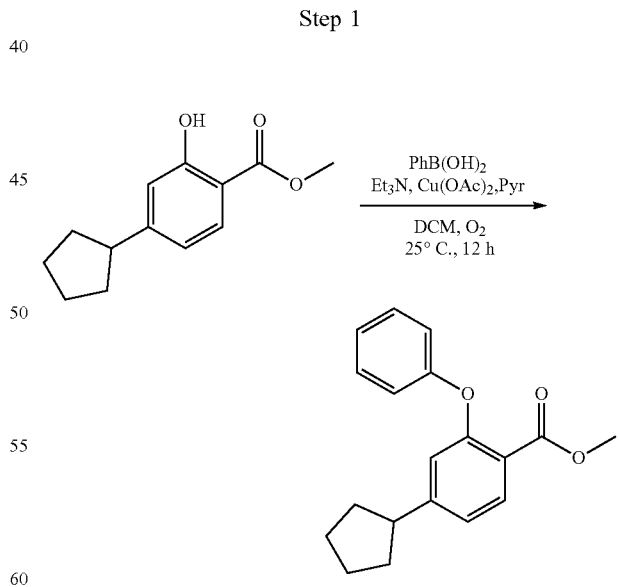

To a solution of copper diacetate (82.5 mg, 0.45 mmol) and methyl 4-cyclopentyl-2-hydroxy-benzoate (100 mg, 0.45 mmol) in DCM (3 mL, 0.151 M) was added 4 Å molecular sieves (100 mg) at 25° C. for 5 minutes, then the mixture was added phenylboronic acid (111 mg, 0.91 mmol), triethylamine (0.16 mL, 1.14 mmol) and pyridine (89.8 mg, 1.14 mmol) at 25° C. under O₂. Then the mixture was stirred at 25° C. for 12 hours. The reaction mixture was poured into water (10 mL) and extracted with DCM (3×10 mL). The combined organic layers were washed with brine (10 mL), dried over Na₂SO₄, filtered and concentrated under reduced pressure to give a residue. The residue was purified by prep-TLC (SiO₂, Petroleum ether:Ethyl acetate=10:1) to afford methyl 4-cyclopentyl-2-phenoxy-benzoate as a colorless solid (20 mg, 15% yield).

Following Step 6 with methyl 4-cyclopentyl-2-phenoxy-benzoate and Step 7 with [(E)-3-methylsulfonylallyl]amine 4-methylbenzenesulfonic acid in Procedure A, the title compound was obtained. LC-MS m/z: 400.1 [M+1].

Example 286

(S,E)-4-cyclopentyl-N-(4-(methylsulfonyl)but-3-en-2-yl)-2-phenoxybenzamide

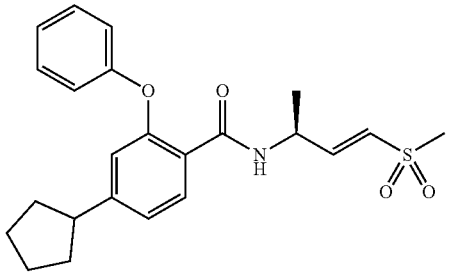 [SMILES: C[C@@H](/C=C/S(C)(=O)=O)NC(=O)c1ccc(C2CCCC2)cc1Oc1ccccc1]

Using [(E,1S)-1-methyl-3-methylsulfonyl-allyl]amine 4-methylbenzenesulfonic acid at the last step of the procedure for the compound of Example 284, the title compound was obtained. LC-MS m/z: 414.2 [M+1].

Example 287

2-cyclopropyl-N-(2-(methylsulfonyl)allyl)-4-phenoxypyrimidine-5-carboxamide

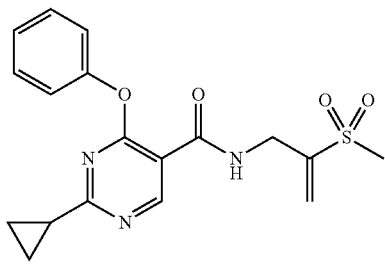 [SMILES: C=C(CNC(=O)c1cnc(C2CC2)nc1Oc1ccccc1)S(C)(=O)=O]

Step 1

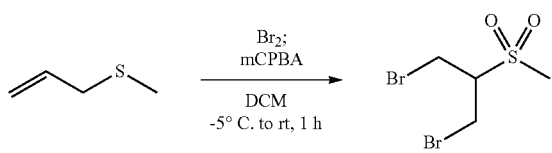

To a solution of allyl(methyl)sulfane (6.7 ml, 61.0 mmol) in DCM (120 ml) was added a solution of bromine in DCM (3.15 ml, 61.0 mmol of bromine in 25 mL of DCM) dropwise over 25 minutes at −5° C. The reaction mixture was allowed to warm to room temperature slowly over 45 minutes and stirred for 0.5 hour. The reaction mixture was diluted with DCM (160 ml) and cooled back to −5° C. 3-chlorobenzoperoxoic acid (35.1 g, 153 mmol) was added portion wise very slowly (control exotherm). After completion of addition, the reaction mixture was stirred at room temperature for 1 hour. The reaction mixture was filtered through a celite pad. The filtrate was washed with saturated aqueous NaHCO₃ solution (3×100 mL) and the combined organic phases were dried over Na₂SO₄, filtered and concentrate under reduced pressure to afford crude 1,3-dibromo-2-(methylsulfonyl)propane (20.1 g).

Step 2

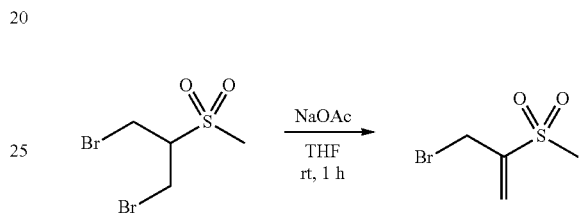

To a solution of 1,3-dibromo-2-(methylsulfonyl)propane (20 g, 71.4 mmol) in THF (120 ml) was added sodium acetate (7.62 g, 93 mmol) at room temperature. The mixture was stirred for 1 hour. The mixture was diluted with EtOAc (250 mL) and filtered through a celite pad. The filtrate was washed with saturated aqueous NaHCO₃ solution (2×100 mL) and the combined organic phases were dried over Na₂SO₄, filtered and concentrate under reduced pressure to give a residue. The residue was purified by flash column chromatography (SiO₂, EtOAc/hexanes=0-100%) to afford 3-bromo-2-methylsulfonyl-prop-1-ene (8.0 g, 56% yield).

Step 3

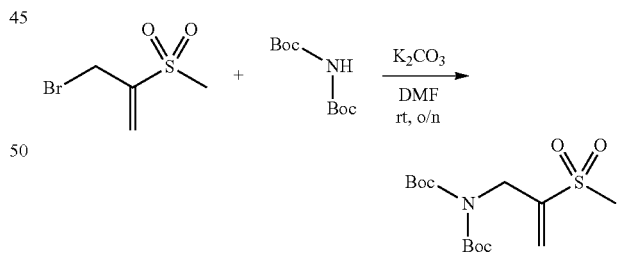

To a solution of 3-bromo-2-methylsulfonyl-prop-1-ene (3.1 g, 15.57 mmol) in DMF (30 mL, 0.519 M) was added di-tert-butyl-iminodicarboxylate (5.0 g, 23.23 mmol) and potassium carbonate (5.4 g, 38.80 mmol) at 0° C. The mixture was allowed to warm to room temperature and stirred overnight. The mixture was diluted with EtOAc (150 mL), washed with water (3×25 mL) and brine (25 mL), dried over Na₂SO₄, filtered and concentrate under reduced pressure to a residue. The residue was purified by flash column chromatography (SiO₂, EtOAc/hexanes=0-20%) to afford tert-butyl (tert-butoxycarbonyl)(2-(methylsulfonyl)allyl) carbamate as a white solid (4.8 g, 92% yield).

Step 4

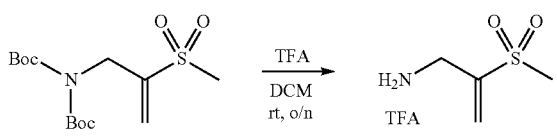

A solution of tert-butyl (tert-butoxycarbonyl)(2-(methyl-sulfonyl)allyl)carbamate (1.0 g, 2.98 mmol) in DCM (5 mL, 0.596 M) was added trifluoroacetic acid (3.4 g, 29.8 mmol) at room temperature. After overnight, the mixture was concentrated to dryness under reduced pressure to afford crude 2-(methylsulfonyl)prop-2-en-1-amine trifluoroacetic acid as a sticky opaque semi solid (0.90 g).

Following Step 7 in Procedure A with 2-(methylsulfonyl)prop-2-en-1-amine trifluoroacetic acid, the title compound was obtained. LC-MS m/z: 374.0 [M+1].

Biological Examples

Example B-1

Cell Growth Assay Protocol

The effects of compound on cellular viability were determined using the CellTiter-Glo® 2.0 Luminescent Cell Viability Assay (Promega, Madison, WI). The CellTiter-Glo® 2.0 Luminescent Cell Viability Assay is a homogeneous method of determining the number of viable cells in culture based on quantitation of the ATP present, an indicator of metabolically active cells. The assay system contains a proprietary thermostable luciferase and a beetle luciferin substrate, in a cell lysis buffer that also contains inhibitors of endogenous enzymes that are released during cells lysis (e.g., ATPases). Upon cell lysis, the luciferin substrate is mono-oxygenated by the luciferase in the presence of $Mg^{2+}$, ATP and molecular oxygen, generating a stable "glow-type" luminescent signal that is proportional to the amount of ATP present.

The cell line HCT 116 (a microsatellite instable-high (MSI-H) cell line isolated from the colon of a male colorectal cancer patient) and SW480 cell line (a microsatellite stable (MSS) cell line isolated from the large intestine of a male Dukes C colorectal cancer patient) were used to determine cell viability after treatment with test compounds.

HCT 116 cells were seeded in a 384-well clear-bottom TC-treated assay plate at 500 cells per well in McCoy's 5A Medium with 10% fetal bovine serum (FBS). SW480 cells were seeded at 1,000 cells per well in Eagle's Minimum Essential Medium (EMEM) with 10% FBS. Both cell lines were seeded in a volume of 50 µL medium per well. After 24 hours at 37° C. in 5% $CO_2$, baseline cell viability was measured by adding 35 µL of CellTiter-Glo® 2.0 reagent to 6 test wells, incubating for 10 minutes at room temperature and then reading the plate on a Clariostar plate reader (BMG Labtech, Cary, NC) in luminescence mode. Compound dilutions were then added to remaining cells starting at a concentration of 100 µM with 3-fold dilutions for 9 additional points using the HP D300e Digital Dispenser (Hewlett Packard, Palo Alto, CA). The final DMSO concentration was 1%. The concentration range was adjusted as needed for compounds of different potencies. The cells treated with compounds were incubated for 5 days at 37° C. in 5% $CO_2$. At the end of the 5-day incubation period, 35 µL of Cell-Titer-Glo® 2.0 reagent was added to each well and incubated for 10 minutes at room temperature. The plate was then read on a Clariostar plate reader (BMG Labtech, Cary, NC) in luminescence mode. The previously measured baseline cell viability was subtracted from the luminescence value of each well, and cell viability (% of DMSO) was plotted as a function of log compound concentration. The $EC_{50}$ was then calculated for each compound using Dotmatics Software (San Diego, CA). Finally, the ratio of MSS cell line $EC_{50}$ to MSI-H cell line $EC_{50}$ was calculated.

Example B-2

Helicase Assay for WRN Inhibition

Effects of compounds on WRN helicase activity were assessed with the Helicase Assay for WRN Inhibition. This is an ATP-dependent (inclusion of ATP is important and is required for this assay) fluorescence based assay using recombinant WRN and a fluorogenic DNA substrate.

TABLE 1

| Reagents | Reagent working solutions | Stock conc | End conc |
|---|---|---|---|
| Assay Buffer (AB) | -TRIS pH 7.5 (Life Technologies: Tris-HCL pH 7.5 #15567-027) | 1 M | 50 mM |
| | | 1 M | 2 mM |
| | -MgCL2 (SIGMA; M1028-100 ml) | 5 M | 100 mM |
| | -NaCL (Invitrogen; AM9760G) | 10% in H2O | 0.01% |
| | -Tween-20 (SIGMA-ALDRICH; P 9416-100 ml) | 2.5 Units/ml | 0.0025 |
| | -PolyIC (deoxyinosinic-deoxycytidylic) acid sodium salt (SIGMA; P4929) | 30% in H2O | U/ml |
| | | 1 M | 0.003% |
| | -BSA (SIGMA, A9576) | | 1 mM |
| | -DTT | | |
| Protein | hWRN(519-1227)_C-H3CV-GFP-10His ("10His" is disclosed as SEQ ID NO: 2) | Lot dependent | 20 nM |
| Substrate | ATP (SIGMA; A7699) | 500 mM in H2O | 2 mM |
| DNA duplex TAMRA | OLIGOA-BHQ2: TTTTTTTTTTTT TTTTTTTTTTTT TTTTTCGTACC CGATGTGTTCGT TC/BHQ2 (SEQ ID NO: 3) OLIGOB-TAMRA: TAMRA/ GAACGAACACAT CGGGTACGTTTT TTTTTTTTTTT TTTTTTTTTTT TT (SEQ ID NO: 4) | 100 µM in H2O | 0.1 µM |

TABLE 1-continued

| | | | |
|---|---|---|---|
| Capturing Strand | GAACGAACACAT CGGGTACG (SEQ ID NO: 5) | 500 M in H2O | 1 uM |
| Reagents | | Plate brand and type | Cat. No |
| Assay Plate | | Corning 384 NBS treated, Black, black bottom LV | Producer: Corning #3820 |

WRN protein (hWRN(519-1227)_C-H3CV-GFP-10His) ("10His" is disclosed as SEQ ID NO: 2) was diluted in Assay buffer with 0.2 mM ATP (inclusion of ATP is important and is required in this assay) and plated in assay plate, 10 μl/well. WRN was treated with serial dilutions of test compounds were preincubated for 30 minutes at room temperature, final DMSO concentration of 0.5%. The mixture was briefly centrifuged (1000 rpm for 30 seconds). Following preincubation, the reaction was initiated by addition of a 10 μl/well mixture containing ATP, the capturing strand and the TAMPA-labeled DNA duplex DNA. The mixture was briefly centrifuged (1000 rpm for 30 seconds). The reaction was allowed to continue for 30 minutes at room temperature followed by endpoint measurement of fluorescence (Ex. 535 nm, em 585 nm) on a Clariostar plate reader (BMG Labtech, Cary, NC). WRN activity was normalized to signal from wells without WRN protein (background, 0% activity) and wells with protein treated only with DMSO (positive control, 100% activity). For each compound the potency of inhibition (IC50) was determined using Graphpad Prism.

Example B-3

Target Engagement Protocol:

Cells or cell lysates were treated with a dose response of compound followed by probe treatment, which labels solvent exposed cysteines. Proteins were enzymatically digested with trypsin and probe-labelled peptides were enriched with streptavidin. Isolated peptides were then separated using reversed-phase liquid chromatography on a C18 column (Dionex Ultimated 3000 nano-LC, Thermo). Peptides were analyzed by parallel reaction monitoring mass spectrometry (Exploris 120, Thermo). WRN_C727 peak areas were quantified and normalized to a set of control peptides from highly abundant proteins found in all samples.

Target engagement (%) is calculated relative to DMSO treated control samples.

TABLE 2

Biological data

| Compound of Example # | Cell Growth Inhibition $GI_{50}$ [μM] | | WRN Helicase $IC_{50}$ [μM] | OCI-AML2 WRN C727 $TE_{50}$ [μM] | |
|---|---|---|---|---|---|
| | HCT-116 | SW480 | | in situ (cell) | in vitro (lysate) |
| 1 | 2.1 | >10 | 4.1 | 1.84 | 4.99 |
| 2 | 0.2171 | >11.59 | 0.7281 | 0.531 | 3.356 |
| 3 | 5.9 | >10 | 18.43 | | |
| 4 | | | 30 | 10.77 | 75 |
| 5 | | | 32 | | |
| 6 | 0.2142 | 11.81 | 0.4395 | 0.2 | 5 |
| 7 | 1.159 | >19.49 | 2.7 | | 14.05 |
| 8 | 0.04402 | 6.716 | 0.07576 | | 0.195 |
| 9 | 0.043 | 15 | 0.16 | | 0.31 |
| 10 | 0.07244 | 27.39 | 0.13 | | 0.24 |
| 11 | | | 87.05 | 50 | >100 |
| 12 | 8.9 | >10 | 14 | 50 | >100 |
| 13 | 2.1 | >10 | 5.9 | 0.68 | 9.72 |
| 14 | 5.4 | >10 | 10 | 2.09 | 20 |
| 15 | 0.36 | >10 | 0.94 | 0.76 | 4.53 |
| 16 | 0.08495 | 24.27 | 0.18 | | 0.65 |
| 17 | 6.3 | >10 | 7.621 | 5.99 | 80 |
| 18 | 0.38 | >10 | 1.098 | 1.53 | 6.84 |
| 19 | 0.13 | 21.79 | 0.3647 | | 0.74 |
| 20 | 0.745 | 15.43 | 1.7 | | 9.36 |
| 21 | 3.1 | 14 | 6.1 | | >100 |
| 22 | 2.5 | 6.1 | 3.5 | | |
| 23 | 1.1 | 2.8 | 3.4 | | 8.83 |
| 24 | 7.7 | >10 | 20 | | >100 |
| 25 | 5 | >10 | 12 | | >100 |
| 26 | 18 | 54 | 103 | | >100 |
| 27 | | | 34 | | |
| 28 | 0.6055 | 37.15 | 1.5 | | 6.74 |
| 29 | 0.1649 | 37.42 | 0.645 | | 1.68 |
| 30 | 0.12 | 16 | 0.45 | | 1.43 |
| 31 | 0.63 | 28 | 0.88 | | 3.24 |
| 32 | | | 35 | | >100 |
| 33 | 1.3 | >100 | 2.5 | | 4.64 |
| 34 | | | 26 | | >100 |
| 35 | 0.1711 | 18.08 | 1.009 | 0.29 | 5 |
| 36 | 0.05902 | 17.66 | 0.1849 | | 0.45 |

TABLE 2-continued

| | Biological data | | | |
|---|---|---|---|---|
| | Cell Growth Inhibition | | | OCI-AML2 WRN C727 TE$_{50}$ [μM] |
| Compound of | GI$_{50}$ [μM] | | WRN Helicase | in situ | in vitro |
| Example # | HCT-116 | SW480 | IC$_{50}$ [μM] | (cell) | (lysate) |
| 37 | 0.03594 | 28.57 | 0.24 | | 0.45 |
| 38 | 0.1566 | 11.67 | 0.4337 | | 0.8 |
| 39 | 0.11 | 14 | 0.24 | | 0.64 |
| 40 | 1.2 | 49 | 2.7 | | 3.48 |
| 41 | 0.72 | 33 | 1.4 | | 2.06 |
| 42 | 0.355 | 5.196 | 1.7 | | 4.44 |
| 43 | 0.67 | 7.8 | 1.5 | | 18.72 |
| 44 | 0.27 | >10 | 0.91 | 0.26 | 1.18 |
| 45 | 0.03674 | 12.96 | 0.086 | | 0.11 |
| 46 | 0.1243 | >11.89 | 0.287 | | 0.99 |
| 47 | 0.2915 | >12.65 | 0.77 | | 0.99 |
| 48 | 0.0365 | 5.97 | 0.062 | | 0.035 |
| 49 | 0.06016 | 5.194 | 0.092 | | 0.22 |
| 50 | 0.09471 | 7.505 | 0.22 | | 0.28 |
| 51 | 0.1838 | 8.521 | 0.45 | | 3.3 |
| 52 | | | 66 | | >100 |
| 53 | 0.97 | >10 | 3.6 | | 14.51 |
| 54 | 0.77 | >10 | 2.6 | | 50 |
| 55 | 0.15 | 6.2 | 0.91 | | 8.68 |
| 56 | 0.3776 | 10.55 | 0.8425 | 0.43 | 4.9 |
| 57 | 0.07178 | >11.82 | 0.2369 | 0.0927 | 0.56 |
| 58 | 0.02347 | 8.728 | 0.05769 | 0.016 | 0.448 |
| 59 | | | 54 | | >100 |
| 60 | 0.2 | 13 | 0.41 | | 2.87 |
| 61 | 1.3 | 7.5 | 3.5 | | >100 |
| 62 | 0.265 | 13.15 | 0.65 | | 4.09 |
| 63 | 0.0306 | 31.01 | 0.08793 | | 0.5 |
| 64 | 2.3 | 36 | 8.6 | | >100 |
| 65 | 0.08695 | 25.42 | 0.3 | | 1.17 |
| 66 | 0.03022 | 21.82 | 0.1129 | | 0.38 |
| 67 | 0.0439 | 9.783 | 0.14 | | 0.5 |
| 68 | 0.2296 | 31.43 | 0.18 | | 1 |
| 69 | 1.215 | 51.57 | 3.388 | | 10.97 |
| 70 | 0.1298 | >58.68 | 0.24 | | 0.79 |
| 71 | 0.11 | 41.35 | 0.27 | | |
| 72 | 0.04672 | 45.18 | 0.16 | | 0.6 |
| 73 | 0.3 | 16 | 0.15 | | 0.47 |
| 74/75 | | | 84 | | >100 |
| 74/75 | 0.72 | 12 | 1.2 | | 50 |
| 76 | 3.4 | >10 | 4.9 | | 50 |
| 77 | 0.43 | >5 | 1.5 | 1.14 | 25.995 |
| 78 | 2.6 | >10 | 9.327 | | 50 |
| 79 | | | 18 | | >100 |
| 80 | | | 148.4 | 20.39 | >100 |
| 81 | 0.54 | >10 | 0.87 | 0.27 | 2.51 |
| 82 | 0.28 | 20 | 0.55 | | 0.7 |
| 83 | 0.2015 | 19.05 | 0.2383 | | 0.38 |
| 84 | 0.05109 | 8.775 | 0.08 | 0.016 | 0.2 |
| 85 | 0.04844 | 11.53 | 0.12 | | 0.22 |
| 86 | 0.2236 | 41.67 | 0.4546 | | 1.91 |
| 87 | 0.04322 | 23.45 | 0.1316 | 0.065 | 0.575 |
| 88 | 0.08295 | 32.45 | 0.22 | | |
| 89 | 0.0575 | 37.5 | 0.2167 | | 0.28 |
| 90 | 0.3265 | 19.18 | 0.69 | | |
| 91 | 0.2515 | 26.12 | 0.6 | | |
| 92 | 0.2449 | 42.99 | 1.1 | | 10 |
| 93 | 0.1284 | 87.47 | 0.46 | | 4.19 |
| 94/95 | 0.21 | 16 | 0.4583 | | 2 |
| 94/95 | 2.1 | 12 | 4.3 | | 30 |
| 96 | 0.03692 | 27.5 | 0.2 | | 0.4 |
| 97 | 0.07 | 40 | 0.22 | | |
| 98 | 0.0547 | 4.696 | 0.14 | | 1 |
| 99 | 0.74 | 40 | 2 | | 10 |
| 100 | 0.06599 | 24.38 | 0.1738 | 0.15 | 0.8533 |
| 101 | 0.3742 | 7.859 | 1.1 | | 6.03 |
| 102 | 0.08177 | 4.142 | 0.13 | 0.16 | 0.53 |
| 103 | 0.3587 | 20.35 | 1.5 | | 3.43 |
| 104 | | | 19 | | 21.78 |
| 105 | 6 | >10 | 8.6 | 6.2 | >100 |
| 106 | | | 24 | | >100 |
| 107 | | | 82 | | >100 |

TABLE 2-continued

| | Biological data | | | |
|---|---|---|---|---|
| | Cell Growth Inhibition | | | OCI-AML2 WRN C727 TE$_{50}$ [μM] |
| Compound of | GI$_{50}$ [μM] | | WRN Helicase | in situ | in vitro |
| Example # | HCT-116 | SW480 | IC$_{50}$ [μM] | (cell) | (lysate) |
| 108 | | | 87 | 50 | >100 |
| 109 | | | 182.7 | | >100 |
| 110 | 6.6 | >10 | 6.2 | | 22.43 |
| 111 | 4.2 | >10 | 3.8 | | |
| 112 | 4.8 | >10 | 4.6 | | 7.43 |
| 113 | 1.1 | 6.2 | 1.8 | | 2.33 |
| 114 | 0.56 | >10 | 1.1 | | 4.68 |
| 115 | 2.1 | >10 | 2.9 | | 30.15 |
| 116 | 2.5 | >10 | 2.2 | 1.5 | 22.338 |
| 117 | 6 | 7.4 | 6.7 | | >100 |
| 118 | 3.2 | >10 | 3.2 | 3.47 | 15.64 |
| 119 | | | 24 | | >100 |
| 120 | 4.3 | 4.8 | 4.9 | | |
| 121 | 5 | 5.5 | 5.2 | | 2.56 |
| 122 | | | 22 | 8.07 | >100 |
| 123 | | | 29 | 20 | >100 |
| 124 | >10 | >10 | 14 | | 6.92 |
| 125 | 3.1 | >10 | 12.49 | | 52.19 |
| 126 | | | 44.43 | | >100 |
| 127 | 1.3 | 5.3 | 4.271 | | 7.28 |
| 128 | 2.5 | 4.2 | 5.9 | | 25.11 |
| 129 | | | 85 | | >100 |
| 130 | | | 50 | | >100 |
| 131 | | | 24 | | >100 |
| 132 | | | 30 | | >100 |
| 133 | | | 31 | | |
| 134 | | | 53 | | >100 |
| 135 | | | 70 | | 75 |
| 136 | 5.1 | >10 | 11 | | 18.53 |
| 137 | 0.98 | >10 | 3.4 | | 10 |
| 138 | | | 19 | | >100 |
| 139 | | | 191.6 | >100 | >100 |
| 140 | 0.33 | 32 | 1.9 | | |
| 141 | | | 118.3 | | >100 |
| 142 | | | 20 | | 50 |
| 143 | 3.4 | 13 | 14 | | |
| 144 | 0.6929 | >15.98 | 1.889 | 0.8 | 20 |
| 145 | | | 59 | | >100 |
| 146 | | | 53 | | |
| 147/148 | | | 56 | | |
| 147/148 | 3.5 | >10 | 10 | | |
| 149 | 2.5 | >10 | 7.8 | | |
| 150 | | | 43 | | >100 |
| 151 | | | 59 | | >100 |
| 152 | 0.08062 | 14.42 | 0.33 | | |
| 153 | 0.1649 | >10 | 0.5 | 0.16 | 1.88 |
| 154 | 0.222 | 8.967 | 0.33 | 0.14 | 1.33 |
| 155 | | | 15 | | 20 |
| 156 | | | 15 | | 40 |
| 157 | 1.1 | >10 | 4 | | 15 |
| 158 | 0.36 | 40 | 1.5 | | |
| 159 | 2.5 | 12 | 6.9 | | |
| 160 | 0.15 | 3.4 | 0.9 | | 6 |
| 161 | | | 153.9 | | >100 |
| 162 | | | 128 | | >100 |
| 163 | 0.4 | 3.9 | 0.74 | 0.56 | 1.76 |
| 164 | 7.1 | >10 | 12 | 21.43 | >100 |
| 165 | 2.7 | >10 | 4.1 | | 22.61 |
| 166 | 0.69 | >10 | 3.6 | | 8.93 |
| 167 | | | 15.56 | 7.08 | >100 |
| 168 | 1.6 | 17 | 4.4 | | 9.23 |
| 169 | | | 110.4 | | |
| 170 | | | 136.6 | | >100 |
| 171 | 0.4338 | 8.097 | 1.187 | | 4.45 |
| 172 | | | 13 | | 31.16 |
| 173 | | | 48 | | >100 |
| 174 | 2.2 | 11 | 6.8 | | 11.22 |
| 175 | 2.2 | 12 | 6.8 | | 20 |
| 176 | 0.44 | 13 | 1.6 | | 1.66 |
| 177 | 0.086 | 12 | 0.37 | | |
| 178 | 3.2 | 45 | 15 | | |

TABLE 2-continued

Biological data

| Compound of Example # | Cell Growth Inhibition GI$_{50}$ [µM] | | WRN Helicase IC$_{50}$ [µM] | OCI-AML2 WRN C727 TE$_{50}$ [µM] | |
|---|---|---|---|---|---|
| | HCT-116 | SW480 | | in situ (cell) | in vitro (lysate) |
| 179 | 0.1976 | 7 | 1.039 | | |
| 180 | 0.05822 | 3.4 | 0.4395 | | |
| 181 | 0.08836 | 17 | 0.8699 | | 27.23 |
| 182 | 0.108 | 19 | 1.1 | | 4.86 |
| 183 | | | 2.9 | | 64.43 |
| 184 | 0.1907 | 3.1 | 2.4 | | 1.3 |
| 185 | 0.02736 | 5.4 | 0.2392 | | 1.72 |
| 186 | 0.01953 | 3.3 | 0.2 | | 0.42 |
| 187 | | | 52 | | >100 |
| 188 | 0.3912 | >15.17 | 1.1 | 0.49 | |
| 189 | 0.1021 | >13.82 | 0.2415 | 0.1 | 0.64 |
| 190 | 0.53 | 5.4 | 0.31 | | 0.69 |
| 191 | 0.26 | 7.4 | 0.91 | | 2.19 |
| 192/193 | | | 54 | | >100 |
| 192/193 | 0.023 | 24 | 0.1844 | | 0.655 |
| 194/195 | 0.073 | 41 | 0.34 | | |
| 194/195 | | | 29 | | |
| 196 | 0.27 | 4.3 | 0.46 | 0.18 | 3.84 |
| 197 | 0.7094 | 6.187 | 1.688 | | 6.24 |
| 198 | | | 27 | | |
| 199 | 0.57 | >10 | 1.5 | 1.7 | 8.36 |
| 200 | 3.6 | >10 | 4.5 | | 21.74 |
| 201 | 0.26 | 9 | 0.7 | 0.16 | 4.04 |
| 202 | 7.2 | >10 | 8.6 | | 75 |
| 203 | | | 77 | | |
| 204 | | | 96 | | |
| 205 | | | 20 | | >100 |
| 206 | 5.7 | 8.6 | 11 | | 20 |
| 207 | | | 52 | | >100 |
| 208 | 1.2 | 19 | 5.5 | | 13.04 |
| 209 | | | 18 | | >100 |
| 210 | | | | | |
| 211 | | | 51 | | >100 |
| 212 | | | 31 | | >100 |
| 213 | 2.156 | 12.65 | 11 | | >100 |
| 214 | 2.474 | >19.49 | 10 | | >100 |
| 215 | 1.4 | 8.2 | 2.2 | | 9.62 |
| 216 | 2.2 | >10 | 7.736 | | 13.75 |
| 217 | 0.5586 | >10 | 0.96 | 0.44 | 1.65 |
| 218 | 1.378 | >29.33 | 4.3 | | 17.06 |
| 219 | 0.3225 | >24.49 | 1.2 | | 2.78 |
| 220 | 0.0827 | 36.06 | 0.14 | 0.1 | 0.38 |
| 221 | 2 | 52 | 8.3 | | 20 |
| 222 | 0.1334 | >15.04 | 0.4437 | | 1.3 |
| 223 | 0.05389 | 19 | 0.18 | | 0.23 |
| 224 | 0.01699 | 13.64 | 0.04833 | 0.00875 | 0.09323 |
| 225 | 0.017 | 17.97 | 0.05444 | 0.016 | 0.119 |
| 226 | 0.02298 | 27.87 | 0.09295 | 0.016 | 0.116 |
| 227/228 | 2.337 | 13.42 | 14 | | >100 |
| 227/228 | 0.007386 | 13 | 0.044 | | 0.42 |
| 229 | 0.013 | 13 | 0.058 | | |
| 230 | 0.01664 | 14 | 0.11 | | 0.81 |
| 231 | 0.038 | 61 | 0.21 | | 0.42 |
| 232 | 0.06991 | 28.14 | 0.3 | | 2.36 |
| 233 | 0.01989 | 16.97 | 0.072 | | 0.48 |
| 234 | 0.011 | 6.1 | 0.056 | | |
| 235 | 0.03944 | 8.3 | 0.08926 | | 70 |
| 236 | 0.012 | 4.5 | 0.042 | | |
| 237 | | | 17 | | 0.5 |
| 238 | | | 53 | | >100 |
| 239 | | | 148.2 | | >100 |
| 240 | | | 67 | | >100 |
| 241 | 8.4 | >10 | 12 | | |
| 242 | 2.8 | >10 | 9.8 | | |
| 243 | | | 43 | | >100 |
| 244 | | | 20 | | 0.49 |
| 245 | 0.1396 | 36 | 1.1 | | |
| 246 | 0.64 | 16 | 8 | | |
| 247 | 6.5 | >10 | 8.5 | | 30 |
| 248 | | | 63 | | |
| 249 | | | 39 | | |

TABLE 2-continued

Biological data

| Compound of Example # | Cell Growth Inhibition GI$_{50}$ [μM] HCT-116 | Cell Growth Inhibition GI$_{50}$ [μM] SW480 | WRN Helicase IC$_{50}$ [μM] | OCI-AML2 WRN C727 TE$_{50}$ [μM] in situ (cell) | OCI-AML2 WRN C727 TE$_{50}$ [μM] in vitro (lysate) |
|---|---|---|---|---|---|
| 250 | 1.14 | 44.9 | 4.5 | | 0.62 |
| 251 | | | 103.2 | | |
| 252 | 2.1 | >30 | 12 | | 0.35 |
| 253 | 0.24 | >10 | 0.94 | 0.2 | |
| 255 | 0.3286 | >12.65 | 1.141 | | 3.77 |
| 256 | | | 42 | | >100 |
| 259 | | | 7 | | 0.12 |
| 260 | 1.8 | 41 | 8.2 | | >100 |
| 261 | 0.35 | 37.95 | 0.88 | | 1.79 |
| 262 | 1.7 | 3 | 6.5 | | |
| 263 | 1.4 | 2.3 | 5.5 | | |
| 264 | 3.8 | 8.1 | 2.3 | 6.65 | 16.32 |
| 265 | 8.5 | >10 | 7.2 | | |
| 266 | | | 115.8 | | |
| 267 | | | 29 | | |
| 268 | 2.1 | 14 | 1.7 | | 23.27 |
| 269 | 3.298 | 17.89 | 6.1 | | 25 |
| 270 | 0.51 | 11 | 0.91 | | 8.53 |
| 271 | 0.3974 | 12 | 0.9859 | | 17.35 |
| 272 | 0.21 | 7.8 | 0.38 | 3.96 | 8.28 |
| 273/274 | | | 70 | | 4.07 |
| 273/274 | 0.1221 | 16 | 0.7697 | | >100 |
| 275/276 | 5.2 | 10 | 14 | | |
| 275/276 | 0.08585 | 9.4 | 0.23 | | |
| 278/279 | | | 65 | | |
| 278/279 | 0.35 | 11 | 1.2 | | |
| 280 | | | 62 | 21.34 | 8.49 |
| 281 | | | 51 | | 41.83 |
| 282 | 12 | 10 | 11 | 8.91 | 24.84 |
| 283 | | | 64 | | |
| 284 | | | 15 | | >100 |
| 285 | 6.1 | >10 | 3.3 | 4.47 | 14.165 |
| 286 | 0.6 | >10 | 1.4 | | 3.58 |
| 287 | 3.5 | 3.9 | 8 | | |

Some aspects relate to a Werner syndrome helicase (WRN helicase). The WRN helicase may include an amino acid sequence. Table 3 below includes an example of a WRN helicase amino acid sequence.

TABLE 3

| SEQ ID NO: | PROTEIN | PROTEIN AMINO ACID SEQUENCE |
|---|---|---|
| 1 | WRN_HUMAN (Reference: UniProt KB-Q14191) | MSEKKLETTAQQRKCPEWMNVQNKRCAVEERKAC VRKSVFEDDLPFLEFTGSIVYSYDAS DCSFLSEDISMSLSDGDVVGFDMEWPPLYNRGKL GKVALIQLCVSESKCYLPHVSSMSVF PQGLKMLLENKAVKKAGVGIEGDQWKLLRDFDIK LKNPFVELTDVANKKLKCTETWSLNSL VKHLLGKQLLKDKSIRCSNWSKFPLTEDQKLYAA TDAYAGFIIYRNLEILDDTVQRFAIN KEEEILLSDMNKQLTSISEEVMDLAKHLPHAFSK LENPRRVSILLKDISENLYSLRRMII GSTNIETELRPSNNLNLLSFEDSTTGGVQQKQIR EHEVLIHVEDETWDPTLDHLAKHDGE DVLGNKVERKEDGFEDGVEDNKLKENMERACLMS LDITEHELQILEQQSQEEYLSDIAYK STEHLSPNDNENDTSYVIESDEDLEMEMLKHLSP NDNENDTSYVIESDEDLEMEMLKSLE NLNSGTVEPTHSKCLKMERNLGLPTKEEEEDDEN EANEGEEDDDKDFLWPAPNEEQVTCL KMYFGHSSFKPVQWKVIHSVLEERRDNVAVMATG YGKSLCFQYPPVYVGKIGLVISPLIS LMEDQVLQLKMSNIPACFLGSAQSENVLTDIKLG KYRIVYVTPEYCSGNMGLLQQLEADI GITLIAVDEAHCISEWGHDFRDSFRKLGSLKTAL PMVPIVALTATASSSIREDIVRCLNL RNPQITCTGFDRPNLYLEVRRKTGNILQDLQPFL VKTSSHWEFEGPTIIYCPSRKMTQQV TGELRKLNLSCGTYHAGMSFSTRKDIHHRFVRDE IQCVIATIAFGMGINKADIRQVIHYG APKDMESYYQEIGRAGRDGLQSSCHVLWAPADIN LNRHLLTEIRNEKFRLYKLKMMAKME KYLHSSRCRRQIILSHFEDKQVQKASLGIMGTEK CCDNCRSRLDHCYSMDDSEDTSWDFG PQAFKLLSAVDILGEKFGIGLPILFLRGSNSQRL ADQYRRHSLFGTGKDQTESWWKAFSR QLITEGFLVEVSRYNKFMKICALTKKGRNWLHKA NTESQSLILQANEELCPKKLLLPSSK TVSSGTKEHCYNQVPVELSTEKKSNLEKLYSYKP CDKISSGSNISKKSIMVQSPEKAYSS SQPVISAQEQETQIVLYGKLVEARQKHANKMDVP PAILATNKILVDMAKMRPTTVENVKR IDGVSEGKAAMLAPLLEVIKHFCQTNSVQTDLFS STKPQEEQKTSLVAKNKICTLSQSMA ITYSLFQEKKMPLKSIAESRILPLMTIGMHLSQA VKAGCPLDLERAGLTPEVQKIIADVI |

TABLE 3-continued

| SEQ ID NO: | PROTEIN | PROTEIN AMINO ACID SEQUENCE |
|---|---|---|
| | | RNPPVNSDMSKISLIRMLVPENIDTYLIHMAIEI LKHGPDSGLQPSCDVNKRRCFPGSEE ICSSSKRSKEEVGINTETSSAERKRRLPVWFAKG SDTSKKLMDKTKRGGLFS |

Some aspects relate to a WRN helicase or a variant thereof. Some aspects include a WRN helicase variant. Some examples of natural WRN helicase variants are shown in Table 4 below, and are also described further in the UniProt database (www.uniprot.org/uniprot/Q14191, last modified May 25, 2022). The examples in Table 4 include substitution differences at given positions with relation to SEQ ID NO: 1.

TABLE 4

Natural variants of WRN

| Feature key | Position | Description |
|---|---|---|
| Natural variant VAR_017453 | 32 | K → R |
| Natural variant VAR_036318 | 92 | G → V |
| Natural variant VAR_017454 | 114 | V → I |
| Natural variant VAR_026588 | 125 | K → N |
| Natural variant VAR_026589 | 135 | K → E |
| Natural variant VAR_017455 | 172 | T → P |
| Natural variant VAR_017456 | 240 | N → K |
| Natural variant VAR_006904 | 324 | T → A |
| Natural variant VAR_020450 | 329 | Q → R |
| Natural variant VAR_018941 | 343 | E → K |
| Natural variant VAR_020451 | 383 | L → F |
| Natural variant VAR_017457 | 383 | L → W |
| Natural variant VAR_006905 | 387 | M → I |
| Natural variant VAR_018942 | 533 | N → S |
| Natural variant VAR_018943 | 612 | S → C |
| Natural variant VAR_018944 | 708 | S → F |
| Natural variant VAR_057124 | 711 | R → W |
| Natural variant VAR_017458 | 724 | Q → L |
| Natural variant VAR_014913 | 834 | R → C |
| Natural variant VAR_018945 | 912 | I → S |
| Natural variant VAR_007903 | 1074 | L → F |
| Natural variant VAR_014914 | 1079 | S → L |
| Natural variant VAR_018946 | 1133 | S → A |
| Natural variant VAR_054162 | 1141 | S → L |
| Natural variant VAR_017459 | 1269 | K → E |
| Natural variant VAR_018947 | 1339 | V → I |
| Natural variant VAR_006906 | 1367 | C → R |

In some embodiments, the WRN helicase or variant thereof comprises the amino acid sequence of SEQ ID NO: 1. For example, the WRN helicase may include or consist of the amino acid sequence of SEQ ID NO: 1.

In some embodiments, the WRN helicase or variant thereof comprises an amino acid sequence that is not identical to SEQ ID NO: 1. In some embodiments, the WRN helicase or variant thereof comprises an amino acid sequence that is about 70%, about 75%, about 80%, about 85%, about 90%, about 91%, about 92%, about 93%, about 94%, about 95%, about 96%, about 97%, about 98%, about 99%, or about 100% identical to SEQ ID NO: 1. In some embodiments, the WRN helicase or variant thereof comprises an amino acid sequence that is 70%, 75%, 80%, 85%, 90%, 91%, 92%, 93%, 94%, 95%, 96%, 97%, 98%, 99%, or 100% identical to SEQ ID NO: 1. In some embodiments, the WRN helicase or variant thereof comprises an amino acid sequence that is about 99.0%, about 99.1%, about 99.2%, about 99.3%, about 99.4%, about 99.5%, about 99.6%, about 99.7%, about 99.8%, about 99.9%, or about 100% identical to SEQ ID NO: 1. In some embodiments, the WRN helicase or variant thereof comprises an amino acid sequence that is 99.0%, 99.1%, 99.2%, 99.3%, 99.4%, 99.5%, 99.6%, 99.7%, 99.8%, 99.9%, or 100% identical to SEQ ID NO: 1. In some embodiments, the WRN helicase or variant thereof may comprise an amino acid sequence with a sequence identity within a range of any of the aforementioned percentages. In some embodiments, the WRN helicase or variant thereof comprises an amino acid sequence at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical, to the amino acid sequence of SEQ ID NO: 1. In some embodiments, the WRN helicase or variant thereof comprises an amino acid sequence at least 90.0% identical, at least 90.1% identical, at least 90.2% identical, at least 90.3% identical, at least 90.4% identical, at least 90.5% identical, at least 90.6% identical, at least 90.7% identical, at least 90.8% identical, or at least 90.9% identical, to the amino acid sequence of SEQ ID NO: 1. In some embodiments, the WRN helicase or variant thereof comprises an amino acid sequence no more than 75% identical, no more than 80% identical, no more than 85% identical, no more than 90% identical, no more than 91% identical, no more than 92% identical, no more than 93% identical, no more than 94% identical, no more than 95% identical, no more than 96% identical, no more than 97% identical, no more than 98% identical, or no more than 99% identical, to the amino acid sequence of SEQ ID NO: 1. In some embodiments, the WRN helicase or variant thereof comprises an amino acid sequence no more than 90.0% identical, no more than 90.1% identical, no more than 90.2% identical, no more than 90.3% identical, no more than 90.4% identical, no more than 90.5% identical, no more than 90.6% identical, no more than 90.7% identical, no more than 90.8% identical, or no more than 90.9% identical, to the amino acid sequence of SEQ ID NO: 1.

In some embodiments, the WRN helicase variant includes a WRN helicase fragment. In some embodiments, the WRN helicase variant includes a fragment of any of the aforementioned sequences. In some embodiments, the WRN helicase fragment includes at least 500, at least 600, at least 700, at least 800, at least 900, at least 1000, at least 1100, at least 1200, at least 1300, or at least 1400, amino acids of a WRN helicase or variant thereof described herein. In some embodiments, the WRN helicase fragment includes no more than 500, no more than 600, no more than 700, no more than 800, no more than 900, no more than 1000, no more than 1100, no more than 1200, no more than 1300, or no more than 1400, amino acids of a WRN helicase or variant thereof described herein.

In some embodiments, where an amino acid at a position is described (e.g. amino acid positions 1-726, 727, or 728-1432 of a WRN helicase), an equivalent position may be included in a variant or fragment, even if the exact amino acid numbering is not the same.

The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled. This application refers to various issued patents, published patent applications, journal articles, and other publications, each of which are incorporated herein by reference in its entirety.

The invention claimed is:
1. A compound of Formula (I):

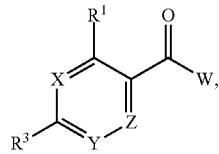

(I)

or a pharmaceutically acceptable salt thereof, wherein:
X is N;
Y is N;
Z is $CR^5$;
  or Y and Z taken together form an optionally substituted five- to six-membered heteroaryl, or an optionally substituted five- to six-membered heterocyclyl;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
  or $R^1$ together with the carbon atoms to which it is shown attached and X form an optionally substituted five- to six-membered heterocyclyl;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl);
  or $R^3$ taken together with the carbon atom to which it is shown attached and Y form an optionally substituted five- to six-membered heterocyclyl or heterocyclenyl;
$R^5$ is H, $C_1$-$C_6$ alkyl, —$NR_2$, or —N(R)—C(=O)—($C_1$-$C_6$ alkyl);
each R independently is H, or optionally substituted $C_1$-$C_6$ alkyl;
W is $W^1$, $W^2$, $W^3$, $W^4$, or $W^5$;
$W^1$ is:

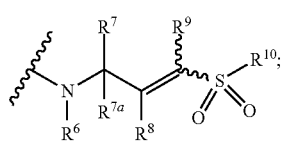

wherein:
the bonds represented by ⌇ indicate that

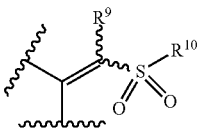

can exist as either a (Z)- or (E)-geometric isomer wherein

indicates the point of attachment;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;
$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl;
  or $R^6$ together with the nitrogen atom to which it is shown attached and $R^7$ and $R^{7a}$ together with the carbon atom to which they are shown attached form an azetidinyl ring;
  or $R^6$ together with the nitrogen atom to which it is shown attached and $R^7$, $R^{7a}$, and $R^8$ together with the carbon atoms to which they are shown attached form an azetidinyl or pyrrolodinyl ring;
  or $R^6$ together with the nitrogen atom to which it is shown attached and $R^7$, $R^{7a}$, $R^8$, and $R^9$ together with the carbon atoms to which they are shown attached form a dihydropyrrolyl ring;
  or $R^8$, $R^9$, and $R^{10}$ together with the carbon atoms to which they are shown attached form a 1,1-dioxido-2H-thietyl ring;
$W^2$ is:

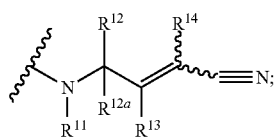

wherein:
the bonds represented by ⌇ indicate that

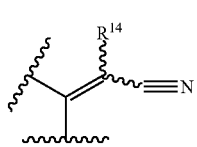

can exist as either a (Z)- or (E)-geometric isomer, wherein

indicates the point of attachment;
$R^{11}$ is H;
$R^{12}$ is H or optionally substituted $C_1$-$C_6$ alkyl;
$R^{12a}$ is H; and
$R^{13}$ and $R^{14}$ are each H;
  or $R^{11}$ together with the nitrogen atom to which it is shown attached and $R^{12}$, $R^{12a}$, and $R^{13}$ together with the carbon atoms to which they are shown attached form an optionally substituted azetidinyl ring;
$W^3$ is:

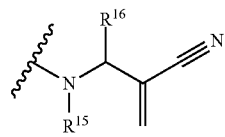

wherein:

indicates the point of attachment;
$R^{15}$ is H;
$R^{16}$ is H or optionally substituted $C_1$-$C_6$ alkyl, or optionally substituted $C_3$-$C_8$ cycloalkyl;
$W^4$ is:

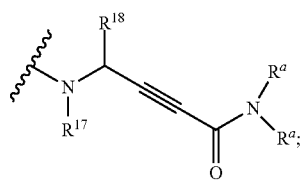

wherein:

indicates the point of attachment;
$R^{17}$ is H;
$R^{18}$ is H or optionally substituted $C_1$-$C_6$ alkyl; and
each $R^a$ independently is optionally substituted $C_1$-$C_6$ alkyl; and $W^5$ is:

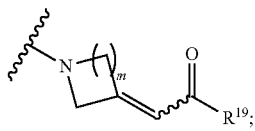

wherein:
  the bond represented by ～ indicates that

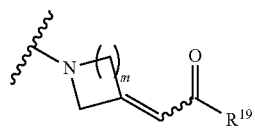

can exist as either a (Z)- or (E)-geometric isomer, and wherein

indicates the point of attachment;
m is 1, 2, or 3; and
$R^{19}$ is selected from the group consisting of $C_1$-$C_6$ alkyl and —O—($C_1$-$C_6$ alkyl).

2. The compound according to claim 1, or a pharmaceutically acceptable salt thereof, wherein:
X is N;
Y is N;
Z is $CR^5$;
$R^1$ is H, —O-(optionally substituted $C_3$-$C_8$ cycloalkyl), —O-(optionally substituted $C_1$-$C_6$ alkyl), —O-(optionally substituted $C_6$-$C_{10}$ aryl), —O-(optionally substituted five- to six-membered heteroaryl), —O-(optionally substituted five- to six-membered heterocyclyl), or optionally substituted $C_3$-$C_8$ cycloalkyl;
$R^3$ is optionally substituted $C_3$-$C_8$ cycloalkyl, optionally substituted $C_3$-$C_8$ cycloalkenyl, optionally substituted $C_6$-$C_{10}$ aryl, optionally substituted $C_1$-$C_6$ alkyl, optionally substituted $C_1$-$C_6$ alkenyl, —$NR_2$, —N(R)(optionally substituted $C_3$-$C_8$ cycloalkyl), —S-(optionally substituted $C_1$-$C_6$ alkyl), —O-(optionally substituted $C_1$-$C_6$ alkyl), —O-(optionally substituted $C_3$-$C_8$ cycloalkyl), optionally substituted four- to six-membered heterocyclyl or heterocyclenyl, optionally substituted five- to six-membered heteroaryl, or —O-(optionally substituted $C_3$-$C_8$ cycloalkyl); $R^5$ is H, $C_1$-$C_6$ alkyl, —$NR_2$, or —N(R)—C(=O)—($C_1$-$C_6$ alkyl);
each R independently is H, or optionally substituted $C_1$-$C_6$ alkyl;
W is $W^1$;
$R^6$ is H;
$R^7$ is H, optionally substituted $C_1$-$C_6$ alkyl, optionally substituted $C_3$-$C_8$ cycloalkyl, or optionally substituted five- to six-membered heterocyclyl;

$R^{7a}$ is H or deuterium;
$R^8$ is H;
$R^9$ is H; and
$R^{10}$ is optionally substituted $C_1$-$C_6$ alkyl, optionally substituted $C_3$-$C_8$ cycloalkyl, or optionally substituted five- to six-membered heterocyclyl.

3. The compound according to claim 2, or a pharmaceutically acceptable salt thereof, wherein:
$R^1$ is —O—($C_6$-$C_{10}$ aryl);
$R^3$ is fluoro substituted $C_1$-$C_6$ alkyl;
$R^5$ is H;
$R^6$ is H;
$R^7$ is $C_3$-$C_8$ cycloalkyl;
$R^{7a}$ is H or deuterium;
$R^8$ is H;
$R^9$ is H; and
$R^{10}$ is $C_1$-$C_6$ alkyl.

4. The compound according to claim 1, or a pharmaceutically acceptable salt thereof, wherein:
in $R^1$:
the optional substituents of the —O-(optionally substituted $C_3$-$C_8$ cycloalkyl) are 1-3 substituents selected from the group consisting of halo, cyano, and hydroxy; or when there are two substituents on the same ring carbon atom of the $C_3$-$C_8$ cycloalkyl, the substituents together with the ring carbon atom to which they are attached form a $C_3$-$C_6$ cycloalkyl; or when there are two substituents on adjacent ring carbon atoms of the $C_3$-$C_8$ cycloalkyl, the substituents taken together with the ring carbon atoms to which they are attached form a $C_3$-$C_6$ cycloalkyl;
the optional substituents of the —O-(optionally substituted $C_6$-$C_{10}$ aryl) are 1-3 substituents selected from the group consisting of halo, $C_1$-$C_6$ alkyl, cyano, hydroxy, and —NH$_2$, or 1-5 deuterium atoms;
or when $R^1$ together with the carbon atoms to which it is shown attached and X form an optionally substituted five- to six-membered heterocyclyl, two substituents on the same ring carbon atom of the five- to six-membered heterocyclyl together with the ring carbon atom to which they are attached form a five- to six-membered cycloalkyl;
in $R^3$:
the optional substituents of the optionally substituted $C_3$-$C_8$ cycloalkyl are 1-3 substituents selected from hydroxy, halo, $C_1$-$C_6$ alkyl, and $C_6$-$C_{10}$ aryl; or when there are two substituents on the same carbon atom of the $C_3$-$C_8$ cycloalkyl, the substituents together with the ring carbon atom to which they are attached form a $C_3$-$C_6$ cycloalkyl; or when there are two substituents on adjacent ring carbon atoms of the $C_3$-$C_8$ cycloalkyl, the substituents taken together with the ring carbon atoms to which they are attached form $C_6$-$C_{10}$ aryl;
or when $R^3$ taken together with the carbon atom to which it is shown attached and Y form an optionally substituted five- to six-membered heterocyclyl or heterocyclenyl, the optional substituents are 1-3 substituents selected from the group consisting of halo and $C_1$-$C_6$ alkyl;
the optional substituents of the optionally substituted $C_6$-$C_{10}$ aryl are 1-3 substituents selected from the group consisting of halo;
the optional substituents of the optionally substituted $C_1$-$C_6$ alkyl or $C_6$ alkenyl are 1-5 substituents selected from the group consisting of halo, hydroxy, —O—($C_1$-$C_6$ alkyl), and optionally substituted $C_3$-$C_6$ cycloalkyl, wherein the optional substituents of the $C_3$-$C_6$ cycloalkyl are 1-3 substituents selected from the group consisting of $C_1$-$C_6$ alkyl;
the optional substituents of the $C_1$-$C_6$ alkyl of R of —NR$_2$ are 1-3 substituents selected from the group consisting of halo; and
the optional substituents of the optionally substituted four- to six-membered heterocyclyl are 1-3 substituents selected from the group consisting of —O—($C_1$-$C_6$ alkyl), $C_1$-$C_6$ alkyl, halo; or when there are two substituents on the same carbon atom of the optionally substituted four- to six-membered heterocyclyl, the substituents together with the ring carbon atom to which they are attached form a $C_3$-$C_6$ cycloalkyl.

5. The compound according to claim 1, or a pharmaceutically acceptable salt thereof, wherein W is $W^1$.

6. The compound according to claim 1, or a pharmaceutically acceptable salt thereof, wherein W is $W^2$.

7. The compound according to claim 6, or a pharmaceutically acceptable salt thereof, wherein $W^2$ is:

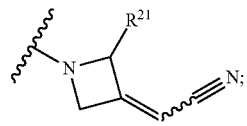

wherein:
$R^{21}$ is H or $C_1$-$C_6$ alkyl;
the bond represented by ⌇⌇⌇ indicates that

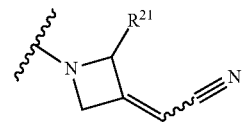

can exist as either a (Z)- or (E)-geometric isomer, and wherein

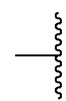

indicates the point of attachment.

8. The compound according to claim 1, or a pharmaceutically acceptable salt thereof, wherein W is $W^3$.

9. The compound according to claim 8, or a pharmaceutically acceptable salt thereof, wherein:
the optionally substituted $C_1$-$C_6$ alkyl of $R^{16}$ is methyl; and
the optionally substituted $C_3$-$C_8$ cycloalkyl of $R^{16}$ is cyclopropyl.

10. The compound according to claim 1, or a pharmaceutically acceptable salt thereof, wherein W is $W^4$.

11. The compound according to claim 10, or a pharmaceutically acceptable salt thereof, wherein:
the optionally substituted $C_1$-$C_6$ alkyl of $R^{18}$ is methyl.

12. The compound according to claim 1, or a pharmaceutically acceptable salt thereof, wherein W is $W^5$.

13. The compound according to claim 12, or a pharmaceutically acceptable salt thereof, wherein:
the $C_1$-$C_6$ alkyl of $R^{19}$ is methyl; and
the —O—($C_1$-$C_6$ alkyl) of $R^{19}$ is methoxy.

14. The compound according to claim 1, or a pharmaceutically acceptable salt thereof, wherein the compound is selected from the group consisting of:
(E)-N-(3-(methylsulfonyl)allyl)-4-phenoxy-2-(pyrrolidin-1-yl)pyrimidine-5-carboxamide;
(S,E)-N-(4-(methylsulfonyl)but-3-en-2-yl)-4-phenoxy-2-phenylpyrimidine-5-carboxamide;
(S,E)-2-methyl-N-(4-(methylsulfonyl)but-3-en-2-yl)-4-phenoxypyrimidine-5-carboxamide;
(R,E)-2-cyclopentyl-N-(4-(methylsulfonyl)but-3-en-2-yl)-4-phenoxypyrimidine-5-carboxamide;
(S,E)-2-cyclopentyl-N-(4-(methylsulfonyl)but-3-en-2-yl)-4-phenoxypyrimidine-5-carboxamide;
(S,E)-2-ethyl-N-(4-(methylsulfonyl)but-3-en-2-yl)-4-phenoxypyrimidine-5-carboxamide;
(E)-2-cyclopentyl-N-(3-(methylsulfonyl)allyl)-4-phenoxypyrimidine-5-carboxamide;
(E)-2-isopropyl-N-(3-(methylsulfonyl)allyl)-4-phenoxypyrimidine-5-carboxamide;
(R,E)-2-cyclobutyl-N-(4-(methylsulfonyl)but-3-en-2-yl)-4-phenoxypyrimidine-5-carboxamide;
(S,E)-2-cyclobutyl-N-(4-(methylsulfonyl)but-3-en-2-yl)-4-phenoxypyrimidine-5-carboxamide;
(S,E)-2-cyclohexyl-N-(4-(methylsulfonyl)but-3-en-2-yl)-4-phenoxypyrimidine-5-carboxamide;
(E)-2-ethyl-N-(3-(methylsulfonyl)allyl)-4-phenoxypyrimidine-5-carboxamide;
(S,E)-2-isopropyl-N-(4-(methylsulfonyl)but-3-en-2-yl)-4-phenoxypyrimidine-5-carboxamide;
(S,E)-2-(cyclopentylamino)-N-(4-(methylsulfonyl)but-3-en-2-yl)-4-phenoxypyrimidine-5-carboxamide;
(E)-2-cyclopropyl-N-(3-(methylsulfonyl)allyl)-4-phenoxypyrimidine-5-carboxamide;
(S,E)-2-cyclopropyl-N-(4-(methylsulfonyl)but-3-en-2-yl)-4-phenoxypyrimidine-5-carboxamide;
(E)-2-(tert-butyl)-N-(3-(methylsulfonyl)allyl)-4-phenoxypyrimidine-5-carboxamide;
(R,Z)-2-cyclopentyl-N-(4-(methylsulfonyl)but-3-en-2-yl)-4-phenoxypyrimidine-5-carboxamide;
(S,Z)-2-cyclopentyl-N-(4-(methylsulfonyl)but-3-en-2-yl)-4-phenoxypyrimidine-5-carboxamide;
(E)-2-cyclobutyl-N-(3-(methylsulfonyl)allyl)-4-phenoxypyrimidine-5-carboxamide;
(E)-4-(4-chlorophenoxy)-2-cyclopentyl-N-(3-(methylsulfonyl)allyl)pyrimidine-5-carboxamide;
(S,E)-4-(4-chlorophenoxy)-2-cyclopentyl-N-(4-(methylsulfonyl)but-3-en-2-yl)pyrimidine-5-carboxamide;
(E)-2-cyclopentyl-4-(3-fluorophenoxy)-N-(3-(methylsulfonyl)allyl)pyrimidine-5-carboxamide;
(E)-2-cyclohexyl-N-(3-(methylsulfonyl)allyl)-4-phenoxypyrimidine-5-carboxamide;
(E)-N-(3-(methylsulfonyl)allyl)-2-(methylthio)-4-phenoxypyrimidine-5-carboxamide;
2-cyclopropyl-N-((1,1-dioxido-2H-thiet-3-yl)methyl)-4-phenoxypyrimidine-5-carboxamide;
2-cyclopropyl-N-(1,1-dioxido-2,3-dihydrothiophen-3-yl)-4-phenoxypyrimidine-5-carboxamide;
(E)-2-cyclopentyl-4-(4-fluorophenoxy)-N-(3-(methylsulfonyl)allyl)pyrimidine-5-carboxamide;
(S,E)-2-cyclopentyl-4-(4-fluorophenoxy)-N-(4-(methylsulfonyl)but-3-en-2-yl)pyrimidine-5-carboxamide;
(S,E)-4-(2-chlorophenoxy)-2-cyclopentyl-N-(4-(methylsulfonyl)but-3-en-2-yl)pyrimidine-5-carboxamide;
(S,E)-4-(3-chlorophenoxy)-2-cyclopentyl-N-(4-(methylsulfonyl)but-3-en-2-yl)pyrimidine-5-carboxamide;
(S,E)-2-cyclopentyl-4-(3-fluorophenoxy)-N-(4-(methylsulfonyl)but-3-en-2-yl)pyrimidine-5-carboxamide;
(S,E)-2-cyclopentyl-4-(2-fluorophenoxy)-N-(4-(methylsulfonyl)but-3-en-2-yl)pyrimidine-5-carboxamide;
(S,E)-4-(cyclohexyloxy)-2-cyclopentyl-N-(4-(methylsulfonyl)but-3-en-2-yl)pyrimidine-5-carboxamide;
(E)-2-cyclopentyl-N-methyl-N-(3-(methylsulfonyl)allyl)-4-phenoxypyrimidine-5-carboxamide;
(E)-2-cyclopentyl-N-(3-(methylsulfonyl)allyl)-4-(p-tolyloxy)pyrimidine-5-carboxamide;
(E)-N-(3-(methylsulfonyl)allyl)-4-phenoxy-2-(1H-pyrazol-5-yl)pyrimidine-5-carboxamide;
(E)-4-(3-chlorophenoxy)-2-cyclopentyl-N-(3-(methylsulfonyl)allyl)pyrimidine-5-carboxamide;
(S,E)-2-cyclopentyl-4-(3,5-difluorophenoxy)-N-(4-(methylsulfonyl)but-3-en-2-yl)pyrimidine-5-carboxamide;
(S,E)-2-cyclopentyl-4-(4-fluoro-3-methylphenoxy)-N-(4-(methylsulfonyl)but-3-en-2-yl)pyrimidine-5-carboxamide;
(S,E)-2-cyclopentyl-4-(3,5-dichlorophenoxy)-N-(4-(methylsulfonyl)but-3-en-2-yl)pyrimidine-5-carboxamide;
(S,E)-2-(cyclopentyloxy)-N-(4-(methylsulfonyl)but-3-en-2-yl)-4-phenoxypyrimidine-5-carboxamide;
(2-cyclopropyl-4-phenoxypyrimidin-5-yl)(3-((methylsulfonyl)methylene)azetidin-1-yl)methanone;
(S,E)-2-cyclopentyl-4-(cyclopentyloxy)-N-(4-(methylsulfonyl)but-3-en-2-yl)pyrimidine-5-carboxamide;
(S,E)-4-(4-cyanophenoxy)-2-cyclopentyl-N-(4-(methylsulfonyl)but-3-en-2-yl)pyrimidine-5-carboxamide;
(S,E)-N-(4-(methylsulfonyl)but-3-en-2-yl)-4-phenoxy-2-(tetrahydro-2H-pyran-4-yl)pyrimidine-5-carboxamide;
(S,E)-2-cyclopentyl-4-(3,4-dimethylphenoxy)-N-(4-(methylsulfonyl)but-3-en-2-yl)pyrimidine-5-carboxamide;
(S,E)-2-cyclopentyl-N-(4-(methylsulfonyl)but-3-en-2-yl)-4-(m-tolyloxy)pyrimidine-5-carboxamide;
(S,E)-2-(tert-butyl)-N-(4-(methylsulfonyl)but-3-en-2-yl)-4-phenoxypyrimidine-5-carboxamide;
(S,E)-2-cyclopentyl-4-(4-ethylphenoxy)-N-(4-(methylsulfonyl)but-3-en-2-yl)pyrimidine-5-carboxamide;
(S,E)-2-cyclopentyl-4-(3-ethylphenoxy)-N-(4-(methylsulfonyl)but-3-en-2-yl)pyrimidine-5-carboxamide;
(S,E)-2-cyclopentyl-N-(4-(methylsulfonyl)but-3-en-2-yl)-4-(o-tolyloxy)pyrimidine-5-carboxamide;
(S,E)-2-cyclopentyl-N-(4-(methylsulfonyl)but-3-en-2-yl)-4-((tetrahydro-2H-pyran-4-yl)oxy)pyrimidine-5-carboxamide;
(S,E)-2-(cyclopropylmethyl)-N-(4-(methylsulfonyl)but-3-en-2-yl)-4-phenoxypyrimidine-5-carboxamide;
(S,E)-4-cyclobutoxy-2-cyclopentyl-N-(4-(methylsulfonyl)but-3-en-2-yl)pyrimidine-5-carboxamide;
(S,E)-2-(1-hydroxycyclopentyl)-N-(4-(methylsulfonyl)but-3-en-2-yl)-4-phenoxypyrimidine-5-carboxamide;
(S,E)-2-cyclopentyl-N-(1-(methylsulfonyl)pent-1-en-3-yl)-4-phenoxypyrimidine-5-carboxamide;
N—((S,E)-4-(methylsulfonyl)but-3-en-2-yl)-4-phenoxy-2-(tetrahydrofuran-2-yl)pyrimidine-5-carboxamide;
(S,E)-2-cyclopentyl-N-(4-(methylsulfonyl)but-3-en-2-yl)-4-(pyridin-2-yloxy)pyrimidine-5-carboxamide;
(S,E)-2-cyclopentyl-N-(4-(methylsulfonyl)but-3-en-2-yl)-4-(pyridin-3-yloxy)pyrimidine-5-carboxamide;

(S,E)-2-cyclopropyl-N-(4-(methylsulfonyl)but-3-en-2-yl)-4-(spiro[3.3]heptan-2-yloxy)pyrimidine-5-carboxamide;
(S,E)-N-(4-(methylsulfonyl)but-3-en-2-yl)-4-phenoxy-2-(trifluoromethyl)pyrimidine-5-carboxamide;
(S,E)-2-(tert-butyl)-4-(cyclohexyloxy)-N-(4-(methylsulfonyl)but-3-en-2-yl)pyrimidine-5-carboxamide;
(S,E)-2-(tert-butyl)-4-((4,4-difluorocyclohexyl)oxy)-N-(4-(methylsulfonyl)but-3-en-2-yl)pyrimidine-5-carboxamide;
2-cyclopentyl-N—((S,E)-4-(methylsulfonyl)but-3-en-2-yl)-4-(((S)-tetrahydro-2H-pyran-3-yl)oxy)pyrimidine-5-carboxamide;
(S,E)-2-cyclopropyl-N-(4-(methylsulfonyl)but-3-en-2-yl)-4-(spiro[2.3]hexan-5-yloxy)pyrimidine-5-carboxamide;
(S,E)-2-cyclopropyl-4-(cyclopropylmethoxy)-N-(4-(methylsulfonyl)but-3-en-2-yl)pyrimidine-5-carboxamide;
4-((1R,3S)-3-chlorocyclobutoxy)-2-cyclopropyl-N—((S,E)-4-(methylsulfonyl)but-3-en-2-yl)pyrimidine-5-carboxamide;
(S,E)-4-cyclohexyl-2-cyclopentyl-N-(4-(methylsulfonyl)but-3-en-2-yl)pyrimidine-5-carboxamide;
4-[[(1S,5R)-3-bicyclo[3.1.0]hexanyl]oxy]-2-tert-butyl-N—[(E,1S)-1-methyl-3-methylsulfonyl-allyl]pyrimidine-5-carboxamide;
(S,E)-2-(tert-butyl)-4-((1-cyanocyclopentyl)oxy)-N-(4-(methylsulfonyl)but-3-en-2-yl)pyrimidine-5-carboxamide;
(S,E)-2-(tert-butyl)-4-(3,3-difluorocyclobutoxy)-N-(4-(methylsulfonyl)but-3-en-2-yl)pyrimidine-5-carboxamide;
(S,E)-2-cyclopentyl-4-methyl-N-(4-(methylsulfonyl)but-3-en-2-yl)-6-phenoxypyrimidine-5-carboxamide;
(S,E)-2-(1-fluorocyclopentyl)-N-(4-(methylsulfonyl)but-3-en-2-yl)-4-phenoxypyrimidine-5-carboxamide;
(S,E)-2-cyclopentyl-4-(3-hydroxyphenoxy)-N-(4-(methylsulfonyl)but-3-en-2-yl)pyrimidine-5-carboxamide;
(S,E)-2-cyclopentyl-4-(4-hydroxyphenoxy)-N-(4-(methylsulfonyl)but-3-en-2-yl)pyrimidine-5-carboxamide;
(2-(tert-butyl)-4-phenoxypyrimidin-5-yl)(3-((methylsulfonyl)methylene)azetidin-1-yl)methanone;
(S,E)-2-(tert-butyl)-4-(cyclopentyloxy)-N-(4-(methylsulfonyl)but-3-en-2-yl)pyrimidine-5-carboxamide;
(S,E)-2-(cyclopentylmethyl)-N-(4-(methylsulfonyl)but-3-en-2-yl)-4-phenoxypyrimidine-5-carboxamide;
(S,E)-2-(7-azabicyclo[2.2.1]heptan-7-yl)-N-(4-(methylsulfonyl)but-3-en-2-yl)-4-phenoxypyrimidine-5-carboxamide;
N—((S,E)-4-(methylsulfonyl)but-3-en-2-yl)-4-phenoxy-2-(tetrahydrofuran-3-yl)pyrimidine-5-carboxamide;
(S,E)-4-(3-chloro-5-fluorophenoxy)-2-cyclopentyl-N-(4-(methylsulfonyl)but-3-en-2-yl)pyrimidine-5-carboxamide;
(S,E)-2-(cyclohexylmethyl)-N-(4-(methylsulfonyl)but-3-en-2-yl)-4-phenoxypyrimidine-5-carboxamide;
(S,E)-4-(3-aminophenoxy)-2-cyclopentyl-N-(4-(methylsulfonyl)but-3-en-2-yl)pyrimidine-5-carboxamide;
(S,E)-2-(cyclobutylmethyl)-N-(4-(methylsulfonyl)but-3-en-2-yl)-4-phenoxypyrimidine-5-carboxamide;
(S,E)-2-cyclopropyl-N-(4-(cyclopropylsulfonyl)but-3-en-2-yl)-4-phenoxypyrimidine-5-carboxamide;
(Z)-(2-cyclopropyl-4-phenoxypyrimidin-5-yl)(3-(2-(methylsulfonyl)vinyl)azetidin-1-yl)methanone;
(E)-(2-cyclopropyl-4-phenoxypyrimidin-5-yl)(3-(2-(methylsulfonyl)vinyl)azetidin-1-yl)methanone;
(S,E)-4-(cyclopentyloxy)-2-cyclopropyl-N-(4-(methylsulfonyl)but-3-en-2-yl)pyrimidine-5-carboxamide;
2-cyclopentyl-4-(((1R,2R)-2-hydroxycyclohexyl)oxy)-N—((S,E)-4-(methylsulfonyl)but-3-en-2-yl)pyrimidine-5-carboxamide;
(S,E)-4-amino-2-cyclopentyl-N-(4-(methylsulfonyl)but-3-en-2-yl)-6-phenoxypyrimidine-5-carboxamide;
(S,E)-2-cyclopentyl-N-(4-(methylsulfonyl)but-3-en-2-yl)-4-(naphthalen-1-yloxy)pyrimidine-5-carboxamide;
(R,E)-2-(2-fluorophenyl)-N-(4-(methylsulfonyl)but-3-en-2-yl)-4-phenoxypyrimidine-5-carboxamide;
(S,E)-2-cyclopentyl-4-(2-hydroxyphenoxy)-N-(4-(methylsulfonyl)but-3-en-2-yl)pyrimidine-5-carboxamide;
(S,E)-4-(cycloheptyloxy)-2-cyclopentyl-N-(4-(methylsulfonyl)but-3-en-2-yl)pyrimidine-5-carboxamide;
2-cyclopentyl-4-(((1S,2R)-2-hydroxycyclohexyl)oxy)-N—((S,E)-4-(methylsulfonyl)but-3-en-2-yl)pyrimidine-5-carboxamide;
2-cyclopentyl-4-(((1R,2S)-2-hydroxycyclohexyl)oxy)-N—((S,E)-4-(methylsulfonyl)but-3-en-2-yl)pyrimidine-5-carboxamide;
(S,E)-2-(bicyclo[1.1.1]pentan-1-yl)-N-(4-(methylsulfonyl)but-3-en-2-yl)-4-phenoxypyrimidine-5-carboxamide;
2-((1S,3R)-3-methylcyclobutyl)-N—((S,E)-4-(methylsulfonyl)but-3-en-2-yl)-4-phenoxypyrimidine-5-carboxamide;
2-((1R,3S)-3-methylcyclobutyl)-N—((S,E)-4-(methylsulfonyl)but-3-en-2-yl)-4-phenoxypyrimidine-5-carboxamide;
(S,E)-2-(3-methoxyazetidin-1-yl)-N-(4-(methylsulfonyl)but-3-en-2-yl)-4-phenoxypyrimidine-5-carboxamide;
2-cyclopropyl-4-((3,3-difluorocyclopentyl)oxy)-N—((S,E)-4-(methylsulfonyl)but-3-en-2-yl)pyrimidine-5-carboxamide;
2-cyclopropyl-4-(((S)-2,2-difluorocyclopentyl)oxy)-N—((S,E)-4-(methylsulfonyl)but-3-en-2-yl)pyrimidine-5-carboxamide;
2-cyclopropyl-4-(((R)-2,2-difluorocyclopentyl)oxy)-N—((S,E)-4-(methylsulfonyl)but-3-en-2-yl)pyrimidine-5-carboxamide;
(S,E)-N-(4-(methylsulfonyl)but-3-en-2-yl)-4-phenoxy-2-(2-azaspiro[3.3]heptan-2-yl)pyrimidine-5-carboxamide;
2-(bicyclo[4.2.0]octa-1,3,5-trien-7-yl)-N—((S,E)-4-(methylsulfonyl)but-3-en-2-yl)-4-phenoxypyrimidine-5-carboxamide;
N—((S,E)-4-(methylsulfonyl)but-3-en-2-yl)-4-phenoxy-2-(tetrahydro-2H-pyran-3-yl)pyrimidine-5-carboxamide;
(S,E)-2-(5,6-dihydro-2H-pyran-3-yl)-N-(4-(methylsulfonyl)but-3-en-2-yl)-4-phenoxypyrimidine-5-carboxamide;
(S,E)-2-cyclopentyl-N-(4-methyl-1-(methylsulfonyl)pent-1-en-3-yl)-4-phenoxypyrimidine-5-carboxamide;
(S,E)-2-(2-hydroxypropan-2-yl)-N-(4-(methylsulfonyl)but-3-en-2-yl)-4-phenoxypyrimidine-5-carboxamide;
(S,E)-2-isobutyl-N-(4-(methylsulfonyl)but-3-en-2-yl)-4-phenoxypyrimidine-5-carboxamide;
(S,E)-2-(2-methylprop-1-en-1-yl)-N-(4-(methylsulfonyl)but-3-en-2-yl)-4-phenoxypyrimidine-5-carboxamide;
2-((2R,5S)-2,5-dimethylpyrrolidin-1-yl)-N—((S,E)-4-(methylsulfonyl)but-3-en-2-yl)-4-phenoxypyrimidine-5-carboxamide;
2-((2R,5R)-2,5-dimethylpyrrolidin-1-yl)-N—((S,E)-4-(methylsulfonyl)but-3-en-2-yl)-4-phenoxypyrimidine-5-carboxamide;

(S,E)-4-(bicyclo[2.2.1]heptan-1-yloxy)-2-cyclopropyl-N-(4-(methylsulfonyl)but-3-en-2-yl)pyrimidine-5-carboxamide;

(S,E)-2-(3,3-difluoropyrrolidin-1-yl)-N-(4-(methylsulfonyl)but-3-en-2-yl)-4-phenoxypyrimidine-5-carboxamide;

(S,E)-2-(2-methoxypropan-2-yl)-N-(4-(methylsulfonyl)but-3-en-2-yl)-4-phenoxypyrimidine-5-carboxamide;

(S,E)-2-(1,1-difluoroethyl)-N-(4-(methylsulfonyl)but-3-en-2-yl)-4-phenoxypyrimidine-5-carboxamide;

(S,E)-2-cyclopentyl-N-(1-cyclopropyl-3-(methylsulfonyl)allyl)-4-phenoxypyrimidine-5-carboxamide;

(S,E)-2-(1-methylcyclopropyl)-N-(4-(methylsulfonyl)but-3-en-2-yl)-4-phenoxypyrimidine-5-carboxamide;

(2-(1-methylcyclopropyl)-4-phenoxypyrimidin-5-yl)(3-((methylsulfonyl)methylene)azetidin-1-yl)methanone;

(2-(tert-butyl)-4-phenoxypyrimidin-5-yl)(3-(((tetrahydro-2H-pyran-4-yl)sulfonyl)methylene)azetidin-1-yl)methanone;

(2-((1S,3S)-3-methylcyclobutyl)-4-phenoxypyrimidin-5-yl)(3-((methylsulfonyl)methylene)azetidin-1-yl)methanone;

(2-((1r,3r)-3-methylcyclobutyl)-4-phenoxypyrimidin-5-yl)(3-((methylsulfonyl)methylene)azetidin-1-yl)methanone;

(S,E)-N-(4-(methylsulfonyl)but-3-en-2-yl)-4-phenoxy-2-(pyrrolidin-1-yl)pyrimidine-5-carboxamide;

(S,E)-2-(2,2-dimethylpyrrolidin-1-yl)-N-(4-(methylsulfonyl)but-3-en-2-yl)-4-phenoxypyrimidine-5-carboxamide;

2-((S)-2-methylpyrrolidin-1-yl)-N—((S,E)-4-(methylsulfonyl)but-3-en-2-yl)-4-phenoxypyrimidine-5-carboxamide;

2-((R)-2-methylpyrrolidin-1-yl)-N—((S,E)-4-(methylsulfonyl)but-3-en-2-yl)-4-phenoxypyrimidine-5-carboxamide;

1-(1-(2-(tert-butyl)-4-phenoxypyrimidine-5-carbonyl)azetidin-3-ylidene)propan-2-one;

(S,E)-2-((1-methylcyclopropyl)methyl)-N-(4-(methylsulfonyl)but-3-en-2-yl)-4-phenoxypyrimidine-5-carboxamide;

(2-((1-methylcyclopropyl)methyl)-4-phenoxypyrimidin-5-yl)(3-((methylsulfonyl)methylene)azetidin-1-yl)methanone;

(E)-(2-cyclopropyl-4-phenoxypyrimidin-5-yl)(3-((methylsulfonyl)methylene)pyrrolidin-1-yl)methanone;

(S,E)-2-(tert-butyl)-N-(4-(methylsulfonyl)but-3-en-2-yl)-4-(phenoxy-d5)pyrimidine-5-carboxamide;

(S,E)-2-cyclopropyl-N-(4-(methylsulfonyl)but-3-en-2-yl)-4-(phenoxy-d5)pyrimidine-5-carboxamide;

(R,E)-2-(tert-butyl)-N-(1-methoxy-4-(methylsulfonyl)but-3-en-2-yl)-4-phenoxypyrimidine-5-carboxamide;

(S,E)-2-(tert-butyl)-N-(1-methoxy-4-(methylsulfonyl)but-3-en-2-yl)-4-phenoxypyrimidine-5-carboxamide;

(S,E)-N-(4-(methylsulfonyl)but-3-en-2-yl)-4-phenoxy-2-(1-phenylcyclopropyl)pyrimidine-5-carboxamide;

2-((1R,3S)-3-methylcyclopentyl)-N—((S,E)-4-(methylsulfonyl)but-3-en-2-yl)-4-phenoxypyrimidine-5-carboxamide;

(S,E)-2-(tert-butyl)-N-(1-cyclopropyl-4-(methylsulfonyl)but-3-en-2-yl)-4-phenoxypyrimidine-5-carboxamide;

(S,E)-2-cyclopropyl-N-(1-cyclopropyl-4-(methylsulfonyl)but-3-en-2-yl)-4-phenoxypyrimidine-5-carboxamide;

(S,E)-2-(3,3-difluorocyclobutyl)-N-(4-(methylsulfonyl)but-3-en-2-yl)-4-phenoxypyrimidine-5-carboxamide;

(R,E)-2-(1,1-difluoroethyl)-N-(1-methoxy-4-(methylsulfonyl)but-3-en-2-yl)-4-phenoxypyrimidine-5-carboxamide;

(S,E)-2-(tert-butyl)-N-(1-cyclopropyl-3-(methylsulfonyl)allyl)-4-phenoxypyrimidine-5-carboxamide;

(S,E)-2-(tert-butyl)-N-(1-cyclobutyl-3-(methylsulfonyl)allyl)-4-phenoxypyrimidine-5-carboxamide;

(S,E)-N-(1-cyclobutyl-3-(methylsulfonyl)allyl)-2-cyclopropyl-4-phenoxypyrimidine-5-carboxamide;

(S,E)-2-(tert-butyl)-N-(1-(3,3-difluorocyclobutyl)-3-(methylsulfonyl)allyl)-4-phenoxypyrimidine-5-carboxamide;

(S,E)-2-cyclopropyl-N-(1-(3,3-difluorocyclobutyl)-3-(methylsulfonyl)allyl)-4-phenoxypyrimidine-5-carboxamide;

(S,E)-2-(1-fluorocyclopropyl)-N-(4-(methylsulfonyl)but-3-en-2-yl)-4-phenoxypyrimidine-5-carboxamide;

(S,E)-N-(1-cyclopropyl-3-(methylsulfonyl)allyl)-2-(1,1-difluoroethyl)-4-phenoxypyrimidine-5-carboxamide;

(S,E)-4-acetamido-2-cyclopentyl-N-(4-(methylsulfonyl)but-3-en-2-yl)-6-phenoxypyrimidine-5-carboxamide;

(R,E)-2-(tert-butyl)-N-(4-(methylsulfonyl)-1-(methylthio)but-3-en-2-yl)-4-phenoxypyrimidine-5-carboxamide;

(R,E)-2-cyclopropyl-N-(4-(methylsulfonyl)-1-(methylthio)but-3-en-2-yl)-4-phenoxypyrimidine-5-carboxamide;

(S,E)-N-(4-(methylsulfonyl)but-3-en-2-yl)-2-(perfluoroethyl)-4-phenoxypyrimidine-5-carboxamide;

(S,E)-N-(1-cyclopropyl-3-(methylsulfonyl)allyl)-2-isopropyl-4-phenoxypyrimidine-5-carboxamide;

(S,E)-2-cyclopropyl-N-(1-cyclopropyl-3-(methylsulfonyl)allyl)-4-phenoxypyrimidine-5-carboxamide;

(S,E)-N-(1-cyclopropyl-3-(methylsulfonyl)allyl)-2-(2-fluoropropan-2-yl)-4-phenoxypyrimidine-5-carboxamide;

N—((S,E)-1-cyclopropyl-3-(methylsulfonyl)allyl)-2-((1S,3S)-3-methylcyclobutyl)-4-phenoxypyrimidine-5-carboxamide;

N—((S,E)-1-cyclopropyl-3-(methylsulfonyl)allyl)-2-((1R,3R)-3-methylcyclobutyl)-4-phenoxypyrimidine-5-carboxamide;

(2-cyclopropyl-4-phenoxypyrimidin-5-yl)(3-(methylsulfonyl)-2,5-dihydro-1H-pyrrol-1-yl)methanone;

(S,E)-2-cyclopropyl-N-(4-(methylsulfonyl)-1-phenylbut-3-en-2-yl)-4-phenoxypyrimidine-5-carboxamide;

(S,Z)-2-cyclopropyl-N-(4-(methylsulfonyl)-1-phenylbut-3-en-2-yl)-4-phenoxypyrimidine-5-carboxamide;

2-(tert-butyl)-N-((3R,4R,E)-4-methoxy-1-(methylsulfonyl)pent-1-en-3-yl)-4-phenoxypyrimidine-5-carboxamide;

(S,E)-2-(tert-butyl)-N-(3-(methylsulfonyl)-1-(tetrahydro-2H-pyran-4-yl)allyl)-4-phenoxypyrimidine-5-carboxamide;

2-cyclopropyl-N-((3R,4R,E)-4-methoxy-1-(methylsulfonyl)pent-1-en-3-yl)-4-phenoxypyrimidine-5-carboxamide;

(S,E)-2-cyclopropyl-N-(3-(methylsulfonyl)-1-(tetrahydro-2H-pyran-4-yl)allyl)-4-phenoxypyrimidine-5-carboxamide;

(S,E)-N-(1-cyclopropyl-3-(methylsulfonyl)allyl)-2-(cyclopropylmethyl)-4-phenoxypyrimidine-5-carboxamide;

(S,E)-2-(tert-butyl)-N-(4-(methylsulfonyl)-1-phenylbut-3-en-2-yl)-4-phenoxypyrimidine-5-carboxamide;

(S,Z)-2-(tert-butyl)-N-(4-(methylsulfonyl)-1-phenylbut-3-en-2-yl)-4-phenoxypyrimidine-5-carboxamide;

(R,E)-2-cyclopentyl-N-(1-methoxy-4-(methylsulfonyl)but-3-en-2-yl)-4-phenoxypyrimidine-5-carboxamide;
(S,E)-2-cyclobutyl-N-(1-cyclopropyl-3-(methylsulfonyl)allyl)-4-phenoxypyrimidine-5-carboxamide;
(S,E)-N-(1-cyclopropyl-3-(methylsulfonyl)allyl)-2-(cyclopropyldifluoromethyl)-4-phenoxypyrimidine-5-carboxamide;
(S,E)-2-(cyclopropyldifluoromethyl)-N-(4-(methylsulfonyl)but-3-en-2-yl)-4-phenoxypyrimidine-5-carboxamide;
(R,E)-2-(cyclopropyldifluoromethyl)-N-(1-methoxy-4-(methylsulfonyl)but-3-en-2-yl)-4-phenoxypyrimidine-5-carboxamide;
(S,E)-2-(1,1-difluoroethyl)-4-phenoxy-N-(5,5,5-trifluoro-1-(methylsulfonyl)pent-1-en-3-yl)pyrimidine-5-carboxamide;
(S,E)-N-(1-cyclobutyl-3-(methylsulfonyl)allyl)-2-cyclopentyl-4-phenoxypyrimidine-5-carboxamide;
(E)-2-(tert-butyl)-N-(4-(methylsulfonyl)-1-phenoxybut-3-en-2-yl)-4-phenoxypyrimidine-5-carboxamide;
(S,E)-N-(1-cyclobutyl-3-(methylsulfonyl)allyl)-2-(cyclopropyldifluoromethyl)-4-phenoxypyrimidine-5-carboxamide;
(S,E)-N-(1-cyclobutyl-3-(methylsulfonyl)allyl)-2-(1,1-difluoroethyl)-4-phenoxypyrimidine-5-carboxamide;
(S,E)-2-(tert-butyl)-N-(5-(dimethylamino)-1-(methylsulfonyl)-5-oxopent-1-en-3-yl)-4-phenoxypyrimidine-5-carboxamide;
(R,E)-2-(1,1-difluoroethyl)-4-phenoxy-N-(5,5,5-trifluoro-1-(methylsulfonyl)pent-1-en-3-yl)pyrimidine-5-carboxamide;
(S,E)-N-(1-cyclopropyl-3-(methylsulfonyl)allyl)-2-(perfluoroethyl)-4-phenoxypyrimidine-5-carboxamide;
(R,E)-N-(1-methoxy-4-(methylsulfonyl)but-3-en-2-yl)-2-(perfluoroethyl)-4-phenoxypyrimidine-5-carboxamide;
(S,E)-N-(1-cyclopropyl-3-(methylsulfonyl)allyl)-4-phenoxy-2-(trifluoromethyl)pyrimidine-5-carboxamide;
(S,E)-N-(4-(methylsulfonyl)but-3-en-2-yl)-4-phenoxy-2-(1-(trifluoromethyl)cyclopropyl)pyrimidine-5-carboxamide;
(S,E)-N-(1-cyclopropyl-3-(methylsulfonyl)allyl)-4-phenoxy-2-(1-(trifluoromethyl)cyclopropyl)pyrimidine-5-carboxamide;
(S,E)-N-(1-cyclopropyl-3-(methylsulfonyl)allyl)-4-phenoxy-2-(2,2,2-trifluoroethyl)pyrimidine-5-carboxamide;
(S,E)-N-(1-cyclopropyl-3-(methylsulfonyl)allyl)-2-(1-fluorocyclopropyl)-4-phenoxypyrimidine-5-carboxamide;
(S,E)-2-(tert-butyl)-N-(1-(4,4-difluorocyclohexyl)-3-(methylsulfonyl)allyl)-4-phenoxypyrimidine-5-carboxamide;
(S,E)-2-(tert-butyl)-N-(5,5-difluoro-1-(methylsulfonyl)pent-1-en-3-yl)-4-phenoxypyrimidine-5-carboxamide;
(S,E)-N-(5,5-difluoro-1-(methylsulfonyl)pent-1-en-3-yl)-2-(1,1-difluoroethyl)-4-phenoxypyrimidine-5-carboxamide;
(S,E)-N-(1-(4,4-difluorocyclohexyl)-3-(methylsulfonyl)allyl)-2-(1,1-difluoroethyl)-4-phenoxypyrimidine-5-carboxamide;
(R,E)-N-(4-(methylsulfonyl)but-3-en-2-yl)-4-phenoxy-2-(2,2,2-trifluoroethyl)pyrimidine-5-carboxamide;
4-(((1R,3S,5S)-bicyclo[3.1.0]hexan-3-yl)oxy)-2-(tert-butyl)-N—((E)-3-(methylsulfonyl)allyl)pyrimidine-5-carboxamide;
4-(((1R,3S,5S)-bicyclo[3.1.0]hexan-3-yl)oxy)-2-cyclopropyl-N—((E)-3-(methylsulfonyl)allyl)pyrimidine-5-carboxamide;
(R,E)-N-(1-(tert-butoxy)-4-(methylsulfonyl)but-3-en-2-yl)-2-(1,1-difluoroethyl)-4-phenoxypyrimidine-5-carboxamide;
(R,E)-2-(tert-butyl)-N-(4-(methylsulfonyl)-1-phenoxybut-3-en-2-yl)-4-phenoxypyrimidine-5-carboxamide;
(S,E)-2-(tert-butyl)-N-(4-(methylsulfonyl)-1-phenoxybut-3-en-2-yl)-4-phenoxypyrimidine-5-carboxamide;
(S,E)-N-(4-(methylsulfonyl)but-3-en-2-yl)-4-phenoxy-2-(spiro[2.3]hexan-5-yl)pyrimidine-5-carboxamide;
(R,E)-2-(1,1-difluoroethyl)-N-(1-(difluoromethoxy)-4-(methylsulfonyl)but-3-en-2-yl)-4-phenoxypyrimidine-5-carboxamide;
(S,E)-2-(1,1-difluoroethyl)-N-(5-(dimethylamino)-1-(methylsulfonyl)-5-oxopent-1-en-3-yl)-4-phenoxypyrimidine-5-carboxamide;
N—((S,E)-1-cyclopropyl-3-(methylsulfonyl)allyl)-2-(cyclopropylfluoromethyl)-4-phenoxypyrimidine-5-carboxamide;
4-(((1R,3S,5S)-bicyclo[3.1.0]hexan-3-yl)oxy)-2-(tert-butyl)-N—((S,E)-1-cyclopropyl-3-(methylsulfonyl)allyl)pyrimidine-5-carboxamide;
(S,E)-N-(1-(3,3-difluorocyclobutyl)-3-(methylsulfonyl)allyl)-2-(1,1-difluoroethyl)-4-phenoxypyrimidine-5-carboxamide;
(R,E)-N-(1-(3,3-difluorocyclobutyl)-3-(methylsulfonyl)allyl)-2-(1,1-difluoroethyl)-4-phenoxypyrimidine-5-carboxamide;
(S,E)-2-(cyclopropyldifluoromethyl)-N-(1-(3,3-difluorocyclobutyl)-3-(methylsulfonyl)allyl)-4-phenoxypyrimidine-5-carboxamide;
(R,E)-2-(cyclopropyldifluoromethyl)-N-(1-(3,3-difluorocyclobutyl)-3-(methylsulfonyl)allyl)-4-phenoxypyrimidine-5-carboxamide;
2-(1,1-difluoroethyl)-N-((3R,4S,E)-4-methoxy-1-(methylsulfonyl)pent-1-en-3-yl)-4-phenoxypyrimidine-5-carboxamide;
4-(((1R,3R,5S)-bicyclo[3.1.0]hexan-3-yl)oxy)-N—((S,E)-1-cyclopropyl-3-(methylsulfonyl)allyl)-2-(1,1-difluoroethyl)pyrimidine-5-carboxamide;
(R,E)-N-(1-cyclopropoxy-4-(methylsulfonyl)but-3-en-2-yl)-2-(1,1-difluoroethyl)-4-phenoxypyrimidine-5-carboxamide;
(S,E)-N-(1-cyclopropyl-3-(methylsulfonyl)allyl)-2-(dimethylamino)-4-phenoxypyrimidine-5-carboxamide;
(S,E)-N-(1-cyclopropyl-3-(methylsulfonyl)allyl)-2-(methylamino)-4-phenoxypyrimidine-5-carboxamide;
(S,E)-2-cyclopropoxy-N-(1-cyclopropyl-3-(methylsulfonyl)allyl)-4-phenoxypyrimidine-5-carboxamide;
(S,E)-N-(1-cyclopropyl-3-(methylsulfonyl)allyl)-4-phenoxy-2-(2,2,2-trifluoroethoxy)pyrimidine-5-carboxamide;
(S,E)-N-(1-cyclopropyl-3-(methylsulfonyl)allyl)-2-(diethylamino)-4-phenoxypyrimidine-5-carboxamide;
(S,E)-2-(cyclopropyl(methyl)amino)-N-(1-cyclopropyl-3-(methylsulfonyl)allyl)-4-phenoxypyrimidine-5-carboxamide;
(S,E)-N-(1-cyclopropyl-3-(methylsulfonyl)allyl)-2-methoxy-4-phenoxypyrimidine-5-carboxamide;
(S,E)-2-(azetidin-1-yl)-N-(1-cyclopropyl-3-(methylsulfonyl)allyl)-4-phenoxypyrimidine-5-carboxamide;
(S,E)-N-(1-cyclopropyl-3-(methylsulfonyl)allyl)-2-(methyl(2,2,2-trifluoroethyl)amino)-4-phenoxypyrimidine-5-carboxamide;

(S,E)-N-(1-cyclopropyl-3-(methylsulfonyl)allyl)-2-(3-fluoroazetidin-1-yl)-4-phenoxypyrimidine-5-carboxamide;

(S,E)-N-(1-cyclopropyl-3-(methylsulfonyl)allyl)-2-(ethyl(methyl)amino)-4-phenoxypyrimidine-5-carboxamide;

(S,E)-N-(1-cyclopropyl-3-(methylsulfonyl)allyl)-2-(3,3-difluoroazetidin-1-yl)-4-phenoxypyrimidine-5-carboxamide;

(S,E)-N-(1-cyclopropyl-3-(methylsulfonyl)allyl)-2-(1,1-difluoropropyl)-4-phenoxypyrimidine-5-carboxamide;

(S,E)-N-(1-cyclopropyl-3-(methylsulfonyl)allyl-1-d)-2-(1,1-difluoroethyl)-4-phenoxypyrimidine-5-carboxamide;

(S)—N-(3-cyanobut-3-en-2-yl)-2-(cyclopropyldifluoromethyl)-4-phenoxypyrimidine-5-carboxamide;

(S,E)-N-(1-cyclopropyl-3-(methylsulfonyl)allyl)-2-(cyclopropyldifluoromethyl)-4-(phenoxy-d5)pyrimidine-5-carboxamide;

(S,E)-N-(1-cyclopropyl-3-(methylsulfonyl)allyl-1-d)-2-(1,1-difluoroethyl)-4-phenoxypyrimidine-5-carboxamide; and (S,E)-N-(1-cyclopropyl-3-(methylsulfonyl)allyl)-2-(cyclopropyldifluoromethyl)-4-(phenoxy-d5)pyrimidine-5-carboxamide.

15. The compound according to claim 1, or a pharmaceutically acceptable salt thereof, wherein the compound is selected from the group consisting of:
2-(1-(2-cyclopropyl-4-phenoxypyrimidine-5-carbonyl)azetidin-3-ylidene)acetonitrile;
2-(1-(2-cyclopropyl-4-phenoxypyrimidine-5-carbonyl)-2-methylazetidin-3-ylidene)acetonitrile;
(E)-N-(3-cyanoallyl)-2-cyclopropyl-4-phenoxypyrimidine-5-carboxamide; and
(Z)—N-(3-cyanoallyl)-2-cyclopropyl-4-phenoxypyrimidine-5-carboxamide.

16. The compound according to claim 1, or a pharmaceutically acceptable salt thereof, wherein the compound is selected from the group consisting of:
N-(2-cyanoallyl)-2-cyclopropyl-4-phenoxypyrimidine-5-carboxamide;
2-(tert-butyl)-N-(2-cyanoallyl)-4-phenoxypyrimidine-5-carboxamide;
N-(2-cyanoallyl)-2-(1,1-difluoroethyl)-4-phenoxypyrimidine-5-carboxamide;
N-(2-cyanoallyl)-2-cyclopentyl-4-phenoxypyrimidine-5-carboxamide;
N-(2-cyanoallyl)-2-(cyclopropyldifluoromethyl)-4-phenoxypyrimidine-5-carboxamide;
(R)—N-(3-cyanobut-3-en-2-yl)-2-(1,1-difluoroethyl)-4-phenoxypyrimidine-5-carboxamide;
(S)—N-(3-cyanobut-3-en-2-yl)-2-(1,1-difluoroethyl)-4-phenoxypyrimidine-5-carboxamide;
(S)—N-(3-cyanobut-3-en-2-yl)-2-(cyclopropyldifluoromethyl)-4-phenoxypyrimidine-5-carboxamide; and (S)—N-(2-cyano-1-cyclopropylallyl)-2-(1,1-difluoroethyl)-4-phenoxypyrimidine-5-carboxamide.

17. The compound according to claim 1, or a pharmaceutically acceptable salt thereof, wherein the compound is:
(S)-2-(1,1-difluoroethyl)-N-(5-(dimethylamino)-5-oxopent-3-yn-2-yl)-4-phenoxypyrimidine-5-carboxamide.

18. The compound according to claim 1, or a pharmaceutically acceptable salt thereof, wherein the compound is selected from the group consisting of:
1-(1-(2-(tert-butyl)-4-phenoxypyrimidine-5-carbonyl)azetidin-3-ylidene)propan-2-one; and
methyl 2-(1-(2-(tert-butyl)-4-phenoxypyrimidine-5-carbonyl)azetidin-3-ylidene)acetate.

19. A pharmaceutical composition, comprising a compound according to claim 1, or a pharmaceutically acceptable salt thereof, and a pharmaceutically acceptable carrier or excipient.

20. A compound of formula:

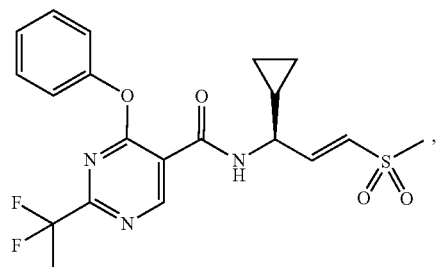 [SMILES: CC(F)(F)c1ncc(C(=O)N[C@H](/C=C/S(C)(=O)=O)C2CC2)c(Oc2ccccc2)n1]

or a pharmaceutically acceptable salt thereof.

21. A pharmaceutical composition comprising the compound according to claim 20, or a pharmaceutically acceptable salt thereof, and a pharmaceutically acceptable carrier or excipient.

22. A compound of formula:

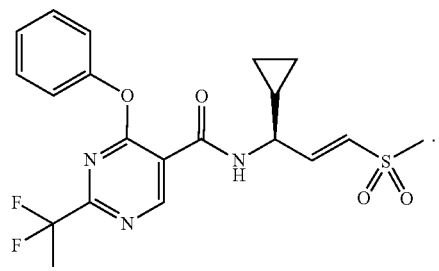 [SMILES: CC(F)(F)c1ncc(C(=O)N[C@H](/C=C/S(C)(=O)=O)C2CC2)c(Oc2ccccc2)n1]

23. A pharmaceutical composition comprising the compound according to claim 22 and a pharmaceutically acceptable carrier or excipient.

* * * * *

```
                            SEQUENCE LISTING

Sequence total quantity: 5
SEQ ID NO: 1            moltype = AA  length = 1432
FEATURE                 Location/Qualifiers
source                  1..1432
                        mol_type = protein
                        organism = Homo sapiens
SEQUENCE: 1
MSEKKLETTA QQRKCPEWMN VQNKRCAVEE RKACVRKSVF EDDLPFLEFT GSIVYSYDAS   60
DCSFLSEDIS MSLSDGDVVG FDMEWPPLYN RGKLGKVALI QLCVSESKCY LFHVSSMSVF  120
PQGLKMLLEN KAVKKAGVGI EGDQWKLLRD FDIKLKNFVE LTDVANKKLK CTETWSLNSL  180
VKHLLGKQLL KDKSIRCSNW SKFPLTEDQK LYAATDAYAG FIIYRNLEIL DDTVQRFAIN  240
KEEEILLSDM NKQLTSISEE VMDLAKHLPH AFSKLENPRR VSILLKDISE NLYSLRRMII  300
GSTNIETELR PSNNLNLLSF EDSTTGGVQQ KQIREHEVLI HVEDETWDPT LDHLAKHDGE  360
DVLGNKVERK EDGFEDGVED NKLKENMERA CLMSLDITEH ELQILEQQSQ EEYLSDIAYK  420
STEHLSPNDN ENDTSYVIES DEDLEMEMLK HLSPNDNEND TSYVIESDED LEMEMLKSLE  480
NLNSGTVEPT HSKCLKMERN LGLPTKEEEE DDENEANEGE EDDDKDFLWP APNEEQVTCL  540
KMYFGHSSFK PVQWKVIHSV LEERRDNVAV MATGYGKSLC FQYPPVYVGK IGLVISPLIS  600
LMEDQVLQLK MSNIPACFLG SAQSENVLTD IKLGKYRIVY VTPEYCSGNM GLLQQLEADI  660
GITLIAVDEA HCISEWGHDF RDSFRKLGSL KTALPMVPIV ALTATASSSI REDIVRCLNL  720
RNPQITCTGF DRPNLYLEVR RKTGNILQDL QPFLVKTSSH WEFEGPTIIY CPSRKMTQQV  780
TGELRKLNLS CGTYHAGMSF STRKDIHHRF VRDEIQCVIA TIAFGMGINK ADIRQVIHYG  840
APKDMESYYQ EIGRAGRDGL QSSCHVLWAP ADINLNRHLL TEIRNEKFRL YKLKMMAKME  900
KYLHSSRCRM QIILSHFEDK QVQKASLGIM GTEKCCDNCR SRLDHCYSMD DSEDTSWDFG  960
PQAFKLLSAV DILGEKFGIG LPILFLRGSN SQRLADQYRR HSLFGTGKDQ TESWWKAFSR 1020
QLITEGFLVE VSRYNKFMKI CALTKKGRNW LHKANTESQS LILQANEELC PKKLLLPSSK 1080
TVSSGTKEHC YNQVPVELST EKKSNLEKLY SYKPCDKISS GSNISKKSIM VQSPEKAYSS 1140
SQPVISAQEQ ETQIVLYGKL VEARQKHANK MDVPPAILAT NKILVDMAKM RPTTVENVKR 1200
IDGVSEGKAA MLAPLLEVIK HFCQTNSVQT DLFSSTKPQE EQKTSLVAKN KICTLSQSMA 1260
ITYSLFQEKK MPLKSIAESR ILPLMTIGMH LSQAVKAGCP LDLERAGLTP EVQKIIADVI 1320
RNPPVNSDMS KISLIRMLVP ENIDTYLIHM AIEILKHGPD SGLQPSCDVN KRRCFPGSEE 1380
ICSSSKRSKE EVGINTETSS AERKRRLPVW FAKGSDTSKK LMDKTKRGGL FS         1432

SEQ ID NO: 2            moltype = AA  length = 10
FEATURE                 Location/Qualifiers
source                  1..10
                        mol_type = protein
                        organism = synthetic construct
SEQUENCE: 2
HHHHHHHHHH                                                          10

SEQ ID NO: 3            moltype = DNA  length = 50
FEATURE                 Location/Qualifiers
source                  1..50
                        mol_type = other DNA
                        organism = synthetic construct
modified_base           50
                        mod_base = OTHER
                        note = 3'black hole quencher-2 modified nucleotide
SEQUENCE: 3
tttttttttt tttttttttt tttttttttt cgtacccgat gtgttcgttc              50

SEQ ID NO: 4            moltype = DNA  length = 50
FEATURE                 Location/Qualifiers
source                  1..50
                        mol_type = other DNA
                        organism = synthetic construct
modified_base           1
                        mod_base = OTHER
                        note = Tetramethylrhodamine (TAMRA) modified nucleotide
SEQUENCE: 4
gaacgaacac atcgggtacg tttttttttt tttttttttt tttttttttt              50

SEQ ID NO: 5            moltype = DNA  length = 20
FEATURE                 Location/Qualifiers
source                  1..20
                        mol_type = other DNA
                        organism = synthetic construct
SEQUENCE: 5
gaacgaacac atcgggtacg                                               20
```